United States Patent
Tremblay et al.

(10) Patent No.: US 9,828,426 B2
(45) Date of Patent: *Nov. 28, 2017

(54) ANTIBODIES AGAINST KIDNEY ASSOCIATED ANTIGEN 1 AND ANTIGEN BINDING FRAGMENTS THEREOF

(71) Applicant: ADC THERAPEUTICS SA, Epalinges (CH)

(72) Inventors: Gilles Bernard Tremblay, La Prairie (CA); Anna N. Moraitis, Laval (CA); Traian Sulea, Kirkland (CA); Mario Filion, Longueuil (CA)

(73) Assignee: ADC Therapeutics SA, Epalinges (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/137,368

(22) Filed: Apr. 25, 2016

(65) Prior Publication Data

US 2016/0304605 A1    Oct. 20, 2016

Related U.S. Application Data

(63) Continuation of application No. 14/558,186, filed on Dec. 2, 2014, now Pat. No. 9,393,302, which is a continuation of application No. 14/036,204, filed as application No. PCT/CA2012/000296 on Mar. 28, 2012, now Pat. No. 8,937,163.

(60) Provisional application No. 61/470,063, filed on Mar. 31, 2011, provisional application No. 61/533,346, filed on Sep. 12, 2011.

(51) Int. Cl.

| | |
|---|---|
| *C07K 9/00* | (2006.01) |
| *C07K 16/28* | (2006.01) |
| *G01N 33/574* | (2006.01) |
| *A61K 47/48* | (2006.01) |
| *C07K 16/30* | (2006.01) |
| *C07K 16/00* | (2006.01) |
| *A61K 38/06* | (2006.01) |
| *A61K 39/395* | (2006.01) |
| *A61K 45/06* | (2006.01) |
| *C07K 16/18* | (2006.01) |

(52) U.S. Cl.
CPC .............. *C07K 16/28* (2013.01); *A61K 38/06* (2013.01); *A61K 39/39558* (2013.01); *A61K 45/06* (2013.01); *A61K 47/48607* (2013.01); *A61K 47/48638* (2013.01); *C07K 16/00* (2013.01); *C07K 16/18* (2013.01); *C07K 16/30* (2013.01); *C07K 16/3038* (2013.01); *C07K 16/3069* (2013.01); *G01N 33/57484* (2013.01); *C07K 2317/21* (2013.01); *C07K 2317/24* (2013.01); *C07K 2317/34* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,745,076 A | 5/1988 | Muller et al. | |
| 5,075,447 A | 12/1991 | Muller et al. | |
| 5,585,279 A | 12/1996 | Davidson | |
| 5,708,022 A | 1/1998 | Bastos et al. | |
| 5,712,127 A | 1/1998 | Malek et al. | |
| 6,057,098 A | 5/2000 | Buechler et al. | |
| 6,288,221 B1 | 9/2001 | Grinstaff et al. | |
| 6,358,953 B1 | 3/2002 | Moheno | |
| 6,806,089 B1 | 10/2004 | Lakowicz et al. | |
| 6,812,339 B1 | 11/2004 | Venter et al. | |
| 6,962,910 B2 | 11/2005 | Brewer et al. | |
| 7,030,236 B2 | 4/2006 | Jhaveri et al. | |
| 7,202,234 B2 | 4/2007 | Chow et al. | |
| 7,429,567 B2 | 9/2008 | Lee et al. | |
| 7,439,051 B2 | 10/2008 | Sokoloff et al. | |
| 7,494,788 B2 | 2/2009 | Dunker et al. | |
| 7,501,485 B2 | 3/2009 | Cowsar | |
| 7,521,197 B2 | 4/2009 | Savage | |
| 7,531,533 B2 | 5/2009 | Shoda et al. | |
| 7,550,501 B2 | 6/2009 | Chow et al. | |
| 7,557,213 B2 | 7/2009 | Melikian et al. | |

(Continued)

FOREIGN PATENT DOCUMENTS

| | | |
|---|---|---|
| CA | 2446185 C | 11/2002 |
| CA | 2615858 A1 | 1/2007 |

(Continued)

OTHER PUBLICATIONS

Abhinandan, K.R. et al, Analysis and improvements to Kabat and structurally correct numbering of antibody variable domains, Molecular Immunology, 45:3832-3839 (2008).

(Continued)

*Primary Examiner* — Sheela J. Huff

(74) *Attorney, Agent, or Firm* — Proskauer Rose LLP; Fangli Chen; Julio J. Mendez

(57) ABSTRACT

Novel antibodies and antigen binding fragments that specifically bind to KAAG1 and which may be used in the treatment, detection and diagnosis of cancer comprising KAAG1-expressing cells are disclosed herein. Cells expressing the antibodies and antigen binding fragments as well as methods of detecting and treating cancer using the antibodies and fragments are also disclosed. Cancer indications which may benefit from such treatment or detection include ovarian cancer, renal cancer, lung cancer, colorectal cancer, breast cancer, brain cancer, and prostate cancer, as well as melanomas.

21 Claims, 32 Drawing Sheets

(56) References Cited

U.S. PATENT DOCUMENTS

| | | |
|---|---|---|
| 7,560,441 B2 | 7/2009 | Wolfman et al. |
| 7,585,839 B2 | 9/2009 | Larsen et al. |
| 7,618,636 B1 | 11/2009 | Masignani et al. |
| 7,628,989 B2 | 12/2009 | Jakobovits et al. |
| 7,641,905 B2 | 1/2010 | Jakobovits et al. |
| 8,216,582 B2 | 7/2012 | Sooknanan et al. |
| 8,937,163 B2 | 1/2015 | Tremblay et al. |
| 2002/0049190 A1 | 4/2002 | Bridger et al. |
| 2002/0106678 A1 | 8/2002 | Robishaw et al. |
| 2002/0177695 A1 | 11/2002 | Grinstaff et al. |
| 2003/0065157 A1 | 4/2003 | Lasek |
| 2003/0087250 A1 | 5/2003 | Monahan et al. |
| 2003/0099974 A1 | 5/2003 | Lillie et al. |
| 2003/0118592 A1 | 6/2003 | Ledbetter et al. |
| 2003/0124579 A1 | 7/2003 | Mack et al. |
| 2003/0133939 A1 | 7/2003 | Ledbetter et al. |
| 2003/0170273 A1 | 9/2003 | O'Hagan et al. |
| 2003/0180767 A1 | 9/2003 | Brewer et al. |
| 2003/0219760 A1 | 11/2003 | Gordon et al. |
| 2004/0009939 A1 | 1/2004 | Chada et al. |
| 2004/0014081 A1 | 1/2004 | Alsobrook et al. |
| 2004/0053824 A1 | 3/2004 | Tang et al. |
| 2004/0101874 A1 | 5/2004 | Ghosh et al. |
| 2004/0172684 A1 | 9/2004 | Kovalic et al. |
| 2004/0214272 A1 | 10/2004 | La Rosa et al. |
| 2004/0242606 A1 | 12/2004 | Bavetsias et al. |
| 2005/0008649 A1 | 1/2005 | Shin et al. |
| 2005/0009851 A1 | 1/2005 | Bavetsias et al. |
| 2005/0053930 A1 | 3/2005 | Anderson et al. |
| 2005/0059624 A1 | 3/2005 | Hoerr et al. |
| 2005/0064481 A1 | 3/2005 | Korfhage |
| 2005/0095592 A1 | 5/2005 | Jazaeri et al. |
| 2005/0113345 A1 | 5/2005 | Chow et al. |
| 2005/0123501 A1 | 6/2005 | Lewis |
| 2005/0147621 A1 | 7/2005 | Higgins et al. |
| 2005/0153333 A1 | 7/2005 | Sooknanan |
| 2005/0170450 A1 | 8/2005 | Durocher et al. |
| 2005/0196754 A1 | 9/2005 | Drmanac et al. |
| 2005/0214826 A1 | 9/2005 | Mor et al. |
| 2005/0214831 A1 | 9/2005 | Monahan et al. |
| 2006/0014686 A1 | 1/2006 | Wonsey et al. |
| 2006/0078941 A1 | 4/2006 | Santin |
| 2006/0084594 A1 | 4/2006 | Santin et al. |
| 2006/0188490 A1 | 8/2006 | Hoerr et al. |
| 2006/0229433 A1 | 10/2006 | De Rouge et al. |
| 2007/0027075 A1 | 2/2007 | Smithrud |
| 2007/0060590 A1 | 3/2007 | Shoda et al. |
| 2007/0093467 A1 | 4/2007 | Zhang et al. |
| 2007/0167409 A1 | 7/2007 | Chow et al. |
| 2007/0167443 A1 | 7/2007 | Melikian et al. |
| 2007/0298093 A1 | 12/2007 | Konur et al. |
| 2007/0299068 A1 | 12/2007 | Karp et al. |
| 2008/0025944 A1 | 1/2008 | Hoerr et al. |
| 2008/0070232 A1 | 3/2008 | Durocher |
| 2008/0166355 A1 | 7/2008 | Moheno et al. |
| 2008/0176790 A1 | 7/2008 | DeFrees |
| 2008/0200650 A1 | 8/2008 | Emery et al. |
| 2008/0213268 A1 | 9/2008 | Watts et al. |
| 2008/0274131 A1 | 11/2008 | Renner et al. |
| 2008/0280317 A1 | 11/2008 | Wu et al. |
| 2008/0280818 A1 | 11/2008 | DeFrees |
| 2008/0300348 A1 | 12/2008 | Haddleton et al. |
| 2008/0306007 A1 | 12/2008 | McCluskey et al. |
| 2008/0311145 A1 | 12/2008 | Campion et al. |
| 2009/0074658 A1 | 3/2009 | Lupold et al. |
| 2009/0075832 A1 | 3/2009 | Neuman et al. |
| 2009/0093621 A1 | 4/2009 | Ferrari et al. |
| 2009/0110662 A1 | 4/2009 | Breitenkamp et al. |
| 2009/0137003 A1 | 5/2009 | Tolstrup et al. |
| 2009/0169520 A1 | 7/2009 | Soreq et al. |
| 2009/0176664 A1 | 7/2009 | Chu |
| 2009/0186855 A1 | 7/2009 | Chow et al. |
| 2009/0197345 A1 | 8/2009 | Seppala |
| 2009/0203542 A1 | 8/2009 | Reichmann et al. |
| 2009/0208507 A1 | 8/2009 | Rohlff |
| 2009/0209463 A1 | 8/2009 | Nakamura et al. |
| 2009/0214467 A1 | 8/2009 | Shakhov et al. |
| 2009/0214585 A1 | 8/2009 | Ciocca et al. |
| 2009/0221032 A1 | 9/2009 | Dunker et al. |
| 2009/0226448 A1 | 9/2009 | Glucksmann et al. |
| 2009/0226451 A1 | 9/2009 | Glucksmann et al. |
| 2009/0226921 A1 | 9/2009 | Afar et al. |
| 2009/0232766 A1 | 9/2009 | Wang et al. |
| 2009/0253156 A1 | 10/2009 | Patton et al. |
| 2009/0275137 A1 | 11/2009 | Kranz et al. |
| 2009/0297401 A1 | 12/2009 | Lundstrom et al. |
| 2009/0305282 A1 | 12/2009 | Yuen et al. |
| 2009/0305962 A1 | 12/2009 | Bakker et al. |
| 2009/0311681 A1 | 12/2009 | Faure |
| 2009/0325869 A1 | 12/2009 | Theil |
| 2010/0003280 A1 | 1/2010 | O'Hagan et al. |
| 2010/0003305 A1 | 1/2010 | Pattanaik |
| 2010/0040606 A1 | 2/2010 | Lantto et al. |
| 2010/0047261 A1 | 2/2010 | Hoerr et al. |
| 2010/0055077 A1 | 3/2010 | Shakhov et al. |
| 2010/0055731 A1 | 3/2010 | Wang et al. |
| 2010/0056459 A1 | 3/2010 | Bonny |
| 2010/0086537 A1 | 4/2010 | Sooknanan et al. |
| 2010/0086541 A1 | 4/2010 | Wu et al. |
| 2010/0105692 A1 | 4/2010 | Moheno et al. |
| 2010/0111993 A1 | 5/2010 | Tureci et al. |
| 2010/0120627 A1 | 5/2010 | Belouchi et al. |
| 2011/0150979 A1 | 6/2011 | Ray et al. |
| 2011/0223107 A1 | 9/2011 | Tremblay et al. |
| 2011/0233107 A1 | 9/2011 | Lockett |
| 2012/0087862 A1 | 4/2012 | Hood et al. |
| 2012/0093819 A1 | 4/2012 | Tremblay et al. |
| 2012/0128661 A1 | 5/2012 | Sooknanan et al. |
| 2012/0288498 A1 | 11/2012 | Sooknanan et al. |
| 2014/0140990 A1 | 5/2014 | Tremblay et al. |

FOREIGN PATENT DOCUMENTS

| | | |
|---|---|---|
| CA | 2655933 A1 | 12/2007 |
| EP | 0178450 A2 | 4/1986 |
| EP | 0636031 A1 | 2/1995 |
| EP | 0816377 A2 | 1/1998 |
| EP | 1318835 B1 | 6/2003 |
| EP | 1422242 A1 | 5/2004 |
| EP | 1458410 B1 | 9/2004 |
| EP | 1465933 A1 | 10/2004 |
| EP | 1547581 A1 | 6/2005 |
| EP | 1550458 A1 | 7/2005 |
| EP | 1646661 B1 | 4/2006 |
| EP | 1751179 | 2/2007 |
| EP | 1847533 A1 | 10/2007 |
| EP | 1905844 A2 | 4/2008 |
| EP | 1970383 A1 | 9/2008 |
| EP | 1987356 | 11/2008 |
| EP | 2002036 | 12/2008 |
| EP | 2021467 | 2/2009 |
| EP | 2057465 | 5/2009 |
| EP | 2161291 A2 | 3/2010 |
| WO | WO-87/04523 A1 | 7/1987 |
| WO | WO-91/09849 A1 | 7/1991 |
| WO | WO-96/13510 A1 | 5/1996 |
| WO | WO-98/58079 A1 | 12/1998 |
| WO | WO-99/31513 A1 | 6/1999 |
| WO | WO-99/58546 A1 | 11/1999 |
| WO | WO-00/01702 A1 | 1/2000 |
| WO | WO-00/14515 A1 | 3/2000 |
| WO | WO-00/23448 A1 | 4/2000 |
| WO | WO-00/25788 A1 | 5/2000 |
| WO | WO-00/56743 A1 | 9/2000 |
| WO | WO-01/19798 A2 | 3/2001 |
| WO | WO-01/46209 A1 | 6/2001 |
| WO | WO-01/70979 A2 | 9/2001 |
| WO | WO-01/98468 A2 | 12/2001 |
| WO | WO-02/070539 A2 | 9/2002 |
| WO | WO-02/086443 A2 | 10/2002 |
| WO | WO-02/102235 A2 | 12/2002 |
| WO | WO-03/043987 A2 | 5/2003 |

(56) References Cited

FOREIGN PATENT DOCUMENTS

| WO | WO-03/047526 A2 | 6/2003 |
|---|---|---|
| WO | WO-03/051401 A2 | 6/2003 |
| WO | WO-03/068054 A2 | 8/2003 |
| WO | WO-03/075952 A1 | 9/2003 |
| WO | WO-03/087768 A2 | 10/2003 |
| WO | WO-03/099205 A2 | 12/2003 |
| WO | WO-2004/030615 A2 | 4/2004 |
| WO | WO-2004/076622 A2 | 9/2004 |
| WO | WO-2004/087874 A2 | 10/2004 |
| WO | WO-2004/104197 A1 | 12/2004 |
| WO | WO-2004/113394 A2 | 12/2004 |
| WO | WO-2005/024055 A1 | 3/2005 |
| WO | WO-2005/039504 A2 | 5/2005 |
| WO | WO-2005/063201 A2 | 7/2005 |
| WO | WO-2005/063288 A1 | 7/2005 |
| WO | WO-2005/070456 A2 | 8/2005 |
| WO | WO-2006/003352 A1 | 1/2006 |
| WO | WO-2006/024518 A1 | 3/2006 |
| WO | WO-2006/027202 A1 | 3/2006 |
| WO | WO-2006/029385 A2 | 3/2006 |
| WO | WO-2006/096989 A2 | 9/2006 |
| WO | WO-2006/102097 A2 | 9/2006 |
| WO | WO-2006/138380 A2 | 12/2006 |
| WO | WO-2007/002559 A1 | 1/2007 |
| WO | WO-2007/002563 A1 | 1/2007 |
| WO | WO-2007/005249 A2 | 1/2007 |
| WO | WO-2007/023287 A1 | 3/2007 |
| WO | WO-2007/045876 A1 | 4/2007 |
| WO | WO-2007/059108 A2 | 5/2007 |
| WO | WO-2007/061853 A2 | 5/2007 |
| WO | WO-2007/073432 A2 | 6/2007 |
| WO | WO-2007/084413 A2 | 7/2007 |
| WO | WO-2007/104948 A2 | 9/2007 |
| WO | WO-2007/110755 A1 | 10/2007 |
| WO | WO-2007/147265 A1 | 12/2007 |
| WO | WO-2008/002267 A1 | 1/2008 |
| WO | WO-2008/016356 A2 | 2/2008 |
| WO | WO-2008/021290 A2 | 2/2008 |
| WO | WO-2008/033932 A2 | 3/2008 |
| WO | WO-2008/052770 A2 | 5/2008 |
| WO | WO-2008/054793 A2 | 5/2008 |
| WO | WO-2008/074004 A2 | 6/2008 |
| WO | WO-2008/082887 A2 | 7/2008 |
| WO | WO-2008/083949 A2 | 7/2008 |
| WO | WO-2008/104804 A2 | 9/2008 |
| WO | WO-2009/004329 A1 | 1/2009 |
| WO | WO-2009/009186 A2 | 1/2009 |
| WO | WO-2009/039854 A2 | 4/2009 |
| WO | WO-2009/044162 A1 | 4/2009 |
| WO | WO-2009/059972 A2 | 5/2009 |
| WO | WO-2009/061681 A2 | 5/2009 |
| WO | WO-2009/069862 A1 | 6/2009 |
| WO | WO-2009/077864 A2 | 6/2009 |
| WO | WO-2009/111088 A2 | 9/2009 |
| WO | WO-2009/114942 A1 | 9/2009 |
| WO | WO-2009/134370 A2 | 11/2009 |
| WO | WO-2009/144230 A1 | 12/2009 |
| WO | WO-2010/003127 A2 | 1/2010 |
| WO | WO-2010/014141 A1 | 2/2010 |
| WO | WO-2010/017479 A1 | 2/2010 |
| WO | WO-2010/033207 A1 | 3/2010 |
| WO | WO-2010/033220 A2 | 3/2010 |
| WO | WO-2010/033240 A2 | 3/2010 |
| WO | WO-2010/037408 A1 | 4/2010 |
| WO | WO-2010/037539 A1 | 4/2010 |
| WO | WO-2010/060186 A1 | 6/2010 |
| WO | WO-2010/096434 A2 | 8/2010 |
| WO | WO-2011/004028 A2 | 1/2011 |
| WO | WO-2011/054112 A1 | 5/2011 |
| WO | WO-2011/112953 A2 | 9/2011 |
| WO | WO-2012/129668 A1 | 10/2012 |
| WO | WO-2013/104050 A2 | 7/2013 |

OTHER PUBLICATIONS

Agrawal, N., et al., RNA Interference: Biology, Mechanism, and Applications, Microbiology and Molecular Biology Reviews, 67(4):657-685 (2003).

An, Z. et al., IgG2m4, an engineered antibody isotype with reduced Fc function, mAbs 1(6):572-579 (2009).

Benoit M.H. et al., Global analysis of chromosome X gene expression in primary cultures of normal ovarian surface epithelial cells and epithelial ovarian cancer cell lines, International Journal of Oncology, 30(1):5-17 (2007).

Berek, J.S. et al., Chapter 115 Ovarian Cancer, in Holland-Frei Cancer Medicine, 5th Edition, Hamilton (ON): B.C. Decker (2000).

Bergers, G. et al., Extrinsic regulators of epithelial tumor progression: metalloproteinases, Current Opinion in Genetics and Development, 10:120-127 (2000).

Bernard, A. et al., A Unique Epitope on the CD2 Molecule Defined by the Monoclonal Antibody 9-1: Epitope-Specific Modulation of the E-Rosette Receptor and Effects on T-Cell Functions, Human Immunology, 17:388-405 (1986).

Bird, R.E. et al., Single-Chain Antigen-Binding Proteins, Science, 242(4877):423-426 (1988).

Bonome, T. et al., Expression Profiling of Serous Low Malignant Potential, Low-Grade, and High-Grade Tumors of the Ovary, Cancer Research, 65(22):10602-10612 (2005).

Bowie, J.U. et al., Deciphering the Message in Protein Sequences: Tolerance to Amino Acid Substitutions, Science, 247(4948):1306-1310 (1990).

Boyer, C.M. et al., Relative Cytotoxic Activity of Immunotoxins Reactive with Different Epitopes on the Extracellular Domain of the c-erbB-2 (Her-2/neu) Gene Product p185, International Journal of Cancer, 82:525-531 (1999).

Bristow, R.E., Surgical standards in the management of ovarian cancer, Current Opinion in Oncology, 12:474-480 (2000).

Brown, E. et al., Carcinosarcoma of the Ovary: 19 Years of Prospective Data from a Single Center, Cancer, 100:2148-2153 (2004).

Brummelkamp, T.R. et al., A System for Stable Expression of Short Interfering RNAs in Mammalian Cells, Science, 296(5567):550-553 (2002).

Burger, R.A., Experience With Bevacizumab in the Management of Epithelial Ovarian Cancer, Journal of Clinical Oncology, 25(20):2902-2908 (2007).

Burgess, W.H. et al., Possible dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, The Journal of Cell Biology, 111:2129-2138 (1990).

Byers, V.S. et al., Therapeutic strategies with monoclonal antibodies and immunoconjugates, Immunology, 65:329-335 (1988).

Cannistra, S.A. et al., Progress in the Management of Gynecologic Cancer, Journal of Clinical Oncology, 25(20):2865-2866 (2007).

Chambers, A.F. et al., Ovarian Cancer Biomarkers in Urine, Clinical Cancer Research, 12(2):323-327 (2006).

Clackson, T. et al., Making antibody fragments using phage display libraries, Nature, 352:624-628 (1991).

Cody, N.A.L. et al., Influence of monolayer, spheroid, and tumor growth conditions on chromosome 3 gene expression in tumorigenic epithelial ovarian cancer cell lines, BMC Medical Genomics, 1:34 (2008).

Cope, N. et al., Strong evidence that KIAA0319 on Chromosome 6p Is a Susceptibility Gene for Developmental Dyslexia, The American Journal of Human Genetics, 76:581-591 (2005).

De Plaen, E. et al., Structure, chromosomal localization, and expression of 12 genes of the MAGE family, Immunogenetics 40:360-369 (1994).

Dennis, C. Off by a whisker, Nature, 442:739-741 (2006).

Dermer, B.G., Another Anniversary for the War on Cancer, Bio/Technology, Vo. 12, p. 320, 1994.

Ebel, W. et al., Preclinical evaluation of MORAb-003, a humanized monoclonal antibody antagonizing folate receptor-alpha. Cancer Immunity, 7:6-13 (2007).

(56) References Cited

OTHER PUBLICATIONS

Elbashir, S.M. et al., Duplexes of 21-nucleotide RNAs mediate RNA interference in cultured mammalian cells, Nature, 411(6836):494-498 (2001).
Freshney, R.i., Culture of Animal Cells, A Manual of Basic Technique, Alan R. Liss, Inc., 1983, New York, p. 4.
Futreal, A.P. et al., A census of human cancer genes, Nature Reviews, 4:177-183 (2004).
GenBank Acc. No. AA744939.1, GI: 2783703, 1998.
GenBank Acc. No. AC002060.4, GI:22507090, first referenced 1997, updated 2002.
GenBank Acc. No. AC068288.6, GI:16418276, first referenced 2001, updated 2005.
GenBank Acc. No. AC104837.2, GI:18249998, first referenced 2001, updated 2002.
GenBank Acc. No. AC109350.5, GI:19526559, first referenced 1998, updated 2002.
GenBank Acc. No. AC117457.11, GI:28557825, first referenced 2002, updated 2003.
GenBank Acc. No. AI922121.1, GI:5658085, first referenced 1999, updated 2000.
GenBank Acc. No. AK092857.1, GI:21751554, first referenced 2002, updated 2004.
GenBank Acc. No. AK092936.1, GI:21751648, first referenced 2002, updated 2004.
GenBank Acc. No. AL157931.17, GI:11493240, first referenced 2000, updated 2009.
GenBank Acc. No. AL583809.3, GI:14250883, 2001.
GenBank Acc. No. AY683003.1, GI:56384942, 2004.
GenBank Acc. No. BC009078.1, GI:14290598, first referenced 2001, updated 2008.
GenBank Acc. No. BC037243, Strausberg et al., Sep. 27, 2002.
GenBank Acc. No. BC073793.1, GI:49258111, first referenced 2002, updated 2006.
GenBank Acc. No. BC092518.1, GI:62201665, first referenced 2002, updated 2005.
GenBank Acc. No. BCO37243.1, GI:23337025, first referenced 2002, updated 2008.
GenBank Acc. No. BG213598.1, GI:13735285, 2001.
GenBank Acc. No. BU595315.1, GI:23247074, 2002.
GenBank Acc. No. NM_000077.3, GI:47132606, first referenced 1994, updated 2004.
GenBank Acc. No. NM_000096.3, GI:189458860, first referenced 1977, updated 2008.
GenBank Acc. No. NM_000170.2, GI:108773800, first referenced 1989, updated 2006.
GenBank Acc. No. NM_000802.2, GI:12056965, first referenced 1990, updated 2001.
GenBank Acc. No. NM_001001887.1, GI:49574525, first referenced 1983, updated 2006.
GenBank Acc. No. NM_001007027.2, GI:91984777, first referenced 1995, updated 2006.
GenBank Acc. No. NM_001017920.2, GI:217272871, first referenced 2002, updated 2008.
GenBank Acc. No. NM_001039548.1, GI:88196793, 2004.
GenBank Acc. No. NM_001463.2, GI:38455387, first referenced 1996, updated 2003.
GenBank Acc. No. NM_001565.2, GI:149999381, first referenced 1985, updated 2007.
GenBank Acc. No. NM_001719.2, GI:187608319, first referenced 1990, updated 2008.
GenBank Acc. No. NM_001826.2, GI:206725531, first referenced 1990, updated 2008.
GenBank Acc. No. NM_001878.2, GI:6382069, first referenced 1991, updated 1999.
GenBank Acc. No. NM_003543.3, GI:21264599, first referenced 1997, updated 2002.
GenBank Acc. No. NM_005101.3, GI:193083170, first referenced 1987, updated 2008.
GenBank Acc. No. NM_005192.3, GI:195927023, first referenced 1993, updated 2008.
GenBank Acc. No. NM_005698.2, GI:16445418, first referenced 1997, updated 2001.
GenBank Acc. No. NM_005733.2, GI:195539383, first referenced 1998, updated 2008.
GenBank Acc. No. NM_005832.3, GI:31317293, first referenced 1999, updated 2003.
GenBank Acc. No. NM_006115.3, GI:46249365, first referenced 1997, updated 2004.
GenBank Acc. No. NM_006681.2, GI:195539393, first referenced 1995, updated 2008.
GenBank Acc. No. NM_006820.2, GI:166706908, first referenced 1997, updated 2008.
GenBank Acc. No. NM_006898.4, GI:23510372, first referenced 1989, updated 2002.
GenBank Acc. No. NM_007019.2, GI:32967292, first referenced 1997, updated 2003.
GenBank Acc. No. NM_012112.4, GI:40354199, first referenced 1997, updated 2003.
GenBank Acc. No. NM_013277.3, GI:186910298, first referenced 1997, updated 2008.
GenBank Acc. No. NM_018279.3, GI:89145418, first referenced 1997, updated 2006.
GenBank Acc. No. NM_021955.3, GI:74316012, first referenced 1984, updated 2005.
GenBank Acc. No. NM_022357.3, GI:193211607, first referenced 2003, updated 2008.
GenBank Acc. No. NM_024501.1, GI:13375631, 1989.
GenBank Acc. No. NM_024626.2, GI:99028880, first referenced 2003, updated 2006.
GenBank Acc. No. NM_033445.2, GI:28872747, first referenced 1998, updated 2003.
GenBank Acc. No. NM_152864.2, GI:42476063, first referenced 2001, updated 2004.
GenBank Acc. No. NM_178580.1, GI:30581108, 2001.
GenBank Acc. No. NM_181337.3, GI:198278499, first referenced 1999, updated 2008.
GenBank Acc. No. NM_202003.1, GI:42544160, 1994.
Gorelik, E. et al., Multiplexed Immunobead-based Cytokine Profiling for Early Detection of Ovarian Cancer, Cancer Epidemiology, Biomarkers & Prevention, 14(4):981-987 (2005).
Guo, H.H. et al., Protein tolerance to random amino acid change, Proceedings of the National Academy of Sciences, 101(25):9205-9210 (2004).
Gura, T. Systems for Identifying New Drugs are Often Faulty, Science, 278(5340):1041-1042 (1997).
Hancok et al., Synthetic Peptides for Antibody Production pp. 13-25, Methods in Molecular Biology, 295: Immunochemical Protocols, Third Edition, 2005.
Hannon, G.J., RNA interference, Nature, 418(6894):244-251 (2002).
Hara et al., Cancer Sci, vol. 99(7), pp. 1471-1478, 2008.
Henry, M.D. et al., A Prostate-Specific Membrane Antigen-Targeted Monoclonal Antibody-Chemotherapeutic Conjugate Designed for the Treatment of Prostate Cancer, Cancer Research, 64:7995-8001 (2004).
Huston, J.S. et al., Protein engineering of antibody binding sites: Recovery of specific activity in an anti-digoxin single-chain Fv analogue produced in *Escherichia coli*, Proceedings of the National Academy of Sciences, 85:5879-5883 (1988).
Idusogie, E.E. et al., Mapping of the C1q Biding Sire of Rituxan, a Chimeric Antibody with a Human IgG1 Fc, The Journal of Immunology, 164:4178-4184 (2000).
International Search Report for PCT/CA2012/000296, 6 pages (Jul. 18, 2012).
Jain, R.K., Barriers to Drug Delivery in Solid Tumors, Sci Am., vol. 271, pp. 58-65, 1994.
Jemal, A. et al., Cancer Statistics, 2005, CA: A Cancer Journal for Clinicians, 55:10-30 (2005).

(56) References Cited

OTHER PUBLICATIONS

Jiang, B. et al., A Novel Peptide Isolated from a Phage Display Peptide Library with Trastuzumab Can Mimic Antigen Epitope of HER-2, The Journal of Biological Chemistry, 280(6):4656-4662 (2005).
Jones, P.T. et al., Replacing the complementarity-determining regions in a human antibody with those from a mouse, Nature, 321(29):522-525 (1986).
Kanapathy Pillai, S.K. et al., Triple-negative breast cancer is associated with EGFR, CK5/6 and c-KIT expression in Malaysian women, BMC Clin. Pathol., 12:18 (2012).
Kelland, L.R., "Of mice and men": values and liabilities of the athymic nude mouse model in anticancer drug development, European Journal of Cancer, 40:827-836 (2004).
Kelly, R. K. et al., An Antibody-cytotoxic Conjugate BIIB015, is a new targeted therapy for Cripto positive tumours, European Journal of Cancer, vol. 47, pp. 1736-1746, 2011.
Kim, K. et al., Both the epitope specificity and isotype are important in the antitumor effect on monoclonal antibodies against HER-2/neu antigen, International Journal of Cancer, 102:428-434 (2002).
Kipps, T.J. et al., Importance of immunoglobulin isotype in human antibody-dependent, cell-mediated cytotoxicity directed by murine monoclonal antibodies, The Journal of Experimental Medicine, 161:1-17 (1985).
Kozak, K.R. et al., Identification of biomarkers for ovarian cancer using strong anion-exchange ProteinChips: Potential use in diagnosis and prognosis, Proceedings of the National Academy of Sciences, 100:12343-12348 (2003).
Larkin, M.A. et al., Clustal W and Clustal X version 2.0, Bioinformatics, 23(21): 2947-2948 (2007).
Lazar, E. et al., Transforming Growth Factor α: Mutation of Aspartic Acid 47 and Leucine 48 Results in Different Biological Activities, Molecular and Cellular Biology, 8(3):1247-1252 (1988).
Leamon, C.P. et al., Folate-mediated targeting: from diagnostics to drug and gene delivery, Drug Discovery Today, 6(1):44-51 (2001).
Lewis, G.D. et al., Differential responses of human tumor cell lines to anti-p185$^{HER2}$ monoclonal antibodies, Cancer Immunology, Immunotherapy, 37:255-263 (1993).
Li, X. et al., Usage of Monoclonal Antibody BG6 in the Diagnosis and Differential Diagnosis of Breast Cancer, Chinese Journal of Clinical Oncology, 9(6):415-417 (1992) (English abstract).
Li, et al., Genbank Acc. No. AY648683; Jun. 15, (2005).
Liang, et al., Genbank Acc. No. AY436928; Mar. 15, 2004.
Luque, L.E. et al., A Highly Conserved Arginine Is Critical for the Functional Folding of Inhibitor of Apoptosis (IAP) BIR Domains, Biochemistry, 41:13663-13671 (2002).
Masui, H. et al., Mechanism of Antitumor Activity in Mice for Anti-Epidermal Growth Factor Receptor Monoclonal Antibodies with Different Isotypes, Cancer Research, 46:5592-5598 (1986).
MacCallum, R.M. et al. Antibody-antigen Interactions: Contact Analysis and Binding Site Topography, J. Mol. Biol. 262, pp. 732-745, 1996.
McDevitt, M.R. et al., An x-Particle Emitting Antibody ([$^{213}$Bi]J591) for Radioimmunotherapy of Prostate Cancer, Cancer Research, 60:6095-6100 (2000).
McIntosh, M.W. et al., Combining CA 125 and SMR serum markers for diagnosis and early detection of ovarian carcinoma, Gynecologic Oncology 95(1):9-15 (2004).
Menon, U. et al., Prospective Study Using the Risk of Ovarian Cancer Algorithm to Screen for Ovarian Cancer, Journal of Clinical Oncology, 23(31):7919-7926 (2005).
Mor, G. et al., Serum protein markers for early detection of ovarian cancer, Proceedings of the National Academy of Sciences, 102(21):7677-7682 (2005).
Mosmann, T., Rapid Colorimetric Assay for Cellular Growth and Survival: Application to Proliferation and Cytotoxicity Assays, Journal of Immunological Methods, 65:55-63 (1983).
Munodzana, D. et al., Conformational Dependence of *Anaplasma marginale* Major Surface Protein 5 Surface-Exposed B-Cell Epitopes, Infection and Immunity, 66(6):2619-2624 (1998).

NCBI Accession No. M32599.1, first referenced 1990.
NCBI Accession No. NM_001238, first referenced 1991.
NCBI Accession No. NM_003376, 1991.
NCBI Accession No. Q9UBP8, 1999.
NCBI Accession No. X00351, first referenced 1984.
Nicodemus, C.F. et al., Monoclonal antibody therapy of ovarian cancer, Expert Review of Anticancer Therapy, 5(1):87-96 (2005).
Oei, A. L. M., et al., The use of monoclonal antibodies for the treatment of epithelial ovarian cancer (Review), International Journal of Oncology, 32(6):1145-1157 (2008).
Panka, D.J. et al., Variable region framework differences result in decreased or increased affinity of variant anti-digoxin antibodies, Proceedings of the National Academy of Sciences USA, 85:3080-3084 (1988).
Paul, Fundamental Immunology, $3^{rd}$ Edition, pp. 292-295, 1993.
Pettersen, R.D. et al., CD47 Signals T Cell Death, The Journal of Immunology, 162(12):7031-7040 (1999).
Polyak, M.J. et al., Alanine-170 and proline-172 are critical determinants for extracellular CD20 epitopes; heterogeneity in the fine specificity of CD20 monoclonal antibodies is defined by additional requirements imposed by both amino acid sequence and quaternary structure, Blood, 99(9):3256-3262 (2002).
Portolano, S. et al., Lack of Promiscuity in Autoantigen-Specific H and L Chain Combinations as Revealed by Human H and L Chain "Roulette", The Journal of Immunology, 150:880-887 (1993).
Press, O. et al., Ricin A-chain Containing Immunotoxins Directed Against Different Epitopes on the CD2 Molecule Differ in their Ability to Kill Normal and Malignant T Cells, The Journal of Immunology, 141(12):4410-4417 (1988).
Provencher, D.M. et al., Characterization of Four Novel Epithelial Ovarian Cancer Cell Lines, In Vitro Cellular & Developmental Biology—Animal, 36:357-361 (2000).
Reinecke, P. et al., Multidrug Resistance phenotype and paclitaxel (Taxol) sensitivity in human renal carcinoma cell lines of different histologic types, Cancer Invest., 18(7): 614-625, 2000.
Riemer, A.B. et al., Matching of trastuzumab (Herceptin®) epitope mimics onto the surface of Her-2/neu—a new method of epitope definition, Molecular Immunology, 42:1121-1124 (2005).
Rudikoff, S. et al., Single amino acid substitution altering antigen-binding specificity, Proceedings of the National Academy of Sciences USA, 79:1979-1983 (1982).
Rudnick, S.I. et al., Influence of Affinity and Antigen Internalization on the Uptake and Penetration of Anti-HER2 Antibodies in Solid Tumors, Cancer Research, 71(6):2250-2259 (2011).
Saijo, N. What are the reasons for negative phase III trials of molecular-targeted-based drugs? Cancer Science, 95(10):772-776 (2004).
Samouelian, V. et al., Chemosensitivity and radiosensitivity profiles of four new human epithelial ovarian cancer cell lines exhibiting genetic alterations in BRCA2, TGFβ-RII, KRAS2, TP53 and/or CDNK2A, Cancer Chemotherapy and Pharmacology, 54:497-504 (2004).
Schorge, J.O. et al., Osteopontin as an Adjunct to CA125 in Detecting Recurrent Ovarian Cancer, Clinical Cancer Research, 10:3474-3478 (2004).
Schumacher, J. et al., Strong Genetic Evidence of DCDC2 as a Susceptibility Gene for Dyslexia, The American Journal of Human Genetics, 78(1):52-62 (2006).
Scholler and Urban, CA125 in Ovarian Cancer, Biomark Med 2007, 1(4):513-523.
Seidman, J.D. et al., Surface Epithelial Tumors of the Ovary, *Blaustein's Pathology of the Female Genital Tract*, Kurman, R.J. (Ed.), 5th Ed., New York: Springer-Verlag (2002), pp. 791-904.
Seton-Rogers, L., Breast Cancer: On the origins of tumour subtypes, Nature Reviews: Cancer, vol. 7, 1 page (2007).
Shih, I. et al., Molecular Pathogenesis of Ovarian Borderline Tumors: New Insights and Old Challenges, Clinical Cancer Research, 11(20):7273-7279 (2005).
Simon, I. et al., B7-H4 is a Novel Membrane-Bound Protein and a Candidate Serum and Tissue Biomarker for Ovarian Cancer, Cancer Research, 66(3):1570-1575 (2006).

(56) References Cited

OTHER PUBLICATIONS

Skolnick, J. et al., From genes to protein structure and function: novel applications of computational approaches in the genomic era, TIBTech 18:37-39 (2000).
Slingluff, C.L. et al., Melanomas with concordant loss of multiple melanocytic differentiation proteins: immune escape that may be overcome by targeting unique or underlined antigens, Cancer Immunology, Immunotherapy, 48:661-672 (2000).
Stancovski, I. et al., Mechanistic aspect of the opposing effects of monoclonal antibodies to the ERBB2 receptor on tumor growth, The Proceedings of the National Academy of Science in the United States of America, 88:8691-8695 (1991).
Subik, K. et al. The Expression Patterns of ER, PR, HER2, CK5/6, EGFR, Ki-67 and AR by Immunohistochemical Analysis in Breast Cancer Cell Lines, Breast Cancer: Basic and Clinical Research, vol. 4, pp. 35-41, 2010.
Takada, I. et al., Alteration of a Single Amino Acid in Peroxisome Proliferator-Activated Receptor-α(PPARα) Generates a PPARS Phenotype, Molecular Endocrinology 14(5):733-740 (2000).
Tamura, M. et al., Structural Correlates of an Anticarcinoma Antibody: Identification of Specifiicity-Determining Residues (SDRs) and Development of a Minimally Immunogenic Antibody Variant by Retention of SDRs Only, The Journal of Immunology, 164:1432-1441 (2000).
Tatusova, T. et al., Blast 2 sequences, a new tool for comparing protein and nucleotide sequences, FEMS Microbiology Letters, 174:247-250 (1999).
Vajdos, F.F., et al., Comprehensive Functional Maps of the Antigen Binding Site of an Anti-Erb2 Antibody Obtained with Shotgun Scanning Mutagenesis, J. Mol. Biol. 320, pp. 415-428, 2002.
Van Den Eynde, B.J. et al., A New Antigen Recognized by Cytolytic T Lymphocytes on a Human Kidney Tumor Results from Reverse Strand transcription, The Journal of Experimental Medicine, 190(12):1793-1799 (1999).
Verhoeyen, M. et al., Reshaping Human Antibodies: Grafting an Antilysozyme Activity, Science, 239:(4847):1534-1535 (1988).
Vogelstein, B. et al., Cancer genes and the pathways they control, Nature Medicine, 10(8):789-799 (2004).
Vucic, D. et al., A Mutational Analysis of the Baculovirus Inhibitor of Apoptosis Op-IAP, The Journal of Biological Chemistry, 273(51):33915-33921 (1998).
Vuist, W.M.J. et al., Two Distinct Mechanisms of Antitumor Activity Mediated by the Combination of Interleukin 2 and Monoclonal Antibodies, Cancer Research, 50:5767-5772 (1990).
Ward, E.S. et al., Binding activities of a repertoire of single immunoglobulin variable domains secreted from *Escherichia coli*, Nature, 341:544-546 (1989).
Woolas, R.P. et al., Elevation of Multiple Serum Markers in Patients with Stage I Ovarian Cancer, Journal of the National Cancer Institute, 85(21):1748-1751 (1993).
Written Opinion for PCT/CA2009/001586, 8 pages (Feb. 2, 2010).
Written Opinion for PCT/CA2013/000011, 9 pages (Feb. 6, 2015).
Written Opinion for PCT/CA2012/000296, 7 pages (Jul. 18, 2012).
Xu, F. et al., Antibody-induced growth inhibition is mediated through immunochemically and functionally distinct epitopes on the extracellular domain of the c-erbB-2 (HER-2/neu) gene product p185, International Journal of Cancer, 53:401-408 (1993).
Allred, C. D. Issues and Updates: Evaluating Estrogen Receptor-α, progesterone receptor, and HER2 in Breast Cancer, Modern Pathology (2010), 23, S52-S59.
Baccala et al., Expression of Prostate-Specific Membrane Antigen in Tumor-Associated Neovasculature of Rnal Neoplasms, Urology (2007), vol. 70, pp. 385-390.

Figure 11A

Variable light chain alignment

```
Mouse VL         DVVMTQTPLSLAVSLGDQASISCRSSQSLLHSNGNTYLEWYLQKPGQSPKLLIHTVSNRF  60
SEQ ID NO.33     DIVMTQTPLSLPVTPGEPASISCRSSQSLLHSNGNTYLEWYLQKPGQSPQLLIYTVSNRF  60
                 *:**********.**:  *:  **************************:***:******

Mouse VL         SGVPDRFSGSGSGTDFTLKISRVEAEDLGVYYCFQGSHVPLTFGAGTRLELK  112
SEQ ID NO.33     SGVPDRFSGSGSGTDFTLKISRVEAEDVGVYYCFQGSHVPLTFGQGTKLEIK  112
                 ***************************:************** ***:**:*
```

Figure 11B

Variable heavy chain alignment

```
Mouse VH         QIQLVQSGPEMVKPGASVKMSCKASGYTFTDDYMSWVKQSHGKSLEWIGDINPYNGDTNY  60
SEQ ID NO.38     QVQLVQSGAEVKKPGASVKVSCKASGYTFTDDYMSWVRQAPGQGLEWMGDINPYNGDTNY  60
                 *:******.*:*.******:*****************:**.*: **:************

Mouse VH         NQKFKGKAILTVDKSSSTAYMQLNSLTSEDSAVYYCARDPGAMDYWGQGTSVTVSS  116
SEQ ID NO.38     NQKFKGRVTITADTSTSTAYMELSSLRSEDTAVYYCARDPGAMDYWGQGTLVTVSS  116
                 ******:. *:*.*:*:***** *** ***:******************* *****
```

| Antibody | ka (1/Ms) | kd (1/s) | $K_D$ (nM) | Fold diff. |
|---|---|---|---|---|
| LcHc | $7.72 \times 10^6$ | $1.21 \times 10^{-4}$ | 0.016 | - |
| Lh1Hh1 | $6.93 \times 10^6$ | $3.28 \times 10^{-3}$ | 0.474 | 29.6 |
| Lh2Hh1 | $6.97 \times 10^6$ | $2.37 \times 10^{-3}$ | 0.341 | 21.3 |
| Lh1Hh2 | $5.65 \times 10^6$ | $1.19 \times 10^{-3}$ | 0.211 | 13.2 |
| Lh2Hh2 | $7.40 \times 10^6$ | $1.81 \times 10^{-3}$ | 0.245 | 15.3 |
| Lh1Hh3 | $6.46 \times 10^6$ | $9.60 \times 10^{-4}$ | 0.149 | 9.3 |
| Lh2Hh3 | $4.46 \times 10^6$ | $1.02 \times 10^{-3}$ | 0.228 | 14.3 |
| Lh1Hh4 | $5.14 \times 10^6$ | $7.64 \times 10^{-4}$ | 0.149 | 9.3 |
| Lh2Hh4 | $4.57 \times 10^6$ | $4.70 \times 10^{-4}$ | 0.103 | 6.4 |

Figure 15

SEQUENCE LISTING

<160> NUMBER OF SEQ ID NOS: 56

<210> SEQ ID NO 1
<211> LENGTH: 348
<212> TYPE: DNA
<213> ORGANISM: Artificial Sequence
<220> FEATURE:
<223> OTHER INFORMATION: 3A4 heavy chain variable region

<400> SEQUENCE: 1
cagatccagt tggtgcaatc tggacctgag atggtgaagc ctggggcttc agtgaagatg      60
tcctgtaagg cttctggata cacattcact gacgactaca tgagctgggt gaaacagagc     120
catggaaaga gccttgagtg gattggagat attaatcctt acaacggtga tactaactac     180
aaccagaagt tcaagggcaa ggccatattg actgtagaca atcctccag cacagcctac     240 atgcagctca acagcctgac atcggaagac tcagcagtct attactgtgc aagagacccg     300
ggggctatgg actactgggg tcaaggaacc tcagtcaccg tctcctca                 348

<210> SEQ ID NO 2
<211> LENGTH: 116
<212> TYPE: PRT
<213> ORGANISM: Artificial Sequence
<220> FEATURE:
<223> OTHER INFORMATION: 3A4 heavy chain variable region

<400> SEQUENCE: 2

Gln Ile Gln Leu Val Gln Ser Gly Pro Glu Met Val Lys Pro Gly Ala
1               5                   10                  15

Ser Val Lys Met Ser Cys Lys Ala Ser Gly Tyr Thr Phe Thr Asp Asp
            20                  25                  30

Tyr Met Ser Trp Val Lys Gln Ser His Gly Lys Ser Leu Glu Trp Ile
        35                  40                  45

Gly Asp Ile Asn Pro Tyr Asn Gly Asp Thr Asn Tyr Asn Gln Lys Phe
    50                  55                  60

Lys Gly Lys Ala Ile Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Pro Gly Ala Met Asp Tyr Trp Gly Gln Gly Thr Ser Val
            100                 105                 110

Thr Val Ser Ser
        115

<210> SEQ ID NO 3
<211> LENGTH: 336
<212> TYPE: DNA
<213> ORGANISM: Artificial Sequence

```
<220> FEATURE:
<223> OTHER INFORMATION: 3A4 light chain variable region

<400> SEQUENCE: 3
gatgttgtga tgacccaaac tccactctcc ctggctgtca gtcttggaga tcaagcctcc      60
atctcttgca gatctagtca gagccttcta catagtaatg gaaacaccta tttagaatgg     120
taccttcaga aaccaggcca gtctccaaag ctcctgatcc acacagtttc caaccgattt     180
tctggggtcc cagacagatt cagtggcagt ggatcaggga cagatttcac actcaagatc     240
agcagagtgg aggctgagga tctgggagtt tattactgct ttcaaggttc acatgttccg     300
ctcacgttcg gtgctgggac caggctggag ctgaaa                               336

<210> SEQ ID NO 4
<211> LENGTH: 112
<212> TYPE: PRT
<213> ORGANISM: Artificial Sequence
<220> FEATURE:
<223> OTHER INFORMATION: 3A4 light chain variable region

<400> SEQUENCE: 4

Asp Val Val Met Thr Gln Thr Pro Leu Ser Leu Ala Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile His Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Arg Leu Glu Leu Lys
            100                 105                 110

<210> SEQ ID NO 5
<211> LENGTH: 10
<212> TYPE: PRT
<213> ORGANISM: Artificial Sequence
<220> FEATURE:
<223> OTHER INFORMATION: 3A4 heavy chain CDR1

<400> SEQUENCE: 5

Gly Tyr Thr Phe Thr Asp Asp Tyr Met Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: 3A4 heavy chain CDR2

<400> SEQUENCE: 6

Asp Ile Asn Pro Tyr Asn Gly Asp Thr Asn
1               5                   10

<210> SEQ ID NO 7
<211> LENGTH: 7
<212> TYPE: PRT
<213> ORGANISM: Artificial Sequence
```

<220> FEATURE:
<223> OTHER INFORMATION: 3A4 heavy chain CDR3

<400> SEQUENCE: 7

Asp Pro Gly Ala Met Asp Tyr
1               5

<210> SEQ ID NO 8
<211> LENGTH: 16
<212> TYPE: PRT
<213> ORGANISM: Artificial Sequence
<220> FEATURE:
<223> OTHER INFORMATION: 3A4 light chain CDR1

<400> SEQUENCE: 8

Arg Ser Ser Gln Ser Leu Leu His Ser Asn Gly Asn Thr Tyr Leu Glu
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: 3A4 light chain CDR2

<400> SEQUENCE: 9

Thr Val Ser Asn Arg Phe Ser
1               5

<210> SEQ ID NO 10
<211> LENGTH: 9
<212> TYPE: PRT
<213> ORGANISM: Artificial Sequence
<220> FEATURE:
<223> OTHER INFORMATION: 3A4 light chain CDR3

<400> SEQUENCE: 10

Phe Gln Gly Ser His Val Pro Leu Thr
1               5

<210> SEQ ID NO 11
<211> LENGTH: 33
<212> TYPE: DNA
<213> ORGANISM: Artificial Sequence
<220> FEATURE:
<223> OTHER INFORMATION: OGS1773 primer

<400> SEQUENCE: 11
gtaagcagcg ctgtggctgc accatctgtc ttc                                33

<210> SEQ ID NO 12
<211> LENGTH: 35
<212> TYPE: DNA
<213> ORGANISM: Artificial Sequence
<220> FEATURE:
<223> OTHER INFORMATION: OGS1774 primer

<400> SEQUENCE: 12
gtaagcgcta gcctaacact ctcccctgtt gaagc                              35

<210> SEQ ID NO 13
<211> LENGTH: 321
<212> TYPE: DNA
<213> ORGANISM: Artificial Sequence
<220> FEATURE:
<223> OTHER INFORMATION: human kappa constant region

<400> SEQUENCE: 13

```
gctgtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata cgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321
```

<210> SEQ ID NO 14
<211> LENGTH: 106
<212> TYPE: PRT
<213> ORGANISM: Artificial Sequence
<220> FEATURE:
<223> OTHER INFORMATION: human kappa constant region

<400> SEQUENCE: 14

```
Ala Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105
```

<210> SEQ ID NO 15
<211> LENGTH: 6385
<212> TYPE: DNA
<213> ORGANISM: Artificial Sequence
<220> FEATURE:
<223> OTHER INFORMATION: pTTVK1 plasmid

<400> SEQUENCE: 15

```
cttgagccgg cggatggtcg aggtgaggtg tggcaggctt gagatccagc tgttggggtg    60
agtactccct ctcaaaagcg ggcattactt ctgcgctaag attgtcagtt ccaaaaacg   120
aggaggattt gatattcacc tggcccgatc tggccataca cttgagtgac aatgacatcc   180
actttgcctt tctctccaca ggtgtccact cccaggtcca gtttaaacg gatctctagc   240
gaattcatga actttctgct gtcttgggtg cattggagcc ttgccttgct gctctacctc   300
caccatgcca gtggtccca ggcttgagac ggagcttaca gcgctgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660
tagggtaccg cggccgcttc gaatgagatc ccccgacctc gacctctggc taataaagga   720
```

```
aatttatttt cattgcaata gtgtgttgga attttttgtg tctctcactc ggaaggacat    780
atgggagggc aaatcatttg gtcgagatcc ctcggagatc tctagctaga gccccgccgc    840
cggacgaact aaacctgact acggcatctc tgcccttct tcgcggggca gtgcatgtaa     900
tcccttcagt tggttggtac aacttgccaa ctgggcctg ttccacatgt gacacggggg     960
gggaccaaac acaaaggggt tctctgactg tagttgacat ccttataaat ggatgtgcac   1020
atttgccaac actgagtggc tttcatcctg gagcagactt tgcagtctgt ggactgcaac   1080
acaacattgc ctttatgtgt aactcttggc tgaagctctt acaccaatgc tgggggacat   1140
gtacctccca ggggcccagg aagactacgg gaggctacac caacgtcaat cagagggggcc  1200 tgtgtagcta ccgataagcg gaccctcaag agggcattag caatagtgtt tataaggccc    1260
ccttgttaac cctaaacggg tagcatatgc ttcccgggta gtagtatata ctatccagac    1320
taaccctaat tcaatagcat atgttaccca acgggaagca tatgctatcg aattagggtt    1380
agtaaaaggg tcctaaggaa cagcgatatc tcccacccca tgagctgtca cggttttatt    1440
tacatggggt caggattcca cgagggtagt gaaccatttt agtcacaagg gcagtggctg    1500
aagatcaagg agcgggcagt gaactctcct gaatcttcgc ctgcttcttc attctccttc    1560
gtttagctaa tagaataact gctgagttgt gaacagtaag gtgtatgtga ggtgctcgaa    1620
aacaaggttt caggtgacgc ccccagaata aatttggac gggggggttca gtggtggcat    1680 tgtgctatga caccaatata accctcacaa acccccttggg caataaatac tagtgtagga   1740
atgaaacatt ctgaatatct ttaacaatag aaatccatgg ggtggggaca agccgtaaag    1800
actggatgtc catctcacac gaatttatgg ctatgggcaa cacataatcc tagtgcaata    1860
tgatactggg gttattaaga tgtgtcccag gcagggacca agacaggtga accatgttgt    1920
tacactctat ttgtaacaag gggaaagaga gtggacgccg acagcagcgg actccactgg    1980
ttgtctctaa caccccgaa aattaaacgg ggctccacgc caatgggcc cataaacaaa     2040 gacaagtggc cactcttttt tttgaaattg tggagtgggg gcacgcgtca gcccccacac    2100
gccgccctgc ggttttggac tgtaaaataa gggtgtaata acttggctga ttgtaacccc    2160
gctaaccact gcggtcaaac cacttgccca caaaccact aatggcaccc cgggggaatac   2220 ctgcataagt aggtgggcgg gccaagatag gggcgcgatt gctgcgatct ggaggacaaa    2280
ttacacacac ttgcgcctga gcgccaagca cagggttgtt ggtcctcata ttcacgaggt    2340
cgctgagagc acggtgggct aatgttgcca tgggtagcat atactaccca aatatctgga    2400
tagcatatgc tatcctaatc tatatctggg tagcataggc tatcctaatc tatatctggg    2460
tagcatatgc tatcctaatc tatatctggg tagtatatgc tatcctaatt tatatctggg    2520
tagcataggc tatcctaatc tatatctggg tagcatatgc tatcctaatc tatatctggg    2580
tagtatatgc tatcctaatc tgtatccggg tagcatatgc tatcctaata gagattaggg    2640
tagtatatgc tatcctaatt tatatctggg tagcatatac tacccaaata tctggatagc    2700
atatgctatc ctaatctata tctgggtagc atatgctatc ctaatctata tctgggtagc    2760
ataggctatc ctaatctata tctgggtagc atatgctatc ctaatctata tctgggtagt    2820
atatgctatc ctaatttata tctgggtagc ataggctatc ctaatctata tctgggtagc    2880
atatgctatc ctaatctata tctgggtagt atatgctatc ctaatctgta tccgggtagc    2940
atatgctatc ctcacgatga taagctgtca aacatgagaa ttaattcttg aagacgaaag    3000
ggcctcgtga tacgcctatt tttataggtt aatgtcatga taataatggt tcttagacg     3060 tcaggtggca cttttcgggg aaatgtgcgc ggaaccccta tttgtttatt tttctaaata    3120
```

```
cattcaaata tgtatccgct catgagacaa taaccctgat aaatgcttca ataatattga    3180
aaaaggaaga gtatgagtat tcaacatttc cgtgtcgccc ttattccctt ttttgcggca    3240
ttttgccttc ctgttttttgc tcacccagaa acgctggtga agtaaaaga tgctgaagat    3300 cagttgggtg cacgagtggg ttacatcgaa ctggatctca acagcggtaa gatccttgag    3360
agttttcgcc ccgaagaacg ttttccaatg atgagcactt ttaaagttct gctatgtggc    3420
gcggtattat cccgtgttga cgccgggcaa gagcaactcg gtcgccgcat acactattct    3480
cagaatgact tggttgagta ctcaccagtc acagaaaagc atcttacgga tggcatgaca    3540
gtaagagaat tatgcagtgc tgccataacc atgagtgata acactgcggc caacttactt    3600
ctgacaacga tcggaggacc gaaggagcta accgcttttt tgcacaacat ggggatcat    3660 gtaactcgcc ttgatcgttg ggaaccggag ctgaatgaag ccataccaaa cgacgagcgt    3720
gacaccacga tgcctgcagc aatggcaaca acgttgcgca aactattaac tggcgaacta    3780
cttactctag cttcccggca acaattaata gactggatgg aggcggataa agttgcagga    3840
ccacttctgc gctcggccct tccggctggc tggtttattg ctgataaatc tggagccggt    3900
gagcgtgggt ctcgcggtat cattgcagca ctggggccag atggtaagcc ctcccgtatc    3960
gtagttatct acacgacggg gagtcaggca actatggatg aacgaaatag acagatcgct    4020
gagataggtg cctcactgat taagcattgg taactgtcag accaagttta ctcatatata    4080
ctttagattg atttaaaact tcatttttaa tttaaaagga tctaggtgaa gatcctttt     4140 gataatctca tgaccaaaat cccttaacgt gagttttcgt tccactgagc gtcagacccc    4200
gtagaaaaga tcaaaggatc ttcttgagat cctttttttc tgcgcgtaat ctgctgcttg    4260
caaacaaaaa aaccaccgct accagcggtg gtttgtttgc cggatcaaga gctaccaact    4320
ctttttccga aggtaactgg cttcagcaga gcgcagatac caaatactgt ccttctagtg    4380
tagccgtagt taggccacca cttcaagaac tctgtagcac cgcctacata cctcgctctg    4440
ctaatcctgt taccagtggc tgctgccagt ggcgataagt cgtgtcttac cgggttggac    4500
tcaagacgat agttaccgga taaggcgcag cggtcgggct gaacgggggg ttcgtgcaca    4560
cagcccagct tggagcgaac gacctacacc gaactgagat acctacagcg tgagcattga    4620
gaaagcgcca cgcttcccga agggagaaag gcggacaggt atccggtaag cggcagggtc    4680
ggaacaggag agcgcacgag ggagcttcca gggggaaacg cctggtatct ttatagtcct    4740
gtcgggtttc gccacctctg acttgagcgt cgatttttgt gatgctcgtc agggggcgg     4800 agcctatgga aaaacgccag caacgcggcc ttttacggt tcctggcctt ttgctggcct     4860
tttgctcaca tgttctttcc tgcgttatcc cctgattctg tggataaccg tattaccgcc    4920
tttgagtgag ctgataccgc tcgccgcagc cgaacgaccg agcgcagcga gtcagtgagc    4980
gaggaagcgg aagagcgccc aatacgcaaa ccgcctctcc ccgcgcgttg gccgattcat    5040
taatgcagct ggcacgacag gtttcccgac tggaaagcgg gcagtgagcg caacgcaatt    5100
aatgtgagtt agctcactca ttaggcaccc caggctttac actttatgct tccggctcgt    5160
atgttgtgtg gaattgtgag cggataacaa tttcacacag gaaacagcta tgaccatgat    5220
tacgccaagc tctagctaga gtcgaccaa ttctcatgtt tgacagctta tcatcgcaga    5280
tccgggcaac gttgttgcat tgctgcaggc gcagaactgg taggtatggc agatctatac    5340
attgaatcaa tattgcaat tagccatatt agtcattggt tatatagcat aaatcaatat    5400
tggctattgg ccattgcata cgttgtatct atatcataat atgtacattt atattggctc    5460
```

```
atgtccaata tgaccgccat gttgacattg attattgact agttattaat agtaatcaat    5520
tacggggtca ttagttcata gcccatatat ggagttccgc gttacataac ttacggtaaa    5580
tggcccgcct ggctgaccgc ccaacgaccc ccgcccattg acgtcaataa tgacgtatgt    5640
tcccatagta acgccaatag ggactttcca ttgacgtcaa tgggtggagt atttacggta    5700
aactgcccac ttggcagtac atcaagtgta tcatatgcca gtccgcccc ctattgacgt    5760 caatgacggt aaatggcccg cctggcatta tgcccagtac atgaccttac ggactttcc    5820 tacttggcag tacatctacg tattagtcat cgctattacc atggtgatgc ggttttggca    5880
gtacaccaat gggcgtggat agcggtttga ctcacgggga tttccaagtc tccaccccat    5940
tgacgtcaat gggagtttgt tttggcacca aaatcaacgg gactttccaa aatgtcgtaa    6000 taacccccgcc ccgttgacgc aaatgggcgg taggcgtgta cggtgggagg tctatataag    6060
cagagctcgt ttagtgaacc gtcagatcct cactctcttc cgcatcgctg tctgcgaggg    6120
ccagctgttg ggctcgcggt tgaggacaaa ctcttcgcgg tctttccagt actcttggat    6180
cggaaacccg tcggcctccg aacggtactc cgccaccgag ggacctgagc gagtccgcat    6240
cgaccggatc ggaaaacctc tcgagaaagg cgtctaacca gtcacagtcg caaggtaggc    6300
tgagcaccgt ggcgggcggc agcgggtggc ggtcggggtt gtttctggcg gaggtgctgc    6360
tgatgatgta attaaagtag gcggt                                           6385

<210> SEQ ID NO 16
<211> LENGTH: 43
<212> TYPE: DNA
<213> ORGANISM: Artificial Sequence
<220> FEATURE:
<223> OTHER INFORMATION: OGS18500 primer

<400> SEQUENCE: 16
atgccaagtg gtcccaggct gatgttgtga tgacccaaac tcc                      43

<210> SEQ ID NO 17
<211> LENGTH: 35
<212> TYPE: DNA
<213> ORGANISM: Artificial Sequence
<220> FEATURE:
<223> OTHER INFORMATION: OGS2084 primer

<400> SEQUENCE: 17
gggaagatga agacagatgg tgcagccaca gtccg                               35

<210> SEQ ID NO 18
<211> LENGTH: 50
<212> TYPE: DNA
<213> ORGANISM: Artificial Sequence
<220> FEATURE:
<223> OTHER INFORMATION: OGS1769 primer

<400> SEQUENCE: 18
gtaagcgcta gcgcctcaac gaagggccca tctgtctttc ccctggcccc               50

<210> SEQ ID NO 19
<211> LENGTH: 37
<212> TYPE: DNA
<213> ORGANISM: Artificial Sequence
<220> FEATURE:
<223> OTHER INFORMATION: OGS1770 primer

<400> SEQUENCE: 19
gtaagcgaat tcacaagatt tgggctcaac tttcttg                             37
```

<210> SEQ ID NO 20
<211> LENGTH: 309
<212> TYPE: DNA
<213> ORGANISM: Artificial Sequence
<220> FEATURE:
<223> OTHER INFORMATION: human immunoglobulin CH1 region

<400> SEQUENCE: 20

```
gcctccacca agggcccatc ggtcttcccc ctggcaccct cctccaagag cacctctggg      60
ggcacagcag ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgt                                                             309
```

<210> SEQ ID NO 21
<211> LENGTH: 103
<212> TYPE: PRT
<213> ORGANISM: Artificial Sequence
<220> FEATURE:
<223> OTHER INFORMATION: human immunoglobulin CH1 region

<400> SEQUENCE: 21

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
            100
```

<210> SEQ ID NO 22
<211> LENGTH: 5379
<212> TYPE: DNA
<213> ORGANISM: Artificial Sequence
<220> FEATURE:
<223> OTHER INFORMATION: plasmid

<400> SEQUENCE: 22

```
cttgagccgg cggatggtcg aggtgaggtg tggcaggctt gagatccagc tgttggggtg      60
agtactccct ctcaaaagcg ggcattactt ctgcgctaag attgtcagtt ccaaaaacg     120 aggaggattt gatattcacc tggcccgatc tggccataca cttgagtgac aatgacatcc     180
actttgcctt tctctccaca ggtgtccact cccaggtcca gtttgccgc caccatggag     240 acagacacac tcctgctatg ggtactgctg ctctgggttc caggttccac tggcggagac     300
ggagcttacg ggcccatctg tctttcccct ggcccctcc tccaagagca cctctggggg     360
cacagcggcc ctgggctgcc tggtcaagga ctacttcccc gaaccggtga cggtgtcgtg     420
gaactcaggc gccctgacca gcggcgtgca caccttcccg gctgtcctac agtcctcagg     480
```

| | |
|---|---|
| actctactcc ctcagcagcg tggtgaccgt gccctccagc agcttgggca cccagaccta | 540 |
| catctgcaac gtgaatcaca agcccagcaa caccaaggtg acaagaaag ttgagcccaa | 600 |
| atcttgtgaa ttcactcaca catgcccacc gtgcccagca cctgaactcc tggggggacc | 660 |
| gtcagtcttc ctcttccccc caaaacccaa ggacaccctc atgatctccc ggaccnctga | 720 |
| ggtcacatgc gtggtggtgg acgtgagcca cgaagaccct gaggtcaagt tcaactggta | 780 |
| cgtggacggc gtggaggtgc ataatgccaa gacaaagccg cgggaggagc agtacaacag | 840 |
| cacgtaccgt gtggtcagcg tcctcaccgt cctgcaccag gactggctga atggcaagga | 900 |
| gtacaagtgc aaggtctcca acaaagccct cccagccccc atcgagaaaa ccatctccaa | 960 |
| agccaaaggg cagccccgag aaccacaggt gtacaccctg cccccatccc gggatgagct | 1020 |
| gaccaagaac caggtcagcc tgacctgcct ggtcaaaggc ttctatccca gcgacatcgc | 1080 |
| cgtggagtgg gagagcaatg ggcagccgga gaacaactac aagaccacgc ctcccgtgct | 1140 |
| ggactccgac ggctccttct tcctctacag caagctcacc gtggacaaga gcaggtggca | 1200 |
| gcaggggaac gtcttctcat gctccgtgat gcatgaggct ctgcacaacc actacacgca | 1260 |
| gaagagcctc tccctgtctc ccgggaaatg atccccgac ctcgacctct ggctaataaa | 1320 |
| ggaaatttat tttcattgca atagtgtgtt ggaattttt gtgtctctca ctcggaagga | 1380 |
| catatgggag ggcaaatcat ttggtcgaga tccctcggag atctctagct agagcccgc | 1440 |
| cgccggacga actaaacctg actacggcat ctctgccct tcttcgcggg gcagtgcatg | 1500 |
| taatcccttc agttggttgg tacaacttgc caactgaacc ctaaacgggt agcatatgct | 1560 |
| tcccgggtag tagtatatac tatccagact aaccctaatt caatagcata tgttacccaa | 1620 |
| cgggaagcat atgctatcga attagggtta gtaaaagggt cctaaggaac agcgatgtag | 1680 |
| gtgggcgggc caagataggg gcgcgattgc tgcgatctgg aggacaaatt acacacactt | 1740 |
| gcgcctgagc gccaagcaca gggttgttgg tcctcatatt cacgaggtcg ctgagagcac | 1800 |
| ggtgggctaa tgttgccatg ggtagcatat actacccaaa tatctggata gcatatgcta | 1860 |
| tcctaatcta tatctgggta gcataggcta tcctaatcta tatctgggta gcatatgcta | 1920 |
| tcctaatcta tatctgggta gtatatgcta tcctaattta tatctgggta gcataggcta | 1980 |
| tcctaatcta tatctgggta gcatatgcta tcctaatcta tatctgggta gtatatgcta | 2040 |
| tcctaatctg tatccgggta gcatatgcta tcctaataga gattagggta gtatatgcta | 2100 |
| tcctaattta tatctgggta gcatatacta cccaaatatc tggatagcat atgctatcct | 2160 |
| aatctatatc tgggtagcat atgctatcct aatctatatc tgggtagcat aggctatcct | 2220 |
| aatctatatc tgggtagcat atgctatcct aatctatatc tgggtagtat atgctatcct | 2280 |
| aatttatatc tgggtagcat aggctatcct aatctatatc tgggtagcat atgctatcct | 2340 |
| aatctatatc tgggtagtat atgctatcct aatctgtatc cgggtagcat atgctatcct | 2400 |
| cacgatgata agctgtcaaa catgagaatt aattcttgaa gacgaaaggg cctcgtgata | 2460 |
| cgcctatttt tataggttaa tgtcatgata ataatggttt cttagacgtc aggtggcact | 2520 |
| tttcggggaa atgtgcgcgg aaccctatt tgtttatttt tctaaataca ttcaaatatg | 2580 |
| tatccgctca tgagacaata accctgataa atgcttcaat aatattgaaa aggaagagt | 2640 |
| atgagtattc aacatttccg tgtcgccctt attccctttt tgcggcatt ttgccttcct | 2700 |
| gttttgctc acccagaaac gctggtgaaa gtaaaagatg ctgaagatca gttgggtgca | 2760 |
| cgagtgggtt acatcgaact ggatctcaac agcggtaaga tccttgagag ttttcgcccc | 2820 |

```
gaagaacgtt ttccaatgat gagcactttt aaagttctgc tatgtggcgc ggtattatcc   2880
cgtgttgacg ccgggcaaga gcaactcggt cgccgcatac actattctca gaatgacttg   2940
gttgagtact caccagtcac agaaaagcat cttacggatg gcatgacagt aagagaatta   3000
tgcagtgctg ccataaccat gagtgataac actgcggcca acttacttct gacaacgatc   3060
ggaggaccga aggagctaac cgcttttttg cacaacatgg gggatcatgt aactcgcctt   3120
gatcgttggg aaccggagct gaatgaagcc ataccaaacg acgagcgtga caccacgatg   3180
cctgcagcaa tggcaacaac gttgcgcaaa ctattaactg gcgaactact tactctagct   3240
tcccggcaac aattaataga ctggatggag gcggataaag ttgcaggacc acttctgcgc   3300
tcggcccttc cggctggctg gtttattgct gataaatctg gagccggtga gcgtgggtct   3360
cgcggtatca ttgcagcact ggggccagat ggtaagccct cccgtatcgt agttatctac   3420
acgacgggga gtcaggcaac tatggatgaa cgaaatagac agatcgctga ataggtgcc   3480 tcactgatta agcattggta actgtcagac caagtttact catatatact ttagattgat   3540
ttaaaacttc attttaatt taaaaggatc taggtgaaga tcctttttga taatctcatg   3600
accaaaatcc cttaacgtga gttttcgttc cactgagcgt cagaccccgt agaaaagatc   3660
aaaggatctt cttgagatcc ttttttttctg cgcgtaatct gctgcttgca acaaaaaaa   3720 ccaccgctac cagcggtggt ttgtttgccg gatcaagagc taccaactct ttttccgaag   3780
gtaactggct tcagcagagc gcagatacca atactgtcc ttctagtgta gccgtagtta   3840
ggccaccact tcaagaactc tgtagcaccg cctacatacc tcgctctgct aatcctgtta   3900
ccagtggctg ctgccagtgg cgataagtcg tgtcttaccg ggttggactc aagacgatag   3960
ttaccggata aggcgcagcg gtcgggctga acgggggt cgtgcacaca gcccagcttg   4020
gagcgaacga cctacaccga actgagatac ctacagcgtg agcattgaga aagcgccacg   4080
cttcccgaag ggagaaaggc ggacaggtat ccggtaagcg cagggtcgg aacaggagag   4140 cgcacgaggg agcttccagg gggaaacgcc tggtatcttt atagtcctgt cgggtttcgc   4200
cacctctgac ttgagcgtcg attttttgtga tgctcgtcag ggggcggag cctatggaaa   4260 aacgccagca acgcggcctt tttacggttc ctggccttt gctggccttt tgctcacatg   4320
ttctttcctg cgttatcccc tgattctgtg gataaccgta ttaccgcctt tgagtgagct   4380
gataccgctc gccgcagccg aacgaccgag cgcagcgagt cagtgagcga ggaagcgtac   4440
atttatattg gctcatgtcc aatatgaccg ccatgttgac attgattatt gactagttat   4500
taatagtaat caattacggg gtcattagtt catagcccat atatggagtt ccgcgttaca   4560
taacttacgg taaatggccc gcctggctga ccgcccaacg acccccgccc attgacgtca   4620
ataatgacgt atgttcccat agtaacgcca tagggacttt ccattgacg tcaatgggtg   4680 gagtatttac ggtaaactgc ccacttggca gtacatcaag tgtatcatat gccaagtccg   4740 cccctattg acgtcaatga cggtaaatgg cccgcctggc attatgccca gtacatgacc   4800
ttacgggact ttcctacttg gcagtacatc tacgtattag tcatcgctat taccatggtg   4860
atgcggtttt ggcagtacac caatgggcgt ggatagcggt ttgactcacg ggatttcca   4920 agtctccacc ccattgacgt caatgggagt ttgttttggc accaaaatca acgggacttt   4980
ccaaaatgtc gtaataaccc cgccccgttg acgcaaatgg gcggtaggcg tgtacggtgg   5040
gaggtctata taagcagagc tcgtttagtg aaccgtcaga tcctcactct cttccgcatc   5100
gctgtctgcg agggccagct gttgggctcg cggttgagga caaactcttc gcggtctttc   5160
cagtactctt ggatcggaaa cccgtcggcc tccgaacggt actccgccac cgagggacct   5220
```

```
gagcgagtcc gcatcgaccg gatcggaaaa cctctcgaga aaggcgtcta accagtcaca    5280
gtcgcaaggt aggctgagca ccgtggcggg cggcagcggg tggcggtcgg ggttgtttct    5340
ggcggaggtg ctgctgatga tgtaattaaa gtaggcggt                           5379
```

<210> SEQ ID NO 23  
<211> LENGTH: 43  
<212> TYPE: DNA  
<213> ORGANISM: Artificial Sequence  
<220> FEATURE:  
<223> OTHER INFORMATION: OGS1879 primer

<400> SEQUENCE: 23

```
gggttccagg ttccactggc cagatccagt tggtgcaatc tgg                         43
```

<210> SEQ ID NO 24  
<211> LENGTH: 38  
<212> TYPE: DNA  
<213> ORGANISM: Artificial Sequence  
<220> FEATURE:  
<223> OTHER INFORMATION: OGS1810 primer

<400> SEQUENCE: 24

```
ggggccaggg gaaagacaga tgggcccttc gttgaggc                               38
```

<210> SEQ ID NO 25  
<211> LENGTH: 33  
<212> TYPE: DNA  
<213> ORGANISM: Artificial Sequence  
<220> FEATURE:  
<223> OTHER INFORMATION: primer

<400> SEQUENCE: 25

```
gtaagcggat ccatggatga cgacgcggcg ccc                                    33
```

<210> SEQ ID NO 26  
<211> LENGTH: 36  
<212> TYPE: DNA  
<213> ORGANISM: Artificial Sequence  
<220> FEATURE:  
<223> OTHER INFORMATION: primer

<400> SEQUENCE: 26

```
gtaagcaagc ttaggccgct gggacagcgg aggtgc                                 36
```

<210> SEQ ID NO 27  
<211> LENGTH: 33  
<212> TYPE: DNA  
<213> ORGANISM: Artificial Sequence  
<220> FEATURE:  
<223> OTHER INFORMATION: primer

<400> SEQUENCE: 27

```
gtaagcaagc ttggcagcag cgccaggtcc agc                                    33
```

<210> SEQ ID NO 28  
<211> LENGTH: 885  
<212> TYPE: DNA  
<213> ORGANISM: Homo sapiens  
<300> PUBLICATION INFORMATION:  
<301> AUTHORS: Van den Eynde, B. J. et al.,  
<302> TITLE: A new antigen recognized by cytolytic T lymphocytes on a human kidney tumor results from reverse strand transcription  
<303> JOURNAL: J. Exp. Med.  
<304> VOLUME: 190  
<305> ISSUE: 12

<306> PAGES: 1793-1799
<307> DATE: 1999-12-20
<308> DATABASE ACCESSION NUMBER: Q9UBP8
<309> DATABASE ENTRY DATE: 1999-12-20

<400> SEQUENCE: 28

```
gagggggcatc aatcacaccg agaagtcaca gccccctcaac cactgaggtg tgggggggta      60
gggatctgca tttcttcata tcaaccccac actataggggc acctaaatgg gtgggcggtg     120
ggggagaccg actcacttga gtttcttgaa ggcttcctgg cctccagcca cgtaattgcc     180
cccgctctgg atctggtcta gcttccggat tcggtggcca gtccgcgggg tgtagatgtt     240
cctgacggcc ccaaagggtg cctgaacgcc gccggtcacc tccttcagga agacttcgaa     300
gctggacacc ttcttctcat ggatgacgac gcggcgcccc gcgtagaagg ggtccccgtt     360
gcggtacaca agcacgctct tcacgacggg ctgagacagg tggctggacc tggcgctgct     420
gccgctcatc ttccccgctg gccgccgcct cagctcgctg cttcgcgtcg ggaggcacct     480
ccgctgtccc agcggcctca ccgcacccag ggcgcgggat cgcctcctga aacgaacgag     540
aaactgacga atccacaggt gaaagagaag taacggccgt gcgcctaggc gtccacccag     600
aggagacact aggagcttgc aggactcgga gtagacgctc aagtttttca ccgtggcgtg     660
cacagccaat caggacccgc agtgcgcgca ccacaccagg ttcacctgct acgggcagaa     720
tcaaggtgga cagcttctga gcaggagccg gaaacgcgcg gggccttcaa acaggcacgc     780
ctagtgaggg caggagagag gaggacgcac acacacacac acacacaaat atggtgaaac     840
ccaatttctt acatcatatc tgtgctaccc tttccaaaca gccta                     885
```

<210> SEQ ID NO 29
<211> LENGTH: 84
<212> TYPE: PRT
<213> ORGANISM: Homo sapiens
<300> PUBLICATION INFORMATION:
<301> AUTHORS: Van den Eynde, B. J., et al.,
<302> TITLE: A new antigen recognized by cytolytic T lymphocytes on a human kidney tumor from reverse strand
<303> JOURNAL: J. Exp. Med.
<304> VOLUME: 190
<305> ISSUE: 12
<306> PAGES: 1793-1799
<307> DATE: 1999-12-20
<308> DATABASE ACCESSION NUMBER: Q9UBP8
<309> DATABASE ENTRY DATE: 1999-12-20

<400> SEQUENCE: 29

```
Met Asp Asp Asp Ala Ala Pro Arg Val Glu Gly Val Pro Val Ala Val
1               5                   10                  15
His Lys His Ala Leu His Asp Gly Leu Arg Gln Val Ala Gly Pro Gly
            20                  25                  30
Ala Ala Ala Ala His Leu Pro Arg Trp Pro Pro Gln Leu Ala Ala
        35                  40                  45
Ser Arg Arg Glu Ala Pro Pro Leu Ser Gln Arg Pro His Arg Thr Gln
    50                  55                  60
Gly Ala Gly Ser Pro Pro Glu Thr Asn Glu Lys Leu Thr Asn Pro Gln
65                  70                  75                  80
Val Lys Glu Lys
```

<210> SEQ ID NO 30
<211> LENGTH: 112
<212> TYPE: PRT
<213> ORGANISM: Artificial Sequence
<220> FEATURE:

```
<223> OTHER INFORMATION: variant light chain variable region
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is any amino acid
<220> FEATURE:
<221> NAME/KEY: MISC_FEATURE
<222> LOCATION: (17)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (50)..(50)
<223> OTHER INFORMATION: Xaa is any amino acid
<220> FEATURE:
<221> NAME/KEY: MISC_FEATURE
<222> LOCATION: (88)..(88)
<223> OTHER INFORMATION: Xaa is any amino acid
<220> FEATURE:
<221> NAME/KEY: MISC_FEATURE
<222> LOCATION: (105)..(105)
<223> OTHER INFORMATION: Xaa is any amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: MISC_FEATURE
<222> LOCATION: (111)..(111)
<223> OTHER INFORMATION: Xaa is any amino acid

<400> SEQUENCE: 30

Asp Xaa Val Met Thr Gln Thr Pro Leu Ser Leu Xaa Val Xaa Xaa Gly
1               5                   10                  15

Xaa Xaa Ala Ser Ile Ser Cys Arg Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Xaa Leu Leu Ile His Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Phe Gln Gly
                85                  90                  95

Ser His Val Pro Leu Thr Phe Gly Xaa Gly Thr Xaa Leu Glu Xaa Lys
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: variant light chain variable region
<220> FEATURE:
<221> NAME/KEY: MISC_FEATURE
<222> LOCATION: (2)..(2)
```

```
<223> OTHER INFORMATION: Xaa is a hydrophobic amino acid
<220> FEATURE:
<221> NAME/KEY: MISC_FEATURE
<222> LOCATION: (12)..(12)
<223> OTHER INFORMATION: Xaa is A or P
<220> FEATURE:
<221> NAME/KEY: MISC_FEATURE
<222> LOCATION: (14)..(14)
<223> OTHER INFORMATION: Xaa is a neutral hydrophilic amino acid
<220> FEATURE:
<221> NAME/KEY: MISC_FEATURE
<222> LOCATION: (15)..(15)
<223> OTHER INFORMATION: Xaa is L or P
<220> FEATURE:
<221> NAME/KEY: MISC_FEATURE
<222> LOCATION: (17)..(17)
<223> OTHER INFORMATION: Xaa is an acidic amino acid
<220> FEATURE:
<221> NAME/KEY: MISC_FEATURE
<222> LOCATION: (18)..(18)
<223> OTHER INFORMATION: Xaa is Q or P
<220> FEATURE:
<221> NAME/KEY: MISC_FEATURE
<222> LOCATION: (50)..(50)
<223> OTHER INFORMATION: Xaa is a basic amino acid
<220> FEATURE:
<221> NAME/KEY: MISC_FEATURE
<222> LOCATION: (88)..(88)
<223> OTHER INFORMATION: Xaa is a hydrophobic amino acid
<220> FEATURE:
<221> NAME/KEY: MISC_FEATURE
<222> LOCATION: (105)..(105)
<223> OTHER INFORMATION: Xaa is A or Q
<220> FEATURE:
<221> NAME/KEY: MISC_FEATURE
<222> LOCATION: (108)..(108)
<223> OTHER INFORMATION: Xaa is a basic amino acid
<220> FEATURE:
<221> NAME/KEY: MISC_FEATURE
<222> LOCATION: (111)..(111)
<223> OTHER INFORMATION: Xaa is a hydrophobic amino acid

<400> SEQUENCE: 31

Asp Xaa Val Met Thr Gln Thr Pro Leu Ser Leu Xaa Val Xaa Xaa Gly
1               5                   10                  15

Xaa Xaa Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Xaa Leu Leu Ile His Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Phe Gln Gly
                85                  90                  95

Ser His Val Pro Leu Thr Phe Gly Xaa Gly Thr Xaa Leu Glu Xaa Lys
                100                 105                 110

<210> SEQ ID NO 32
<211> LENGTH: 112
<212> TYPE: PRT
<213> ORGANISM: Artificial Sequence
<220> FEATURE:
<223> OTHER INFORMATION: variant light chain variable region
<220> FEATURE:
<221> NAME/KEY: MISC_FEATURE
<222> LOCATION: (2)..(2)
<223> OTHER INFORMATION: Xaa is V or I
<220> FEATURE:
<221> NAME/KEY: MISC_FEATURE
<222> LOCATION: (12)..(12)
```

<223> OTHER INFORMATION: Xaa is A or P
<220> FEATURE:
<221> NAME/KEY: MISC_FEATURE
<222> LOCATION: (14)..(14)
<223> OTHER INFORMATION: Xaa is S or T
<220> FEATURE:
<221> NAME/KEY: MISC_FEATURE
<222> LOCATION: (15)..(15)
<223> OTHER INFORMATION: Xaa is L or P
<220> FEATURE:
<221> NAME/KEY: MISC_FEATURE
<222> LOCATION: (17)..(17)
<223> OTHER INFORMATION: Xaa is D or E
<220> FEATURE:
<221> NAME/KEY: MISC_FEATURE
<222> LOCATION: (18)..(18)
<223> OTHER INFORMATION: Xaa is Q or P
<220> FEATURE:
<221> NAME/KEY: MISC_FEATURE
<222> LOCATION: (50)..(50)
<223> OTHER INFORMATION: Xaa is K or Q
<220> FEATURE:
<221> NAME/KEY: MISC_FEATURE
<222> LOCATION: (88)..(88)
<223> OTHER INFORMATION: Xaa is L or V
<220> FEATURE:
<221> NAME/KEY: MISC_FEATURE
<222> LOCATION: (105)..(105)
<223> OTHER INFORMATION: Xaa is A or Q
<220> FEATURE:
<221> NAME/KEY: MISC_FEATURE
<222> LOCATION: (108)..(108)
<223> OTHER INFORMATION: Xaa is R or K
<220> FEATURE:
<221> NAME/KEY: MISC_FEATURE
<222> LOCATION: (111)..(111)
<223> OTHER INFORMATION: Xaa is L or I

<400> SEQUENCE: 32

Asp Xaa Val Met Thr Gln Thr Pro Leu Ser Leu Xaa Val Xaa Xaa Gly
1               5                   10                  15

Xaa Xaa Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Xaa Leu Leu Ile His Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Phe Gln Gly
                85                  90                  95

Ser His Val Pro Leu Thr Phe Gly Xaa Gly Thr Xaa Leu Glu Xaa Lys
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: variant 1 light chain variable region: Lvh1

<400> SEQUENCE: 33

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

```
Pro Gln Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gln Gly Thr Lys Leu Glu Ile Lys
                100                 105                 110

<210> SEQ ID NO 34
<211> LENGTH: 112
<212> TYPE: PRT
<213> ORGANISM: Artificial Sequence
<220> FEATURE:
<223> OTHER INFORMATION: variant 2 light chain variable region: Lvh2

<400> SEQUENCE: 34

Asp Val Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Thr Val Ser Asn Arg Phe Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gln Gly Thr Lys Leu Glu Ile Lys
                100                 105                 110

<210> SEQ ID NO 35
<211> LENGTH: 116
<212> TYPE: PRT
<213> ORGANISM: Artificial Sequence
<220> FEATURE:
<223> OTHER INFORMATION: variant heavy chain variable region
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is any amino acid
<220> FEATURE:
<221> NAME/KEY: MISC_FEATURE
<222> LOCATION: (38)..(38)
<223> OTHER INFORMATION: Xaa is any amino acid
<220> FEATURE:
<221> NAME/KEY: MISC_FEATURE
<222> LOCATION: (40)..(40)
<223> OTHER INFORMATION: Xaa is any amino acid
```

```
<220> FEATURE:
<221> NAME/KEY: MISC_FEATURE
<222> LOCATION: (41)..(41)
<223> OTHER INFORMATION: Xaa is any amino acid
<220> FEATURE:
<221> NAME/KEY: MISC_FEATURE
<222> LOCATION: (43)..(43)
<223> OTHER INFORMATION: Xaa is any amino acid
<220> FEATURE:
<221> NAME/KEY: MISC_FEATURE
<222> LOCATION: (44)..(44)
<223> OTHER INFORMATION: Xaa is any amino acid
<220> FEATURE:
<221> NAME/KEY: MISC_FEATURE
<222> LOCATION: (48)..(48)
<223> OTHER INFORMATION: Xaa is any amino acid
<220> FEATURE:
<221> NAME/KEY: MISC_FEATURE
<222> LOCATION: (67)..(67)
<223> OTHER INFORMATION: Xaa is any amino acid
<220> FEATURE:
<221> NAME/KEY: MISC_FEATURE
<222> LOCATION: (68)..(68)
<223> OTHER INFORMATION: Xaa is any amino acid
<220> FEATURE:
<221> NAME/KEY: MISC_FEATURE
<222> LOCATION: (69)..(69)
<223> OTHER INFORMATION: Xaa is any amino acid
<220> FEATURE:
<221> NAME/KEY: MISC_FEATURE
<222> LOCATION: (70)..(70)
<223> OTHER INFORMATION: Xaa is any amino acid
<220> FEATURE:
<221> NAME/KEY: MISC_FEATURE
<222> LOCATION: (72)..(72)
<223> OTHER INFORMATION: Xaa is any amino acid
<220> FEATURE:
<221> NAME/KEY: MISC_FEATURE
<222> LOCATION: (74)..(74)
<223> OTHER INFORMATION: Xaa is any amino acid
<220> FEATURE:
<221> NAME/KEY: MISC_FEATURE
<222> LOCATION: (76)..(76)
<223> OTHER INFORMATION: Xaa is any amino acid
<220> FEATURE:
<221> NAME/KEY: MISC_FEATURE
<222> LOCATION: (82)..(82)
<223> OTHER INFORMATION: Xaa is any amino acid
<220> FEATURE:
<221> NAME/KEY: MISC_FEATURE
<222> LOCATION: (84)..(84)
<223> OTHER INFORMATION: Xaa is any amino acid
<220> FEATURE:
<221> NAME/KEY: MISC_FEATURE
<222> LOCATION: (87)..(87)
<223> OTHER INFORMATION: Xaa is any amino acid
<220> FEATURE:
<221> NAME/KEY: MISC_FEATURE
<222> LOCATION: (91)..(91)
<223> OTHER INFORMATION: Xaa is any amino acid
<220> FEATURE:
<221> NAME/KEY: MISC_FEATURE
<222> LOCATION: (111)..(111)
<223> OTHER INFORMATION: Xaa is any amino acid

<400> SEQUENCE: 35

Gln Xaa Gln Leu Val Gln Ser Gly Xaa Glu Xaa Xaa Lys Pro Gly Ala
1               5                   10                  15

Ser Val Lys Xaa Ser Cys Lys Ala Ser Gly Tyr Thr Phe Thr Asp Asp
            20                  25                  30

Tyr Met Ser Trp Val Xaa Gln Xaa Xaa Gly Xaa Xaa Leu Glu Trp Xaa
        35                  40                  45

Gly Asp Ile Asn Pro Tyr Asn Gly Asp Thr Asn Tyr Asn Gln Lys Phe
    50                  55                  60
```

```
Lys Gly Xaa Xaa Xaa Thr Xaa Asp Xaa Ser Xaa Ser Thr Ala Tyr
 65                  70                  75                  80

Met Xaa Leu Xaa Ser Leu Xaa Ser Glu Asp Xaa Ala Val Tyr Tyr Cys
             85                  90                  95

Ala Arg Asp Pro Gly Ala Met Asp Tyr Trp Gly Gln Gly Thr Xaa Val
            100                 105                 110

Thr Val Ser Ser
            115

<210> SEQ ID NO 36
<211> LENGTH: 116
<212> TYPE: PRT
<213> ORGANISM: Artificial Sequence
<220> FEATURE:
<223> OTHER INFORMATION: variant heavy chain variable region
<220> FEATURE:
<221> NAME/KEY: MISC_FEATURE
<222> LOCATION: (2)..(2)
<223> OTHER INFORMATION: Xaa is a hydrophobic amino acid
<220> FEATURE:
<221> NAME/KEY: MISC_FEATURE
<222> LOCATION: (9)..(9)
<223> OTHER INFORMATION: Xaa is A or P
<220> FEATURE:
<221> NAME/KEY: MISC_FEATURE
<222> LOCATION: (11)..(11)
<223> OTHER INFORMATION: Xaa is a hydrophobic amino acid
<220> FEATURE:
<221> NAME/KEY: MISC_FEATURE
<222> LOCATION: (12)..(12)
<223> OTHER INFORMATION: Xaa is V or K
<220> FEATURE:
<221> NAME/KEY: MISC_FEATURE
<222> LOCATION: (20)..(20)
<223> OTHER INFORMATION: Xaa is a hydrophobic amino acid
<220> FEATURE:
<221> NAME/KEY: MISC_FEATURE
<222> LOCATION: (38)..(38)
<223> OTHER INFORMATION: Xaa is a basic amino acid
<220> FEATURE:
<221> NAME/KEY: MISC_FEATURE
<222> LOCATION: (40)..(40)
<223> OTHER INFORMATION: Xaa is S or A
<220> FEATURE:
<221> NAME/KEY: MISC_FEATURE
<222> LOCATION: (41)..(41)
<223> OTHER INFORMATION: Xaa is H or P
<220> FEATURE:
<221> NAME/KEY: MISC_FEATURE
<222> LOCATION: (43)..(43)
<223> OTHER INFORMATION: Xaa is a basic amino acid
<220> FEATURE:
<221> NAME/KEY: MISC_FEATURE
<222> LOCATION: (44)..(44)
<223> OTHER INFORMATION: Xaa is S or G
<220> FEATURE:
<221> NAME/KEY: MISC_FEATURE
<222> LOCATION: (48)..(48)
<223> OTHER INFORMATION: Xaa is a hydrophobic amino acid
<220> FEATURE:
<221> NAME/KEY: MISC_FEATURE
<222> LOCATION: (67)..(67)
<223> OTHER INFORMATION: Xaa is a basic amino acid
<220> FEATURE:
<221> NAME/KEY: MISC_FEATURE
<222> LOCATION: (68)..(68)
<223> OTHER INFORMATION: Xaa is a hydrophobic amino acid
<220> FEATURE:
<221> NAME/KEY: MISC_FEATURE
<222> LOCATION: (69)..(69)
<223> OTHER INFORMATION: Xaa is I or T
<220> FEATURE:
<221> NAME/KEY: MISC_FEATURE
<222> LOCATION: (70)..(70)
<223> OTHER INFORMATION: Xaa is a hydrophobic amino acid
```

```
<220> FEATURE:
<221> NAME/KEY: MISC_FEATURE
<222> LOCATION: (72)..(72)
<223> OTHER INFORMATION: Xaa is hydrophobic amino acid
<220> FEATURE:
<221> NAME/KEY: MISC_FEATURE
<222> LOCATION: (74)..(74)
<223> OTHER INFORMATION: Xaa is K or T
<220> FEATURE:
<221> NAME/KEY: MISC_FEATURE
<222> LOCATION: (76)..(76)
<223> OTHER INFORMATION: Xaa is a neutral amino acid
<220> FEATURE:
<221> NAME/KEY: MISC_FEATURE
<222> LOCATION: (82)..(82)
<223> OTHER INFORMATION: Xaa is Q or E
<220> FEATURE:
<221> NAME/KEY: MISC_FEATURE
<222> LOCATION: (84)..(84)
<223> OTHER INFORMATION: Xaa is N or S
<220> FEATURE:
<221> NAME/KEY: MISC_FEATURE
<222> LOCATION: (87)..(87)
<223> OTHER INFORMATION: Xaa is T or R
<220> FEATURE:
<221> NAME/KEY: MISC_FEATURE
<222> LOCATION: (91)..(91)
<223> OTHER INFORMATION: Xaa is a neutral hydrophilic amino acid
<220> FEATURE:
<221> NAME/KEY: MISC_FEATURE
<222> LOCATION: (111)..(111)
<223> OTHER INFORMATION: Xaa is S or L

<400> SEQUENCE: 36

Gln Xaa Gln Leu Val Gln Ser Gly Xaa Glu Xaa Xaa Lys Pro Gly Ala
  1               5                  10                  15

Ser Val Lys Xaa Ser Cys Lys Ala Ser Gly Tyr Thr Phe Thr Asp Asp
             20                  25                  30

Tyr Met Ser Trp Val Xaa Gln Xaa Xaa Gly Xaa Xaa Leu Glu Trp Xaa
         35                  40                  45

Gly Asp Ile Asn Pro Tyr Asn Gly Asp Thr Asn Tyr Asn Gln Lys Phe
 50                  55                  60

Lys Gly Xaa Xaa Xaa Xaa Thr Xaa Asp Xaa Ser Xaa Ser Thr Ala Tyr
 65                  70                  75                  80

Met Xaa Leu Xaa Ser Leu Xaa Ser Glu Asp Xaa Ala Val Tyr Tyr Cys
             85                  90                  95

Ala Arg Asp Pro Gly Ala Met Asp Tyr Trp Gly Gln Gly Thr Xaa Val
            100                 105                 110

Thr Val Ser Ser
            115

<210> SEQ ID NO 37
<211> LENGTH: 116
<212> TYPE: PRT
<213> ORGANISM: Artificial Sequence
<220> FEATURE:
<223> OTHER INFORMATION: variant heavy chain variable region
<220> FEATURE:
<221> NAME/KEY: MISC_FEATURE
<222> LOCATION: (2)..(2)
<223> OTHER INFORMATION: Xaa is I or V
<220> FEATURE:
<221> NAME/KEY: MISC_FEATURE
<222> LOCATION: (9)..(9)
<223> OTHER INFORMATION: Xaa is P or A
<220> FEATURE:
<221> NAME/KEY: MISC_FEATURE
<222> LOCATION: (11)..(11)
<223> OTHER INFORMATION: Xaa is M or V
<220> FEATURE:
```

-continued

```
<221> NAME/KEY: MISC_FEATURE
<222> LOCATION: (12)..(12)
<223> OTHER INFORMATION: Xaa is V or K
<220> FEATURE:
<221> NAME/KEY: MISC_FEATURE
<222> LOCATION: (20)..(20)
<223> OTHER INFORMATION: Xaa is M or V
<220> FEATURE:
<221> NAME/KEY: MISC_FEATURE
<222> LOCATION: (38)..(38)
<223> OTHER INFORMATION: Xaa is K or R
<220> FEATURE:
<221> NAME/KEY: MISC_FEATURE
<222> LOCATION: (40)..(40)
<223> OTHER INFORMATION: Xaa is S or A
<220> FEATURE:
<221> NAME/KEY: MISC_FEATURE
<222> LOCATION: (41)..(41)
<223> OTHER INFORMATION: Xaa is H or P
<220> FEATURE:
<221> NAME/KEY: MISC_FEATURE
<222> LOCATION: (43)..(43)
<223> OTHER INFORMATION: Xaa is K or Q
<220> FEATURE:
<221> NAME/KEY: MISC_FEATURE
<222> LOCATION: (44)..(44)
<223> OTHER INFORMATION: Xaa is S or G
<220> FEATURE:
<221> NAME/KEY: MISC_FEATURE
<222> LOCATION: (48)..(48)
<223> OTHER INFORMATION: Xaa is I or M
<220> FEATURE:
<221> NAME/KEY: MISC_FEATURE
<222> LOCATION: (67)..(67)
<223> OTHER INFORMATION: Xaa is K or R
<220> FEATURE:
<221> NAME/KEY: MISC_FEATURE
<222> LOCATION: (68)..(68)
<223> OTHER INFORMATION: Xaa is A or V
<220> FEATURE:
<221> NAME/KEY: MISC_FEATURE
<222> LOCATION: (69)..(69)
<223> OTHER INFORMATION: Xaa is I or T
<220> FEATURE:
<221> NAME/KEY: MISC_FEATURE
<222> LOCATION: (70)..(70)
<223> OTHER INFORMATION: Xaa is L or I
<220> FEATURE:
<221> NAME/KEY: MISC_FEATURE
<222> LOCATION: (72)..(72)
<223> OTHER INFORMATION: Xaa is V or A
<220> FEATURE:
<221> NAME/KEY: MISC_FEATURE
<222> LOCATION: (74)..(74)
<223> OTHER INFORMATION: Xaa is K or T
<220> FEATURE:
<221> NAME/KEY: MISC_FEATURE
<222> LOCATION: (76)..(76)
<223> OTHER INFORMATION: Xaa is S or T
<220> FEATURE:
<221> NAME/KEY: MISC_FEATURE
<222> LOCATION: (82)..(82)
<223> OTHER INFORMATION: Xaa is Q or E
<220> FEATURE:
<221> NAME/KEY: MISC_FEATURE
<222> LOCATION: (84)..(84)
<223> OTHER INFORMATION: Xaa is N or S
<220> FEATURE:
<221> NAME/KEY: MISC_FEATURE
<222> LOCATION: (87)..(87)
<223> OTHER INFORMATION: Xaa is T or R
<220> FEATURE:
<221> NAME/KEY: MISC_FEATURE
<222> LOCATION: (91)..(91)
<223> OTHER INFORMATION: Xaa is S or T
<220> FEATURE:
<221> NAME/KEY: MISC_FEATURE
<222> LOCATION: (111)..(111)
<223> OTHER INFORMATION: Xaa is S or L
```

<400> SEQUENCE: 37

Gln Xaa Gln Leu Val Gln Ser Gly Xaa Glu Xaa Xaa Lys Pro Gly Ala
1               5                   10                  15

Ser Val Lys Xaa Ser Cys Lys Ala Ser Gly Tyr Thr Phe Thr Asp Asp
            20                  25                  30

Tyr Met Ser Trp Val Xaa Gln Xaa Xaa Gly Xaa Xaa Leu Glu Trp Xaa
        35                  40                  45

Gly Asp Ile Asn Pro Tyr Asn Gly Asp Thr Asn Tyr Asn Gln Lys Phe
    50                  55                  60

Lys Gly Xaa Xaa Xaa Xaa Thr Xaa Asp Xaa Ser Xaa Ser Thr Ala Tyr
65                  70                  75                  80

Met Xaa Leu Xaa Ser Leu Xaa Ser Glu Asp Xaa Ala Val Tyr Tyr Cys
        85                  90                  95

Ala Arg Asp Pro Gly Ala Met Asp Tyr Trp Gly Gln Gly Thr Xaa Val
            100                 105                 110

Thr Val Ser Ser
        115

<210> SEQ ID NO 38
<211> LENGTH: 116
<212> TYPE: PRT
<213> ORGANISM: Artificial Sequence
<220> FEATURE:
<223> OTHER INFORMATION: variant 1 heavy chain variable region: Hvh1

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Arg Gln Ala Pro Gly Gln Gly Leu Glu Trp Met
        35                  40                  45

Gly Asp Ile Asn Pro Tyr Asn Gly Asp Thr Asn Tyr Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
        85                  90                  95

Ala Arg Asp Pro Gly Ala Met Asp Tyr Trp Gly Gln Gly Thr Leu Val
            100                 105                 110

Thr Val Ser Ser
        115

<210> SEQ ID NO 39
<211> LENGTH: 116
<212> TYPE: PRT
<213> ORGANISM: Artificial Sequence
<220> FEATURE:
<223> OTHER INFORMATION: variant 2 heavy chain variable region: Hvh2

<400> SEQUENCE: 39

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Arg Gln Ala Pro Gly Gln Gly Leu Glu Trp Met
        35                  40                  45

Gly Asp Ile Asn Pro Tyr Asn Gly Asp Thr Asn Tyr Asn Gln Lys Phe
         50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Asp Pro Gly Ala Met Asp Tyr Trp Gly Gln Gly Thr Leu Val
             100                 105                 110

Thr Val Ser Ser
         115

<210> SEQ ID NO 40
<211> LENGTH: 116
<212> TYPE: PRT
<213> ORGANISM: Artificial Sequence
<220> FEATURE:
<223> OTHER INFORMATION: variant 3 heavy chain variable region: Hvh3

<400> SEQUENCE: 40

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
                 20                  25                  30

Tyr Met Ser Trp Val Arg Gln Ala Pro Gly Gln Gly Leu Glu Trp Ile
             35                  40                  45

Gly Asp Ile Asn Pro Tyr Asn Gly Asp Thr Asn Tyr Asn Gln Lys Phe
         50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Asp Pro Gly Ala Met Asp Tyr Trp Gly Gln Gly Thr Leu Val
             100                 105                 110

Thr Val Ser Ser
         115

<210> SEQ ID NO 41
<211> LENGTH: 116
<212> TYPE: PRT
<213> ORGANISM: Artificial Sequence
<220> FEATURE:
<223> OTHER INFORMATION: variant 4 heavy chain variable region: Hvh4

<400> SEQUENCE: 41

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
                 20                  25                  30

Tyr Met Ser Trp Val Lys Gln Ala Pro Gly Gln Gly Leu Glu Trp Ile
             35                  40                  45

Gly Asp Ile Asn Pro Tyr Asn Gly Asp Thr Asn Tyr Asn Gln Lys Phe
         50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                 85                  90                  95

Ala Arg Asp Pro Gly Ala Met Asp Tyr Trp Gly Gln Gly Thr Leu Val

Thr Val Ser Ser
        115

<210> SEQ ID NO 42
<211> LENGTH: 219
<212> TYPE: PRT
<213> ORGANISM: Artificial Sequence
<220> FEATURE:
<223> OTHER INFORMATION: 3A4 murine light (kappa) chain

<400> SEQUENCE: 42

Asp Val Val Met Thr Gln Thr Pro Leu Ser Leu Ala Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile His Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Arg Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 43
<211> LENGTH: 219
<212> TYPE: PRT
<213> ORGANISM: Artificial Sequence
<220> FEATURE:
<223> OTHER INFORMATION: 3A4 humanized light (kappa) chain variant 1:
      Lh1

<400> SEQUENCE: 43

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 44
<211> LENGTH: 219
<212> TYPE: PRT
<213> ORGANISM: Artificial Sequence
<220> FEATURE:
<223> OTHER INFORMATION: 3A4 humanized light (kappa) chain variant 2: Lh2

<400> SEQUENCE: 44

```
Asp Val Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Thr Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Leu Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

-continued

```
            195                 200                 205
Pro Val Thr Lys Ser Phe Asn Arg Gly Glu Cys
    210                 215

<210> SEQ ID NO 45
<211> LENGTH: 446
<212> TYPE: PRT
<213> ORGANISM: Artificial Sequence
<220> FEATURE:
<223> OTHER INFORMATION: 3A4 murine heavy (Igg1) chain

<400> SEQUENCE: 45

Gln Ile Gln Leu Val Gln Ser Gly Pro Glu Met Val Lys Pro Gly Ala
1               5                   10                  15

Ser Val Lys Met Ser Cys Lys Ala Ser Gly Tyr Thr Phe Thr Asp Asp
            20                  25                  30

Tyr Met Ser Trp Val Lys Gln Ser His Gly Lys Ser Leu Glu Trp Ile
        35                  40                  45

Gly Asp Ile Asn Pro Tyr Asn Gly Asp Thr Asn Tyr Asn Gln Lys Phe
    50                  55                  60

Lys Gly Lys Ala Ile Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Pro Gly Ala Met Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
```

```
            340                 345                 350
Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 46
<211> LENGTH: 446
<212> TYPE: PRT
<213> ORGANISM: Artificial Sequence
<220> FEATURE:
<223> OTHER INFORMATION: 3A4 humanized heavy (Igg1) chain variant 1: Hh1

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Arg Gln Ala Pro Gly Gln Gly Leu Glu Trp Met
        35                  40                  45

Gly Asp Ile Asn Pro Tyr Asn Gly Asp Thr Asn Tyr Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
              260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 47
<211> LENGTH: 446
<212> TYPE: PRT
<213> ORGANISM: Artificial Sequence
<220> FEATURE:
<223> OTHER INFORMATION: 3A4 humanized heavy (Igg1) chain variant 2: Hh2

<400> SEQUENCE: 47

Gln Ile Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Asp
            20                  25                  30
Tyr Met Ser Trp Val Arg Gln Ala Pro Gly Gln Gly Leu Glu Trp Met
        35                  40                  45
Gly Asp Ile Asn Pro Tyr Asn Gly Asp Thr Asn Tyr Asn Gln Lys Phe
    50                  55                  60
Lys Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Pro Gly Ala Met Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
```

```
            180                 185                 190
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Lys Thr His Thr
            210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
            245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
            325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445

<210> SEQ ID NO 48
<211> LENGTH: 446
<212> TYPE: PRT
<213> ORGANISM: Artificial Sequence
<220> FEATURE:
<223> OTHER INFORMATION: 3A4 humanized heavy (Igg1) chain variant 3: Hh3

<400> SEQUENCE: 48

Gln Ile Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Asp
            20                  25                  30
Tyr Met Ser Trp Val Arg Gln Ala Pro Gly Gln Gly Leu Glu Trp Ile
            35                  40                  45
Gly Asp Ile Asn Pro Tyr Asn Gly Asp Thr Asn Tyr Asn Gln Lys Phe
        50                  55                  60
Lys Gly Arg Ala Thr Leu Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
            85                  90                  95
Ala Arg Asp Pro Gly Ala Met Asp Tyr Trp Gly Gln Gly Thr Leu Val
```

```
            100                 105                 110
Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 49
<211> LENGTH: 446
<212> TYPE: PRT
<213> ORGANISM: Artificial Sequence
<220> FEATURE:
<223> OTHER INFORMATION: 3A4 humanized heavy (Igg1) chain variant 4: Hh4

<400> SEQUENCE: 49

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
```

```
                    20                  25                  30
Tyr Met Ser Trp Val Lys Gln Ala Pro Gly Gln Gly Leu Glu Trp Ile
                35                  40                  45
Gly Asp Ile Asn Pro Tyr Asn Gly Asp Thr Asn Tyr Asn Gln Lys Phe
 50                  55                  60
Lys Gly Lys Ala Thr Leu Thr Val Asp Lys Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Asp Pro Gly Ala Met Asp Tyr Trp Gly Gln Gly Thr Leu Val
                100                 105                 110
Thr Val Ser Ser Ala Ser Thr Lys Gly Pro Ser Val Phe Pro Leu Ala
                115                 120                 125
Pro Ser Ser Lys Ser Thr Ser Gly Gly Thr Ala Ala Leu Gly Cys Leu
                130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Lys Val Glu Pro Lys Ser Cys Asp Lys Thr His Thr
                210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
                275                 280                 285
Lys Pro Arg Glu Glu Gln Tyr Asn Ser Thr Tyr Arg Val Val Ser Val
                290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Asp Glu Leu Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys
                435                 440                 445
```

<210> SEQ ID NO 50
<211> LENGTH: 34
<212> TYPE: DNA
<213> ORGANISM: Artificial Sequence
<220> FEATURE:
<223> OTHER INFORMATION: primer

<400> SEQUENCE: 50
atacccaagc ttgccaccat ggagacagac acac                         34

<210> SEQ ID NO 51
<211> LENGTH: 33
<212> TYPE: DNA
<213> ORGANISM: Artificial Sequence
<220> FEATURE:
<223> OTHER INFORMATION: primer

<400> SEQUENCE: 51
atacccaagc ttcatttccc gggagacagg gag                          33

<210> SEQ ID NO 52
<211> LENGTH: 41
<212> TYPE: DNA
<213> ORGANISM: Artificial Sequence
<220> FEATURE:
<223> OTHER INFORMATION: primer

<400> SEQUENCE: 52
atacccaagc ttgggccacc atgaactttc tgctgtcttg g                 41

<210> SEQ ID NO 53
<211> LENGTH: 34
<212> TYPE: DNA
<213> ORGANISM: Artificial Sequence
<220> FEATURE:
<223> OTHER INFORMATION: primer

<400> SEQUENCE: 53
atacccaagc ttctaacact ctcccctgtt gaag                         34

<210> SEQ ID NO 54
<211> LENGTH: 3962
<212> TYPE: DNA
<213> ORGANISM: Artificial Sequence
<220> FEATURE:
<223> OTHER INFORMATION: pK-CR5 plasmid

<400> SEQUENCE: 54
ctaaattgta agcgttaata ttttgttaaa attcgcgtta aattttgtt aaatcagctc    60 attttttaac caataggccg aaatcggcaa aatcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt ttttttgggt cgaggtgccg taaagcacta aatcggaacc ctaaagggag   300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600

```
taaaacgacg gccagtgagc gcgcgtaata cgactcacta tagggcgaat ggagctcca      660
ccgcggtggc ggccgctcta gaactagtgg atccacatcg gcgcgccaaa tgatttgccc      720
tcccatatgt ccttccgagt gagagacaca aaaaattcca acacactatt gcaatgaaaa      780
taaatttcct ttattagcca gaggtcgaga tttaaataag cttgctagca gatctttgga      840
cctgggagtg gacacctgtg gagagaaagg caaagtggat gtcattgtca ctcaagtgta      900
tggccagatc gggccaggtg aatatcaaat cctcctcgtt tttggaaact gacaatctta      960
gcgcagaagt aatgcccgct tttgagaggg agtactcacc ccaacagctg gatctcaagc     1020
ctgccacacc tcacctcgac catccgccgt ctcaagaccg cctactttaa ttacatcatc     1080
agcagcacct ccgccagaaa caaccccgac cgccacccgc tgccgcccgc cacggtgctc     1140
agcctacctt gcgactgtga ctggttagac gcctttctcg agaggttttc cgatccggtc     1200
gatgcggact cgctcaggtc cctcggtggc ggagtaccgt tcggaggccg acgggtttcc     1260
gatccaagag tactgaaaag accgcgaaga gtttgtcctc aaccgcgagc ccaacagctg     1320
gccctcgcag acagcgatgc ggaagagagt gaccgcggag gctggatcgg tcccggtgtc     1380
ttctatggag gtcaaaacag cgtggatggc gtctccaggc gatctgacgg ttcactaaac     1440
gagctctgct tatataggcc tcccaccgta cacgcctacc tcgacccggg taccaatctt     1500
ataatacaaa cagaccagat tgtctgtttg ttataataca aacagaccag attgtctgtt     1560
tgttataata caaacagacc agattgtctg tttgttataa cacaaacaga ccagattgtc     1620
tgtttgttat aatacaaaca gaccagattg tctgtttgtt ataatacaaa cagaccagat     1680
tgtctgtttg ttaaggttgt cgagtgaaga cgaaagggtt cattaaggcg cgccgtcgac     1740
ctcgaggggg ggcccggtac ccagcttttg ttccctttag tgagggttaa ttgcgcgctt     1800
ggcgtaatca tggtcatagc tgtttcctgt gtgaaattgt tatccgctca caattccaca     1860
caacatacga gccggaagca taaagtgtaa agcctggggt gcctaatgag tgagctaact     1920
cacattaatt gcgttgcgct cactgcccgc tttccagtcg ggaaacctgt cgtgccagct     1980
gcattaatga atcggccaac gcgcgggag aggcggtttg cgtattgggc gctcttccgc     2040
ttcctcgctc actgactcgc tgcgctcggt cgttcggctg cggcgagcgg tatcagctca     2100
ctcaaaggcg gtaatacggt tatccacaga atcagggat aacgcaggaa agaacatgtg     2160
agcaaaaggc cagcaaaagg ccaggaaccg taaaaaggcc gcgttgctgg cgttttccca     2220
taggctccgc cccctgacg agcatcacaa aaatcgacgc tcaagtcaga ggtggcgaaa     2280
cccgacagga ctataaagat accaggcgtt tccccctgga agctccctcg tgcgctctcc     2340
tgttccgacc ctgccgctta ccggatacct gtccgccttt ctcccttcgg gaagcgtggc     2400
gctttctcat agctcacgct gtaggtatct cagttcggtg taggtcgttc gctccaagct     2460
gggctgtgtg cacgaacccc ccgttcagcc cgaccgctgc gccttatccg gtaactatcg     2520
tcttgagtcc aacccggtaa gacacgactt atcgccactg gcagcagcca ctggtaacag     2580
gattagcaga gcgaggtatg taggcggtgc tacagagttc ttgaagtggt ggcctaacta     2640
cggctacact agaaggacag tatttggtat ctgcgctctg ctgaagccag ttaccttcgg     2700
aaaaagagtt ggtagctctt gatccggcaa acaaaccacc gctggtagcg gtggtttttt     2760
tgtttgcaag cagcagatta cgcgcagaaa aaaaggatct caagaagatc ctttgatctt     2820
ttctacgggg tctgacgctc agtggaacga aaactcacgt taagggattt tggtcatgag     2880
attatcaaaa aggatcttca cctagatcct ttttaaatta aaaatgaagtt ttaaatcaat     2940
ctaaagtata tatgagtaaa cttggtctga cagttaccaa tgcttaatca gtgaggcacc     3000
```

```
tatctcagcg atctgtctat ttcgttcatc catagttgcc tgactcccccg tcgtgtagat    3060 aactacgata cgggagggct taccatctgg ccccagtgct gcaatgatac cgcgagaccc    3120
acgctcaccg gctccagatt tatcagcaat aaaccagcca gccggaaggg ccgagcgcag    3180
aagtggtcct gcaactttat ccgcctccat ccagtctatt aattgttgcc gggaagctag    3240
agtaagtagt tcgccagtta atagtttgcg caacgttgtt gccattgcta caggcatcgt    3300
ggtgtcacgc tcgtcgtttg gtatggcttc attcagctcc ggttcccaac gatcaaggcg    3360
agttacatga tcccccatgt tgtgcaaaaa agcggttagc tccttcggtc ctccgatcgt    3420
tgtcagaagt aagttggccg cagtgttatc actcatggtt atggcagcac tgcataattc    3480
tcttactgtc atgccatccg taagatgctt ttctgtgact ggtgagtact caaccaagtc    3540
attctgagaa tagtgtatgc ggcgaccgag ttgctcttgc ccggcgtcaa tacgggataa    3600
taccgcgcca catagcagaa ctttaaaagt gctcatcatt ggaaaacgtt cttcggggcg    3660
aaaactctca aggatcttac cgctgttgag atccagttcg atgtaaccca ctcgtgcacc    3720
caactgatct tcagcatctt ttactttcac cagcgtttct gggtgagcaa aaacaggaag    3780
gcaaaatgcc gcaaaaaagg gaataagggc gacacggaaa tgttgaatac tcatactctt    3840 ccttttttcaa tattattgaa gcatttatca gggttattgt ctcatgagcg gatacatatt    3900
tgaatgtatt tagaaaaata aacaaatagg ggttccgcgc acatttcccc gaaaagtgcc    3960
ac                                                                   3962

<210> SEQ ID NO 55
<211> LENGTH: 6530
<212> TYPE: DNA
<213> ORGANISM: Artificial Sequence
<220> FEATURE:
<223> OTHER INFORMATION: pMPG-CR5 plasmid

<400> SEQUENCE: 55
gtcgacgata ccgtgcactt aattaagcgc gctcgaccaa atgatttgcc ctcccatatg      60
tccttccgag tgagagacac aaaaaattcc aacacactat tgcaatgaaa ataaatttcc     120
tttattagcc agaggtcgag gtcgggggat ccgtttaaac ttggacctgg gagtggacac     180
ctgtggagag aaaggcaaag tggatgtcat tgtcactcaa gtgtatggcc agatcgggcc     240
aggtgaatat caaatcctcc tcgttttttgg aaactgacaa tcttagcgca gaagtaatgc     300
ccgcttttga gagggagtac tcaccccaac agctggatct caagcctgcc acacctcacc     360
tcgaccatcc gccgtctcaa gaccgcctac tttaattaca tcatcagcag cacctccgcc     420
agaaacaacc ccgaccgcca cccgctgccg cccgccacgg tgctcagcct accttgcgac     480
tgtgactggt tagacgcctt tctcgagagg ttttccgatc cggtcgatgc ggactcgctc     540
aggtccctcg gtggcggagt accgttcgga ggccgacggg tttccgatcc aagagtactg     600
gaaagaccgc gaagagtttg tcctcaaccg cgagcccaac agctggccct cgcagacagc     660
gatgcggaag agagtgaccg cggaggctgg atcggtcccg gtgtcttcta tggaggtcaa     720
aacagcgtgg atggcgtctc caggcgatct gacggttcac taaacgagct ctgcttatat     780
aggcctccca ccgtacacgc ctacctcgac ccgggtacca atcttataat acaaacagac     840
cagattgtct gtttgttata atacaaacag accagattgt ctgtttgtta taatacaaac     900
agaccagatt gtctgtttgt tataatacaa acagaccaga ttgtctgttt gttataatac     960
aaacagacca gattgtctgt tgttataat acaaacagac cagattgtct gtttgttaag    1020
```

-continued

```
gttgtcgagt gaagacgaaa gggttaatta aggcgcgccg tcgactagct tggcacgcca    1080
gaaatccgcg cggtggtttt tgggggtcgg gggtgtttgg cagccacaga cgcccggtgt    1140
tcgtgtcgcg ccagtacatg cggtccatgc ccaggccatc caaaaaccat gggtctgtct    1200
gctcagtcca gtcgtggacc agaccccacg caacgcccaa aataataacc cccacgaacc    1260
ataaaccatt ccccatgggg gaccccgtcc ctaacccacg gggccagtgg ctatggcagg    1320
gcctgccgcc ccgacgttgg ctgcgagccc tgggccttca cccgaacttg ggggtgggg    1380
tggggaaaag gaagaaacgc gggcgtattg gccccaatgg ggtctcggtg gggtatcgac    1440
agagtgccag ccctgggacc gaaccccgcg tttatgaaca aacgacccaa cacccgtgcg    1500
ttttattctg tcttttttatt gccgtcatag cgcgggttcc ttccggtatt gtctccttcc    1560
gtgtttcagt tagcctcccc catctcccct attcctttgc cctcggacga gtgctggggc    1620
gtcggtttcc actatcggcg agtacttcta cacagccatc ggtccagacg gccgcgcttc    1680
tgcgggcgat ttgtgtacgc ccgacagtcc cggctccgga tcggacgatt gcgtcgcatc    1740
gaccctgcgc ccaagctgca tcatcgaaat tgccgtcaac caagctctga tagagttggt    1800
caagaccaat gcggagcata tacgcccgga gccgcggcga tcctgcaagc tccggatgcc    1860
tccgctcgaa gtagcgcgtc tgctgctcca tacaagccaa ccacggcctc cagaagaaga    1920
tgttggcgac ctcgtattgg gaatccccga acatcgcctc gctccagtca atgaccgctg    1980
ttatgcggcc attgtccgtc aggacattgt tggagccgaa atccgcgtgc acgaggtgcc    2040
ggacttcggg gcagtcctcg gcccaaagca tcagctcatc gagagcctgc gcgacggacg    2100
cactgacggt gtcgtccatc acagtttgcc agtgatacac atgggatca gcaatcgcgc    2160
atatgaaatc acgccatgta gtgtattgac cgattccttg cggtccgaat gggccgaacc    2220
cgctcgtctg gctaagatcg gccgcagcga tcgcatccat ggcctccgcg accggctgca    2280
gaacagcggg cagttcggtt tcaggcaggt cttgcaacgt gacaccctgt gcacggcggg    2340
agatgcaata ggtcaggctc tcgctgaatt ccccaatgtc aagcacttcc ggaatcggga    2400
gcgcggccga tgcaaagtgc cgataaacat aacgatcttt gtagaaacca tcggcgcagc    2460
tatttacccg caggacatat ccacgccctc ctacatcgaa gctgaaagca cgagattctt    2520
cgccctccga gagctgcatc aggtcggaga cgctgtcgaa cttttcgatc agaaacttct    2580
cgacagacgt cgcggtgagt tcaggctttt tcatatctca ttgcccggga tctgcggcac    2640
gctgttgacg ctgttaagcg ggtcgctgca gggtcgctcg gtgttcgagg ccacacgcgt    2700
caccttaata tgcgaagtgg acctgggacc gcgccgcccc gactgcatct gcgtgttcga    2760
attcgccaat gacaagacgc tgggcggggt tgtgtcatc atagaactaa agacatgcaa    2820
atatatttct tccggggaca ccgccagcaa acgcgagcaa cgggcacgg ggatgaagca    2880
gggcatggcg gccgacgcgc tgggctacgt cttgctggcg ttcgcgacgc gaggctggat    2940
ggccttcccc attatgattc ttctcgcttc cggcggcatc gggatgcccg cgttgcaggc    3000
catgctgtcc aggcaggtag atgacgacca tcagggacag cttcaaggat cgctcgcggc    3060
tcttaccagc ctaacttcga tcactggacc gctgatcgtc acggcgattt atgccgcctc    3120
ggcgagcaca tggaacgggt tggcatggat tgtaggcgcc gccctatacc ttgtctgcct    3180
ccccgcgttg cgtcgcggtg catggagccg ggccacctcg acctgaatgg aagccggcgg    3240
cacctcgcta acggattcac cactccaaga attggagcca atcaattctt gcggagaact    3300
gtgaatgcgc aaaccaaccc ttggcagaac atatccatcg cgtccgccat ctccagcagc    3360
cgcacgcggc gcagcaaaag gccaggaacc gtaaaaaggc cgcgttgctg cgttttttcc    3420
```

```
ataggctccg ccccctgac gagcatcaca aaaatcgacg ctcaagtcag aggtggcgaa   3480
acccgacagg actataaaga taccaggcgt ttccccctgg aagctccctc gtgcgctctc   3540
ctgttccgac cctgccgctt accggatacc tgtccgcctt tctcccttcg ggaagcgtgg   3600
cgctttctca tagctcacgc tgtaggtatc tcagttcggt gtaggtcgtt cgctccaagc   3660
tgggctgtgt gcacgaaccc cccgttcagc ccgaccgctg cgccttatcc ggtaactatc   3720
gtcttgagtc caacccggta agacacgact tatcgccact ggcagcagcc actggtaaca   3780
ggattagcag agcgaggtat gtaggcggtg ctacagagtt cttgaagtgg tggcctaact   3840
acggctacac tagaaggaca gtatttggta tctgcgctct gctgaagcca gttaccttcg   3900
gaaaaagagt tggtagctct tgatccggca acaaaccac cgctggtagc ggtggttttt   3960
ttgtttgcaa gcagcagatt acgcgcagaa aaaaggatc tcaagaagat cctttgatct   4020
tttctacggg gtctgacgct cagtggaacg aaaactcacg ttaagggatt ttggtcatga   4080
gattatcaaa aaggatcttc acctagatcc ttttaaatta aaaatgaagt tttaaatcaa   4140
tctaaagtat atatgagtaa acttggtctg acagttacca atgcttaatc agtgaggcac   4200
ctatctcagc gatctgtcta tttcgttcat ccatagttgc ctgactcccc gtcgtgtaga   4260
taactacgat acgggagggc ttaccatctg gccccagtgc tgcaatgata ccgcgagacc   4320
cacgctcacc ggctccagat ttatcagcaa taaaccagcc agccggaagg gccgagcgca   4380
gaagtggtcc tgcaacttta tccgcctcca tccagtctat taattgttgc cgggaagcta   4440
gagtaagtag ttcgccagtt aatagtttgc gcaacgttgt tgccattgct gcaggcatcg   4500
tggtgtcacg ctcgtcgttt ggtatggctt cattcagctc cggttcccaa cgatcaaggc   4560
gagttacatg atcccccatg ttgtgcaaaa aagcggttag ctccttcggt cctccgatcg   4620
ttgtcagaag taagttggcc gcagtgttat cactcatggt tatggcagca ctgcataatt   4680
ctcttactgt catgccatcc gtaagatgct tttctgtgac tggtgagtac tcaaccaagt   4740
cattctgaga atagtgtatg cggcgaccga gttgctcttg cccggcgtca acacgggata   4800
ataccgcgcc acatagcaga actttaaaag tgctcatcat tggaaaacgt tcttcggggc   4860
gaaaactctc aaggatctta ccgctgttga tccagttc gatgtaaccc actcgtgcac   4920
ccaactgatc ttcagcatct tttactttca ccagcgtttc tgggtgagca aaaacaggaa   4980
ggcaaaatgc cgcaaaaaag gaataagggc gacacggaa atgttgaata ctcatactct   5040
tcctttttca atattattga agcatttatc agggttattg tctcatgagc ggatacatat   5100
ttgaatgtat ttagaaaaat aaacaaatag gggttccgcg cacatttccc cgaaaagtgc   5160
cacctgacgt ctaagaaacc attattatca tgacattaac ctataaaaat aggcgtatca   5220
cgaggccctt tcgtcttcaa gaattctcat gtttgacagc ttatctctag cagatccgga   5280
attccctcc ccaatttaaa tgaggaccta acctgtggaa atctactgat gtgggaggct   5340
gtaactgtac aaacagaggt tattggaata actagcatgc ttaaccttca tgcagggtca   5400
caaaaagtgc atgacgatgg tggaggaaaa cctattcaag gcagtaattt ccacttcttt   5460
gctgttggtg gagacccctt ggaaatgcag ggagtgctaa tgaattacag gacaaagtac   5520
ccagatggta ctataacccc taaaaaccca acagcccagt cccaggtaat gaatactgac   5580
cataaggcct attttggacaa aaacaatgct tatccagttg agtgctgggt tcctgatcct   5640
agtgaaaatg aaaatactag gtattttggg actttcacag gaggggaaaa tgttcccca   5700
gtacttcatg tgaccaacac agctaccaca gtgttgctag atgaacaggg tgtggggcct   5760
```

```
ctttgtaaag ctgatagcct gtatgtttca gctgctgata tttgtggcct gtttactaac    5820
agctctggaa cacaacagtg gagaggcctt gcaagatatt ttaagatccg cctgagaaaa    5880
agatctgtaa agaatcctta cctaatttcc tttttgctaa gtgaccttat aaacaggaga    5940
acccagagag tggatgggca gcctatgtat ggtatggaat cccaggtaga agaggttagg    6000
gtgtttgatg gcacagaaag acttccaggg gacccagata tgataagata tattgacaaa    6060
cagggacaat tgcaaaccaa aatgctttaa acaggtgctt ttattgtaca tatacattta    6120
ataaatgctg cttttgtata agccacttttt aagcttgtgt tattttgggg gtggtgtttt   6180 aggccttttta aaacactgaa agcctttaca caaatgcaac tcttgactat gggggtctga   6240
cctttgggaa tgttcagcag gggctgaagt atctgagact tgggaagagc attgtgattg    6300
ggattcagtg cttgatccat gtccagagtc ttcagtttct gaatcctctt ctcttgtaat    6360
atcaagaata catttcccca tgcatatatt atatttcatc cttgaaaaag tatacatact    6420
tatctcagaa tccagccttt ccttccattc aacaattcta gaagttaaaa ctggggtaga    6480
tgctattaca gaggtagaat gcttcctaaa cccagaaatg ggggatctgc                6530
```

<210> SEQ ID NO 56
<211> LENGTH: 17
<212> TYPE: PRT
<213> ORGANISM: Artificial Sequence
<220> FEATURE:
<223> OTHER INFORMATION: 3A4 heavy chain CDR2

<400> SEQUENCE: 56

```
Asp Ile Asn Pro Tyr Asn Gly Asp Thr Asn Tyr Asn Gln Lys Phe Lys
1               5                   10                  15

Gly
```

ANTIBODIES AGAINST KIDNEY ASSOCIATED ANTIGEN 1 AND ANTIGEN BINDING FRAGMENTS THEREOF

PRIORITY CLAIM

This patent application is a continuation of U.S. Ser. No. 14/558,186 filed on Dec. 2, 2014 which is a continuation of U.S. Ser. No. 14/036,204 filed on Sep. 25, 2013 now U.S. Pat. No. 8,937,163, which is a national stage filing under 35 U.S.C. §371 of international application No. PCT/CA2012/000296 filed on Mar. 28, 2012 which claimed priority to U.S. provisional application No. 61/470,063 filed Mar. 31, 2011 and U.S. provisional application No. 61/533,346 filed on Sep. 12, 2011. The entire contents of each of these priority applications are incorporated herein by reference.

SEQUENCE LISTING

In accordance with 37 C.F.R. §1.52(e)(5), a Sequence Listing in the form of a text file (entitled "Sequence Listing", created on Apr. 25, 2016 of 90 kilobytes) is incorporated herein by reference in its entirety.

FIELD OF THE INVENTION

The present invention relates to specific antibodies or antigen binding fragments that specifically bind to kidney associated antigen 1 (KAAG1) and their use for the treatment, detection and diagnosis of cancer. Delivery of a therapeutic agent to cells with these antibodies or antigen binding fragments is particularly contemplated.

BACKGROUND OF THE INVENTION

Among gynecologic malignancies, ovarian cancer accounts for the highest tumor-related mortality in women in the United States (Jemal et al., 2005). It is the fourth leading cause of cancer-related death in women in the U.S (Menon et al., 2005). The American Cancer Society estimated a total of 22,220 new cases in 2005 and attributed 16,210 deaths to the disease (Bonome et al., 2005). For the past 30 years, the statistics have remained largely the same—the majority of women who develop ovarian cancer will die of this disease (Chambers and Vanderhyden, 2006). The disease carries a 1:70 lifetime risk and a mortality rate of >60% (Chambers and Vanderhyden, 2006). The high mortality rate is due to the difficulties with the early detection of ovarian cancer when the malignancy has already spread beyond the ovary. Indeed, >80% of patients are diagnosed with advanced staged disease (stage III or IV) (Bonome et al., 2005). These patients have a poor prognosis that is reflected in <45% 5-year survival rate, although 80% to 90% will initially respond to chemotherapy (Berek et al., 2000). This increased success compared to 20% 5-year survival rate years earlier is, at least in part, due to the ability to optimally debulk tumor tissue when it is confined to the ovaries, which is a significant prognostic factor for ovarian cancer (Bristow R. E., 2000; Brown et al., 2004). In patients who are diagnosed with early disease (stage I), the 5-yr survival ranges from >90 (Chambers and Vanderhyden, 2006).

Ovarian cancer comprises a heterogeneous group of tumors that are derived from the surface epithelium of the ovary or from surface inclusions. They are classified into serous, mucinous, endometrioid, clear cell, and Brenner (transitional) types corresponding to the different types of epithelia in the organs of the female reproductive tract (Shih and Kurman, 2005). Of these, serous tumors account for ~60% of the ovarian cancer cases diagnosed. Each histologic subcategory is further divided into three groups: benign, intermediate (borderline tumor or low malignancy potential (LMP)), and malignant, reflecting their clinical behavior (Seidman et al., 2002). LMP represents 10% to 15% of tumors diagnosed as serous and is a conundrum as they display atypical nuclear structure and metastatic behavior, yet they are considerably less aggressive than high-grade serous tumors. The 5-year survival for patients with LMP tumors is 95% in contrast to a <45% survival for advanced high-grade disease over the same period (Berek et al., 2000).

Presently, the diagnosis of ovarian cancer is accomplished, in part, through routine analysis of the medical history of patients and by performing physical, ultrasound and x-ray examinations, and hematological screening. Two alternative strategies have been reported for early hematological detection of serum biomarkers. One approach is analysis of serum samples by mass spectrometry to find proteins or protein fragments of unknown identity that detects the presence or absence of cancer (Mor et al., 2005; Kozak et al., 2003). However, this strategy is expensive and not broadly available. Alternatively, the presence or absence of known proteins/peptides in the serum is being detected using antibody microarrays, ELISA, or other similar approaches. Serum testing for a protein biomarker called CA-125 (cancer antigen-125) has long been widely performed as a marker for ovarian cancer. However, although ovarian cancer cells may produce an excess of these protein molecules, there are some other cancers, including cancer of the fallopian tube or endometrial cancer (cancer of the lining of the uterus), 60% of people with pancreatic cancer, and 20%-25% of people with other malignancies with elevated levels of CA-125. The CA-125 test only returns a true positive result for about 50% of Stage I ovarian cancer patients and has a 80% chance of returning true positive results from stage II, III, and IV ovarian cancer patients. The other 20% of ovarian cancer patients do not show any increase in CA-125 concentrations. In addition, an elevated CA-125 test may indicate other benign activity not associated with cancer, such as menstruation, pregnancy, or endometriosis. Consequently, this test has very limited clinical application for the detection of early stage disease when it is still treatable, exhibiting a positive predictive value (PPV) of <10%. Even with the addition of ultrasound screening to CA-125, the PPV only improves to around 20% (Kozak et al., 2003). Thus, this test is not an effective screening test.

Despite improved knowledge of the etiology of the disease, aggressive cytoreductive surgery, and modern combination chemotherapy, there has been only little change in mortality. Poor outcomes have been attributed to (1) lack of adequate screening tests for early disease detection in combination with only subtle presentation of symptoms at this stage—diagnosis is frequently being made only after progression to later stages, at which point the peritoneal dissemination of the cancer limits effective treatment and (2) the frequent development of resistance to standard chemotherapeutic strategies limiting improvement in the 5-year survival rate of patients. The initial chemotherapy regimen for ovarian cancer includes the combination of carboplatin (Paraplatin) and paclitaxel (taxol). Years of clinical trials have proved this combination to be most effective after effective surgery—reduces tumor volume in about 80% of the women with newly diagnosed ovarian cancer and 40% to 50% will have complete regression—but studies continue to look for ways to improve patient response. Recent abdominal infusion of chemotherapeutics to target hard-to-reach cells in combination with intravenous delivery has increased the effectiveness. However, severe side effects often lead to an incomplete course of treatment. Some other chemotherapeutic agents include doxorubicin, cisplatin, cyclophosphamide, bleomycin, etoposide, vinblastine, topotecan hydrochloride, ifosfamide, 5-fluorouracil and melphalan. More recently, clinical trials have demonstrated that intraperitoneal administration of cisplatin confers a survival advantage compared to systemic intravenous chemotherapy (Cannistra and McGuire, 2007). The excellent survival rates for women with early stage disease receiving chemotherapy provide a strong rationale for research efforts to develop strategies to improve the detection of ovarian cancer. Furthermore, the discovery of new ovarian cancer-related biomarkers will lead to the development of more effective therapeutic strategies with minimal side effects for the future treatment of ovarian cancer.

Notwithstanding these recent advances in the understanding and the treatment for ovarian cancer, the use of chemotherapy is invariably associated with severe adverse reactions, which limit their use. Consequently, the need for more specific strategies such as combining antigen tissue specificity with the selectivity of monoclonal antibodies should permit a significant reduction in off-target-associated side effects. The use of monoclonal antibodies for the therapy of ovarian cancer is beginning to emerge with an increasing number of ongoing clinical trials (Oei et al., 2008; Nicodemus and berek, 2005). Most of these trials have examined the use of monoclonal antibodies conjugated to radioisotopes, such as yttrium-90, or antibodies that target tumor antigens already identified in other cancer types. An example of this is the use of bevacizumab, which targets vascular endothelial growth factor (Burger, 2007). There are very few ovarian cancer specific antigens that are currently under investigation as therapeutic targets for monoclonal antibodies. Some examples include the use of a protein termed B7-H4 (Simon et al., 2006) and more recently folate receptor-alpha (Ebel et al., 2007), the latter of which has recently entered Phase II clinical trials.

Kidney associated antigen 1 (KAAG1) was originally cloned from a cDNA library derived from a histocompatibility leukocyte antigen-B7 renal carcinoma cell line as an antigenic peptide presented to cytotoxic T lymphocytes (Van den Eynde et al., 1999; Genebank accession no. Q9UBP8, SEQ ID NOs.:28; 29). The locus containing KAAG1 was found to encode two genes transcribed on opposite DNA strands. The sense strand was found to encode a transcript that encodes a protein termed DCDC2. Expression studies by these authors found that the KAAG1 antisense transcript was tumor specific and exhibited very little expression in normal tissues whereas the DCDC2 sense transcript was ubiquitously expressed (Van den Eynde et al., 1999). The expression of the KAAG1 transcript in cancer, and in particular ovarian cancer, renal cancer, lung cancer, colon cancer, breast cancer and melanoma was disclosed in the published patent application No. PCT/CA2007/001134 (the entire content of which is incorporated herein by reference). Van den Eynde et al., also observed RNA expression in renal carcinomas, colorectal carcinomas, melanomas, sarcomas, leukemias, brain tumors, thyroid tumors, mammary carcinomas, prostatic carcinomas, oesophageal carcinomas, bladder tumor, lung carcinomas and head and neck tumors. Recently, strong genetic evidence obtained through linkage disequilibrium studies found that the VMP/DCDC2/KAAG1 locus was associated with dyslexia (Schumacher et al., 2006; Cope et al., 2005). One of these reports pointed to the DCDC2 marker as the culprit in dyslexic patients since the function of this protein in cortical neuron migration was in accordance with symptoms of these patients who often display abnormal neuronal migration and maturation (Schumacher et al., 2006).

SUMMARY OF THE INVENTION

The invention relates to specific anti-KAAG1 antibodies and antigen binding fragments and their use for the treatment, detection and diagnosis of cancer comprising tumor cells expressing KAAG1 or a KAAG1 variant. Exemplary embodiments of such cancer includes, for example, ovarian cancer, skin cancer, renal cancer, colorectal cancer, sarcoma, leukemia, brain cancer, cancer of the thyroid, breast cancer, prostate cancer, cancer of the oesophagus, bladder cancer, lung cancer and head and neck cancer.

The antibodies or antigen binding fragments may be particularly effective at targeting KAAG1 or KAAG1 variant expressed at the surface of the tumor cells.

In fact, the antibodies and antigen binding fragments of the present invention appear to have improved ability to bind to KAAG1-expressing tumor cells in comparison with, for example, the 3D3 and 3G10 antibodies disclosed in PCT/CA2009/001586 (the entire content of which is incorporated herein by reference). These antibodies and antigen binding fragments are also internalized and may therefore be useful to deliver therapeutic agents to tumor cells. Our results suggest that antibodies and antigen binding fragments having the desired characteristics (e.g., improved binding and internalization) generally bind to a C-terminal region of KAAG1 delimited by amino acids 61 to 84. However, although both the 3A4 and 3G10 antibodies bind to the same region, the 3A4 antibody appears to bind to the surface of tumor cells more efficiently than the 3G10 antibody. In particular, cancer cells that express the KAAG1 antigen require approximately 10-fold less 3A4 compared to 3G10 in flow cytometry experiments, an approach that measures the direct binding of the antibodies to the surface of the cells. In addition, in binding experiments using surface plasmon resonance, it was discovered that the affinity of 3A4 for KAAG1 is below 10 picomolar, whereas antibodies 3D3 and 3G10 exhibited affinities greater than 200 nanomolar (20-fold lower affinity). Therefore, these increases in binding ability of 3A4 are expected to translate into improved therapeutic activity.

The present invention provides in one aspect thereof, an isolated or substantially purified antibody or antigen binding fragment which may be capable of specific binding to a sequence which is identical to at least 10 (e.g., 10 to 20 or more) consecutive amino acids located between amino acids 61 to 84 of KAAG1 (SEQ ID NO.:29)

The present invention also provides isolated antibodies or antigen binding fragments capable of competing with the antibody or antigen binding fragment described herein.

In a further aspect, the invention relates to specific antibodies or antigen binding fragments having the amino acid sequences described herein. Such antibodies or antigen binding fragments may be in the form of monoclonal antibodies, polyclonal antibodies, chimeric antibodies, humanized antibodies and human antibodies (isolated) as well as antigen binding fragments having the characteristics described herein. Antibodies or antigen binding fragments encompassing permutations of the light and/or heavy chains between a monoclonal, chimeric, humanized or human antibody are also encompassed herewith.

The antibodies or antigen binding fragments of the present invention may thus comprise amino acids of a human constant region and/or framework amino acids of a human antibody.

The term "antibody" refers to intact antibody, monoclonal or polyclonal antibodies. The term "antibody" also encompasses multispecific antibodies such as bispecific antibodies. Human antibodies are usually made of two light chains and two heavy chains each comprising variable regions and constant regions. The light chain variable region comprises 3 CDRs, identified herein as CDRL1 or L1, CDRL2 or L2 and CDRL3 or L3 flanked by framework regions. The heavy chain variable region comprises 3 CDRs, identified herein as CDRH1 or H1, CDRH2 or H2 and CDRH3 or H3 flanked by framework regions. The CDRs of the humanized antibodies of the present invention have been identified using the Kabat and Chotia definitions (e.g., CDRH2 set forth in SEQ ID NO.:56). However, others (Abhinandan and Martin, 2008) have used modified approaches based loosely on Kabat and Chotia resulting in the delineation of shorter CDRs (e.g., CDRH2 set forth in SEQ ID NO.:6).

The term "antigen-binding fragment", as used herein, refers to one or more fragments of an antibody that retain the ability to bind to an antigen (e.g., KAAG1, secreted form of KAAG1 or variants thereof). It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), e.g., $V_H$ CDR3. Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "humanized antibody" encompasses fully humanized antibody (i.e., frameworks are 100% humanized) and partially humanized antibody (e.g., at least one variable domain contains one or more amino acids from a human antibody, while other amino acids are amino acids of a non-human parent antibody). Typically a "humanized antibody" contains CDRs of a non-human parent antibody (e.g., mouse, rat, rabbit, non-human primate, etc.) and frameworks that are identical to those of a natural human antibody or of a human antibody consensus. In such instance, those "humanized antibodies" are characterized as fully humanized. A "humanized antibody" may also contain one or more amino acid substitutions that have no correspondence to those of the human antibody or human antibody consensus. Such substitutions include, for example, back-mutations (e.g., re-introduction of non-human amino acids) that may preserve the antibody characteristics (e.g., affinity, specificity etc.). Such substitutions are usually in the framework region. A "humanized antibody" optionally also comprise at least a portion of a constant region (Fc) which is typically that of a human antibody. Typically, the constant region of a "humanized antibody" is identical to that of a human antibody.

The term "natural human antibody" refers to an antibody that is encoded (encodable) by the human antibody repertoire, i.e., germline sequence.

The term "chimeric antibody" refers to an antibody having non-human variable region(s) and human constant region.

The term "hybrid antibody" refers to an antibody comprising one of its heavy or light chain variable region (its heavy or light chain) from a certain types of antibody (e.g., humanized) while the other of the heavy or light chain variable region (the heavy or light chain) is from another type (e.g., murine, chimeric).

In some embodiments, the heavy chain and/or light chain framework region of the humanized antibody may comprises from one to thirty amino acids from the non-human antibody which is sought to be humanized and the remaining portion being from a natural human antibody or a human antibody consensus. In some instances, the humanized antibody may comprise from 1 to 6 non-human CDRs and often the six CDRs are non-human.

The natural human antibody selected for humanization of the non-human parent antibody may comprise a variable region having a three-dimensional structure similar to that of (superimposable to) a (modeled) variable region of the non-human parent antibody. As such, the humanized antibody has a greater chance of having a three-dimensional structure similar to that of the non-human parent antibody.

The light chain variable region of the natural human antibody selected for humanization purposes, may have, for example an overall (over the entire light chain variable region) of at least 70%, 75%, 80%, etc. identity with that of the non-human parent antibody. Alternatively, the light chain framework region of the natural human antibody selected for humanization purposes, may have, for example, at least 70% 75%, 80%, 85% etc. sequence identity with the light chain framework region of the non-human parent antibody. In some embodiments, the natural human antibody selected for humanization purposes may have the same or substantially the same number of amino acids in its light chain complementarity determining region to that of a light chain complementarity determining region of the non-human parent antibody.

The heavy chain variable region of the natural human antibody selected for humanization purposes, may have, for example an overall (over the entire heavy chain variable region) of at least 60%, 70%, 75%, 80%, etc. identity with that of the non-human parent antibody. Also in accordance with the present invention, the human framework region amino acid residues of the humanized antibody heavy chain may be from a natural human antibody heavy chain framework region having at least 70%, 75%, 89% etc. identity with a heavy chain framework region of the non-human parent antibody. In some embodiments, the natural human antibody selected for humanization purposes may have the same or substantially the same number of amino acids in its heavy chain complementarity determining region to that of a heavy chain complementarity determining region of the non-human parent antibody.

The natural human antibody that is selected for humanization of the non-human parent antibody may comprise a variable region having a three-dimensional structure similar to that of (superimposable to) a (modeled) variable region of the non-human parent antibody. As such, the humanized or hybrid antibody has a greater chance of having a three-dimensional structure similar to that of the non-human parent antibody.

For example, the natural human antibody heavy chain variable region which may be selected for humanization purposes may have the following characteristics: a) a three-dimensional structure similar to or identical (superimposable) to that of a heavy chain of the non-human antibody and/or b) a framework region having an amino acid sequence at least 70% identical to a heavy chain framework region of the non-human antibody. Optionally, (a number of) amino acid residues in a heavy chain CDR (e.g., all three CDRs) is the same or substantially the same as that of the non-human heavy chain CDR amino acid residues.

Alternatively, the natural human antibody light chain variable region which may be selected for humanization purposes may have the following characteristics: a) a three-dimensional structure similar to or identical (superimposable) to that of a light chain of the non-human antibody, and/or b) a framework region having an amino acid sequence at least 70% identical to a light chain framework region of the non-human antibody. Optionally, (a number of) amino acid residues in a light chain CDR (e.g., all three CDRs) that is the same or substantially the same as that of the non-human light chain CDR amino acid residues.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding.

Antibodies and/or antigen binding fragments of the present invention may originate, for example, from a mouse, a rat or any other mammal or from other sources such as through recombinant DNA technologies.

Further scope, applicability and advantages of the present invention will become apparent from the non-restrictive detailed description given hereinafter. It should be understood, however, that this detailed description, while indicating exemplary embodiments of the invention, is given by way of example only, with reference to the accompanying drawings.

BRIEF DESCRIPTION OF THE DRAWINGS

FIG. 11A is an alignment of murine 3A4 light chain variable region (SEQ ID NO.:4) with a light chain variable region variant (SEQ ID NO.:33) using the ClustalW2 program (Larkin M. A., et al., (2007) ClustalW and ClustalX version 2. *Bioinformatics* 2007 23(21): 2947-2948) where an "*" (asterisk) indicates positions which have a single, fully conserved residue, wherein ":" (colon) indicates conservation between groups of strongly similar properties—scoring >0.5 in the Gonnet PAM 250 matrix and where "." (period) indicates conservation between groups of weakly similar properties—scoring=<0.5 in the Gonnet PAM 250 matrix.

FIG. 11B is an alignment of murine 3A4 heavy chain variable region (SEQ ID NO.:2) with a light chain variable region variant (SEQ ID NO.:38) using the ClustalW2 program (Larkin M. A., et al., (2007) ClustalW and ClustalX version 2. *Bioinformatics* 2007 23(21): 2947-2948) where an "*" (asterisk) indicates positions which have a single, fully conserved residue, wherein ":" (colon) indicates conservation between groups of strongly similar properties—scoring >0.5 in the Gonnet PAM 250 matrix and where "." (period) indicates conservation between groups of weakly similar properties—scoring=<0.5 in the Gonnet PAM 250 matrix.

FIG. 15 is a Table listing the rate and affinity constants for the murine and humanized variants of the 3A4 antibody.

DETAILED DESCRIPTION OF THE INVENTION

Figure 1:
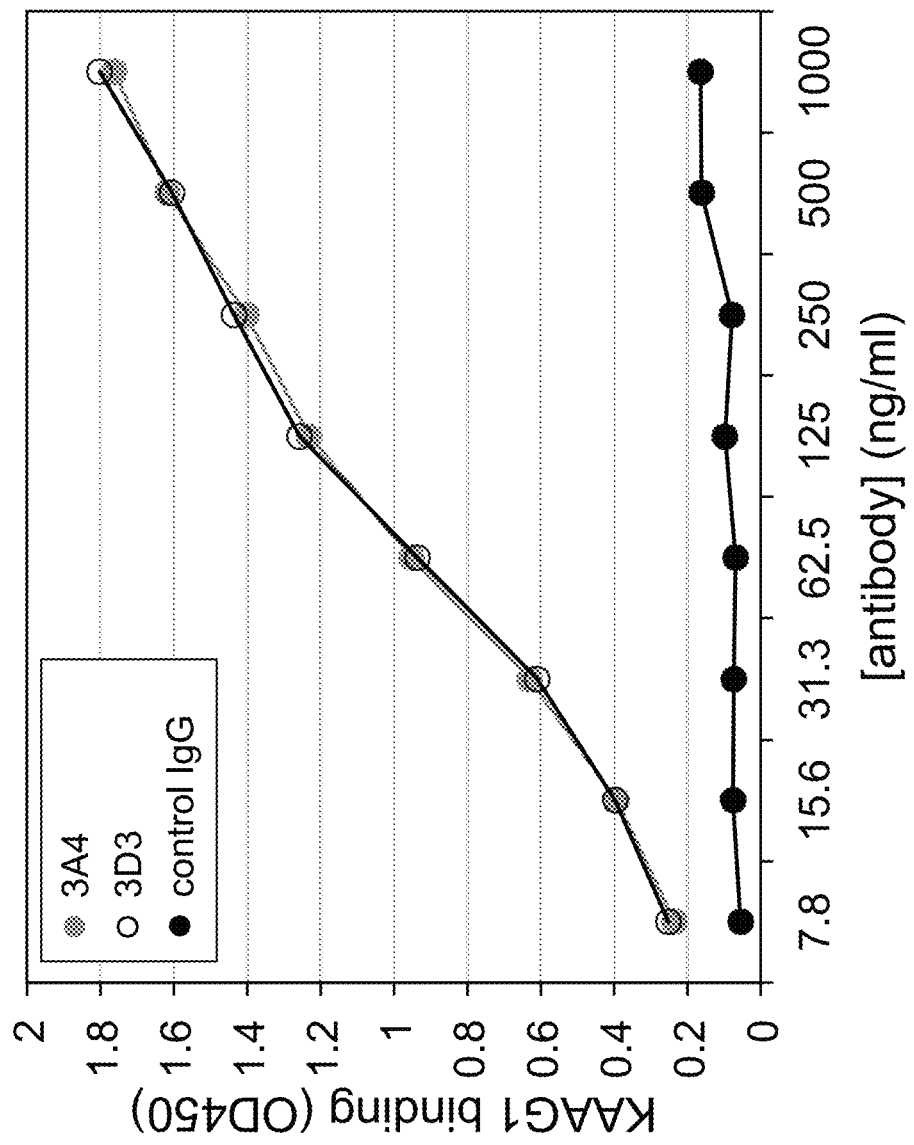
FIG. 1 shows the results from the ELISA that compares the binding of the 3A4 chimeric anti-KAAG1 antibody with a control antibody when incubated with increasing concentrations of recombinant human KAAG1. The binding curve of 3A4 is shown by the lighter colored line.

The Expression and Biological Activity of KAAG1 in Cancer Cells

The present invention relates to the use of antibodies to target tumors found in various cancer types, in particular ovarian cancer. In order to direct the antibodies to the tumors, the identification of tumor-specific antigens that are expressed at the cell surface of the cancer cells must be carried out. There are several technologies that are available to identify tumor-specific antigens and the method that was used to identify KAAG1 in ovarian tumors, an innovative discovery platform called Subtractive Transcription-based Amplification of mRNA (STAR), is described in the published patent application No. PCT/CA2007/001134 published under No. WO/2007/147265 on Dec. 27, 2007.

Analysis of the ovarian cancer STAR libraries yielded many genes that encode secreted and cell surface proteins. One of these, termed AB-0447, contained an open reading frame that encoded a polypeptide of 84 amino acids, corresponding to SEQ ID NO.:29 that was encoded by a cDNA of 885 base pairs with the nucleotide sequence shown in SEQ ID NO.:28. A search of publicly available databases revealed that the AB-0447 nucleotide sequence was identical to that of a gene called KAAG1. Bioinformatic analysis predicted a membrane-anchored protein that presents its functional domain to the extracellular compartment. KAAG1 was originally cloned from a kidney cancer library as a cell surface antigen, a result that confirms its membrane localization. Additionally, our studies showed that the protein was processed at its amino-terminus, a result that was consistent with cleavage of a functional signal peptide at or between amino acids 30 and 34. Furthermore, transient expression of the full-length cDNA resulted in detection of cleaved KAAG1 in the culture medium. This last finding indicated that this membrane-anchored protein could be shed from the cells when expressed at high levels. In contrast, expression of an amino-truncated mutant of KAAG1 resulted in intra-cellular retention of the protein. There are currently no published reports that shed any light on its function and the over-expression of KAAG1 in ovarian cancer, as disclosed by this invention, has never been previously documented.

We have thus investigated whether KAAG1 could be used for antibody-based diagnostics and therapeutics.

Several ovarian cancer cell-based models have been established, such as TOV-21G, TOV-112D, OV-90, and others, and are familiar to those skilled in the art. These cells are part of a collection of human ovarian cancer cell lines derived from patients with ovarian tumors or ascites fluid. These cell lines have undergone an in-depth analysis, including global gene expression patterns on microarrays that make them excellent cell-based models for human ovarian cancer. The growth properties, gene expression patterns, and response to chemotherapeutic drugs indicated that these cell lines are very representative of ovarian tumor behavior in vivo (Benoit et al., 2007). RT-PCR analysis of total RNA isolated from these ovarian cancer cell lines showed that the KAAG1 transcript was weakly expressed in the cell lines derived from primary tumors. In contrast, cell lines derived from ascitic fluid contained high levels of KAAG1 expression. The increased expression of KAAG1 in cells from the ascitic fluid suggested that the environment of the cells influences the regulation of the KAAG1 gene. Ascitic cells are associated with advanced disease and this pattern of expression implies that increased KAAG1 levels are associated with anchorage-independent growth. In concordance with this latter suggestion, KAAG1 expression was found to significantly increase in cell lines derived from primary tumors when these cells were cultured as spheroids in 3D cultures. These spheroids have been extensively characterized and were found to display many properties associated with tumors in vivo (Cody et al., 2008). Thus, expression of KAAG1 was found to be significantly increased in models that mimic tumor progression, in particular during the evolution of ovarian cancer.

With the demonstration that KAAG1 expression is regulated in ovarian cancer cells, the function of this gene in ovarian cancer cell behavior was examined in cell-based assays. To that effect, RNA interference (RNAi) was used to knock down the expression of the endogenous KAAG1 gene in the ovarian cancer cell lines and it was found that decreased expression of KAAG1 resulted in a significant reduction in the migration of the cells as determined in a standard cell motility assay, as exemplified by a wound healing (or scratch) assay. This type of assay measures the speed at which cells fill a denuded area in a confluent monolayer. Decreased expression of KAAG1 resulted in a reduction in the survival of ovarian cancer cell lines as measured by a clonogenic assay, such as a colony survival assay. Those skilled in the art may use other methods to evaluate the requirement of KAAG1 in the behavior of cancer cells, in particular ovarian cancer cells.

Based on the expression of KAAG1 in a large proportion of ovarian tumors, its limited expression in normal tissues, and a concordance between expression levels and increased malignancy, and a putative biological role for KAAG1 in the behavior of ovarian cancer cell lines, KAAG1 was chosen as a therapeutic target for the development of antibodies for the detection, prevention, and treatment of ovarian cancer. Expression of KAAG1 in cancers, other than ovarian cancer also lead the Applicant to the evaluation of therapeutic or diagnostic antibodies for other cancer indications.

The present invention therefore provides anti-KAAG1 antibodies and antigen binding fragments thereof which specifically target KAAG1 and which may be used, for example, as an antibody-drug conjugate.

Such antibodies and antigen binding fragments include for example, monoclonal antibodies, polyclonal antibodies, chimeric antibodies, humanized antibodies, antibody fragments, single chain antibodies, domain antibodies, and polypeptides having an antigen binding region.

Antibodies and Antigen Binding Fragments that Binds to KAAG1

Antibodies were initially isolated from Fab libraries for their specificity towards the antigen of interest.

The variable regions of the antibodies or antigen binding fragments described herein may be fused with constant regions of a desired species thereby allowing recognition of the antibody by effector cells of the desired species. The constant region may originate, for example, from an IgG1, IgG2, IgG3, or IgG4 subtype. Cloning or synthesizing a constant region in frame with a variable region is well within the scope of a person of skill in the art and may be performed, for example, by recombinant DNA technology. Thus, antibodies comprising constant region of a human antibody as well as antibodies or antigen binding fragments comprising framework amino acids of a human antibody are also encompassed by the present invention.

The present invention therefore provides in an exemplary embodiment, an isolated antibody or antigen binding fragment comprising a light chain variable region having;
  a. a CDRL1 sequence comprising SEQ ID NO.:8 or as set forth in SEQ ID NO.:8;
  b. a CDRL2 sequence comprising SEQ ID NO.:9 or as set forth in SEQ ID NO.:9, or;
  c. a CDRL3 sequence comprising SEQ ID NO.:10 or as set forth in SEQ ID NO.:10.

The isolated antibody or antigen binding fragment may also comprise a heavy chain variable region having;
  a. a CDRH1 sequence comprising SEQ ID NO.:5 or as set forth in SEQ ID NO.:5;
  b. a CDRH2 sequence comprising SEQ ID NO.:6 or as set forth in SEQ ID NO.:6, or;
  c. a CDRH3 sequence comprising SEQ ID NO.:7 or as set forth in SEQ ID NO.:7.

In an exemplary embodiment, the antibody or antigen binding fragment may comprise any individual CDR or a combination of CDR1, CDR2 and/or CDR3 of the light chain variable region. The CDR3 may more particularly be selected. Combination may include for example, CDRL1 and CDRL3; CDRL1 and CDRL2; CDRL2 and CDRL3 and; CDRL1, CDRL2 and CDRL3.

In another exemplary embodiment, the antibody or antigen binding fragment may comprise any individual CDR or a combination of CDR1, CDR2 and/or CDR3 of the heavy chain variable region. The CDR3 may more particularly be selected. Combination may include for example, CDRH1 and CDRH3; CDRH1 and CDRH2; CDRH2 and CDRH3 and; CDRH1, CDRH2 and CDRH3.

In accordance with the present invention, the antibody or antigen binding fragment may comprise at least two CDRs of a CDRL1, a CDRL2 or a CDRL3.

Also in accordance with the present invention, the antibody or antigen binding fragment may comprise one CDRL1, one CDRL2 and one CDRL3.

Further in accordance with the present invention, the antibody or antigen binding fragment may comprise:
  a. At least two CDRs of a CDRL1, CDRL2 or CDRL3 and;
  b. At least two CDRs of a CDRH1, one CDRH2 or one CDRH3.

The antibody or antigen binding fragment may more preferably comprise one CDRL1, one CDRL2 and one CDRL3.

The antibody or antigen binding fragment may also more preferably comprise one CDRH1, one CDRH2 and one CDRH3.

In accordance with the present invention, the antibody or antigen binding fragment may comprise one CDRH1, one CDRH2 or one CDRH3.

In accordance with the present invention, the antibody or antigen binding fragment may also comprise one CDRH1, one CDRH2 and one CDRH3.

When only one of the light chain variable region or the heavy chain variable region is available, an antibody or antigen-binding fragment may be reconstituted by screening a library of complementary variable regions using methods known in the art (Portolano et al. The Journal of Immunology (1993) 150:880-887, Clarkson et al., Nature (1991) 352:624-628).

Also encompassed by the present invention are polypeptides or antibodies comprising variable chains having at least one conservative amino acid substitution in at least one of the CDRs described herein (in comparison with the original CDR).

The present invention also encompasses polypeptides or antibodies comprising variable chains having at least one conservative amino acid substitution in at least two of the CDRs (in comparison with the original CDRs).

The present invention also encompasses polypeptides or antibodies comprising variable chains having at least one conservative amino acid substitution in the 3 CDRs (in comparison with the original CDRs).

The present invention also encompasses polypeptides or antibodies comprising variable chains having at least two conservative amino acid substitutions in at least one of the CDRs (in comparison with the original CDRs).

The present invention also encompasses polypeptides or antibodies comprising variable chains having at least two conservative amino acid substitutions in at least two of the CDRs (in comparison with the original CDRs).

The present invention also encompasses polypeptides or antibodies comprising variable chains having at least two conservative amino acid substitutions in the 3 CDRs (in comparison with the original CDRs).

In another aspect, the present invention relates to a polypeptide, antibody or antigen binding fragment comprising (on a single polypeptide chain or on separate polypeptide chains) at least one complementarity-determining region of a light chain variable region and at least one complementarity-determining region of a heavy chain variable region of one of the antibodies or antigen binding fragment described herein.

The present invention relates in another aspect thereof to anti-KAAG1 antibodies that may comprise (on a single polypeptide chain or on separate polypeptide chains) all six complementarity-determining regions (CDRs) of the antibody or antigen binding fragment described herein.

Variant Antibody and Antigen Binding Fragments

The present invention also encompasses variants of the antibodies or antigen binding fragments described herein. Variant antibodies or antigen binding fragments included are those having a variation in the amino acid sequence. For example, variant antibodies or antigen binding fragments included are those having at least one variant CDR (two, three, four, five or six variant CDRs or even twelve variant CDRs), a variant light chain variable region, a variant heavy chain variable region, a variant light chain and/or a variant heavy chain. Variant antibodies or antigen binding fragments included in the present invention are those having, for example, similar or improved binding affinity in comparison with the original antibody or antigen binding fragment.

As used herein the term "variant" applies to any of the sequence described herein and includes for example, a variant CDR (either CDRL1, CDRL2, CDRL3, CDRH1, CDRH2 and/or CDRH3), a variant light chain variable region, a variant heavy chain variable region, a variant light chain, a variant heavy chain, a variant antibody, a variant antigen binding fragment and a KAAG1 variant.

Variant antibodies or antigen binding fragments encompassed by the present invention are those which may comprise an insertion, a deletion or an amino acid substitution (conservative or non-conservative). These variants may have at least one amino acid residue in its amino acid sequence removed and a different residue inserted in its place.

The antibody or antigen binding fragment of the present invention may have a light chain variable region and/or heavy chain variable region as described above and may further comprise amino acids of a constant region, such as, for example, amino acids of a constant region of a human antibody.

In an exemplary embodiment, the antibody or antigen binding fragment of the present invention may comprise, for example, a human IgG1 constant region.

In accordance with another exemplary embodiment of the invention, the antigen binding fragment may be, for example, a scFv, a Fab, a Fab' or a (Fab')$_2$.

A site of interest for substitutional mutagenesis includes the hypervariable regions (CDRs), but modifications in the framework region or even in the constant region are also contemplated. Conservative substitutions may be made by exchanging an amino acid (of a CDR, variable chain, antibody, etc.) from one of the groups listed below (group 1 to 6) for another amino acid of the same group.

Other exemplary embodiments of conservative substitutions are shown in Table 1A under the heading of "preferred substitutions". If such substitutions result in a undesired property, then more substantial changes, denominated "exemplary substitutions" in Table 1A, or as further described below in reference to amino acid classes, may be introduced and the products screened.

It is known in the art that variants may be generated by substitutional mutagenesis and retain the biological activity of the polypeptides of the present invention. These variants have at least one amino acid residue in the amino acid sequence removed and a different residue inserted in its place. For example, one site of interest for substitutional mutagenesis may include a site in which particular residues obtained from various species are identical. Examples of substitutions identified as "conservative substitutions" are shown in Table 1A. If such substitutions result in a change not desired, then other type of substitutions, denominated "exemplary substitutions" in Table 1A, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

| | |
|---|---|
| (group 1) | hydrophobic: norleucine, methionine (Met), Alanine (Ala), Valine (Val), Leucine (Leu), Isoleucine (Ile) |
| (group 2) | neutral hydrophilic: Cysteine (Cys), Serine (Ser), Threonine (Thr) |
| (group 3) | acidic: Aspartic acid (Asp), Glutamic acid (Glu) |
| (group 4) | basic: Asparagine (Asn), Glutamine (Gln), Histidine (His), Lysine (Lys), Arginine (Arg) |
| (group 5) | residues that influence chain orientation: Glycine (Gly), Proline (Pro); and |
| (group 6) | aromatic: Tryptophan (Trp), Tyrosine (Tyr), Phenylalanine (Phe) |

Non-conservative substitutions will entail exchanging a member of one of these classes for another.

TABLE 1A

Amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg, Asp | Gln |
| Asp (D) | Glu, Asn | Glu |
| Cys (C) | Ser, Ala | Ser |
| Gln (Q) | Asn; Glu | Asn |
| Glu (E) | Asp, Gln | Asp |
| Gly (G) | Ala | Ala |
| His (H) | Asn, Gln, Lys, Arg, | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Tyr |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Variant antibody or antigen binding fragment may have substantial sequence similarity and/or sequence identity in its amino acid sequence in comparison with that the original antibody or antigen binding fragment amino acid sequence. The degree of similarity between two sequences is based upon the percentage of identities (identical amino acids) and of conservative substitution.

Generally, the degree of similarity and identity between variable chains has been determined herein using the Blast2 sequence program (Tatiana A. Tatusova, Thomas L. Madden (1999), "Blast 2 sequences—a new tool for comparing protein and nucleotide sequences", FEMS Microbiol Lett. 174:247-250) using default settings, i.e., blastp program, BLOSUM62 matrix (open gap 11 and extension gap penalty 1; gapx dropoff 50, expect 10.0, word size 3) and activated filters.

Percent identity will therefore be indicative of amino acids which are identical in comparison with the original peptide and which may occupy the same or similar position.

Percent similarity will be indicative of amino acids which are identical and those which are replaced with conservative amino acid substitution in comparison with the original peptide at the same or similar position.

Variants of the present invention therefore comprise those which may have at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an original sequence or a portion of an original sequence.

Exemplary embodiments of variants are those having at least 81% sequence identity to a sequence described herein and 81%, 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 82% sequence identity to a sequence described herein and 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Further exemplary embodiments of variants are those having at least 85% sequence identity to a sequence described herein and 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 90% sequence identity to a sequence described herein and 90%, 91%, 92%, 93%, 94%, 95%, 96%, 97%, 98%, 99% or 100% sequence similarity with an original sequence or a portion of an original sequence.

Additional exemplary embodiments of variants are those having at least 95% sequence identity to a sequence described herein and 95%, 96%, 97%, 98%, 99% or 100% sequence similarity with an original sequence or a portion of an original sequence.

Yet additional exemplary embodiments of variants are those having at least 97% sequence identity to a sequence described herein and 97%, 98%, 99% or 100% sequence similarity with an original sequence or a portion of an original sequence.

For a purpose of concision the applicant provides herein a Table 1B illustrating exemplary embodiments of individual variants encompassed by the present invention and comprising the specified % sequence identity and % sequence similarity. Each "X" is to be construed as defining a given variant.

heavy chains, antibodies and/or antigen binding fragments which comprise at least 80% identity with the sequence described herein.

Exemplary embodiments of the antibody or antigen binding fragment of the present invention are those comprising a light chain variable region comprising a sequence at least 70%, 75%, 80% identical to SEQ ID NO.:4.

These light chain variable region may comprise a CDRL1 sequence at least 80% identical to SEQ ID NO.:8, a CDRL2 sequence at least 80% identical to SEQ ID NO.:9 and a CDRL3 sequence at least 80% identical to SEQ ID NO.:10.

In an exemplary embodiment of the present invention, any of the antibodies provided herein may comprise a CDRL1 sequence which may be at least 90% identical to SEQ ID NO.:8.

In another exemplary embodiment of the present invention, any of the antibodies provided herein may comprise a CDRL1 sequence which may be 100% identical to SEQ ID NO.:8.

In another exemplary embodiment of the present invention, any of the antibodies provided herein may comprise a CDRL2 sequence at least 90% identical to SEQ ID NO.:9.

In yet another exemplary embodiment of the present invention, any of the antibodies provided herein may comprise a CDRL2 sequence which may be 100% identical to SEQ ID NO.:9.

In another exemplary embodiment of the present invention, any of the antibodies provided herein may comprise a CDRL3 sequence which may be at least 90% identical to SEQ ID NO.:10.

In an additional exemplary embodiment of the present invention, any of the antibodies provided herein may comprise a CDRL3 sequence which may be 100% identical to SEQ ID NO.:10.

In an exemplary embodiment, the antibody or antigen binding fragment may comprise a heavy chain variable region comprising a sequence at least 70%, 75%, 80% identical to SEQ ID NO.:2.

TABLE 1B

| | | Percent (%) sequence identity | | | | | | | | | | | | | | | | | | | |
|---|---|---|---|---|---|---|---|---|---|---|---|---|---|---|---|---|---|---|---|---|---|
| | | 80 | 81 | 82 | 83 | 84 | 85 | 86 | 87 | 88 | 89 | 90 | 91 | 92 | 93 | 94 | 95 | 96 | 97 | 98 | 99 | 100 |
| Percent (%) sequence similarity | 80 | X | | | | | | | | | | | | | | | | | | | | |
| | 81 | X | X | | | | | | | | | | | | | | | | | | | |
| | 82 | X | X | X | | | | | | | | | | | | | | | | | | |
| | 83 | X | X | X | X | | | | | | | | | | | | | | | | | |
| | 84 | X | X | X | X | X | | | | | | | | | | | | | | | | |
| | 85 | X | X | X | X | X | X | | | | | | | | | | | | | | | |
| | 86 | X | X | X | X | X | X | X | | | | | | | | | | | | | | |
| | 87 | X | X | X | X | X | X | X | X | | | | | | | | | | | | | |
| | 88 | X | X | X | X | X | X | X | X | X | | | | | | | | | | | | |
| | 89 | X | X | X | X | X | X | X | X | X | X | | | | | | | | | | | |
| | 90 | X | X | X | X | X | X | X | X | X | X | X | | | | | | | | | | |
| | 91 | X | X | X | X | X | X | X | X | X | X | X | X | | | | | | | | | |
| | 92 | X | X | X | X | X | X | X | X | X | X | X | X | X | | | | | | | | |
| | 93 | X | X | X | X | X | X | X | X | X | X | X | X | X | X | | | | | | | |
| | 94 | X | X | X | X | X | X | X | X | X | X | X | X | X | X | X | | | | | | |
| | 95 | X | X | X | X | X | X | X | X | X | X | X | X | X | X | X | X | | | | | |
| | 96 | X | X | X | X | X | X | X | X | X | X | X | X | X | X | X | X | X | | | | |
| | 97 | X | X | X | X | X | X | X | X | X | X | X | X | X | X | X | X | X | X | | | |
| | 98 | X | X | X | X | X | X | X | X | X | X | X | X | X | X | X | X | X | X | X | | |
| | 99 | X | X | X | X | X | X | X | X | X | X | X | X | X | X | X | X | X | X | X | X | |
| | 100 | X | X | X | X | X | X | X | X | X | X | X | X | X | X | X | X | X | X | X | X | X |

The present invention encompasses CDRs, light chain variable regions, heavy chain variable regions, light chains, These heavy chain variable regions may comprise a CDRH1 sequence at least 80% identical to SEQ ID NO.:5, a CDRH2 sequence at least 80% identical to SEQ ID NO.:6 and a CDRH3 sequence at least 80% identical to SEQ ID NO.:7.

In an exemplary embodiment of the present invention, any of the antibodies provided herein may comprise a CDRH1 sequence which may be at least 90% identical to SEQ ID NO.:5.

In another exemplary embodiment of the present invention, any of the antibodies provided herein may comprise a CDRH1 sequence which may be 100% identical to SEQ ID NO.:5.

In yet another exemplary embodiment of the present invention, any of the antibodies provided herein may comprise a CDRH2 sequence which may be at least 90% identical to SEQ ID NO.:6.

In a further exemplary embodiment of the present invention, any of the antibodies provided herein may comprise a CDRH2 sequence which may be 100% identical to SEQ ID NO.:6.

In yet a further exemplary embodiment of the present invention, any of the antibodies provided herein may comprise a CDRH3 sequence which may be at least 90% identical to SEQ ID NO.:7.

In an additional exemplary embodiment of the present invention, any of the antibodies provided herein may comprise a CDRH3 sequence which may be 100% identical to SEQ ID NO.:7.

In some instances, the variant antibody heavy chain variable region may comprise amino acid deletions or additions (in combination or not with amino acid substitutions). Often 1, 2, 3, 4 or 5 amino acid deletions or additions may be tolerated.

Exemplary embodiments of variant antibody or antigen binding fragments include those having a light chain variable region as set forth in SEQ ID NO.:30:

```
                                         SEQ ID NO.: 30
DXVMTQTPLSLXVXXGXXASISCRSSQSLLHSNGNTYLEVVYLQKPGQSP
XLLIHTVSNRFSGVPDRFSGSGSGTDFTLKISRVEAEDXGVYYCFQGSHV
PLTFGXGTXLEXK,
``` wherein at least one of the amino acids identified by X is an amino acid substitution (conservative or non-conservative) in comparison with a corresponding amino acid in the polypeptide set forth in SEQ ID NO.:4. The amino acid substitution may be, for example, an amino acid found at a corresponding position of a natural human antibody or a human antibody consensus. The amino acid substitution may be, for example conservative.

Another exemplary embodiment of a variant antibody or antigen binding fragment include those having a light chain variable region as set forth in SEQ ID NO.:31:

```
                                         SEQ ID NO.: 31
DX_{a1}VMTQTPLSLX_{a2}VX_{a3}X_{a4}GX_{a5}X_{a6}ASISCRSSQSLLHSNGNTYL
EWYLQKPGQSPX_{a7}LLIHTVSNRFSGVPDRFSGSGSGTDFTLKISRVEAE
DX_{a8}GVYYCFQGSHVPLTFGX_{a9}GTX_{a10}LEX_{a11}K,
```

Wherein $X_{a1}$ may be a hydrophobic amino acid;
Wherein $X_{a2}$ may be A or P;
Wherein $X_{a3}$ may be neutral hydrophilic amino acid;
Wherein $X_{a4}$ may be L or P;
Wherein $X_{a5}$ may be an acidic amino acid;
Wherein $X_{a6}$ may be Q or P;
Wherein $X_{a7}$ may be a basic amino acid;
Wherein $X_{a8}$ may be a hydrophobic amino acid;
Wherein $X_{a9}$ may be A or Q;
Wherein $X_{a10}$ may be a basic amino acid; or
Wherein $X_{a11}$ may be a hydrophobic amino acid, wherein at least one of the amino acid identified by X is an amino acid substitution (conservative or non-conservative) in comparison with a corresponding amino acid in the polypeptide set forth in SEQ ID NO.:4.

An additional exemplary embodiment of a variant antibody or antigen binding fragment include those having a light chain variable region as set forth in SEQ ID NO.:32:

```
                                         SEQ ID NO.: 32
DX_{41}VMTQTPLSLX_{42}VX_{43}X_{44}GX_{45}X_{46}ASISCRSSQSLLHSNGNTYLEV
VYLQKPGQSPX_{47}LLIHTVSNRFSGVPDRFSGSGSGTDFTLKISRVEAE
DX_{48}GVYYCFQGSHVPLTFGX_{49}GTX_{410}LEX_{411}K
```

Wherein $X_{41}$ may be V or I
Wherein $X_{42}$ may be A or P
Wherein $X_{43}$ may be S or T
Wherein $X_{44}$ may be L or P
Wherein $X_{45}$ may be D or E
Wherein $X_{46}$ may be Q or P
Wherein $X_{47}$ may be K or Q
Wherein $X_{48}$ may be L or V
Wherein $X_{49}$ may be A or Q
Wherein $X_{410}$ may be R or K or
Wherein $X_{411}$ may be L or I, wherein at least one of the amino acid identified by X is an amino acid substitution (conservative or non-conservative) in comparison with a corresponding amino acid in the polypeptide set forth in SEQ ID NO.:4.

In accordance with an embodiment, the light chain variable domain variant may have a sequence as set forth in SEQ ID NO.:33 or 34:

```
                                         SEQ ID NO.: 33
DIVMTQTPLSLPVTPGEPASISCRSSQSLLHSNGNTYLEWYLQKPGQSPQ
LLIYTVSNRFSGVPDRFSGSGSGTDFTLKISRVEAEDVGVYYCFQGSHVP
LTFGQGTKLEIK.

SEQ ID NO.: 34
DVVMTQTPLSLPVTPGEPASISCRSSQSLLHSNGNTYLEVVYLQKPGQSP
KLLIYTVSNRFSGVPDRFSGSGSGTDFTLKISRVEAEDVGVYYCFQGSHV
PLTFGQGTKLEIK.
```

Exemplary embodiments of variant antibody or antigen binding fragments include those having a heavy chain variable region as set forth in SEQ ID NO.:35.

```
                                         SEQ ID NO.: 35
QXQLVQSGXEXXKPGASVKXSCKASGYTFTDDYMSVVVXQXXGXXLEWXG
DINPYNGDTNYNQKFKGXXXXTXDXSXSTAYMXLXSLXSEDXAVYYCARD
PGAMDYWGQGTXVTVSS,
``` wherein at least one of the amino acid identified by X is an amino acid substitution (conservative or non-conservative) in comparison with a corresponding amino acid in the polypeptide set forth in SEQ ID NO.:2. The amino acid substitution may be, for example, an amino acid found at a corresponding position of a natural human antibody or a human antibody consensus. The amino acid substitution may be, for example conservative.

Another exemplary embodiment of a variant antibody or antigen binding fragment include those having a heavy chain variable region as set forth in SEQ ID NO.:36:

SEQ ID NO.: 36

QX$_{b1}$QLVQSGX$_{b2}$EX$_{b3}$X$_{b4}$KPGASVKX$_{b5}$SCKASGYTFTDDYMSWVX$_{b6}$QX$_{b7}$

X$_{b8}$GX$_{b9}$X$_{b10}$LEWX$_{b11}$GDINPYNGDTNYNQKFKGX$_{b12}$X$_{b13}$X$_{b14}$X$_{b15}$TX$_{b16}$

DX$_{b17}$SX$_{b18}$STAYMX$_{b19}$LX$_{b20}$SLX$_{b21}$SEDX$_{b22}$AVYYCARDPGAMDYWGQG

TX$_{b23}$VTVSS,

Wherein X$_{b1}$ may be a hydrophobic amino acid;
Wherein X$_{b2}$ may be P or A;
Wherein X$_{b3}$ may be a hydrophobic amino acid;
Wherein X$_{b4}$ may be V or K;
Wherein X$_{b5}$ may be a hydrophobic amino acid;
Wherein X$_{b6}$ may be a basic amino acid;
Wherein X$_{b7}$ may be S or A;
Wherein X$_{b8}$ may be H or P;
Wherein X$_{b9}$ may be a basic amino acid;
Wherein X$_{b10}$ may be S or G;
Wherein X$_{b11}$ may be a hydrophobic amino acid;
Wherein X$_{b12}$ may be a basic amino acid;
Wherein X$_{b13}$ may be a hydrophobic amino acid;
Wherein X$_{b14}$ may be I or T;
Wherein X$_{b15}$ may be a hydrophobic amino acid;
Wherein X$_{b16}$ may be a hydrophobic amino acid;
Wherein X$_{b17}$ may be K or T;
Wherein X$_{b18}$ may be a neutral hydrophilic amino acid;
Wherein X$_{b19}$ may be Q or E;
Wherein X$_{b20}$ may be N or S;
Wherein X$_{b21}$ may be T or R;
Wherein X$_{b22}$ may be a neutral hydrophilic amino acid; or
Wherein X$_{b23}$ may be S or L,
wherein at least one of the amino acid identified by X is an amino acid substitution (conservative or non-conservative) in comparison with a corresponding amino acid in the polypeptide set forth in SEQ ID NO.:2.

An additional exemplary embodiment of a variant antibody or antigen binding fragment include those having a heavy chain variable region as set forth in SEQ ID NO.:37:

SEQ ID NO.: 37

QX$_{B1}$QLVQSGX$_{B2}$EX$_{B3}$X$_{B4}$KPGASVKX$_{B5}$SCKASGYTFTDDYMSWVX$_{B6}$Q

X$_{B7}$X$_{B8}$GX$_{B9}$X$_{B10}$LEWX$_{B11}$GDINPYNGDTNYNQKPKGX$_{B12}$X$_{B13}$X$_{B14}$X$_{B15}$T

X$_{B16}$DX$_{B17}$SX$_{B18}$STAYMX$_{B19}$LX$_{B20}$SLX$_{B21}$SEDX$_{B22}$AVYYCARDPGAMDY

WGQGTX$_{B23}$VTVSS

Wherein X$_{B1}$ may be I or V;
Wherein X$_{B2}$ may be P or A;
Wherein X$_{B3}$ may be M or V;
Wherein X$_{B4}$ may be V or K;
Wherein X$_{B5}$ may be M or V;
Wherein X$_{B6}$ may be K or R;
Wherein X$_{B7}$ may be S or A;
Wherein X$_{B8}$ may be H or P;
Wherein X$_{B9}$ may be K or Q;
Wherein X$_{B10}$ may be S or G;
Wherein X$_{B11}$ may be I or M;
Wherein X$_{B12}$ may be K or R;
Wherein X$_{B13}$ may be A or V;
Wherein X$_{B14}$ may be I or T;
Wherein X$_{B15}$ may be L or I;
Wherein X$_{B16}$ may be V or A;
Wherein X$_{B17}$ may be K or T;
Wherein X$_{B18}$ may be S or T;
Wherein X$_{B19}$ may be Q or E;
Wherein X$_{B20}$ may be N or S;
Wherein X$_{B21}$ may be T or R;
Wherein X$_{B22}$ may be S or T; or
Wherein X$_{B23}$ is S or L,
wherein at least one of the amino acid identified by X is an amino acid substitution (conservative or non-conservative) in comparison with a corresponding amino acid in the polypeptide set forth in SEQ ID NO.:2.

In accordance with an embodiment, the heavy chain variable domain variant may have a sequence as set forth in any one of SEQ ID NO.38 to 41:

SEQ ID NO.: 38
QVQLVQSGAEVKKPGASVKVSCKASGYTFTDDYMSWVRQAPGQGLEWMGD
INPYNGDTNYNQKFKGRVTITADTSTSTAYMELSSLRSEDTAVYYCARDP
GAMDYWGQGTLVTVSS.

SEQ ID NO.: 39
QIQLVQSGAEVKKPGASVKVSCKASGYTFTDDYMSWVRQAPGQGLEWMGD
INPYNGDTNYNQKFKGRVTITADKSTSTAYMELSSLRSEDTAVYYCARDP
GAMDYWGQGTLVTVSS.

SEQ ID NO.: 40
QIQLVQSGAEVKKPGASVKVSCKASGYTFTDDYMSWVRQAPGQGLEWIGD
INPYNGDTNYNQKFKGRATLTVDKSTSTAYMELSSLRSEDTAVYYCARDP
GAMDYWGQGTLVTVSS.

SEQ ID NO.: 41
QIQLVQSGAEVKKPGASVKVSCKASGYTFTDDYMSWVKQAPGQGLEWIGD
INPYNGDTNYNQKFKGKATLTVDKSTSTAYMELSSLRSEDTAVYYCARDP
GAMDYWGQGTLVTVSS.

Production of the Antibodies in Cells

The anti-KAAG1 antibodies that are disclosed herein can be made by a variety of methods familiar to those skilled in the art, such as hybridoma methodology or by recombinant DNA methods.

In an exemplary embodiment of the invention, an anti-KAAG1 antibodies (e.g., an antibody which can compete with the antibodies disclosed herewith) may be produced by the conventional hybridoma technology, where a mouse is immunized with an antigen, spleen cells isolated and fused with myeloma cells lacking HGPRT expression and hybrid cells selected by hypoxanthine, aminopterin and thymine (HAT) containing media.

In an additional exemplary embodiment of the invention, the anti-KAAG1 antibodies may be produced by recombinant DNA methods.

In order to express the anti-KAAG1 antibodies, nucleotide sequences able to encode any one of a light and heavy immunoglobulin chains described herein or any other may be inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express a polypeptide or RNA derived from nucleotide sequences able to encode any one of a light and heavy immunoglobulin chains described herein. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, nucleotide sequences able to encode any one of a light and heavy immunoglobulin chains described herein may be transformed into cell lines using expression vectors that may contain viral origins of replication and/or endogenous expression elements and a selectable or visible marker gene on the same or on a separate vector. The invention is not to be limited by the vector or host cell employed. In certain embodiments of the present invention, the nucleotide sequences able to encode any one of a light and heavy immunoglobulin chains described herein may each be ligated into a separate expression vector and each chain expressed separately. In another embodiment, both the light and heavy chains able to encode any one of a light and heavy immunoglobulin chains described herein may be ligated into a single expression vector and expressed simultaneously.

Alternatively, RNA and/or polypeptide may be expressed from a vector comprising nucleotide sequences able to encode any one of a light and heavy immunoglobulin chains described herein using an in vitro transcription system or a coupled in vitro transcription/translation system respectively.

In general, host cells that contain nucleotide sequences able to encode any one of a light and heavy immunoglobulin chains described herein and/or that express a polypeptide encoded by the nucleotide sequences able to encode any one of a light and heavy immunoglobulin chains described herein, or a portion thereof, may be identified by a variety of procedures known to those of skill in the art. These procedures include, but are not limited to, DNA/DNA or DNA/RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

Host cells comprising nucleotide sequences able to encode any one of a light and heavy immunoglobulin chains described herein may thus be cultured under conditions for the transcription of the corresponding RNA (mRNA, etc.) and/or the expression of the polypeptide from cell culture. The polypeptide produced by a cell may be secreted or may be retained intracellularly depending on the sequence and/or the vector used. In an exemplary embodiment, expression vectors containing nucleotide sequences able to encode any one of a light and heavy immunoglobulin chains described herein may be designed to contain signal sequences that direct secretion of the polypeptide through a prokaryotic or eukaryotic cell membrane.

Due to the inherent degeneracy of the genetic code, other DNA sequences that encode the same, substantially the same or a functionally equivalent amino acid sequence may be produced and used, for example, to express a polypeptide encoded by nucleotide sequences able to encode any one of a light and heavy immunoglobulin chains described herein. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. In an exemplary embodiment, anti-KAAG1 antibodies that contain particular glycosylation structures or patterns may be desired. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and antibody epitopes such as monoclonal antibody epitopes.

In yet a further aspect, the present invention relates to a polynucleotide which may comprise a nucleotide sequence encoding a fusion protein. The fusion protein may comprise a fusion partner (e.g., HA, Fc, etc.) fused to the polypeptide (e.g., complete light chain, complete heavy chain, variable regions, CDRs etc.) described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Antibody Conjugates

The antibody or antigen binding fragment of the present invention may be conjugated with a detectable moiety (i.e., for detection or diagnostic purposes) or with a therapeutic moiety (for therapeutic purposes).

A "detectable moiety" is a moiety detectable by spectroscopic, photochemical, biochemical, immunochemical, chemical and/or other physical means. A detectable moiety may be coupled either directly and/or indirectly (for example via a linkage, such as, without limitation, a DOTA or NHS linkage) to antibodies and antigen binding fragments thereof of the present invention using methods well known in the art. A wide variety of detectable moieties may be used, with the choice depending on the sensitivity required, ease of conjugation, stability requirements and available instrumentation. A suitable detectable moiety include, but is not limited to, a fluorescent label, a radioactive label (for example, without limitation, $^{125}$I, In$^{111}$, Tc$^{99}$, I$^{131}$ and including positron emitting isotopes for PET scanner etc), a nuclear magnetic resonance active label, a luminiscent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

In another exemplary embodiment of the invention, the antibody or antigen binding fragment thereof may be coupled (modified) with a therapeutic moiety (e.g., drug, cytotoxic moiety, anti-cancer agent).

In an exemplary embodiment, the anti-KAAG1 antibodies and antigen binding fragments may comprise a chemotherapeutic, a cytotoxic agent or an anti-cancer drug (e.g., small molecule). Such chemotherapeutic or cytotoxic agents include, but are not limited to, Yttrium-90, Scandium-47, Rhenium-186, Iodine-131, Iodine-125, and many others recognized by those skilled in the art (e.g., lutetium (e.g., Lu$^{177}$), bismuth (e.g., Bi$^{213}$), copper (e.g., Cu$^{67}$)). In other instances, the chemotherapeutic, cytotoxic agent or anticancer drug may be comprised of, among others known to those skilled in the art, 5-fluorouracil, adriamycin, irinotecan, taxanes, *pseudomonas* endotoxin, ricin, auristatins (e.g., monomethyl auristatin E, monomethyl auristatin F), maytansinoids (e.g., mertansine) and other toxins.

Alternatively, in order to carry out the methods of the present invention and as known in the art, the antibody or antigen binding fragment of the present invention (conjugated or not) may be used in combination with a second molecule (e.g., a secondary antibody, etc.) which is able to specifically bind to the antibody or antigen binding fragment of the present invention and which may carry a desirable detectable, diagnostic or therapeutic moiety.

Pharmaceutical Compositions of the Antibodies and their Use

Pharmaceutical compositions of the anti-KAAG1 antibodies or antigen binding fragments (conjugated or not) are also encompassed by the present invention. The pharmaceutical composition may comprise an anti-KAAG1 antibody or an antigen binding fragment and may also contain a pharmaceutically acceptable carrier.

Other aspects of the invention relate to a composition which may comprise the antibody or antigen binding fragment described herein and a carrier.

The present invention also relates to a pharmaceutical composition which may comprise the antibody or antigen binding fragment described herein and a pharmaceutically acceptable carrier.

In addition to the active ingredients, a pharmaceutical composition may contain pharmaceutically acceptable carriers comprising water, PBS, salt solutions, gelatins, oils, alcohols, and other excipients and auxiliaries that facilitate processing of the active compounds into preparations that may be used pharmaceutically. In other instances, such preparations may be sterilized.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), antioxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the ED$_{50}$ (the dose therapeutically effective in 50% of the population) and LD$_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The term "treatment" for purposes of this disclosure refers to both therapeutic treatment and prophylactic or preventative measures, wherein the object is slow down (lessen) the targeted pathologic condition or disorder. Those in need of treatment include those already with the disorder as well as those prone to have the disorder or those in whom the disorder is to be prevented. Particularly, subjects in need include subjects with an elevated level of one or more cancer markers.

The anti-KAAG1 antibodies and antigen binding fragments thereof may have therapeutic uses in the treatment of various cancer types, such as ovarian cancer, renal cancer, colon cancer, lung cancer, melanoma, etc. In an exemplary embodiment, the antibodies and fragments have therapeutic uses in ovarian cancer. In a more particular embodiment the subject may have, for example, a recurrent ovarian cancer. In yet another embodiment, the subject may have, for example, a metastatic cancer.

In certain instances, the anti-KAAG1 antibodies and fragments may block the interaction of KAAG1 with its protein partners. The anti-KAAG1 antibodies of the present invention may particularly be used to deliver a therapeutic moiety to a cell expressing KAAG1.

The anti-KAAG1 antibodies and antigen binding fragments thereof may have therapeutic uses in the treatment of various types of ovarian cancer. Several different cell types may give rise to different ovarian cancer histotypes. The most common form of ovarian cancer is comprised of tumors that originate in the epithelial cell layer of the ovary or the fallopian tube. Such epithelial ovarian cancers include serous tumors, endometroid tumors, mucinous tumors, clear cell tumors, and borderline tumors. In other embodiments, the anti-KAAG1 antibodies and antigen binding fragments thereof have uses in the treatment of other types of ovarian cancer such as germ line and sex cord ovarian cancer.

In certain instances, the anti-KAAG1 antibodies and antigen binding fragments thereof may be administered concurrently in combination with other treatments given for the same condition. As such, the antibodies may be administered with anti-mitotics (eg., taxanes), platinum-based agents (eg., cisplatin), DNA damaging agents (eg. Doxorubicin) and other anti-cancer therapies that are known to those skilled in the art. In other instances, the anti-KAAG1 antibodies and antigen binding fragments thereof may be administered with other therapeutic antibodies. These include, but are not limited to, antibodies that target EGFR, CD-20, and Her2.

The present invention relates in a further aspect thereof to a method for inhibiting the growth of a KAAG1-expressing cell, the method which may comprise contacting the cell with an effective amount of the antibody or antigen binding fragment described herein.

The present invention also encompasses method of treating cancer or inhibiting the growth of a KAAG1 expressing cells in a mammal, the method may comprise administering the antibody or antigen binding fragment, for example, conjugated with a therapeutic moiety described herein to a subject in need.

In further aspects, the present invention provides method of treatment, diagnostic methods and method of detection using the antibody or antigen binding fragment of the present invention and the use of these antibodies or antigen binding fragment in the manufacture of a pharmaceutical composition or drug for such purposes.

The invention therefore relates to the use of the isolated antibody or antigen binding fragment described herein in the (manufacture of a pharmaceutical composition for) treatment of cancer.

The antibody or antigen binding fragment may more particularly be applicable for malignant tumors including, for example, a malignant tumor having the ability to metastasize and/or tumor cells characterized by anchorage-independent growth.

The antibody or antigen binding fragment of the present invention may also be used in the diagnosis of cancer. The diagnosis of cancer may be performed in vivo by administering the antibody or antigen binding fragment of the present invention to a mammal having or suspected of having a cancer. The diagnosis may also be performed ex vivo by contacting a sample obtained from the mammal with the antibody or antigen binding fragment and determining the presence or absence of cells (tumor cells) expressing KAAG1 or a KAAG1 variant.

The present invention therefore also encompasses method of detecting cancer or detecting a KAAG1 expressing cells in a mammal, the method may comprise administering the antibody or antigen binding fragment described herein to a subject in need.

The present invention relates in another aspect thereof to a method for detecting a cell expressing KAAG1 or a KAAG1 variant, the method may comprise contacting the cell with an antibody or antigen binding fragment described herein and detecting a complex formed by the antibody and the KAAG1- or KAAG1 variant-expressing cell. Exemplary embodiments of antibodies or antigen binding fragments used in detection methods are those which are capable of binding to the extracellular region of KAAG1.

Other exemplary embodiments of antibodies or antigen binding fragments used in detection methods are those which bind to KAAG1 or KAAG1 variant expressed at the surface of a tumor cells.

Subject in need which would benefit from treatment, detection or diagnostic methods described herein are those which have or are suspected of having cancer, e.g., ovarian cancer (e.g., serous, endometroid, clear cell or mucinous), skin cancer (e.g., melanomas, squamous cell carcinomas), renal cancer (e.g., papillary cell carcinomas, clear cell carcinomas), colorectal cancer (e.g., colorectal carcinomas), sarcoma, leukemia, brain tumor, thyroid tumor, breast cancer (e.g., mammary carcinomas), prostate cancer (e.g., prostatic carcinomas), oesophageal tumor, bladder tumor, lung tumor (e.g., lung carcinomas) or head and neck tumor and especially when the cancer is characterized as being malignant and/or when the cells expressing KAAG1 or a KAAG1 variant are characterized by anchorage-independent growth.

Subjects having cancer may be identified by imaging, tissue biopsy, genetic testing. Alternatively, subjects having cancer may be identified by the presence of cancer markers in their bodily fluids using standard assays (e.g., ELISA and the like).

Especially encompassed by the present invention are patients having or susceptible of having ovarian cancer (e.g., serous, endometroid, clear cell or mucinous), skin cancer (e.g., melanomas, squamous cell carcinomas) or renal cancer (e.g., papillary cell carcinomas) and especially when the cancer is characterized as being malignant and/or when the cells expressing KAAG1 or a KAAG1 variant are characterized by anchorage-independent growth.

Another aspect of the invention relates to a method for detecting KAAG1 (SEQ ID NO.:29), a KAAG1 variant having at least 80% sequence identity with SEQ ID NO.:29 or a secreted form of circulating form of KAAG1 or KAAG1 variant, the method may comprise contacting a cell expressing KAAG1 or the KAAG1 variant or a sample (biopsy, serum, plasma, urine etc.) comprising or suspected of comprising KAAG1 or the KAAG1 variant with the antibody or antigen binding fragments described herein and measuring binding. The sample may originate from a mammal (e.g., a human) which may have cancer (e.g., ovarian cancer, a metastatic cancer) or may be suspected of having cancer (e.g., ovarian cancer, a metastatic cancer). The sample may be a tissue sample obtained from the mammal or a cell culture supernatant.

In accordance with the invention the sample may be a serum sample, a plasma sample, a blood sample, semen or ascitic fluid obtained from the mammal. The antibody or antigen binding fragment described herein may advantageously detect a secreted or circulating form (circulating in blood) of KAAG1.

The method may comprise quantifying the complex formed by the antibody or antigen binding fragment bound to KAAG1 or to the KAAG1 variant.

The binding of an antibody to an antigen will cause an increase in the expected molecular weight of the antigen. A physical change therefore occurs upon specific binding of the antibody or antigen binding fragment and the antigen.

Such changes may be detected using, for example, electrophoresis followed by Western blot and coloration of the gel or blot, mass spectrometry, HPLC coupled with a computer, FACS or else. Apparatus capable of computing a shift in molecular weight are known in the art and include for example, Phosphorimager™.

When the antibody comprises for example a detectable label, the antigen-antibody complex may be detected by the fluorescence emitted by the label, radiation emission of the label, enzymatic activity of a label provided with its substrate or else.

Detection and/or measurement of binding between an antibody or antigen binding fragment and an antigen may be performed by various methods known in the art. Binding between an antibody or antigen binding fragment and an antigen may be monitored with an apparatus capable of detecting the signal emitted by the detectable label (radiation emission, fluorescence, color change etc.). Such apparatus provides data which indicates that binding as occurred and may also provide indication as to the amount of antibody bound to the antigen. The apparatus (usually coupled with a computer) may also be capable of calculating the difference between a background signal (e.g., signal obtained in the absence of antigen-antibody binding) or background noise and the signal obtained upon specific antibody-antigen binding. Such apparatuses may thus provide the user with indications and conclusions as to whether the antigen has been detected or not.

Additional aspects of the invention relates to kits which may include one or more container containing one or more antibodies or antigen binding fragments described herein.

Nucleic Acids, Vectors and Cells

Antibodies are usually made in cells allowing expression of the light chain and heavy chain expressed from a vector(s) comprising a nucleic acid sequence encoding the light chain and/or heavy chain.

The present therefore encompasses nucleic acids capable of encoding any of the CDRs, light chain variable regions, heavy chain variable regions, light chains, heavy chains described herein.

The present invention therefore relates in a further aspect to a nucleic acid encoding a light chain variable region and/or a heavy chain variable region of an antibody which is capable of specific binding to KAAG1.

Exemplary embodiments of nucleic acids of the present invention include nucleic acids encoding a light chain variable region comprising:
 a. a CDRL1 as set forth in SEQ ID NO.:8 or comprising SEQ ID NO.:8;
 b. a CDRL2 as set forth in SEQ ID NO.:9 or comprising SEQ ID NO.:9, or;
 c. a CDRL3 sequence as set forth in SEQ ID NO.:10 or comprising SEQ ID NO.:10.

In accordance with the present invention, the nucleic acid may encode a light chain variable region which may comprise at least two CDRs of a CDRL1, a CDRL2 or a CDRL3.

Also in accordance with the present invention, the nucleic acid may encode a light chain variable region which may comprise one CDRL1, one CDRL2 and one CDRL3.

The present invention also relates to a nucleic acid encoding a heavy chain variable region comprising:
 a. a CDRH1 sequence as set forth in SEQ ID NO.:5 or comprising SEQ ID NO.:5;
 b. a CDRH2 sequence as set forth in SEQ ID NO.:6 or comprising SEQ ID NO.:6, or;
 c. a CDRH3 sequence as set forth in SEQ ID NO.:7 or comprising SEQ ID NO.:7.

In accordance with the present invention, the nucleic acid may encode a heavy chain variable region which may comprise at least two CDRs of a CDRH1, a CDRH2 or a CDRH3.

In accordance with the present invention, the nucleic acid may encode a heavy chain variable region which may comprise one CDRH1, one CDRH2 and one CDRH3.

Also encompassed by the present invention are nucleic acids encoding antibody variants having at least one conservative amino acid substitution.

In accordance with the present invention, the nucleic acid may encode a CDR comprising at least one conservative amino acid substitution.

In accordance with the present invention, the nucleic acid may encode a CDR comprising at least one conservative amino acid substitution in at least two of the CDRs.

In accordance with the present invention, the nucleic acid may encode a CDR comprising at least one conservative amino acid substitution in the 3 CDRs.

In accordance with the present invention, the nucleic acid may encode a CDR comprising at least two conservative amino acid substitutions in at least one of the CDRs.

In accordance with the present invention, the nucleic acid may encode a CDR comprising at least two conservative amino acid substitutions in at least two of the CDRs.

In accordance with the present invention, the nucleic acid may encode a CDR comprising at least two conservative amino acid substitutions in the 3 CDRs.

Other aspects of the invention relate to a nucleic acid encoding a light chain variable region having at least 70%. 75%, 80% sequence identity to SEQ ID NO.:4.

Yet other aspects of the invention relate to a nucleic acid encoding a heavy chain variable region having at least 70%. 75%, 80% sequence identity to SEQ ID NO.:2.

In yet another aspect, the present invention relates to a vector comprising the nucleic acids described herein.

In accordance with the present invention, the vector may be an expression vector.

Vector that contains the elements for transcriptional and translational control of the inserted coding sequence in a particular host are known in the art. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

In another aspect the present invention relates to an isolated cell which may comprise the nucleic acid, antibodies or antigen binding fragment described herein.

The isolated cell may comprise a nucleic acid encoding a light chain variable region and a nucleic acid encoding a heavy chain variable region either on separate vectors or on the same vector. The isolated cell may also comprise a nucleic acid encoding a light chain and a nucleic acid encoding a heavy chain either on separate vectors or on the same vector.

In accordance with the present invention, the cell may be capable of expressing, assembling and/or secreting an antibody or antigen binding fragment thereof.

In another aspect, the present invention provides a cell which may comprise and/or may express the antibody described herein.

In accordance with the invention, the cell may comprise a nucleic acid encoding a light chain variable region and a nucleic acid encoding a heavy chain variable region.

The cell may be capable of expressing, assembling and/or secreting an antibody or antigen binding fragment thereof.

The examples below are presented to further outline details of the present invention.

EXAMPLES

Example 1

This example describes the binding of antibody 3A4 to KAAG1.

The antibodies that bind KAAG1 were generated using the Alere phage display technology. A detailed description of the technology and the methods for generating these antibodies can be found in the U.S. Pat. No. 6,057,098. In addition, a detailed description of the generation of antibodies against KAAG1 can be found in PCT/CA2009/001586. Briefly, the technology utilizes stringent panning of phage libraries that display the antigen binding fragments (Fabs). After a several rounds of panning, a library, termed the Omniclonal, was obtained that was enriched for recombinant Fabs containing light and heavy chain variable regions that bound to KAAG1 with very high affinity and specificity. From this library, more precisely designated Omniclonal AL0003 A2ZB, 96 individual recombinant monoclonal Fabs were prepared from E. coli and tested for KAAG1 binding. The monoclonal designated 3A4 was derived from this 96-well plate of monoclonal antibodies based on its high binding activity for recombinant KAAG1 and its affinity for KAAG1 on the surface of ovarian cancer cells.

The nucleotide sequences of the variable regions of the heavy and light chain immunoglobulin chains are shown in SEQ ID NOS.:1 and 3, respectively and the polypeptide sequences of the variable regions of the heavy and light chain immunoglobulin chains are shown in SEQ ID NOS.:2 and 4, respectively. The complementarity determining regions (CDRs) of the 3A4 heavy chain immunoglobulin are shown in SEQ ID NOS.:5, 6 and 7, respectively and the CDRs of the 3A4 light chain immunoglobulin are shown in SEQ ID NOS.:8, 9 and 10, respectively.

Aside from the possibility of conducting interaction studies between the Fab monoclonals and the KAAG1 protein, the use of Fabs is limited with respect to conducting meaningful in vitro and in vivo studies to validate the biological function of the antigen. Thus, it was necessary to transfer the light and heavy chain variable regions contained in the 3A4 Fabs to full antibody scaffolds, to generate mouse-human chimeric IgG1. The expression vectors for both the light and heavy immunoglobulin chains were constructed such that i) the original bacterial signal peptide sequences upstream of the Fab expression vectors were replaced by mammalian signal peptides and ii) the light and heavy chain constant regions in the mouse antibodies were replaced with human constant regions. The methods to accomplish this transfer utilized standard molecular biology techniques that are familiar to those skilled in the art. A brief overview of the methodology is described here.

Light Chain Expression Vector—an existing mammalian expression plasmid, called pTTVH8G (Durocher et al., 2002), designed to be used in the 293E transient transfection system was modified to accommodate the mouse light chain variable region. The resulting mouse-human chimeric light chain contained a mouse variable region followed by the human kappa constant domain. The cDNA sequence encoding the human kappa constant domain was amplified by PCR with primers OGS1773 and OGS1774 (SEQ ID NOS:11 and 12, respectively). The nucleotide sequence and the corresponding amino acid sequence for the human kappa constant region are shown in SEQ ID NOS:13 and 14, respectively. The resulting 321 base pair PCR product was ligated into pTTVH8G immediately downstream of the signal peptide sequence of human VEGF A (NM_003376). This cloning step also positioned unique restriction endonuclease sites that permitted the precise positioning of the cDNAs encoding the mouse light chain variable regions. The sequence of the final expression plasmid, called pTTVK1, is shown in SEQ ID NO.:15. Based on the 3A4 light chain variable sequence shown in SEQ ID NO.:3, a PCR primer specific for the light chain variable region was designed that incorporated, at its 5'-end, a sequence identical to the last 20 base pairs of the VEGF A signal peptide. The sequence of this primer is shown in SEQ ID NO:16. A reverse primer (SEQ ID NO.:17) incorporated, at its 3'-end, a sequence identical to the first 20 base pairs of the human kappa constant domain. Both the PCR fragments and the digested pTTVK1 were treated with the 3'-5' exonuclease activity of T4 DNA polymerase resulting in complimentary ends that were joined by annealing. The annealing reactions were transformed into competent E. coli and the expression plasmids were verified by sequencing to ensure that the mouse light chain variable regions were properly inserted into the pTTVK1 expression vector.

Heavy Chain Expression Vector—the expression vector that produced the 3A4 heavy chain immunoglobulin was designed in a similar manner to the pTTVK1 described above for production of the light chain immunoglobulins. Plasmid pYD11 (Durocher et al., 2002), which contains the human IgGK signal peptide sequence as well as the CH2 and CH3 regions of the human Fc domain of IgG1, was modified by ligating the cDNA sequence encoding the human constant CH1 region. PCR primers OGS1769 and OGS1770 (SEQ ID NOS:18 and 19), designed to contain unique restriction endonuclease sites, were used to amplify the human IgG1 CH1 region containing the nucleotide sequence and corresponding amino acid sequence shown in SEQ ID NOS:20 and 21. Following ligation of the 309 base pair fragment of human CH1 immediately downstream of the IgGK signal peptide sequence, the modified plasmid (SEQ ID NO.:22) was designated pYD15. When a selected heavy chain variable region is ligated into this vector, the resulting plasmid encodes a full IgG1 heavy chain immunoglobulin with human constant regions. A PCR primers specific for the heavy chain variable region of antibody 3A4 (SEQ ID NOS:1) was designed that incorporated, at its 5'-end, a sequence identical to the last 20 base pairs of the IgGK signal peptide. The sequence of this primers is shown in SEQ ID NOS:23. A reverse primer (SEQ ID NO.:24) incorporated, at its 3'-end, a sequence identical to the first 20 base pairs of the human CH1 constant domain. Both the PCR fragments and the digested pYD15 were treated with the 3'-5' exonuclease activity of T4 DNA polymerase resulting in complimentary ends that were joined by annealing. The annealing reactions were transformed into competent $E.$ $coli$ and the expression plasmids were verified by sequencing to ensure that the mouse heavy chain variable regions were properly inserted into the pYD15 expression vector.

Expression of human 3A4 chimeric IgG1 in 293E cells—The expression vectors prepared above that encoded the light and heavy chain immunoglobulins were expressed in 293E cells using the transient transfection system (Durocher et al., 2002). The ratio of light to heavy chain was optimized in order to achieve the most yield of antibody in the tissue culture medium and it was found to be 9:1 (L:H).

Binding of chimeric 3A4 to KAAG1—To measure the relative binding of the 3A4 monoclonal antibody, recombinant human KAAG1 was produced in 293E cells using the large-scale transient transfection technology (Durocher et al., 2002; Durocher, 2004). The expression and purification of human recombinant KAAG1 as an Fc fusion protein is found in PCT/CA2009/001586. To carry out the binding of Fc-KAAG1 to the antibody preparation, the Fc-KAAG1 was biotinylated with NHS-biotin (Pierce, Rockford, Ill.) and 10 ng/well was coated in a streptavidin 96-well plate for 1 h at room temperature. Purified chimeric 3A4 was added at increasing concentrations and incubated at room temperature for 30 minutes. Bound antibody was detected with HRP-conjugated human anti-kappa light chain antibody in the presence of TMB liquid substrate (Sigma-Aldrich Canada Ltd., Oakville, ON) and readings were conducted at 450 nm in microtiter plate reader. As shown in FIG. 1, 3A4 interacted with the immobilized KAAG1 protein in a dose-dependent manner. When the control unrelated IgG was incubated with the recombinant KAAG1, no binding activity was observed, even at the very highest concentration. This result demonstrated that 3A4 binds to human KAAG1. The binding of 3A4 was compared to the binding of the chimeric 3D3 (described in Tremblay and Filion (2009)), that has different epitope specificity (see Example 2). The binding activity of 3A4 is very similar to 3D3 in this type of assay (see FIG. 1).

Example 2

This example describes the epitope mapping studies to determine which region of KAAG1 the 3A4 antibody binds to.

To further delineate the regions of KAAG1 that are bound by the 3A4 antibody, truncated mutants of KAAG1 were expressed and used in the ELISA. As for the full length KAAG1, the truncated versions were amplified by PCR and ligated into BamHI/HindIII digested pYD5. The primers that were used combined the forward oligonucleotide with the sequence shown in SEQ ID NO.:25 with primers of SEQ ID NOS:26 and 27, to produce Fc-fused fragments that ended at amino acid number 60 and 35 of KAAG1, respectively. The expression of these recombinant mutants was conducted as was described above for the full length Fc-KAAG1 and purified with Protein-A agarose.

Figure 2:
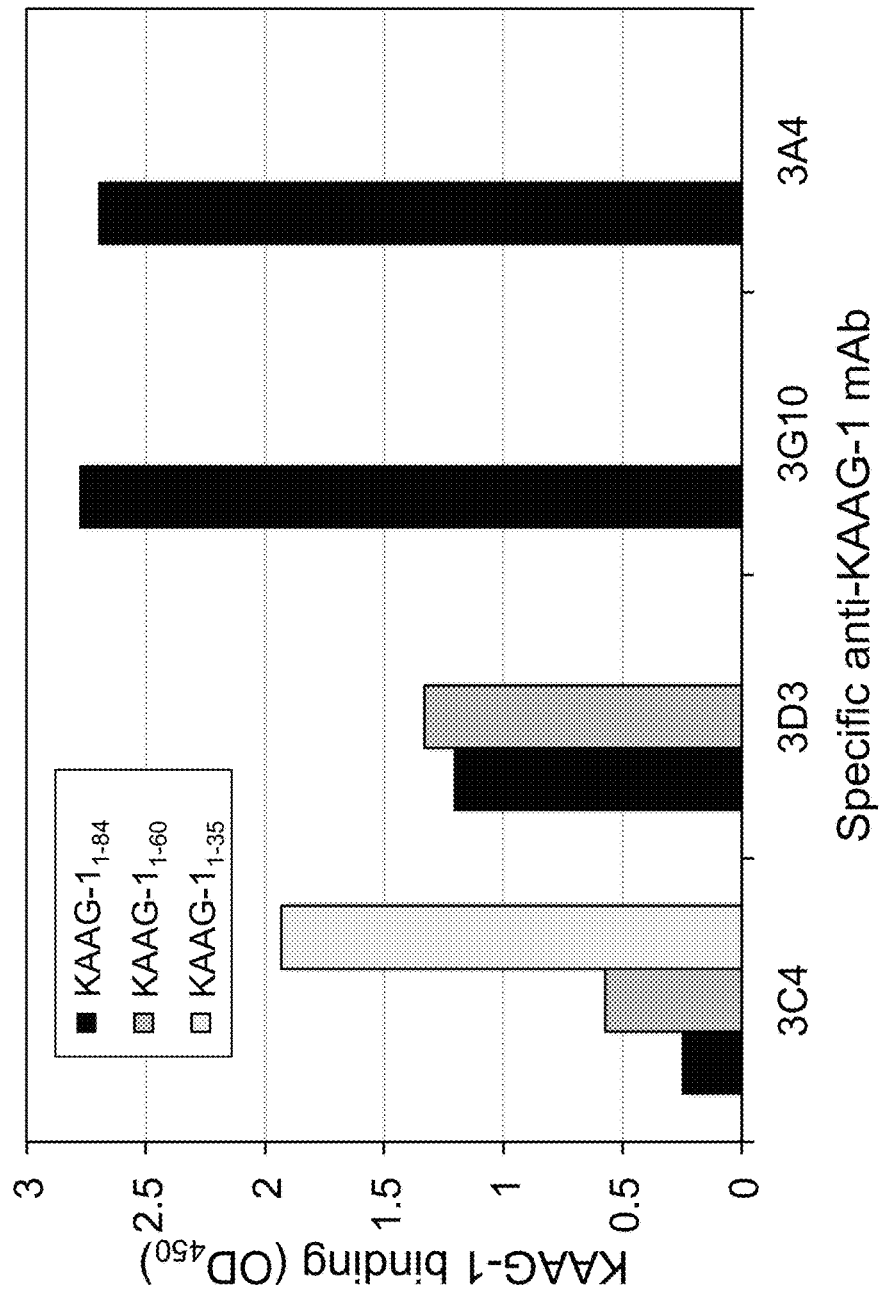
FIG. 2 shows a histogram that describes the results from ELISA analyses to map the epitope specificity of the 3A4 anti-KAAG1 antibody. The results showed that 3A4 interacted with a sequence of amino acids contained in the carboxy-terminus of KAAG1 between amino acids 61-84. The binding of 3A4 was compared with 3C4, 3D3, and 3G10 anti-KAAG1 antibodies that were known to interact with regions 1-35, 36-60, and 61-84 of KAAG1, respectively.

Based on the teachings of Tremblay and Filion (2009), it was known that other antibodies interacted with specific regions of recombinant KAAG1. Thus, anti-KAAG1 antibody 3C4, 3D3, and 3G10 interacted with the regions 1-35, 36-60, and 61-84 of KAAG1, respectively. These binding results were reproduced and are shown in FIG. 2. In order to determine the region in KAAG1 that is bound by the 3A4 antibody, the ELISA was performed using the KAAG1 truncated Fc-fusions according to a similar protocol that was described in Example 1. The only modifications were the use of different biotinylated Fc-KAAG1 truncated mutants. The results show that the binding specificity of 3A4 is similar to 3G10. In KAAG1 mutants that do not have amino acids sequences beyond amino acid 60, the binding of 3A4 to KAAG1 does not occur. This indicates that 3A4 interacts with a region delineated by amino acids 61-84 of human KAAG1. The observation that 3A4 and 3D3 have virtually identical binding activity as measured by ELISA (Example 1) but have very different epitope specificity suggests that the binding properties of 3A4 is quite distinct of 3D3.

Example 3

Figure 3A:
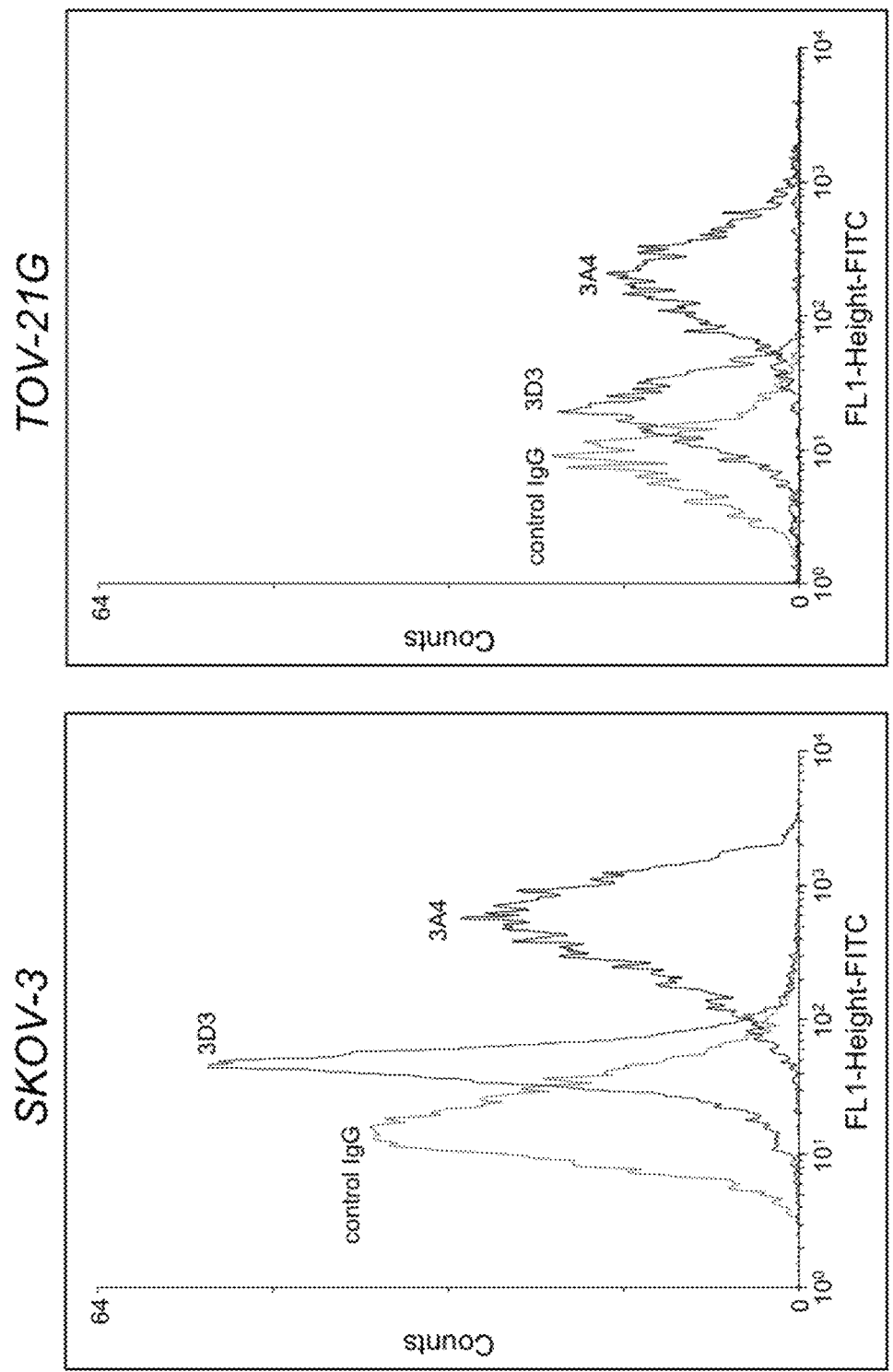
FIG. 3A shows the results of flow cytometry performed on SKOV-3 and TOV-21G ovarian cancer cells with the 3A4 anti-KAAG1 antibody (darker line) compared with a control IgG (lighter line).
Figure 3B:
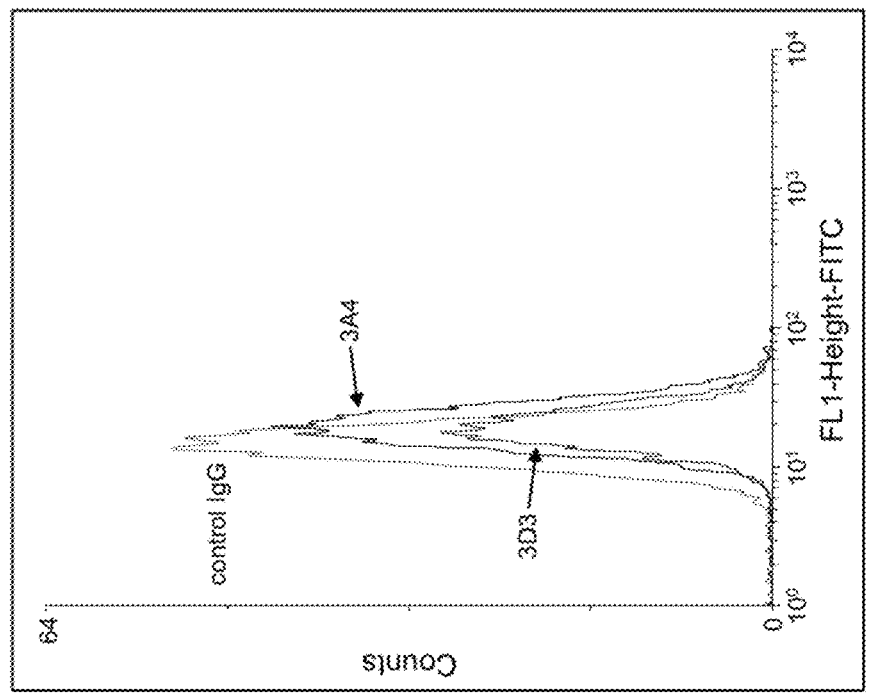
FIG. 3B shows the results of flow cytometry performed on 293E human kidney cells with the 3A4 anti-KAAG1 antibody (darker line) compared with a control IgG (lighter line).

This example describes the ability of 3A4 to bind to KAAG1 on the surface of cancer cell lines Flow cytometry was used to detect KAAG1 on the surface of cell lines. Based on RT-PCR expression analyses using KAAG1 mRNA specific primers, selected cancer cell lines were expected to express KAAG1 protein. To verify this, ovarian cancer cells (SKOV-3 and TOV-21G) and a control cell lines that showed very little KAAG1 expression (293E). The cells were harvested using 5 mM EDTA, counted with a hemocytometer, and resuspended in FCM buffer (0.5% BSA, 10 µg/ml goat serum in 1×PBS) at a cell density of $2\times10^6$ cells/ml. Chimeric 3A4 or a control IgG were added to 100 µl of cells at a final concentration of 5 µg/ml and incubated on ice for 2 h. The cells were washed in cold PBS to remove unbound antibodies, resuspended in 100 µl FCM buffer containing anti-human IgG conjugated to FITC (diluted 1:200) as a secondary antibody and incubated on ice for 45 min on ice. Following another washing step in cold PBS, the cells were resuspended in 250 µl FCM buffer and analyzed with a flow cytometer. The results from this experiment are shown in FIGS. 3A and 3B. Incubation of the cell lines with the control antibody resulted in histograms that corresponded to the signal that was typically obtained when the antibody was omitted from the cells. This established the background signal of these FCM values (FIGS. 3A and 3B). By contrast, incubation of the SKOV-3, TOV-21G with the 3A4 chimeric antibody resulted in a strong fluorescence signal (FIG. 3A). This indicated that the antibody efficiently detects KAAG1 on the surface of these cancer cells. The 293E cells, a human kidney cell line, was expected to show very little KAAG1 expression and indeed, FCM histogram showed almost no shift compared to the control antibody (see FIG. 3B). Therefore, 3A4 specifically detected KAAG1 on the surface of cancer cells. The activity of 3A4 was compared to the 3D3, an anti-KAAG1 antibody described in the teachings of Tremblay and Filion (2009). Based on this patent application, it was known that 3D3 could detect KAAG1 on the surface of cancer cells as measured by FCM. This was confirmed when the 3D3 was incubated in the presence of SKOV-3 and TOV-21G cells (see FIG. 3A). The fluorescence signal was not as high compared to the 3A4, indicating that 3A4 has different and increased ability to detect KAAG1 on the surface of ovarian cancer cells. Other results obtained in our laboratory indicate that 3A4 could detect KAAG1 on the surface of cancer cells under conditions where 3D3 exhibited no activity in this assay (results not shown). Taken together, these observations and the difference in epitope specificity of 3A4 compared to 3D3 suggests that these antibodies have distinct anti-KAAG1 properties.

Example 4

Methods for use of the 3A4 Anti-Kaag1 Antibody as an Antibody Conjugate

Figure 4:
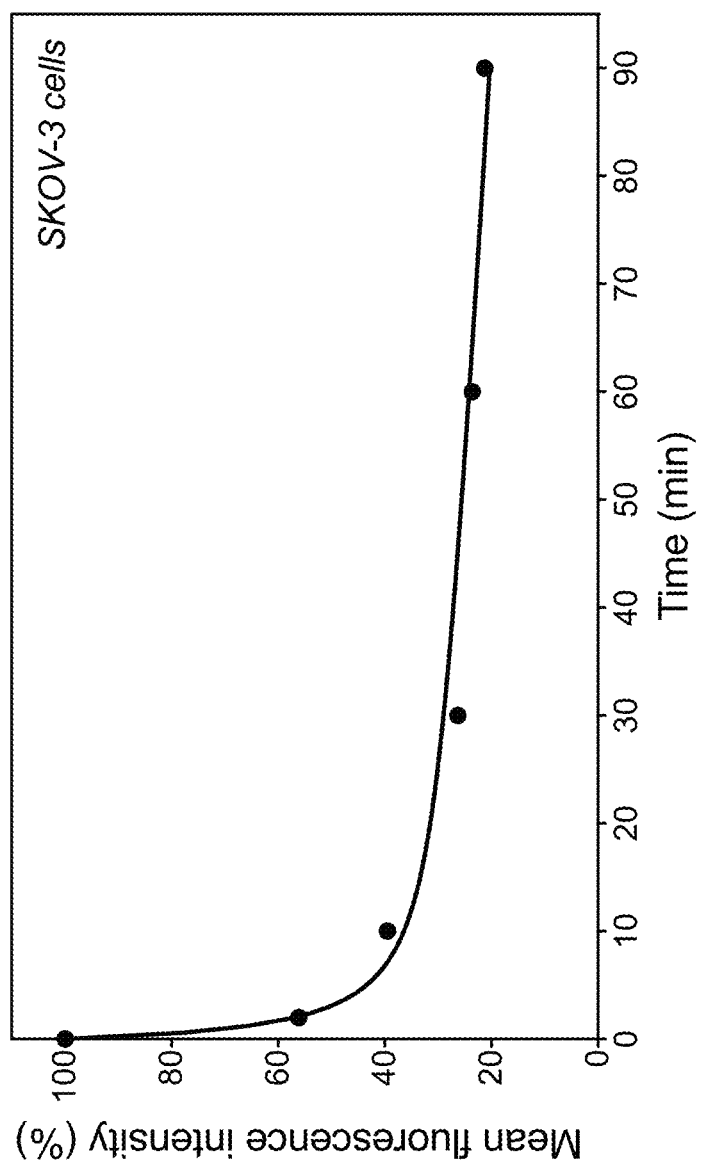
FIG. 4 represents the detection of the KAAG1 antigen on the surface of SKOV-3 cells by flow cytometry with the 3A4 anti-KAAG1 antibody. The fluorescence signal decreases with time when the cells were incubated at 37 C, which suggests that the KAAG1/antibody complex was internalized during the incubation when the cells were incubated with 3A4.

As demonstrated above, the KAAG1 antigen was detected by 3A4 on the surface of cancer cells using flow cytometry. There are several different molecular events that can occur upon binding of an antibody to its target on the surface of cells. These include i) blocking accessibility to another cell-surface antigen/receptor or a ligand, ii) formation of a relatively stable antibody-antigen complex to allow cells to be targeted via ADCC or CDC, iii) signalling events can occur as exemplified by agonistic antibodies, iv) the complex can be internalized, or v) the complex can be shed from the cell surface. To address this question we wished to examine the behavior of the 3A4 antibody-KAAG1 complex on the surface of the cells. SKOV-3 cells were plated, washed, and incubated with 5 µg/ml chimeric 3A4 antibody as described in Example 3. After washing, complete OSE medium was added and the cells placed at 37 C for up to 90 minutes. The cells were removed at the indicated times (see FIG. 4), rapidly cooled, prepared for cytometry with FITC-conjugated anti-human IgG and the results were expressed as the percentage of mean fluorescence intensity (Mean fluorescence intensity, %) remaining. As illustrated in FIG. 4, the fluorescence signal decreases rapidly over a period of 30-45 minutes. This result indicates that the 3A4/KAAG1 complex disappeared from the cells, which indicated that an internalization of the complex likely occurred. Preliminary studies to elucidate the mechanism responsible for this decrease in cell-surface fluorescence have revealed that the complex appears to be internalized.

Figure 5A:
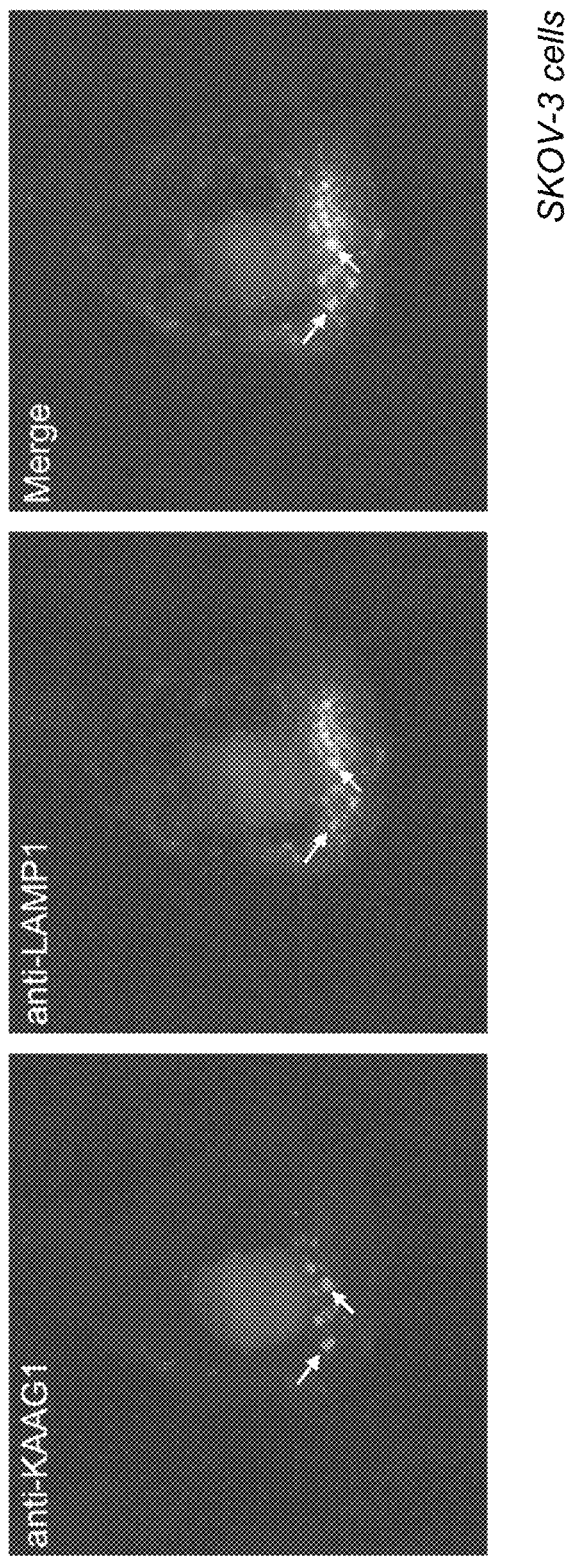
FIG. 5A shows pictures of immunofluorescence data performed on SKOV-3 cells with the 3A4 anti-KAAG1 chimeric antibody and an anti-LAMP1 antibody (left panel: fluorescence signal associated with the anti-KAAG1 antibody; middle panel: fluorescence signal associated with the anti-LAMP1 antibody; right panel: merging of both fluorescence signals).
Figure 5B:
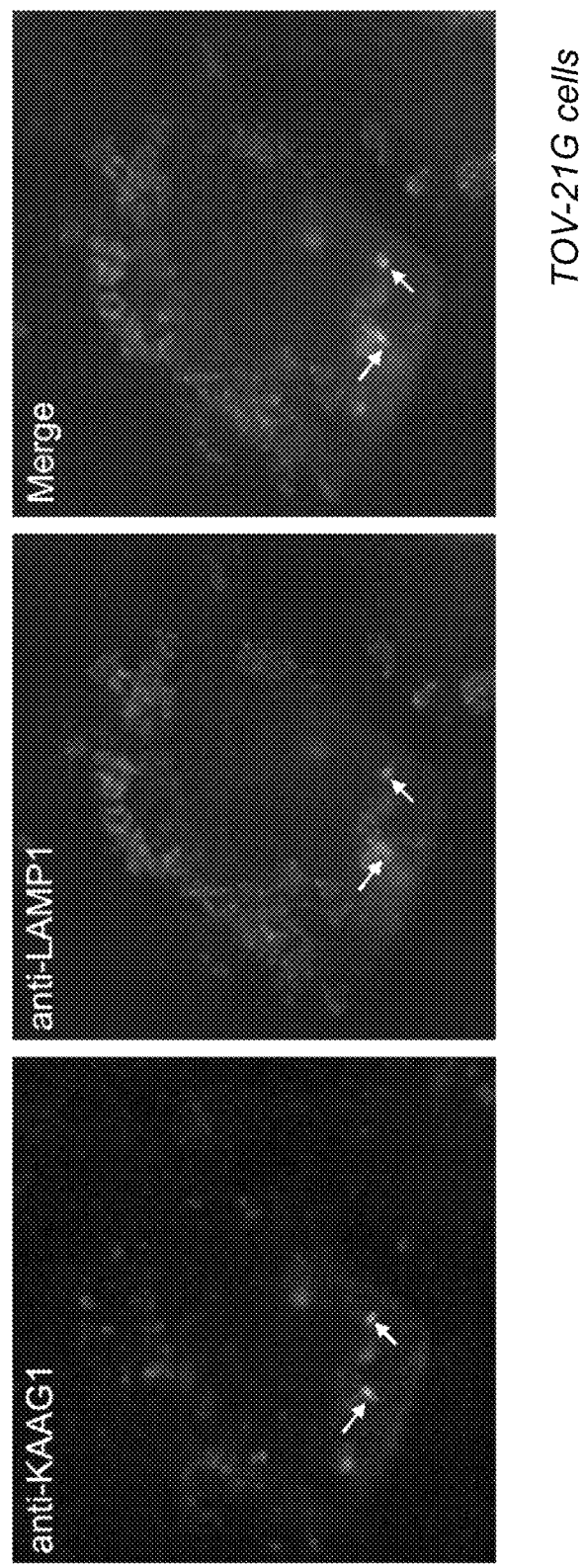
FIG. 5B shows pictures of immunofluorescence data performed on TOV-21G cells with the 3A4 anti-KAAG1 chimeric antibody and an anti-LAMP1 antibody (left panel: fluorescence signal associated with the anti-KAAG1 antibody; middle panel: fluorescence signal associated with the anti-LAMP1 antibody; right panel: merging of both fluorescence signals).

These findings were further confirmed by conducting immunofluorescence on live cells to see if this internalization could be microscopically observed. SKOV-3 cells were seeded on cover slips in full medium (OSE medium (Wisent) containing 10% FBS, 2 mM glutamine, 1 mM sodium-pyruvate, 1× non-essential amino acids, and antibiotics). Once the cells were properly adhered, fresh medium was added containing the 3A4 anti-KAAG1 chimeric antibody at 10 ug/ml and incubating at 37 C for 4 h. The cells were washed in PBS then fixed in 4% paraformaldehyde (in PBS) for 20 min. After washing, the cells were permeabilized with 0.1% Triton X-100 in PBS for 5 min. Blocking was performed with 1.5% dry milk in PBS for 1 h. Lysosomal-associated membrane protein 1 (LAMP1, Chang et al., 2002) was detected by incubating with anti-LAMP1 (Santa Cruz, sc-18821, diluted 1:100) in 1.5% milk in PBS for 2 h. After washing in PBS, the secondary antibodies were added together in 1.5% milk and incubated for 1 h. For the anti-KAAG1 chimeric antibodies the secondary antibody was a Rhodamine Red-X conjugated donkey anti-human IgG (H+L) diluted 1:300. For the anti-LAMP1 antibody the secondary antibody was a DyLight488-conjugated goat anti-mouse IgG (H+L) diluted 1:300. Both secondary antibodies were from Jackson ImmunoResearch. The coverslips were washed in PBS and mounted in ProLong Gold antifade reagent with DAPI. As seen in FIG. 5A, after 4 hours of incubation at 37 C in the presence of SKOV-3 ovarian cancer cells, the 3A4 antibody was able to be detected in complexes predominantly near the peri-nuclear area (arrows, see red staining in the left panel in FIG. 5A), which is typical of endosomal-lysosomal-based internalization pathways. This observation was further confirmed when a lysosomal marker, LAMP1 was visualized and was found to be also expressed in these areas (arrows, see green staining in the middle panel in FIG. 5A). Importantly, the merging of the two images resulted in the appearance of yellow-orange structures indicating that the 3A4 and the anti-LAMP1 antibodies were present in the same structures (arrows, see yellow staining in the right panel in FIG. 5A). The co-localization of 3A4, which binds to KAAG1 on the surface of cancer cells, with LAMP1, a marker of late endosomes/lysosomes, shows that the antibody/antigen complex was internalized and that it follows a pathway that is amenable for the release of a payload that would be conjugated to the 3A4 antibody. Identical results were observed in another cancer cell line, TOV-21G (see FIG. 5B).

Taken together, these studies demonstrated that antibodies specific for KAAG1 such as 3A4 might have uses as an antibody-drug conjugate (ADC). Thus, the high level of ovarian cancer specificity of KAAG1 coupled with the capacity of this target to be internalized in cells would support the development of applications as an ADC.

Example 5

Preferential Detection of KAAG1 on the Surface of Cancer Cells.

Although several antibodies interacting with different epitopes of the KAAG1 protein were developed, the accessibility of these epitopes when KAAG1 is expressed on the surface of intact cancer cells was not fully elucidated. Bioinformatics analysis of the primary amino acid structure of KAAG1 (total number of amino acids in the human protein is 84) did not reveal any obvious sequences that might correspond to a transmembrane domain and therefore how KAAG1 was anchored to the cell membrane was not fully known.

The antibodies generated against KAAG1 were found to bind to three different regions in the KAAG1 protein (see PCT/CA2009/001586). Most of the antibodies interact with amino acids 35-60 in the KAAG1 protein and are exemplified by antibodies 3D3 and 3G12 in this application. Antibodies that interact with the carboxy-terminal end of KAAG1 between amino acids 61-84 are exemplified by antibody 3A4. Finally, antibodies that interact with the amino-terminal region of the protein, as exemplified by 3C4, showed very little binding to cells that express KAAG1.

This application shows that when KAAG1 is expressed in cells, the carboxy-terminal region (amino acids 61-84) is exposed to the extracellular space and that antibodies that target this region are the most efficient at detecting and potentially treating KAAG1-positive cells. Antibodies that bind to the middle region of KAAG1 (amino acids 35-60) can also detect KAAG1 on the cells surface but to a lesser extent than antibodies that interact with the carboxy-terminus.

Figure 6A:
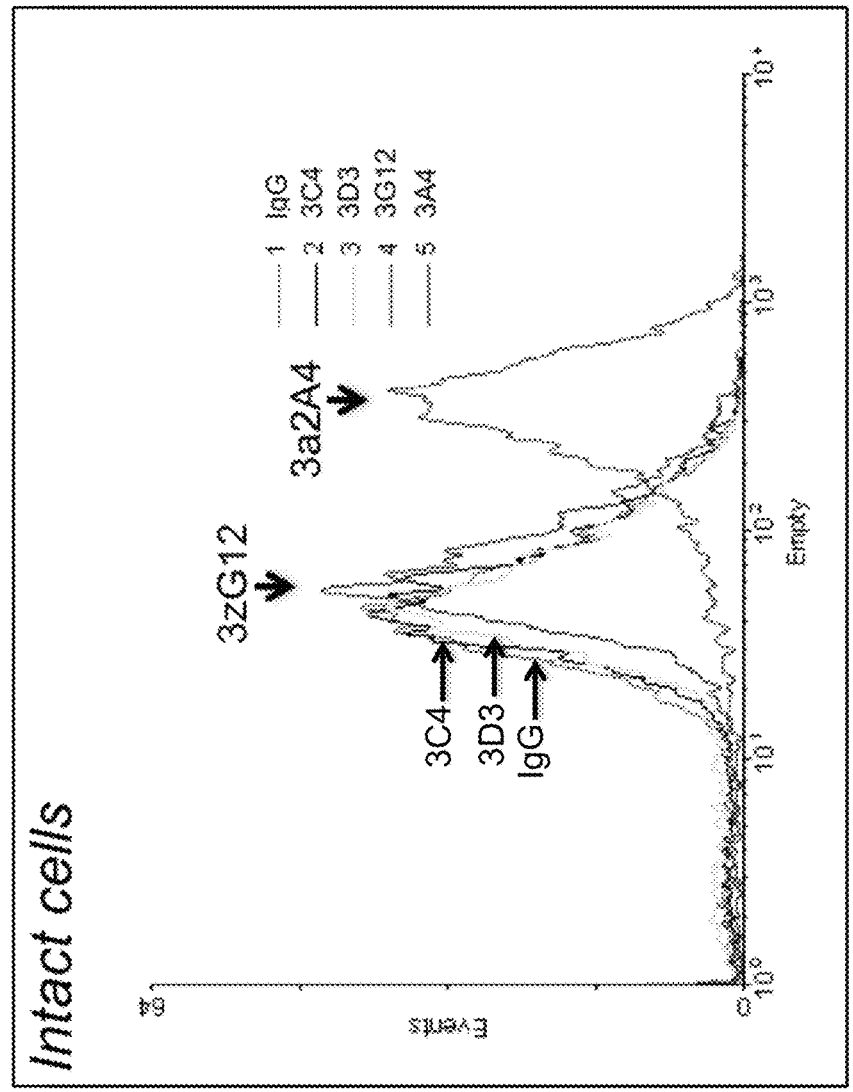
FIGS. 6A and 6B are graphs representing FACs analysis of tumor cells exposed to different anti-KAAG1 antibodies.

Ovarian cancer cell lines such as SKOV-3, are positive for KAAG1 expression. These cells were used to detect the expression KAAG1 by flow cytometry, which is a method that allows the detection of cell surface proteins and is well known by those skilled in the art. Briefly, for each sample 100,000 cells were incubated on ice for 1 h with the primary antibody (either anti-KAAG1, or the control antibody) at a concentration of 1 µg/ml. After several washes with ice-cold PBS, the stained cells were incubated with the secondary antibody that was conjugated to a fluorochrome (FITC) which detects the presence of the primary antibody bound to the cells. After several additional washes, the cells were analyzed with a flow cytometer. The results expressed in FIG. 6 show the Y-axis representing the number of counts (cells) and the X-axis representing the quantity of fluorescence (fluorescence signal). When SKOV-3 cells were incubated with the 3A4 antibody, a large shift in fluorescence was observed indicating that there was abundant KAAG1 protein on the surface of the cells (FIG. 6A) and that it was efficiently recognized by this antibody. Under identical conditions, the antibodies that interact with the middle region of KAAG1, 3G12 and 3D3 (FIG. 6A) were significantly less efficacious for detecting KAAG1. When the cells were incubated with increased concentration of 3G12 or 3D3, KAAG1 could be detected on the cell surface (not shown). When the cells were incubated with either the control IgG (FIG. 6A) or the 3C4, an antibody against the amino terminus of KAAG1 (FIG. 6A), no signal was observed. These results indicate that antibodies that interact with the carboxy-terminus of KAAG1 can detect the antigen on the surface of cancer cells more efficiently then antibodies directed against other regions of KAAG1. This implied that the carboxy-terminus of KAAG1 is exposed to the extracellular (outside) space of the cell. Similar results were obtained for other cancer cell lines that express KAAG1.

Figure 6B:
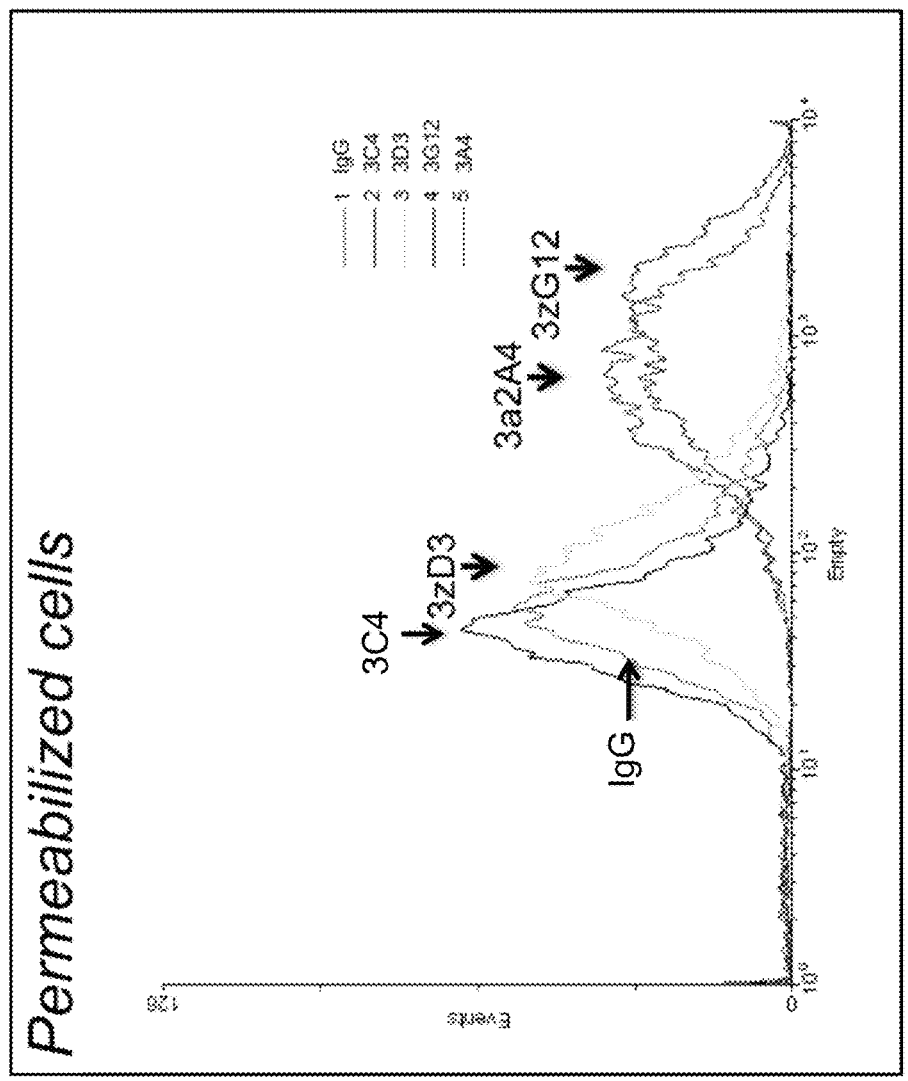

The experiment was also performed in SKOV-3 cells that were permeabilized with Triton X-100. Triton X-100 is typically used to permeabilize cell membranes and release membrane proteins. When the permeabilized cells were incubated with 3A4 and measured in the flow cytometer (see FIG. 6B), the signal was similar to that obtained in intact cells. Strikingly, when the permeabilized cells were incubated with the 3G12 antibody that binds to the middle region of KAAG1 (FIG. 6B), the signal was as strong as the 3A4. These results indicate that the middle region of KAAG1 is likely present in the cell membrane or the inside of the cell. A similar result was obtained with the 3D3 antibody, another middle-region binder (FIG. 6B) but the signal obtained for 3D3 was not as strong. As before, IgG control did not show any detectable signal in this assay (FIG. 6B). Interestingly, incubation of the cells with the 3C4 antibody which binds to the amino region of KAAG1, did not result in any detectable signal (FIG. 6B). This last result suggested that the amino region of KAAG1 is likely cleaved off during the transport of the protein to the cell membrane.

Figure 7:
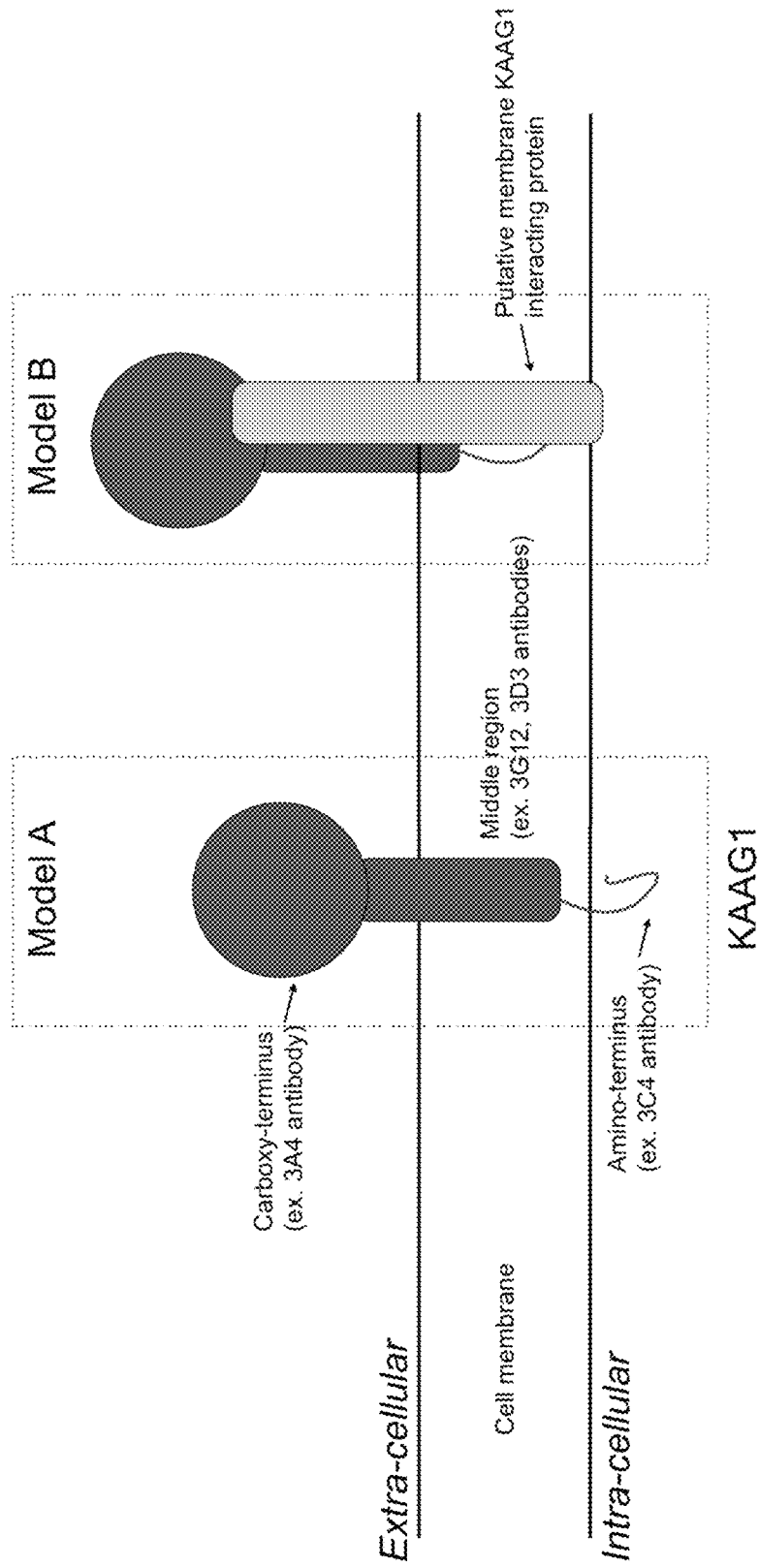
FIG. 7 are schematics representing 2 likely representation of the KAAG1 orientation in the cell membrane.

Overall, these experiments provide much insight into the structure and orientation of the KAAG1 antigen when it is expressed on the surface of cancer cells. Based on these data, two models for the structure of KAAG1 at the cell surface is proposed (FIG. 7). In the first model (FIG. 7, Model A), the data suggests that the middle portion is actually the transmembrane region of KAAG1 that is only partially exposed to the extra-cellular space. This would make the carboxy-terminus of KAAG1 easily detectable and the middle region more difficult to bind. In the second model (FIG. 7, Model B), KAAG1 is anchored to the membrane by another protein that itself is embedded in the cell membrane. Again, the carboxy-terminus would be easily accessible by antibodies such as 3A4 but the interaction between KAAG1 and the protein partner would make access to the middle region difficult. The results showing that antibodies consisting of both the carboxy-terminal binders (as exemplified by 3A4) and middle-region binders (as exemplified by 3G12 and 3D3) tested in the presence of permeabilized cells is in agreement with both models. The inability of the 3C4 antibody to bind to KAAG1 in intact or permeabilized cells is likely due to the lack of amino acids contained in the amino-terminus of the mature processed membrane form of KAAG1 and both models are in agreement with this.

These results imply that antibodies that target the carboxy-terminus of KAAG1 in cancer cells, in particular the region spanned by amino acids 61-84, are the most appropriate for the development of antibodies for uses as therapeutics for the treatment of carcinomas that express KAAG1. In addition, other uses for the KAAG1 antibodies that bind to the carboxy-terminal region include diagnostic reagents for the detection of carcinomas that express KAAG1.

Antibodies or antigen binding fragments having a binding specificity similar to the 3A4 antibody may be generated or isolated by immunizing an animal with the C-terminal portion of KAAG1 according to methods known in the art, including hybridoma technology, by screening a library of antibody or antigen binding fragments with the C-terminal portion of KAAG1 and/or performing competition assay of isolated antibodies or antigen binding fragment with the 3A4 antibody described herein.

Example 6

Humanization by Design of the 3A4 Mouse Monoclonal Antibody

3D Modeling of the Variable Regions of the Mouse 3A4 Monoclonal Antibody.

Figure 8:
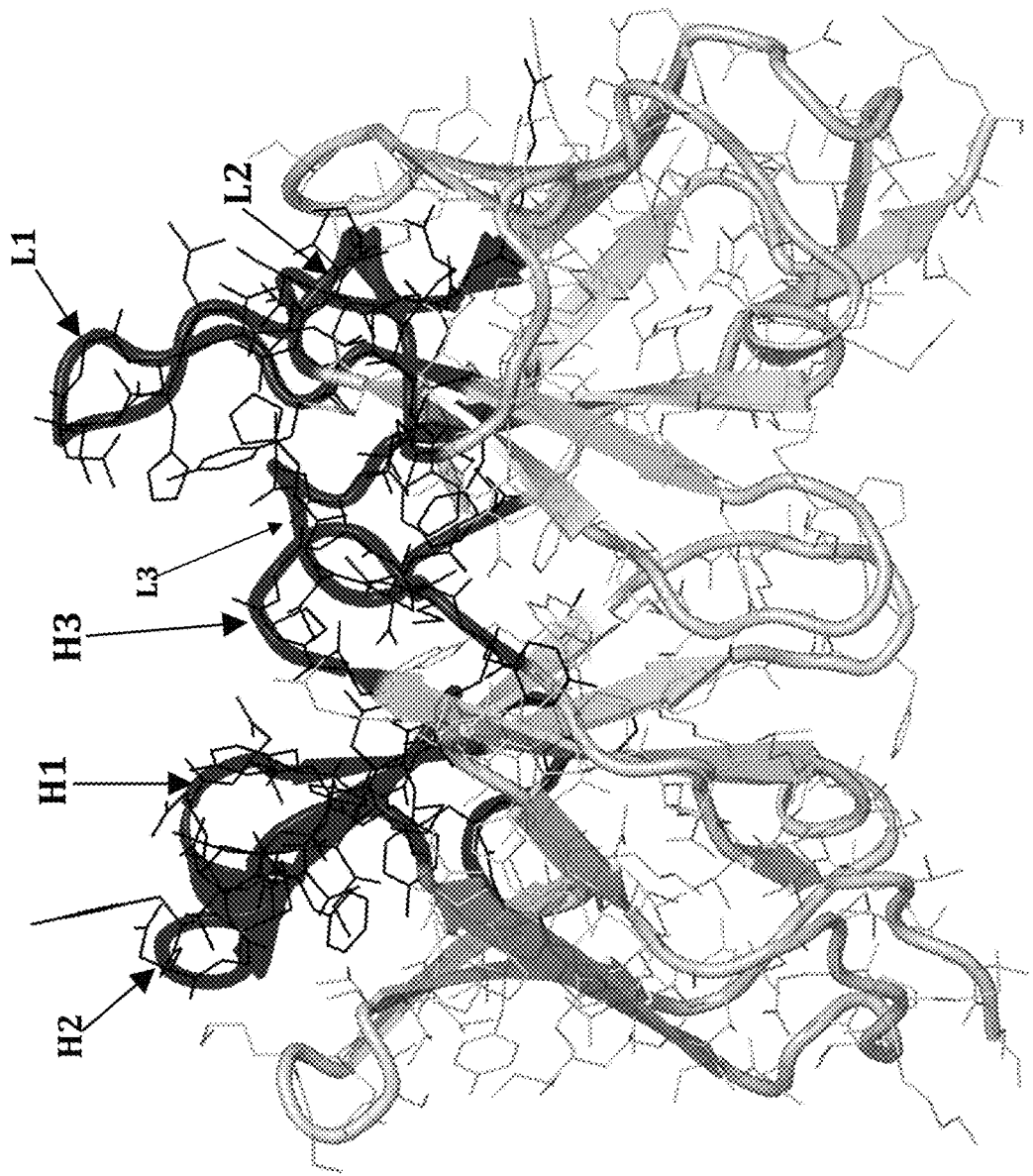
FIG. 8 is a molecular model (ribbon diagram) of the murine 3A4 variable domain. CDR loops are colored in black and labelled L1, L2 and L3 in the light chain and H1, H2 and H3 in the heavy chain. The framework region is shown in gray.
Figure 9A:
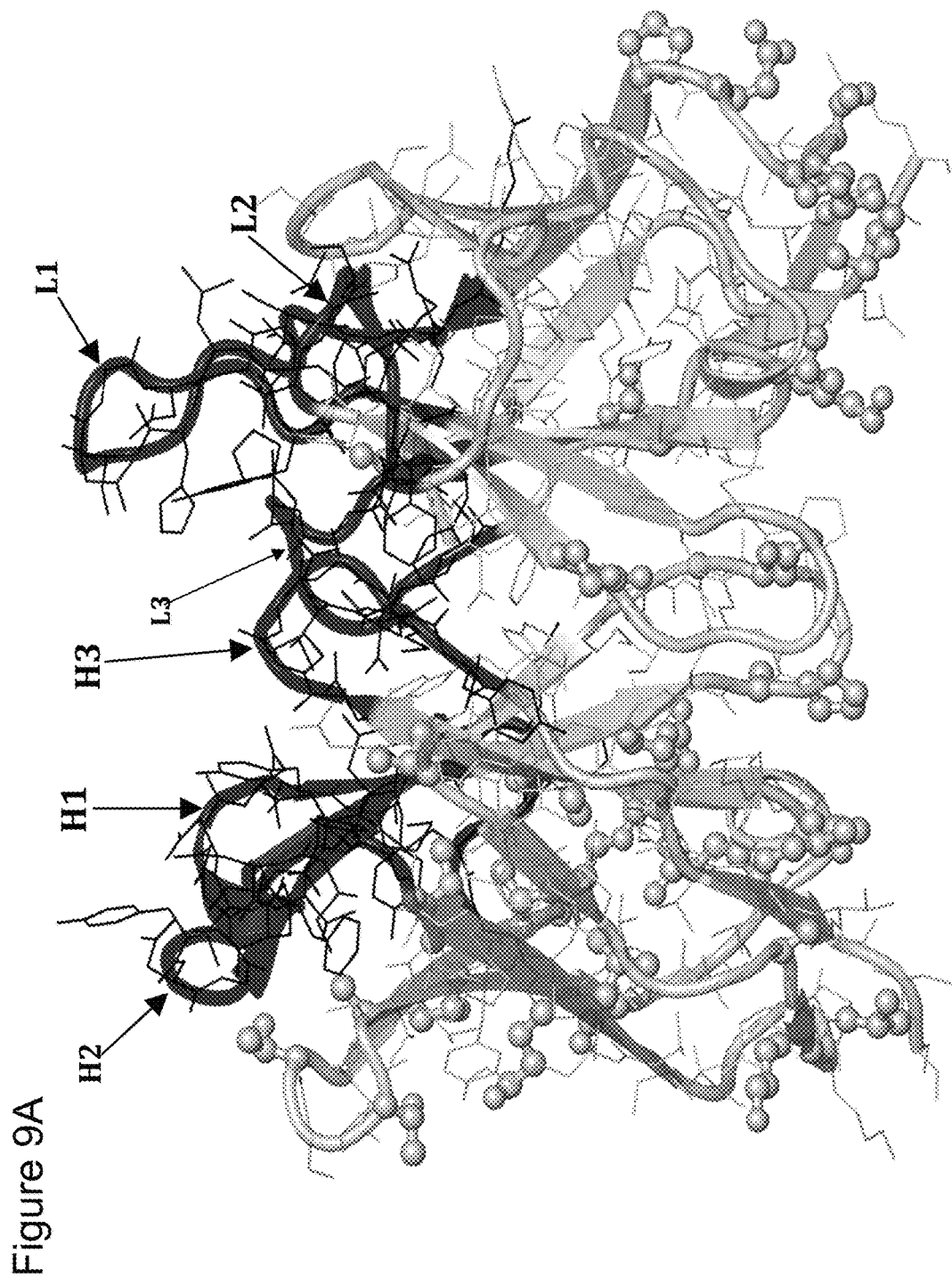
FIG. 9A is a molecular models of humanized antibody Lh1Hh1 (i.e., humanized light chain 1 and humanized heavy chain 1) of 3A4 variable domains. CDR loops are colored in black and labelled L1, L2 and L3 in the light chain and H1, H2 and H3 in the heavy chain. The framework region is shown in gray. The side-chains of residues mutated from murine framework to human framework are rendered in ball-and-stick representation. Lh1 designated the humanized light chain of variant 1 and Hh1 designated the heavy chain of variant 1.
Figure 9B:
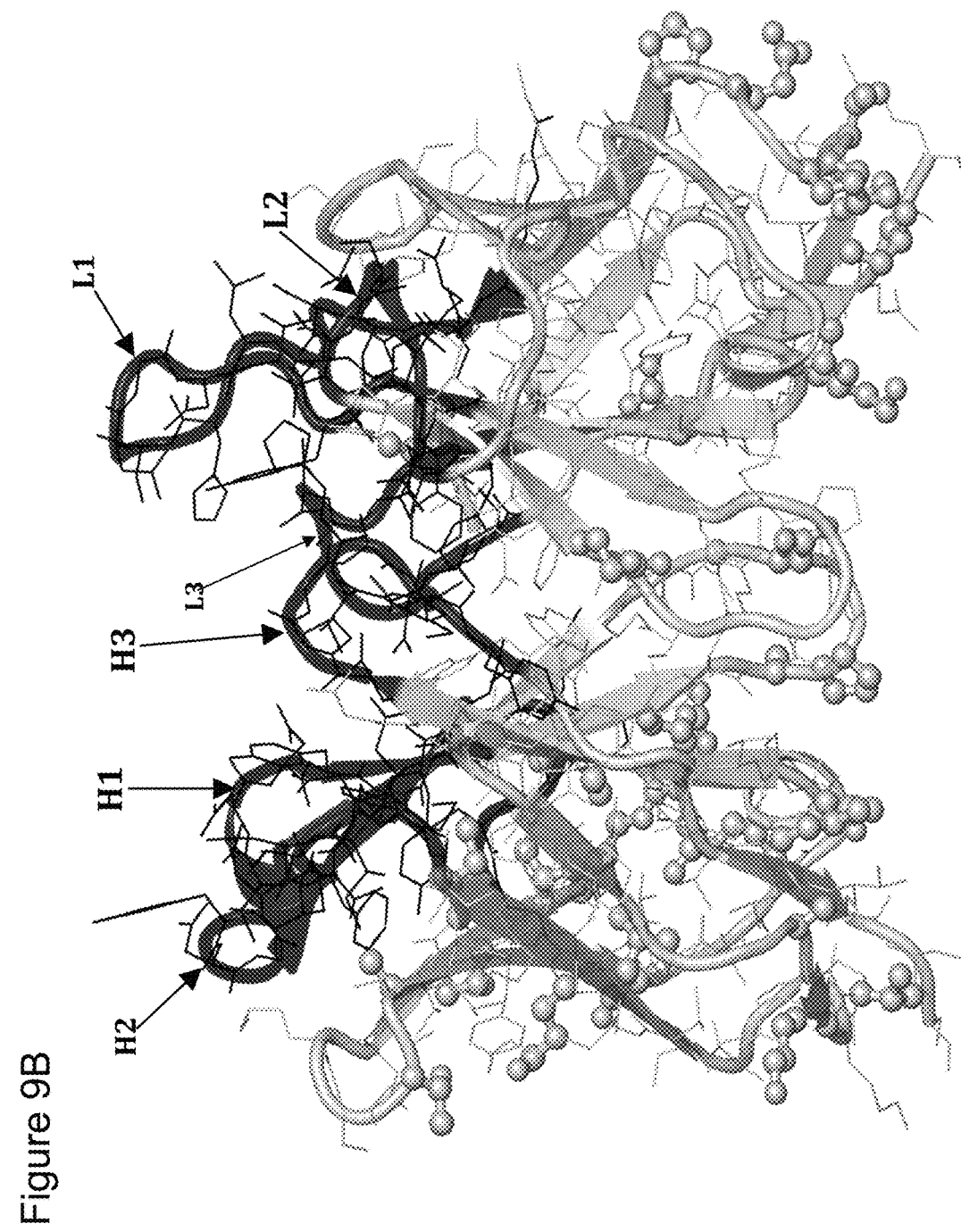
FIG. 9B is a molecular models of humanized antibody Lh1 Hh2 (i.e., humanized light chain 1 and humanized heavy chain 2) of 3A4 variable domains. CDR loops are colored in black and labelled L1, L2 and L3 in the light chain and H1, H2 and H3 in the heavy chain. The framework region is shown in gray. The side-chains of residues mutated from murine framework to human framework are rendered in ball-and-stick representation. Lh1 designated the humanized light chain of variant 1 and Hh2 designated the heavy chain of variant 2.
Figure 9C:
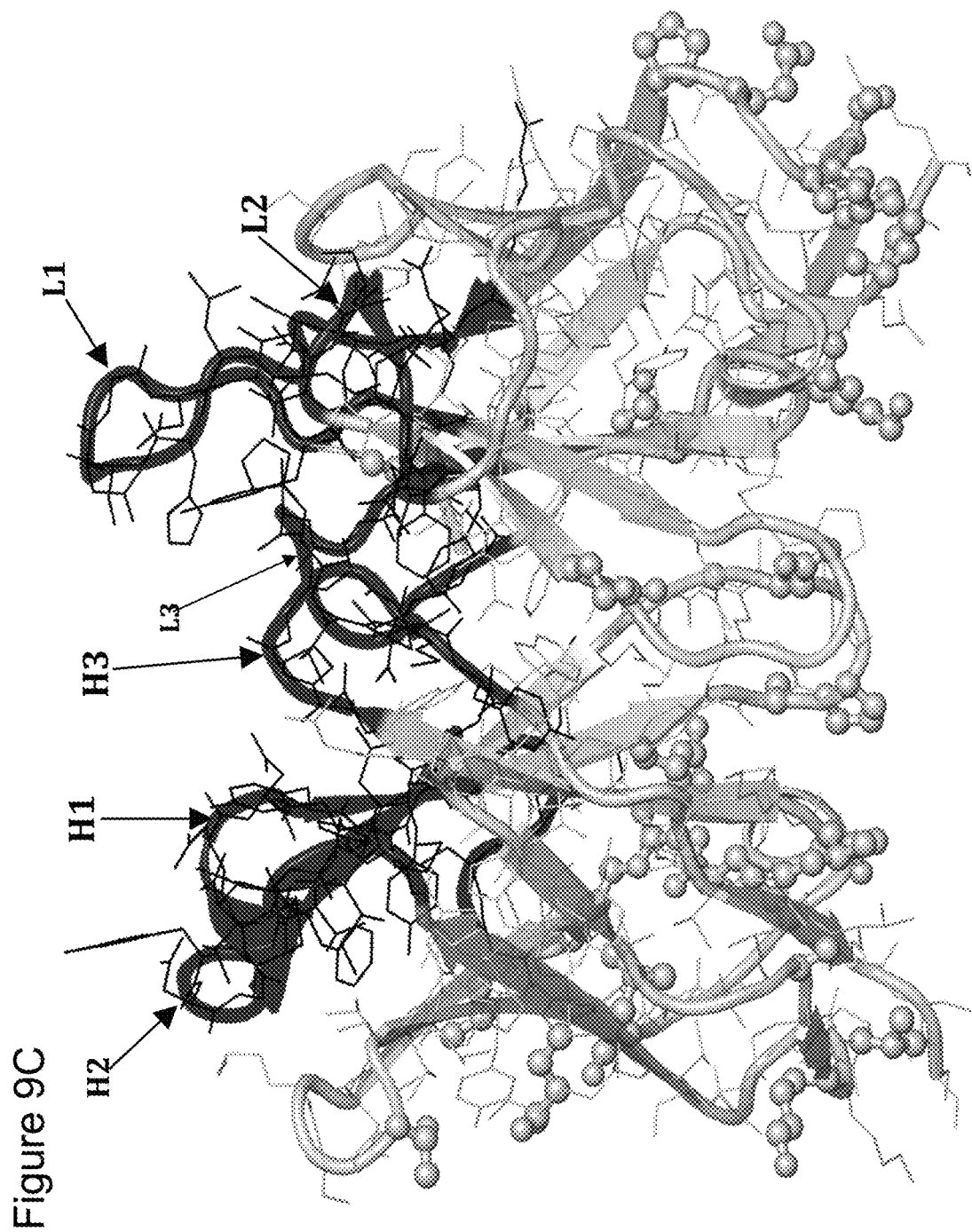
FIG. 9C is a molecular models of humanized antibody Lh1 Hh3 (i.e., humanized light chain 1 and humanized heavy chain 3) of 3A4 variable domains. CDR loops are colored in black and labelled L1, L2 and L3 in the light chain and H1, H2 and H3 in the heavy chain. The framework region is shown in gray. The side-chains of residues mutated from murine framework to human framework are rendered in ball-and-stick representation. Lh1 designated the humanized light chain of variant 1 and Hh3 designated the heavy chain of variant 3.
Figure 9D:
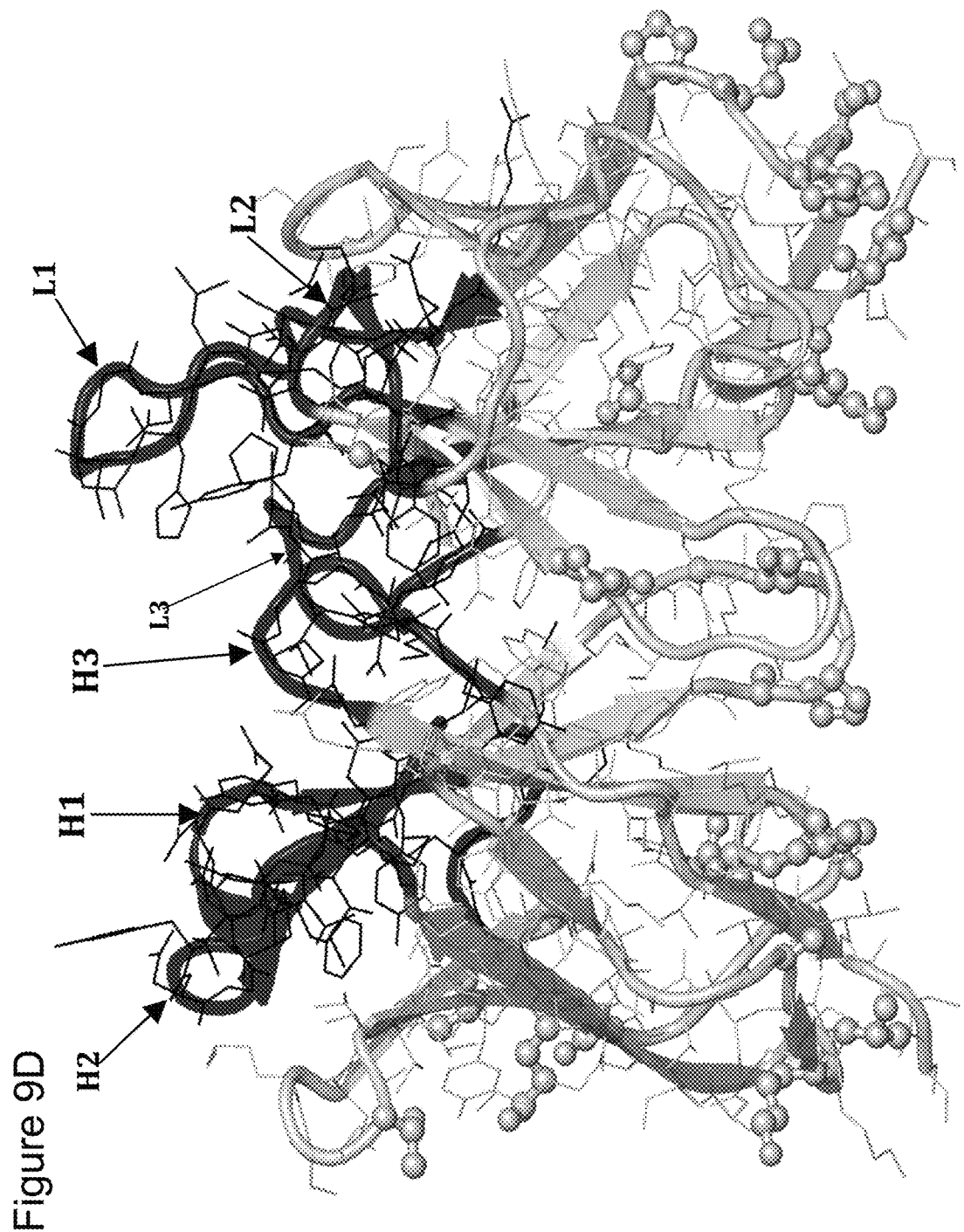
FIG. 9D is a molecular models of humanized antibody Lh1 Hh4 (i.e., humanized light chain 1 and humanized heavy chain 4) of 3A4 variable domains. CDR loops are colored in black and labelled L1, L2 and L3 in the light chain and H1, H2 and H3 in the heavy chain. The framework region is shown in gray. The side-chains of residues mutated from murine framework to human framework are rendered in ball-and-stick representation. Lh1 designated the humanized light chain of variant 1 and Hh4 designated the heavy chain of variant 4.
Figure 9E:
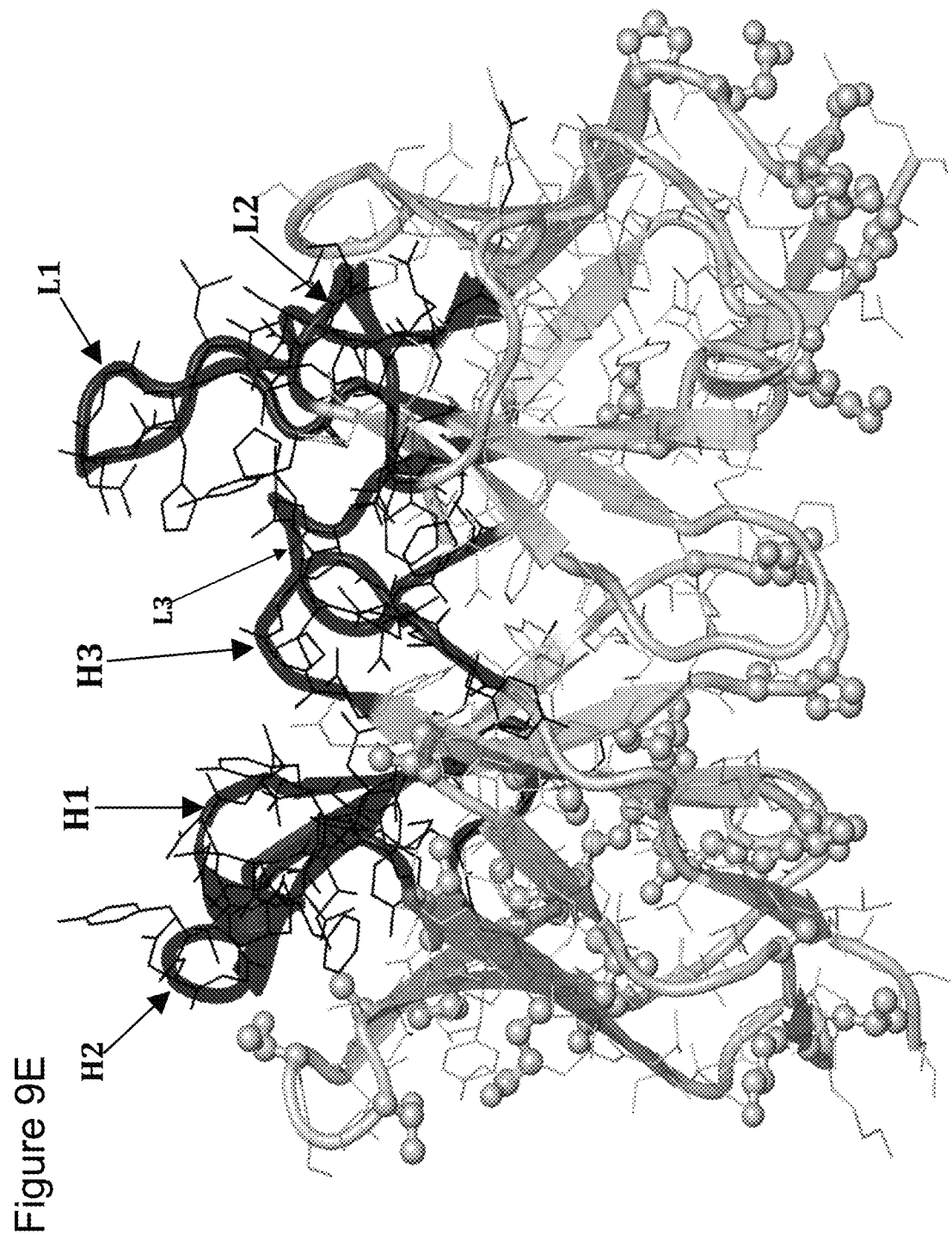
FIG. 9E is a molecular models of humanized antibody Lh2Hh1 (i.e., humanized light chain 2 and humanized heavy chain 1) of 3A4 variable domains. CDR loops are colored in black and labelled L1, L2 and L3 in the light chain and H1, H2 and H3 in the heavy chain. The framework region is shown in gray. The side-chains of residues mutated from murine framework to human framework are rendered in ball-and-stick representation. Lh2 designated the humanized light chain of variant 2 and Hh1 designated the heavy chain of variant 1.
Figure 9F:
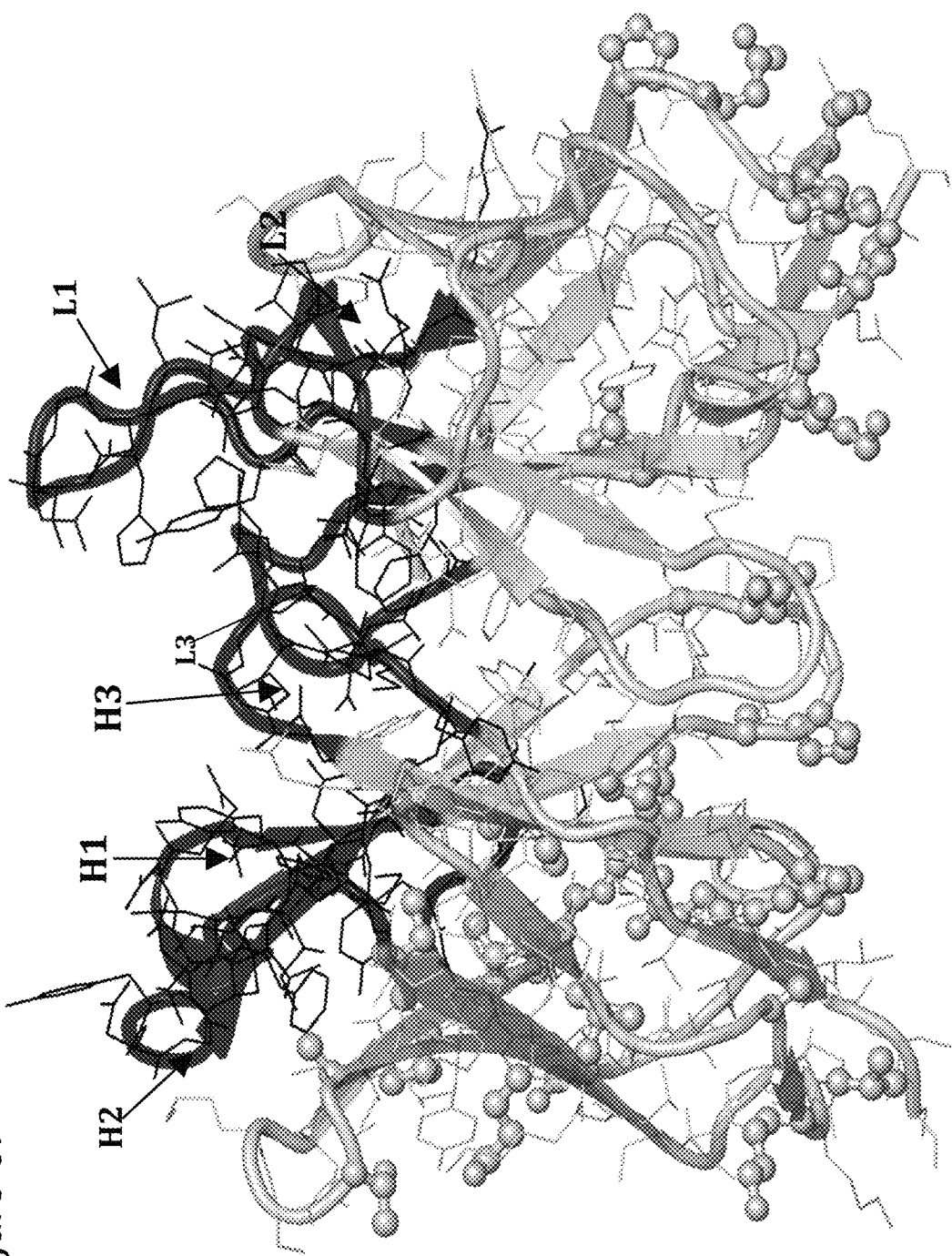
FIG. 9F is a molecular models of humanized antibody Lh2Hh2 (i.e., humanized light chain 2 and humanized heavy chain 2) of 3A4 variable domains. CDR loops are colored in black and labelled L1, L2 and L3 in the light chain and H1, H2 and H3 in the heavy chain. The framework region is shown in gray. The side-chains of residues mutated from murine framework to human framework are rendered in ball-and-stick representation. Lh2 designated the humanized light chain of variant 2 and Hh2 designated the heavy chain of variant 2.
Figure 9G:
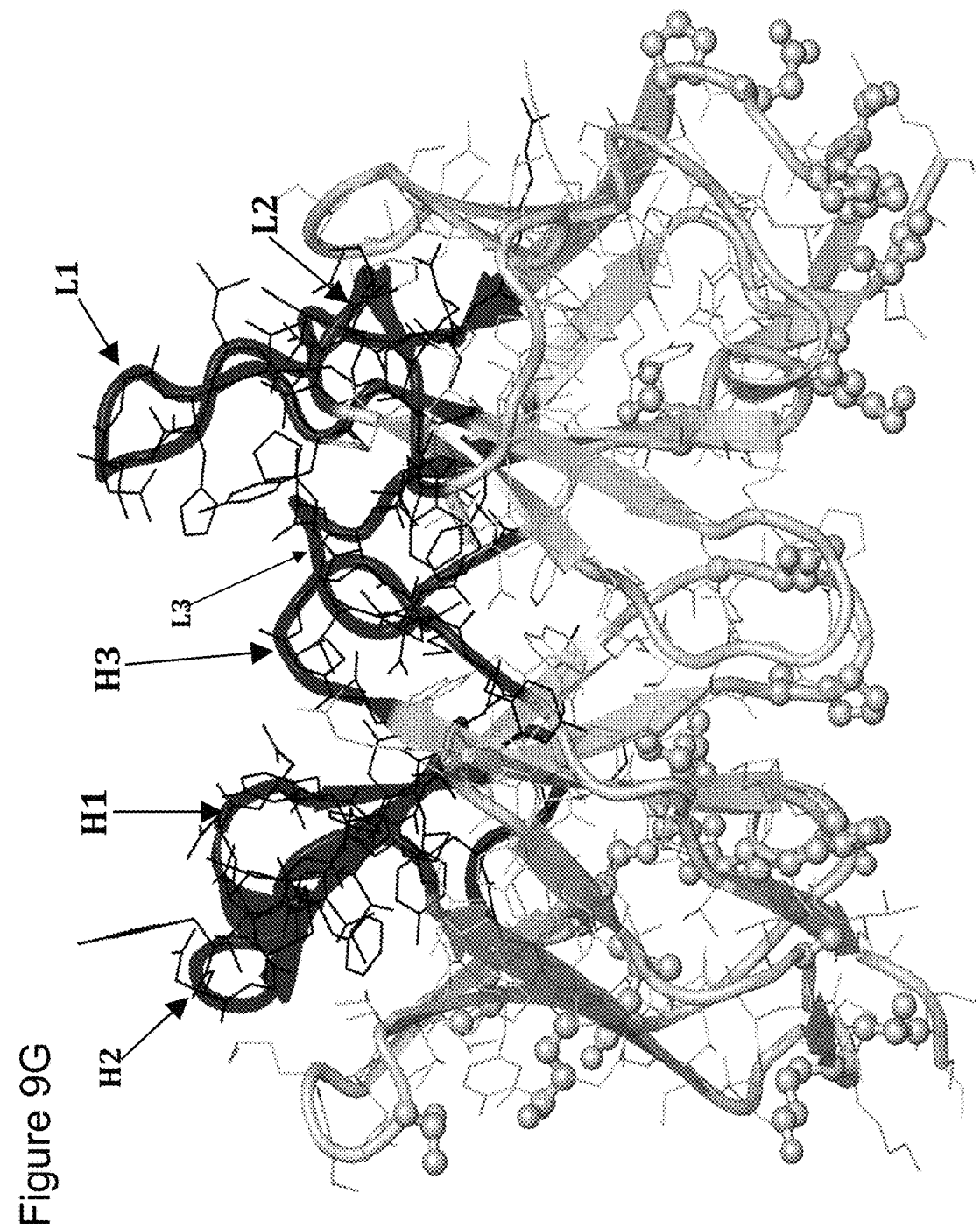
FIG. 9G is a molecular models of humanized antibody Lh2Hh3 (i.e., humanized light chain 2 and humanized heavy chain 3) of 3A4 variable domains. CDR loops are colored in black and labelled L1, L2 and L3 in the light chain and H1, H2 and H3 in the heavy chain. The framework region is shown in gray. The side-chains of residues mutated from murine framework to human framework are rendered in ball-and-stick representation. Lh2 designated the humanized light chain of variant 2 and Hh3 designated the heavy chain of variant 3.
Figure 9H:
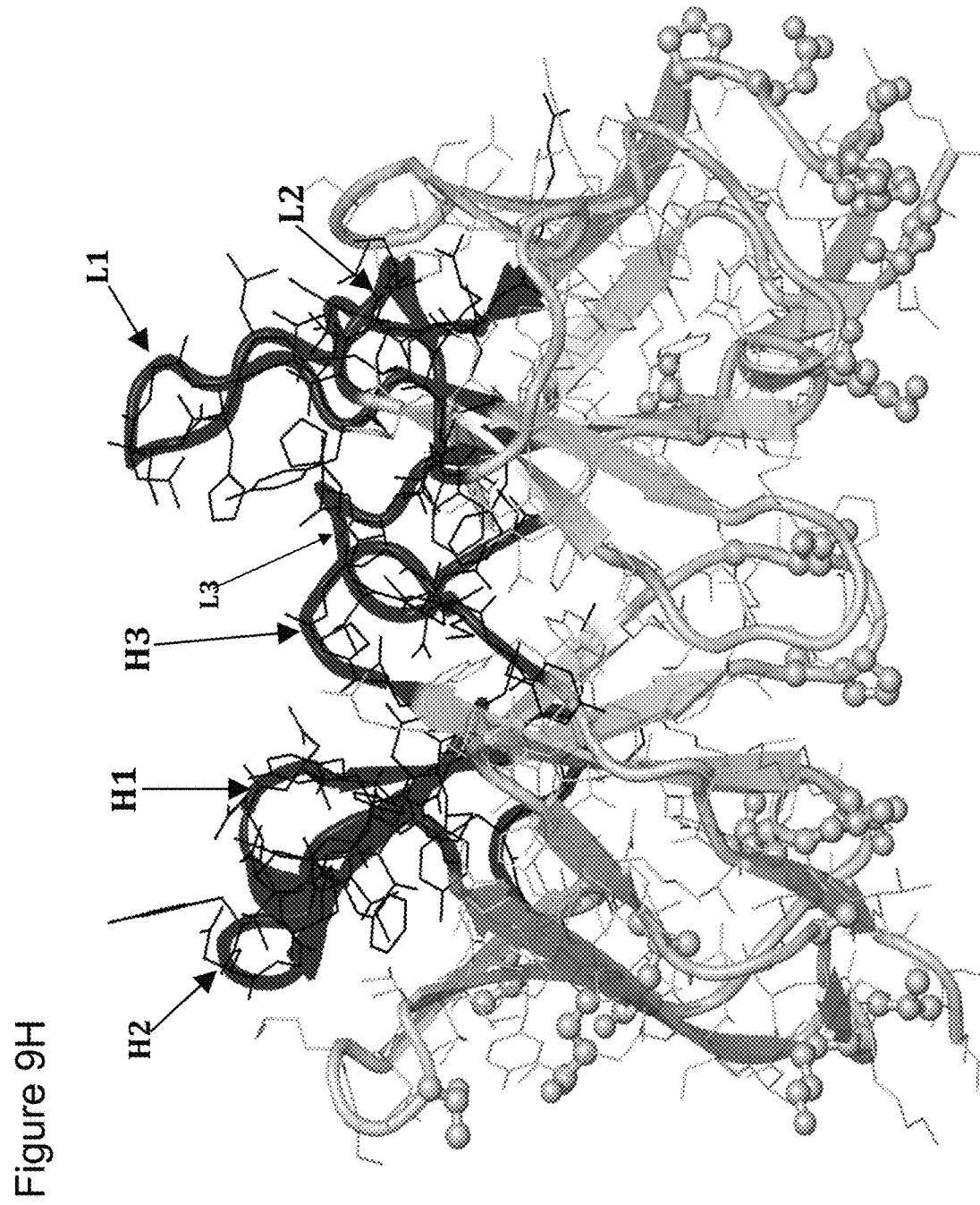
FIG. 9H is a molecular models of humanized antibody Lh2Hh4 (i.e., humanized light chain 2 and humanized heavy chain 4) of 3A4 variable domains. CDR loops are colored in black and labelled L1, L2 and L3 in the light chain and H1, H2 and H3 in the heavy chain. The framework region is shown in gray. The side-chains of residues mutated from murine framework to human framework are rendered in ball-and-stick representation. Lh2 designated the humanized light chain of variant 2 and Hh4 designated the heavy chain of variant 4.

This task was accomplished by homology modeling. The most similar template structures to the murine 3A4 variable region sequences of the light and heavy chains (SEQ ID NOs: 4 and 2) were identified by a BLAST search against PDB. To build an initial model of the mouse 3A4 variable region the following template structures were used (PDB codes): 2IPU (chain L) for the light chain, and 1F11 (chain B) for the heavy chain. Other suitable templates can be found in the PDB entry 2DDQ for the light chain, and in the PDB entries 3IY3, 1KTR, 2VXT, 1A6T ad 1IGI for the heavy chain. Required mutations were operated on these template structures according to the murine 3A4 sequences: 7 mutations in the 2IPU light chain, and 17 mutations plus a 3-residue deletion in the 1F11 heavy chain. The mutated structures corresponding to the heavy and light chains of the murine 3A4 variable regions were assembled into two-chain antibody structures by superimposing the heavy and light chains of the respective template structures. The resulting structure of the assembled 3A4 variable region was first refined by energy minimization with the AMBER force-field and a stepwise release of constraints, ranging from the CDR loops that were relaxed first, to the backbone heavy atoms of the framework region that were fully relaxed only in the last stage. The CDR-H3 loop in each antibody variable region structure was then refined by Monte-Carlo-minimization (MCM) conformational sampling, in which dihedral angles in the CDR-H3 region were sampled in each MCM cycle followed by energy minimization of a predefined region extending 10 Å around the initial conformation of the CDR-H3 loop. A representation of the modeled variable region of the mouse 3A4 antibody is given in FIG. 8. The structures of the human or humanized variable sequences most similar to each of the 3A4 variable sequences were also identified from PDB, and then superimposed onto the modeled structures of the murine 3A4 variable regions. These structures include PDB entries 3QCT, 3AAZ, 1WT5 and 3M8O for the light chain, and PDB entries 1I9R, 3NFP, 1T04, 1ZA6, 3HC4, 2D7T and 1WT5 for the heavy chain. These structures were used to assist in the modeling of mutations in the framework region in order to build the humanized 3D-structures starting from the modeled murine 3D-structure.

Characterization of the Mouse 3A4 Amino-Acid Sequences and Modeled Structure.

This step was carried out to estimate the humanness index, antigen contact propensity index, to delineate the CDRs, canonical residues, inter-chain packing (VH/VL interface residues), variable-/constant-region packing (VH/CH and VL/CL interface residues), unusual framework residues, potential N- and O-glycosylation sites, buried residues, Vernier zone residues, and proximity to CDRs. Internet-available resources and local software were used to assess these properties.

Selection of the Best Human Light-Chain and Heavy-Chain Frameworks for the Mouse CDRs.

This was done by standard sequence homology comparison against a local copy of human germline databases (VBASE), against other sequence libraries (Genbank and SwissProt), as well as the set of human framework consensus sequences. BLAST searches were conducted to retrieve sequence matches with highest homology in the framework region only (thus excluding CDRs) while matching the length of the CDR loops. The human frameworks identified for the light and heavy chains of the 3A4 antibody correspond to the k2 and h1 classes, respectively. Several human germline framework sequences that are most similar to the 3A4 framework sequences were retained in addition to the human consensus sequences for these classes.

Identification of Framework Residues for Back-Mutations and Design of Multiple Humanized Variants.

This is an important step that flags amino-acid residues that should be mutated to the corresponding human sequences with particular care. These residues represent primary candidates for back-mutations to the mouse sequences in case of affinity loss. It is the most difficult and unpredictable step of humanization by design, particularly in the absence of an experimental structure of the antibody-antigen complex. It relies on the identification of residues in one or more of the following categories: canonical, CDR-H3, Vernier zone, unusual, CDR-proximal (within 5 Å), inter-chain packing, and glycosylation-site residues. Such residues might affect antigen-binding site and affinity directly or indirectly. The antigen contact propensity index as well as amino-acid occurrence in human germline databases at each position are also extremely important in deciding whether a certain residue can be safely mutated from the mouse sequence to the human sequence. Humanization of the 3A4 antibody light chain variable region involves 11 mutations to its proposed humanized framework for 100% framework humanization. Humanization of the 3A4 antibody heavy chain variable region involves 23 mutations to its proposed humanized framework for 100% framework humanization. These 100% humanized variable region sequences are labelled Lvh1 and Hvh1, respectively (SEQ ID NOs:33 and 38). Additional humanized sequences were also designed in which several residues from the 3A4 mouse sequences were retained based on careful structural and comparative sequence analyses that indicate a high probability of altering antigen-binding affinity if mutations are to be introduced at these positions. These sequences of the variable regions are labelled Lvh2, Hvh2, Hvh3 and Hvh4 (SEQ ID NOs: 34, 39, 40 and 41).

The two humanized light chain variants (including the constant region) are identified herein as Lh1 (SEQ ID NO.: 43) and Lh2 (SEQ ID NO.:44). The four humanized heavy chain variants (including the constant region_ are identified herein as Hh1 (SEQ ID NO.:46), Hh2 (SEQ ID NO.:47), Hh3 (SEQ ID NO.:48) and Hh4 (SEQ ID NO.:49). The two humanized light chain and 4 humanized heavy chain can be assembled into 8 humanized antibodies (Lh1Hh1, Lh1Hh2, Lh1Hh3, Lh1Hh4, Lh2Hh1, Lh2Hh2, Lh2Hh3, and Lh2Hh4). Molecular models for all these combinations were constructed by homology modeling starting from the 3D model of the murine 3A4 variable region, and are depicted in FIG. 9A to 9H.

Figure 10A:
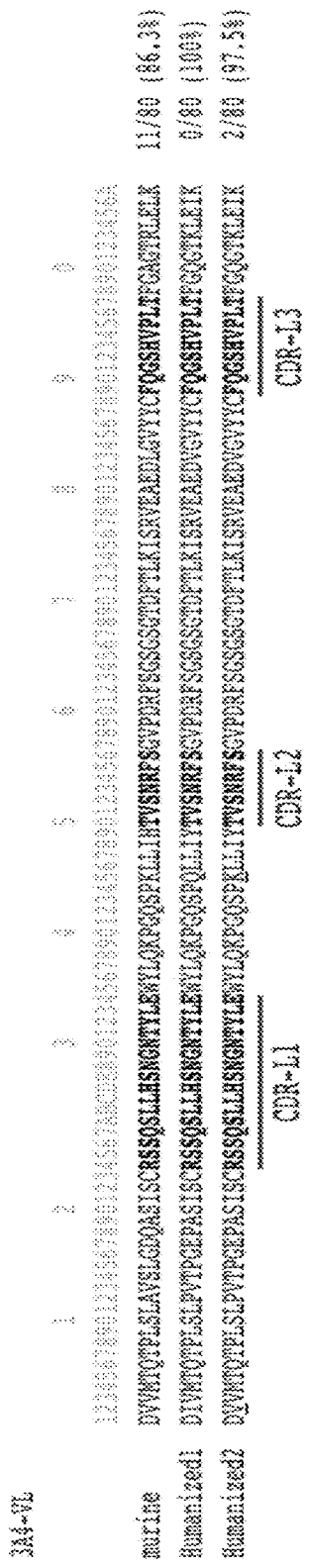
FIG. 10A is an amino acid sequence alignment of the 3A4 variable domains of the murine (SEQ ID NO.: 4) and humanized light chains (Humanized1=SEQ ID NO.:33; Humanized2=SEQ ID NO.:34). The light chain has two humanized variants (Lh1 an Lh2). The CDRs are shown in bold and indicated by CDR-L1, CDR-L2 and CDR-L3. Back mutations in the human framework regions that are murine amino acids are underlined in the humanized sequences.
Figure 10B:
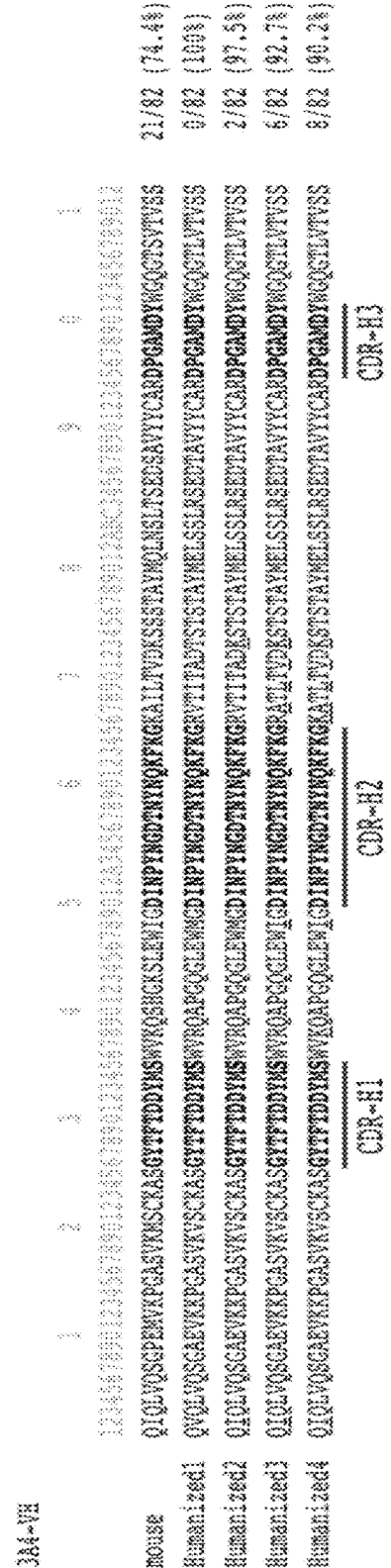
FIG. 10B is an amino acid sequence alignment of the 3A4 variable domains of the murine (SEQ ID NO.:2) and humanized heavy chains (Humanized1=SEQ ID NO.:38; Humanized2=SEQ ID NO.:39, Humanized3=SEQ ID NO.: 40; Humanized4=SEQ ID NO.:41). The heavy chain has four humanized variants (Hh1 to Hh4). The CDRs are shown in bold and indicated by CDR-H1, CDR-H2 and CDR-H3. Back mutations in the human framework regions that are murine amino acids are underlined in the humanized sequences.

In the case of 3A4 light-chain humanized sequence Lvh2 (SEQ ID NO:34), framework residues Val-L2 and Lys-L45 were retained from the mouse sequence since residue L2 is semi-buried, contacts both CDR-L1 and CDR-L3, and has antigen-contacting propensity, while residue L45 approaches the heavy-chain. We note that both these murine residues may occur in human frameworks. In the case of 3A4 heavy-chain humanized sequence Hvh2 (SEQ ID NO:39), framework residues Ile-H2 and Lys-L73 were retained from the mouse sequence since residue H2 is semi-buried, contacts both CDR-H1 and CDR-H3, and has antigen-contacting propensity, while residue H73 belongs to the Vernier zone supporting CDR-H2, and both these murine residues may occur in human frameworks. In the case of 3A4 heavy-chain humanized sequence Hvh3 (SEQ ID NO:40), Ile-H2 and Lys-L73 back-mutations were retained and in addition to these, framework residues Ile-H48, Ala-H67, Leu-H69 and Val-H71 were retained from the mouse sequence since all these additional murine residues are buried residues and belong to the Vernier zone supporting CDR-H2, and also murine residue H71 may occur in human frameworks. In the case of 3A4 heavy-chain humanized sequence Hvh4 (SEQ ID NO:41), all 6 back-mutations of the Hvh3 humanized variant were included plus additional two mouse framework residues Lys-H38 and Lys-H66 since they represent semi-buried residues close to CDR-H2. The resulting amino acid sequences of the murine and humanized chains are listed in Table 1. The alignment of the murine and humanized light chain variable regions is shown in FIG. 10A and the alignment of the murine and humanized heavy chain variable regions is shown in FIG. 10B.

FIGS. 11A and 11B represent alignments of the murine light chain variable region with the 100% humanized light chain variable region and the murine heavy chain variable region with the 100% humanized heavy chain variable region respectively. This figure illustrates the amino acids that are preserved and those that have been chosen for substitution.

Example 7

Assembly and Expression of 3A4 Humanized Variant Antibodies

The purpose of these investigations is to determine the kinetics parameters of anti-clusterin antibodies. In particular, to determine whether the humanization of the 3A4 anti-KAAG1 monoclonal antibody affects the kinetics parameters of its binding to human KAAG1. To this end, a kinetic analysis method was developed using the ProteOn XPR36 instrument from BioRad. Human KAAG1 was immobilized on a sensor chip. Full length antibodies or Fab fragments were injected and allowed to interact with the immobilized KAAG1.

Construction of Plasmid Encoding the Chimeric (Murine) Heavy and Light Chains of 3A4

The heavy and light chains of the chimeric antibody were amplified by PCR from the original murine immunoglobulin chains using the following oligonucleotide primer pairs: heavy chain, 5'-oligo encoded by SEQ ID NO: 50 and 3'-oligo encoded by SEQ ID NO:51; light chain, 5'-oligo encoded by SEQ ID NO: 52 and 3'-oligo encoded by SEQ ID NO:53. The resulting PCR products were digested by Hind III and cloned into pK-CR5 (SEQ ID NO:21) previously digested with Hind III.

Construction of Plasmids Encoding the Humanized Heavy Chain 3A4 Variants 1, 2, 3 and 4

Figure 12A:
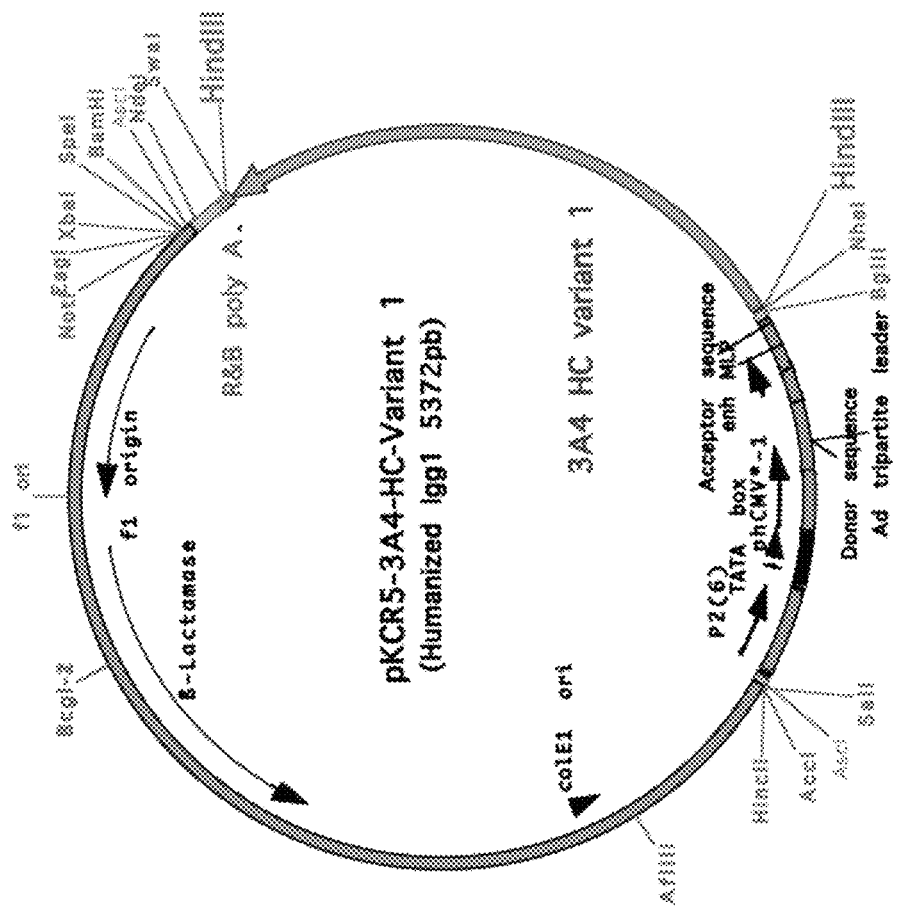
FIG. 12A represents plasmid Map of pKCR5-3A4-HC-Variant 1. The heavy chains of the humanized 3A4 variants were cloned in the same manner into the HindIII site of pK-CR5. Consequently the resulting plasmids are identical to pKCR5-3A4-HC variant 1 except for the sequence of the heavy chain immunoglobulin variable domain.

The fragments coding for the humanized heavy chain region of the antibody 3A4 (Hh1, Hh2, Hh3 and Hh4) were ordered from GenScript (Piscataway, USA). The DNA fragments including the kozak and stop codon sequences were digested with HindIII and cloned into the HindIII site of plasmid pK-CR5 previously dephosphorylated with calf intestinal phosphatase (NEB) to prevent recircularization. FIG. 12A shows the map of the plasmid pK-CR5-3A4-HC-variant1. All heavy chain variants of the humanized 3A4 were constructed in a similar manner.

Construction of Plasmids Encoding the Humanized Light Chain 3A4 Variants 1 and 2

Figure 12B:
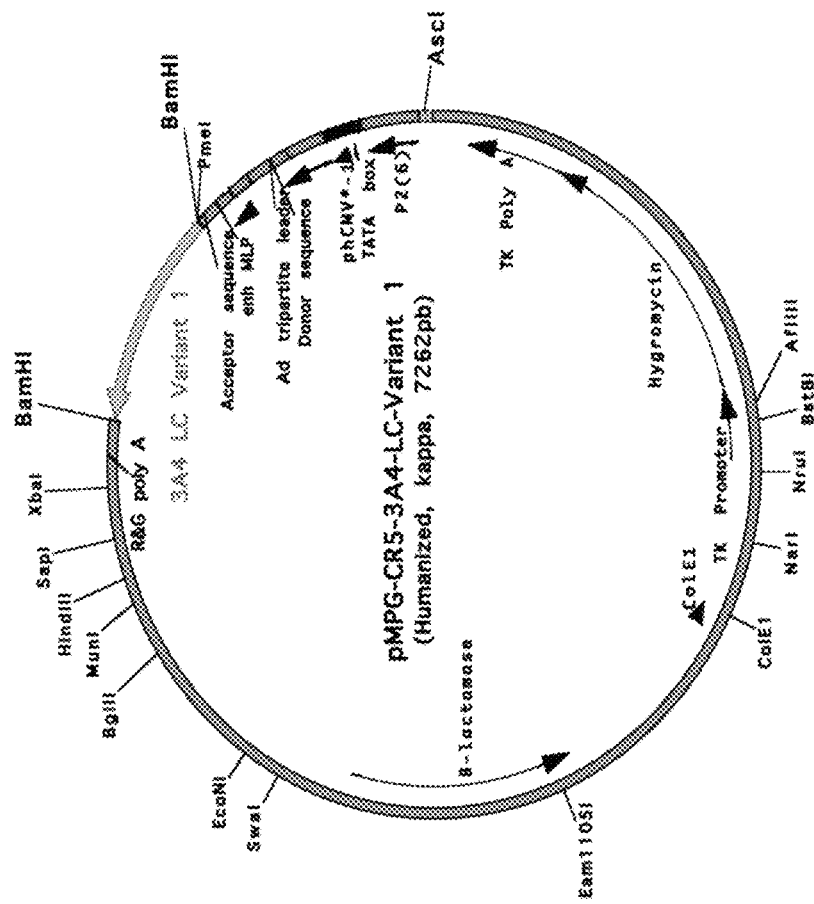
FIG. 12B represents plasmid Map of pMPG-CR5-3A4-LC-Variant 1. The light chains of the humanized variants 1 and 2 of 3A4 antibody were cloned in the same manner into the BamHI site of pMPG-CR5. Consequently, the resulting plasmid is identical to pMPG-CR5-3A4-LC-Variant 1, except for the sequence of the light chain immunoglobulin variable domain.

The fragments coding for the human light chain regions of the antibody 3A4 (Lh1 and Lh2) were ordered from GenScript. The DNA fragments including the kozak and stop codon sequences was digested with BamHI and cloned into the BamHI site of plasmid pMPG-CR5 (SEQ ID NO:55) previously dephosphorylated with calf intestinal phosphatase (NEB) to prevent recircularization. FIG. 12B shows the map of the plasmid pMPG-CR5-3A4-LC-variant1. All light chain variants of the humanized 3A4 were constructed in a similar manner.

Transient Transfection Study

Plasmid DNA was isolated from small cultures of *E. coli* using the Mini-Prep kit (Qiagen Inc, Mississauga, ON) according to the manufacturer's recommendation. Briefly, 2 ml of LB medium containing 100 μg/ml of ampicillin were inoculated with a single colony picked after ligation and transformation. The cultures were incubated at 37° C. overnight with vigorous shaking (250 RPM). The plasmid was then isolated from 1.5 ml of culture using the protocols, buffers, and columns provided by the kit. The DNA was eluted using 50 μl of sterile water. Plasmid DNA was isolated from large culture of *E. coli* using the Plasmid Plus Maxi kit (Qiagen Inc, Mississauga, ON) according to the manufacturer's recommendation. 200 mL of LB medium containing 100 μg/mL ampicillin were inoculated with a single fresh colony of *E. coli* and incubated overnight at 37° C. with vigorous shaking (250 RPM). The bacteria (130 mL of culture for the heavy chain and 180 mL of culture for the light chain) were pelleted by centrifugation at 6000×g, for 15 min, at 4° C. and the plasmid was isolated using the protocols, buffers and columns provided by the kit. The pure plasmids was resuspended in sterile 50 mM Tris, pH8 and quantified by measuring the optical density at 260 nm. Before transfection the purified plasmid were sterilized by extraction with phenol/chloroform followed by ethanol precipitation. The plasmid were resuspended in sterile 50 mM Tris, pH 8 and quantified by optical density at 260 nm.

Before transfection, the cells (CHO-cTA) were washed with PBS and resuspended at a concentration of $4.0 \times 10^6$ cell/ml in growth medium (CD-CHO, Invitrogen) without dextran sulfate for 3 h in suspension culture. For each plasmid combination, 45 ml of cells were transfected by adding slowly 5 ml of CDCHO medium supplemented with 10 μg/ml of each plasmid and 50 μg/ml of polyethylenimine (PEI Max; Polysciences). The final concentration was 1 μg/ml of each plasmid and 5 μg/ml of PEI. After 2 h, the cells were transferred at 30° C. The next days, 50 μg/mL of dextran sulfate and 3.75 ml of each supplement (Efficient Feed A and B Invitrogen) were added to the cells and they were incubated at 30° C. for 13 days. 2.5 ml of Feed A and 2.5 ml of Feed B were added at day 4, 6, 8 and 11. On day 13, the supernatant was clarified by centrifugation and filtered through a 0.22 μM filter.

CHO cells (CHOcTA) were transfected with plasmids encoding the different variants of humanized heavy and light chains of the 3A4 antibody regulated by the CR5 promoter. Transfection with different combinations of light and heavy chains was performed. As control, cells were also transfected with plasmids encoding the chimeric/murine antibody.

Figure 13:
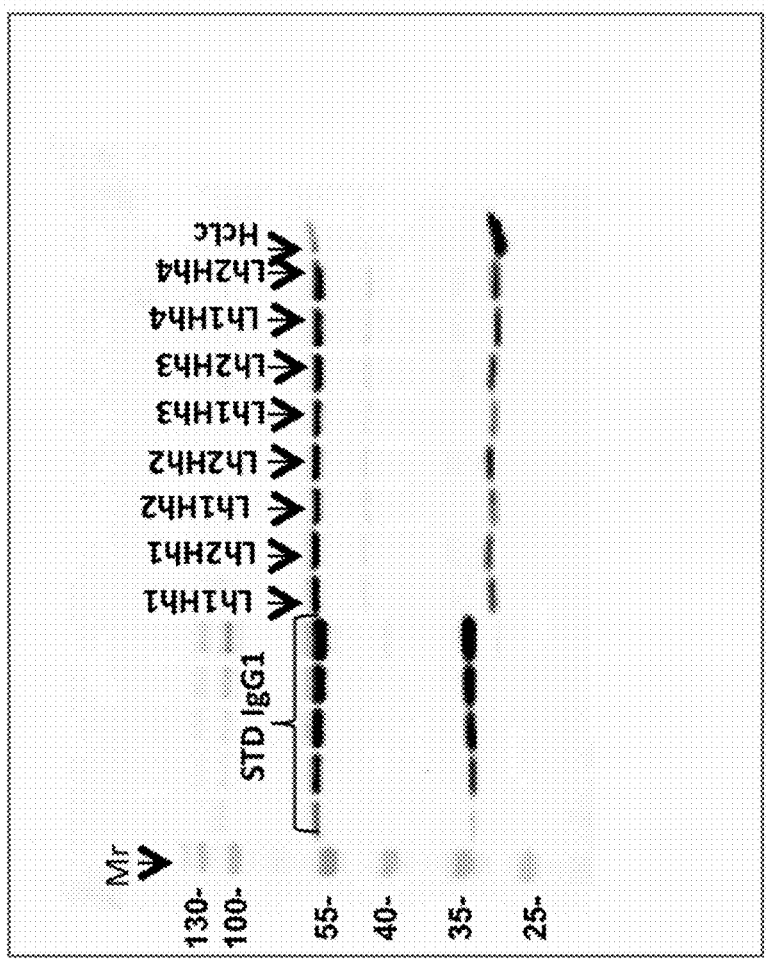
FIG. 13 represents an analysis of antibody production after transient transfection in CHO cells. Supernatant (13 days post-transfection) of CHOcTA cells transfected with the different combinations of light and heavy chains of humanized 3A4 antibody were analyzed by western blot. Quantification of antibody produced in the supernatants was determined after scanning the bands of the western blot against dilution of a known standard (human purified IgG antibody). Mr molecular weight marker (kDa).

Purification of Antibody 15 ml of supernatant from the CHO cell transfections were concentrated by centrifugation using the Amicon Ultra (Ultacell-50k) cassette at 1500 rpm. The concentrated antibody (550 μl) was purified using the Nab spin kit Protein A Plus (Thermo Scientific) according to the manufacture's recommendations. The purified antibodies were then desalted using PBS and the concentrating Amicon Ultra (Ultracel-10K) cassette at 2500 rpm to a final volume of 250 μl. The purified antibody was quantified by reading the $OD_{280}$ using the Nanodrop spectrophotometer and kept frozen at −20° C. An aliquote of the purified antibody was resuspended into an equal volume of Laemmli 2× and heated at 95° C. for 5 min and chilled on ice. A standard curve was made using known amount of purified human IgG1 kappa from Human Myeloma plasma (Athens Research). The samples were separated on a polyacrylamide Novex 10% Tris-Glycine gel (Invitrogen Canada Inc., Burlington, ON) and transferred onto a Hybond-N nitrocellulose membrane (Amersham Bioscience Corp., Baie d'Urfée, QC) for 1 h at 275 mA. The membrane was blocked for 1 h in 0.15% Tween 20, 5% skimmed milk in PBS and incubated for 1 hr with an Goat anti-Human IgG (H+L) conjugated to Cy5 (Jackson, Cat#109-176-099). The signal was revealed and quantified by scanning with the Typhoon Trio+scanner (GE Healthcare). As shown in FIG. 13, all combinations of the 3A4 humanized antibody variants were expressed in CHO cells.

Example 8

Kinetic Analysis of Murine and Humanized 3A4 Antibody Supplies

GLM sensorchips, the Biorad ProteOn amine coupling kit (EDC, sNHS and ethanolamine), and 10 mM sodium acetate buffers were purchased from Bio-Rad Laboratories (Mississauga, ON). HEPES buffer, EDTA, and NaCl were purchased from Sigma-Aldrich (Oakville, ON). Ten percent Tween 20 solution was purchased from Teknova (Hollister, Calif.). The goat anti-human IgG Fc fragment specific antibody was purchased from Jackson ImmunoResearch. The gel filtration column Superdex 75 10/300 GL was purchased from GE Healthcare.

Gel Filtration

Figure 14:
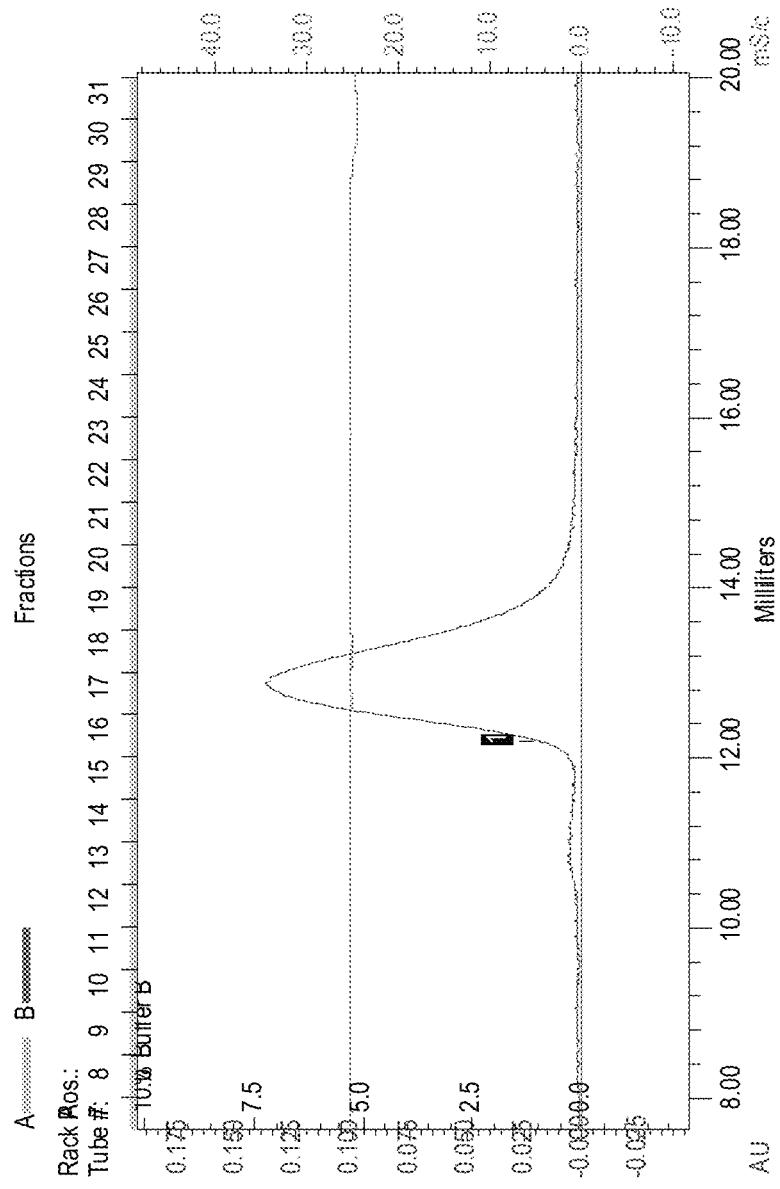
FIG. 14 is a graph of a Superdex G75 gel filtration of recombinant KAAG1 sample. KAAG1 was injected over the gel filtration and separated at 0.4 ml/min. The largest peak between fractions 15-19.

The KAAG1 protein at a concentration of 3.114 mg/ml and a volume of 220 μL was injected onto the Superdex G75 column. The separation was done at 0.4 ml/min in HBST running buffer (see below) without Tween 20. The volume of the fractions collected was 500 μL. Concentration of KAAG1 in each fractions was determined by $OD_{280}$ using an extension coefficient of 5500 and a MW of 8969. FIG. 14 represents the profile of the gel filtration of KAAG1. A small peak of potential aggregate is eluting at around 11 ml. The protein eluting at 13 ml was used as analyte for the SPR assay (fractions 15-19).

SPR Biosensor Assays

All surface plasmon resonance assays were carried out using a BioRad ProteOn XPR36 instrument (Bio-Rad Laboratories Ltd. (Mississauga, ON) with HBST running buffer (10 mM HEPES, 150 mM NaCl, 3.4 mM EDTA, and 0.05% Tween 20 pH 7.4) at a temperature of 25° C. The anti-mouse Fc capture surface was generated using a GLM sensorchip activated by a 1:5 dilution of the standard BioRad sNHS/EDC solutions injected for 300 s at 30 μL/min in the analyte (horizontal) direction. Immediately after the activation, a 13 μg/mL solution of anti-human IgG Fc fragment specific in 10 mM NaOAc pH 4.5 was injected in the analyte direction at a flow rate of 25 μL/min until approximately 8000 resonance units (RUs) were immobilized. Remaining active groups were quenched by a 300 s injection of 1M ethanolamine at 30 μL/min in the analyte direction, and this also ensures mock-activated interspots are created for blank referencing. The screening of the 3A4 variants for binding to KAAG1 occurred in two steps: an indirect capture of 3A4 variants from cell supernatant onto the anti-human IgG Fc fragment specific surface in the ligand direction (vertical) followed by a KAAG1 injection in the analyte direction. Firstly, one buffer injection for 30 s at 100 uL/min in the ligand direction was used to stabilize the baseline. For each 3A4 capture, unpurified 3A4 variants in cell-culture media were diluted to 4% in HBST, or approximately 1.25 μg/mL of purified 3A4 in HBST was used. Four to five 3A4 variants along with wild-type 3A4 were simultaneously injected in individual ligand channels for 240 s at flow 25 μL/min. This resulted in a saturating 3A4 capture of approximately 400-700 RUs onto the anti-human IgG Fc fragment specific surface. The first ligand channel was left empty to use as a blank control if required. This 3A4 capture step was immediately followed by two buffer injections in the analyte direction to stabilize the baseline, and then the gel filtration purified KAAG1 was injected. For a typical screen, five KAAG1 concentrations (8, 2.66, 0.89, 0.29, and 0.098 nM) and buffer control were simultaneously injected in individual analyte channels at 50 μL/min for 120 s with a 600 s dissociation phase, resulting in a set of binding sensorgrams with a buffer reference for each of the captured 3A4 variants. The anti-human IgG Fc fragment specific—3A4 complexes were regenerated by a 18 s pulse of 0.85% phosphoric acid for 18 s at 100 μL/min to prepare the anti-human IgG Fc fragment specific surface for the next injection cycle. Sensorgrams were aligned and double-referenced using the buffer blank injection and interspots, and the resulting sensorgrams were analyzed using ProteOn Manager software v3.0. The kinetic and affinity values were determined by fitting the referenced sensorgrams to the 1:1 Langmuir binding model using local $R_{max}$, and affinity constants ($K_D$ M) were derived from the resulting rate constants ($k_d$ $s^{-1}/k_a$ $M^{-1}$ $s^{-1}$).

Determination of Rate and Affinity Constants

Figure 16A:
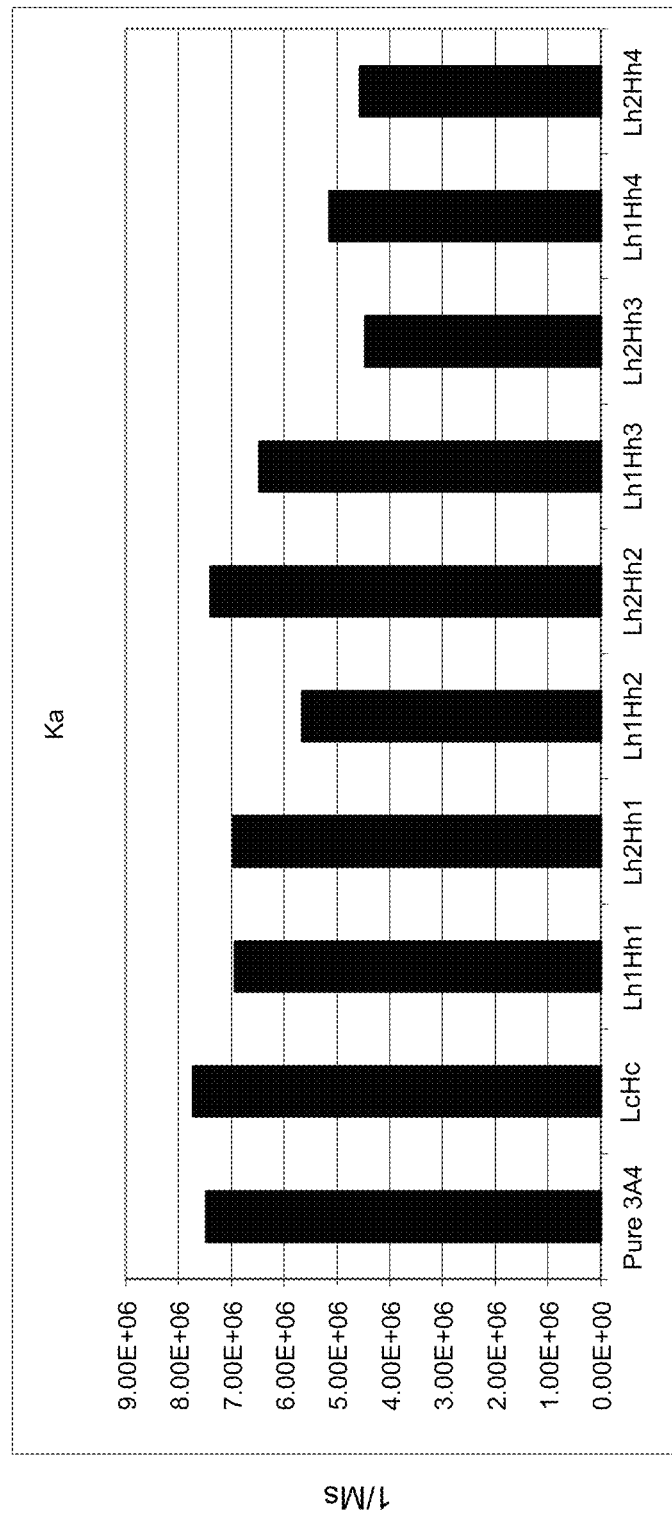
FIG. 16A is an histogram illustrating the association rates ($K_a$) of the humanized antibodies.
Figure 16B:
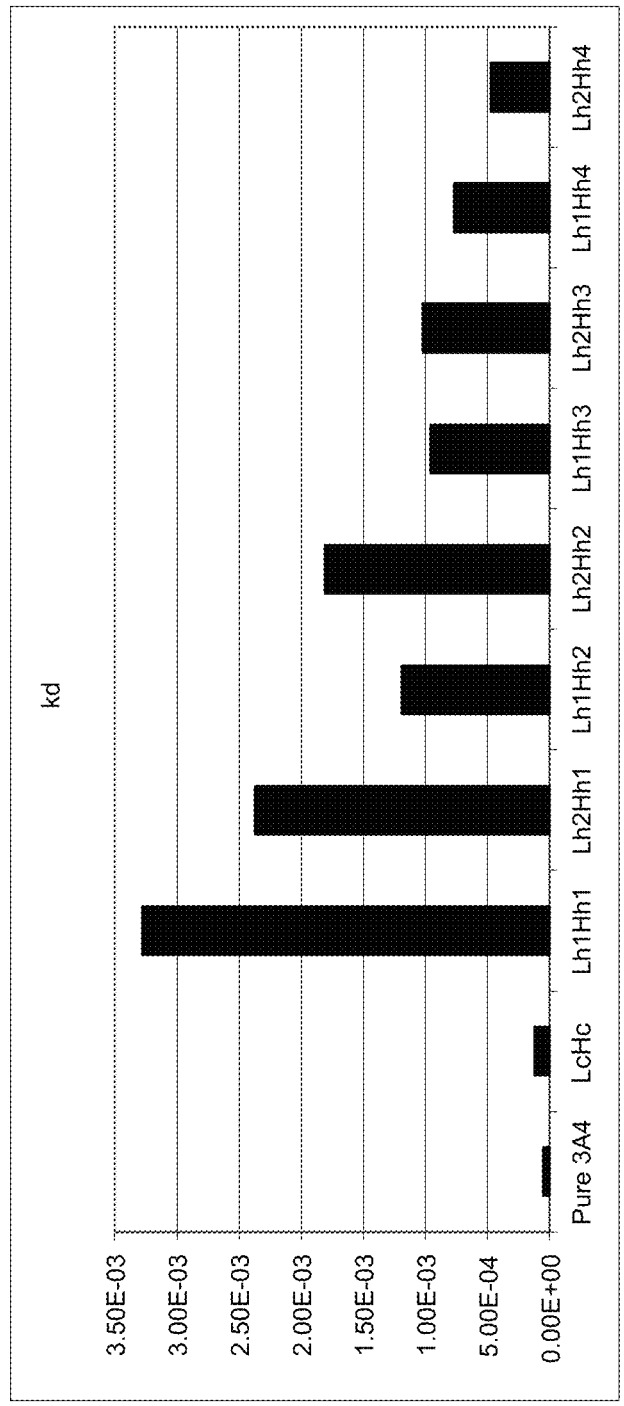
FIG. 16B is an histogram illustrating the dissociation rates ($K_d$) of the humanized antibodies.
Figure 16C:
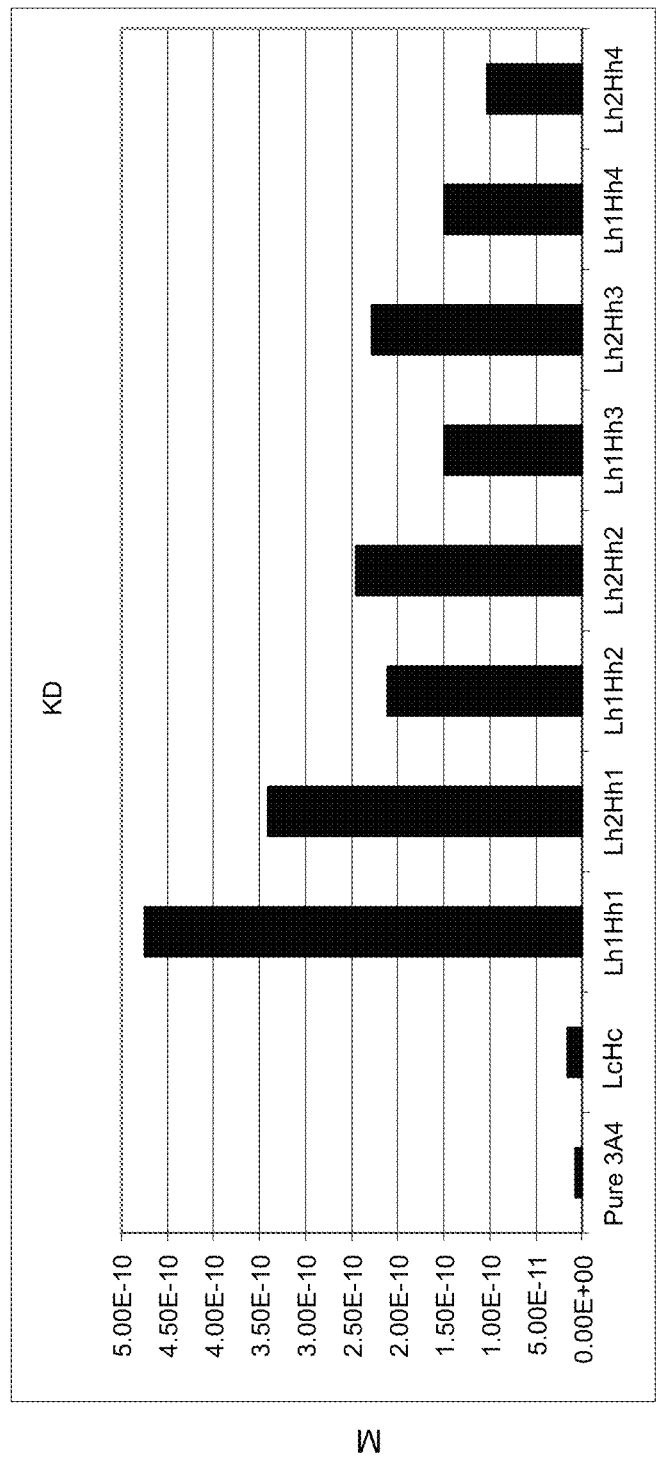
FIG. 16C is an histogram illustrating the affinity constants ($K_D$) of the humanized antibodies.

FIG. 15 summarizes the association ($k_a$, 1/Ms) and dissociation ($k_d$, 1/s) rate constants as well as affinity ($K_D$, M) constants for the interaction of KAAG1 with purified murine 3A4, murine 3A4 transiently expressed as a chimeric and transiently expressed humanized variants. These constants are graphically represented in FIG. 16. The association rate constant is very similar for the pure parental, chimeric and humanized 3A4 variants (FIG. 16A). The dissociation rate constants is similar for the transiently express chimeric as compared to the pure parental 3A4 with suggest that the transfection procedure did not alter the parameters of the interaction of KAAG1 with the antibody (FIG. 16B). However all humanized variants seem to have a slightly altered off rate, i.e. quicker dissociation rate (FIG. 16B). This is reflected in the affinity constants (FIG. 16C). In summary, there is a linear correlation between the binding affinity (log $K_D$) of the humanized variant and the number of back-mutations made in the parent antibody (LcHc) with a decrease in the binding affinity as the number of mutations is increasing. However, the difference in binding affinity is only 4 fold different between the worse variant (H1L1, 0.47 nM) which has no mouse residue retained and the best variant which has 10 mouse residues retained (H4L2, 0.1 nM). Finally, the binding affinity of all variants for KAAG1 was found to be sub-nanomolar and the best variant (H4L2, 0.1 nM) exhibited an affinity about 6-fold weaker than the murine (LcHc, 0.057 nM). Overall, these results indicate that humanization was successful as all of the variants displayed very high affinity for KAAG1.

Example 9

Binding of 3A4 Humanized Variants to KAAG1 in an ELISA

Figure 17A:
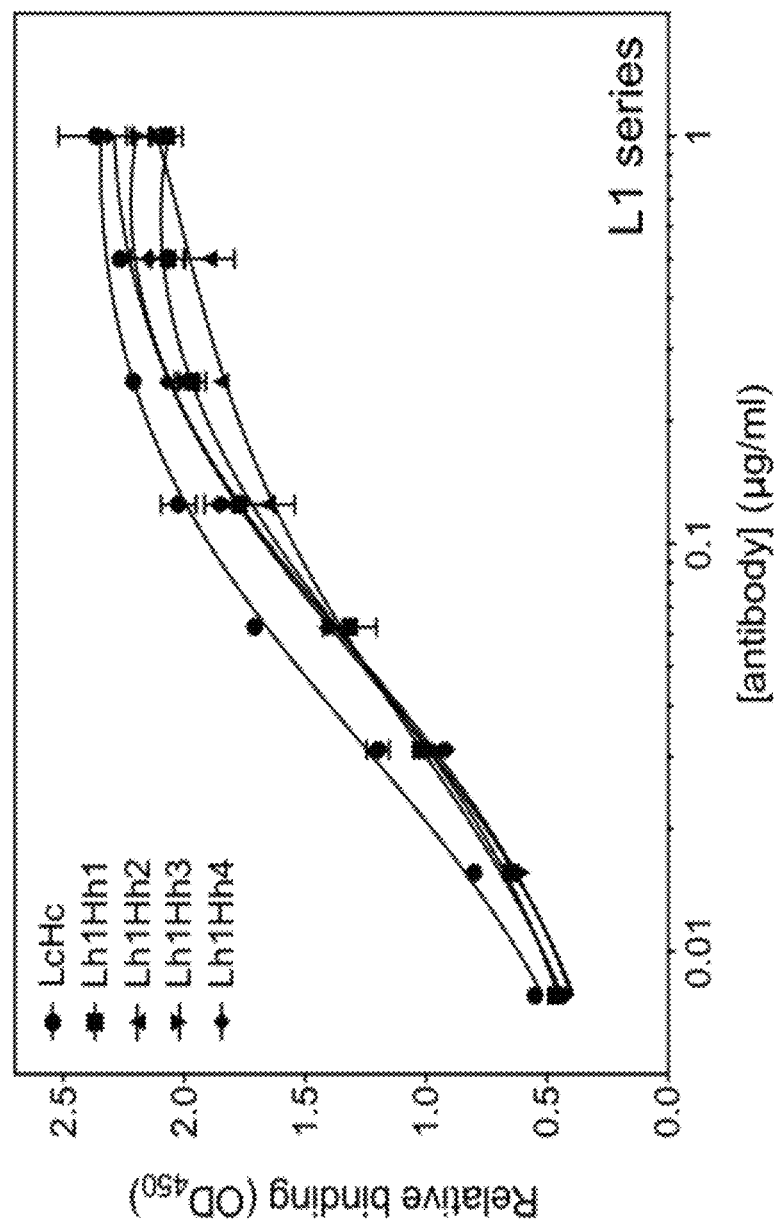
FIG. 17A illustrates humanized 3A4 variants binding to KAAG1 in an ELISA. This figure shows the comparative binding of 3A4 humanized antibody variants and the murine 3A4. Concentration-dependent binding profiles of the humanized heavy chains (Hh1, Hh2, Hh3 and Hh4) assembled with the Lh1 light chain variant.
Figure 17B:
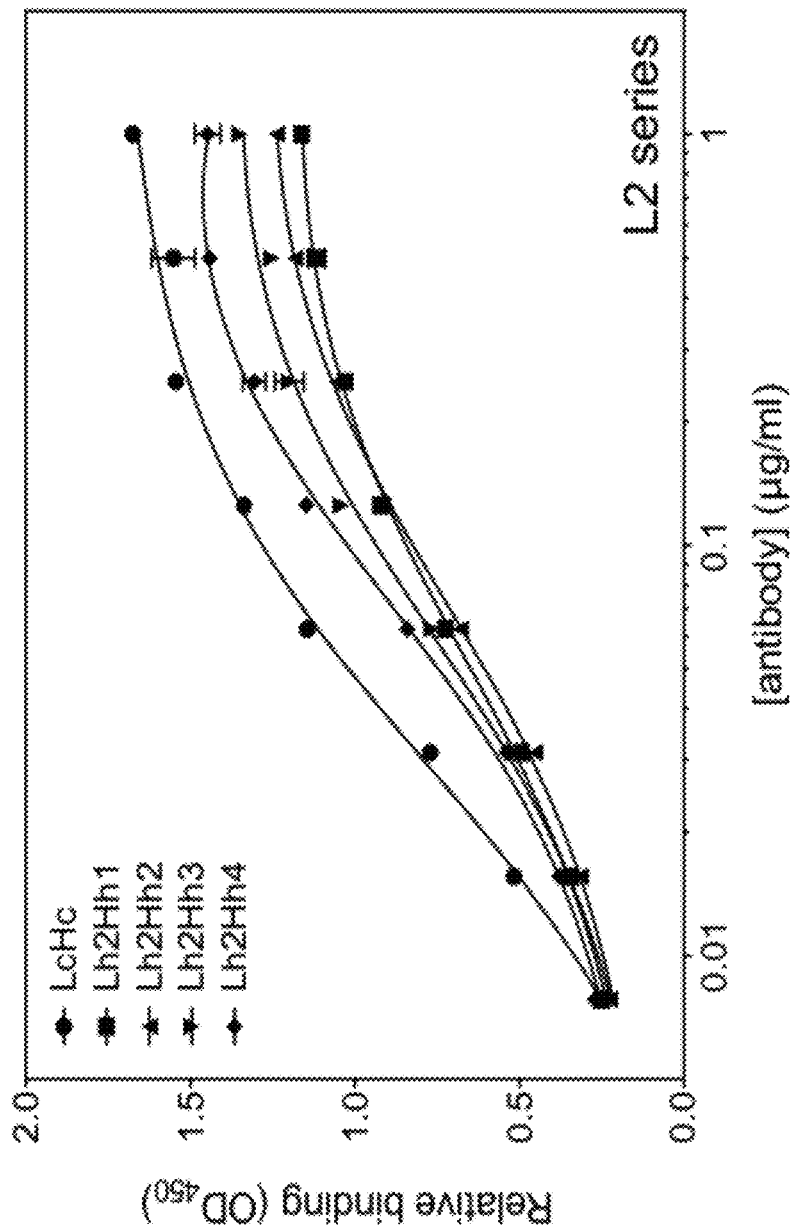
FIG. 17B illustrates humanized 3A4 variants binding to KAAG1 in an ELISA. This figure shows the comparative binding of 3A4 humanized antibody variants and the murine 3A4. Concentration-dependent binding profiles of the humanized heavy chains (Hh1, Hh2, Hh3 and Hh4) assembled with the Lh2 light chain variant.

ELISA methods were also used to compare the binding activity of the humanized 3A4 variants to the murine 3A4 antibody. Recombinant human KAAG1 was coated in 96-well plates O/N, washed and incubated for 1 h at RT with increasing quantities of murine or humanized 3A4 variants. Following another round of washing steps, an anti-human antibody conjugated to HRP was added to the wells and the bound 3A4 antibody was measured calorimetrically at $Abs_{450}$. As shown in FIG. 17A, the humanized variants (Lh1Hh1, Lh1Hh2, Lh1Hh3 and Lh1Hh4) displayed very similar binding to KAAG1 when compared to the murine 3A4 (LcHc). This result indicated that all four humanized heavy chain variants were comparable to the original h3A4 heavy chain when assembled with the L1 variant of the humanized light chain. FIG. 17B shows the results when the heavy chain variants were assembled with Lh2 variant of the 3A4 humanized light chain. In this instance, there was a difference in the binding of the variants. For example, Lh2hh4 was the variant with the closest profile compared to the murine 3A4. This was in agreement with the SPR data (see Example 3), which showed that the variant 4 of the heavy chain had the highest affinity for KAAG1. Taken together, these binding results show that the humanized variants all interact with human KAAG1 in this assay. Although there were some subtle differences, the binding in ELISA was in concordance with the SPR results.

Example 10

Binding of 3A4 Humanized Variants on the Surface of Cancer Cells

Figure 18:
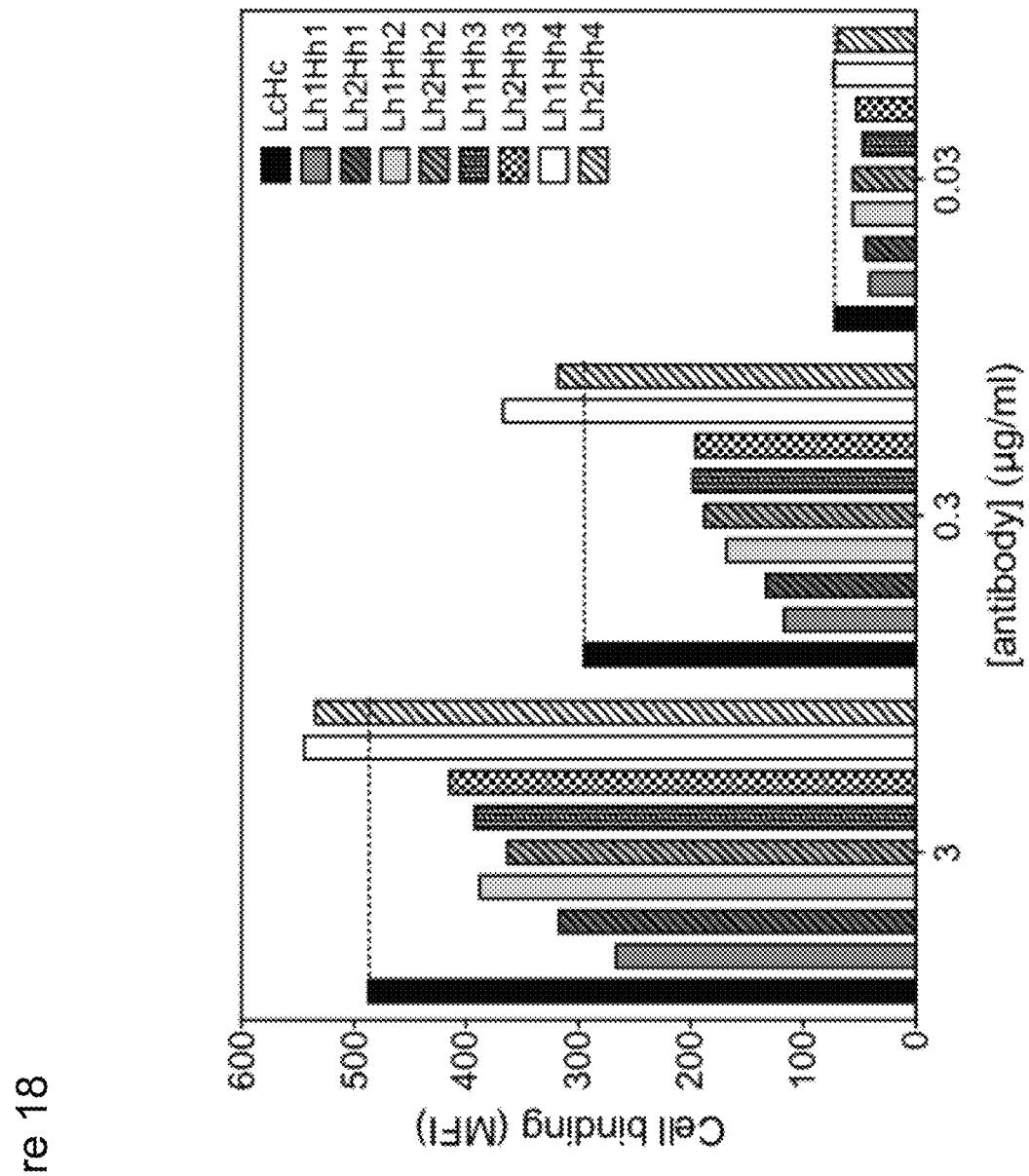
FIG. 18 illustrates humanized 3A4 variants binding to KAAG1 on the surface of cancer cells. This illustration shows the comparative binding activity of the humanized and the murine 3A4 antibodies on the unpermeabilized SKOV-3 ovarian cancer cells.

Flow cytometry was used to evaluate the capacity of the humanized 3A4 variants to interact with KAAG1 expressed on the surface of cancer cells. To this end, SKOV-3 ovarian cancer cells, which we had previously showed were efficiently bound by 3A4 by flow cytometry, were incubated with the eight humanized variants and the original murine antibody. Briefly, SKOV-3 cells were detached from the plate with EDTA and incubated on ice with either 3.0 mg/ml, 0.3 mg/ml or 0.3 mg/ml of the antibodies for 1 h. After three washing steps, the cells were incubated with the secondary antibody, anti-human IgG-conjugated to FITC for 1 h on ice. Cell surface fluorescence was measured in a flow cytometer and the values ae shown in the histogram of FIG. 18. As depicted, all variants could detect KAAG1 on the surface on unpermeabilized and the strongest signals were obtained at the highest concentration of 3A4 antibodies (3 mg/ml) and decreased as the concentration of the antibody was decreased. Among the different variants, the ones with the most murine back-mutations (FIG. 18, see Lh1 Hh4 and Lh2Hh4) interacted with KAAG1 on the surface of cells with the highest activity. In fact, Lh1Hh4 and Lh2hh4 appeared to be slight improved cell surface binding to KAAG1 compared to the murine 3A4 antibody (LcHc).

Publications(the Content of which is hereby Incorporated by Reference)

Jemal A, Murray T, Ward E, Samuels A, Tiwari R C, Ghafoor A, Feuer E J and Thun M J. Cancer statistics, 2005. CA Cancer J Clin 2005; 55: 10-30.

Menon U, Skates S J, Lewis S, Rosenthal A N, Rufford B, Sibley K, Macdonald N, Dawnay A, Jeyarajah A, Bast R C Jr, Oram D and Jacobs I J. Prospective study using the risk of ovarian cancer algorithm to screen for ovarian cancer. J Clin Oncol. 2005; 23(31):7919-26.

Bonome T, Lee J Y, Park D C, Radonovich M, Pise-Masison C, Brady J, Gardner G J, Hao K, Wong W H, Barrett J C, Lu K H, Sood A K, Gershenson D M, Mok S C and Birrer M J. Expression profiling of serous low malignancy potential, low grade, and high-grade tumors of the ovary. Cancer Res 2005; 65: 10602-10612.

Chambers, A and Vanderhyden, B. Ovarian Cancer Biomarkers in Urine. Clin Cancer Res 2006; 12(2): 323-327.

Berek et al. Cancer Medicine. 5th ed. London: B.C. Decker, Inc.; 2000. pp. 1687-1720.

Bristow R. E. Surgical standards in the management of ovarian cancer. Curr Opin Oncol 2000; 12: 474-480.

Brown E, Stewart M, Rye T, Al-Nafussi A, Williams A R, Bradburn M, Smyth J and Gabra H. Carcinosarcoma of the ovary: 19 years of prospective data from a single center. Cancer 2004; 100: 2148-2153.

Shih L-M and Kurman R J. Molecular Pathogenesis of Ovarian Borderline Tumors: New Insights and Old Challenges. Clin Cancer Res 2005; 11(20): 7273-7279.

Seidman J D, Russell P, Kurman R J. Surface epithelial tumors of the ovary. In: Kurman R J, editor. Blaustein's pathology of the female genital tract. 5th ed. New York: Springer-Verlag; 2002. pp. 791-904.

Cannistra S A and McGuire W P. Progress in the management of gynecologic cancer. J. Clin. Oncol. 2007; 25(20): 2865-2866.

Oei A L, Sweep F C, Thomas C M, Boerman O C, Massuger L F. The use of monoclonal antibodies for the treatment of epithelial ovarian cancer. Int. J. Oncol. 2008; 32(6): 1145-1157.

Nicodemus C F and Berek J S. Monoclonal antibody therapy of ovarian cancer. Expert Rev. Anticancer Ther. 2005; 5(1): 87-96.

Burger R A. Experience with bevacizumab in the management of epithelial ovarian cancer. J. Clin. Oncol. 2007; 25(20): 2902-2908.

Simon I, Zhuo S, Corral L, Diamandis E P, Sarno M J, Wolfert R L, Kim N W. B7-H4 is a novel membrane-bound protein and a candidate serum and tissue biomerker for ovarian cancer. Cancer Res. 2006; 66(3): 1570-1575.

Ebel W, Routhier E L, Foley B, Jacob S, McDonough J M, Patel R K, Turchin H A, Chao Q, Kline J B, Old L J, Phillips M D, Nicolaides N C, Sass P M, Grasso L. Preclinical evaluation of MORab-003, a humanized monoclonal antibody antagonizing folate receptor-alpha. Cancer Immun. 2007; 7: 6-13.

Van den Eynde B J, Gaugler B, Probst-Kepper M, Michaux L, Devuyst O, Lorge F, Weynants P, Boon T. A new antigen recognized by cytotoxic T lymphocytes on a human kidney tumor results from reverse strand transcription. J. Exp. Med. 1999; 190(12): 1793-1799.

Sooknanan R, Tremblay G B, Filion M. Polynucleotides and polypeptide sequences involved in cancer. 2007; PCT/CA2007/001134 published under No. WO/2007/147265 on Dec. 27, 2007.

Schumacher J, Anthoni H, Dandouh F, König I R, Hillmer A M, Kluck N, Manthey M, Plume E, Warnke A, Remschmidt H, Hülsmann J, Cichon S, Lindgren C M, Propping P, Zucchelli M, Ziegler A, Peyrard-Janvid M, Schulte-Körne G, Nöthen M M, Kere J. Strong genetic evidence of DCDC2 as a susceptibility gene for dyslexia. Am. J. Hum. Genet. 2006; 78: 52-62.

Cope N, Harold D, Hill G, Moskvina V, Stevenson J, Holmans P, Owen M J, O'Donovan M C, Williams J. Strong evidence that KIAA0319 on chromosome 6p is a susceptibility gene for developmental dyslexia. Am. J. Hum. Genet. 2005; 76: 581-591.

Mor G, Visintin I, Lai Y, Zhao H, Schwartz P, Rutherford T, Yue L, Bray-Ward P and Ward D C Serum protein markers for early detection of ovarian cancer. PNAS 2005; 102: 7677-7682.

Kozak K R, Amneus M W, Pusey S M, Su F, Luong M N, Luong S A, Reddy S T and Farias-Eisner R. Identification of biomarkers for ovarian cancer using strong anion-exchange ProteinChips: potential use in diagnosis and prognosis. PNAS 2003; 100: 12343-12348.

Benoît M H, Hudson T J, Maire G, Squire J A, Arcand S L, Provencher D, Mes-Masson A M, Tonin P N. Global analysis of chromosome X gene expression in primary cultures of normal ovarian surface epithelial cells and epithelial ovarian cancer cell lines. Int. J. Oncol. 2007; 30(1): 5-17.

Cody N A, Zietarska M, Filali-Mouhim A, Provencher D M, Mes-Masson A M, Tonin P N. Influence of monolayer, spheroid, and tumor growth conditions on chromosome 3 gene expression in tumorigenic epithelial ovarian cancer cell lines. BMC Med. Genomics 2008; 1(1):34.

Buechler J, Valkirs G, Gray J. Polyvalent display libraries. 2000; U.S. Pat. No. 6,057,098.

Durocher Y, Kamen A, Perret S, Pham P L. Enhanced production of recombinant proteins by transient transfection of suspension-growing mammalian cells. 2002; Canadian patent application No. CA 2446185.

Durocher Y. Expression vectors for enhanced transient gene expression and mammalian cells expressing them. 2004; U.S. patent application No. 60/662,392.

Tremblay G B, Filion M. Antibodies that specifically block the biological activity of a tumor antigen. 2009; PCT/CA2009/001586.

Durocher Y, Kamen A, Perret S, Pham P L. Enhanced production of recombinant proteins by transient transfection of suspension-growing mammalian cells. 2002; Canadian patent application No. CA 2446185.

Durocher Y. Expression vectors for enhanced transient gene expression and mammalian cells expressing them. 2004; U.S. patent application No. 60/662,392.

Chang M H, Karageorgos L E, Meikle P J. CD107a (LAMP-1) and CD107b (LAMP-2). 2002; J Biol Regul Homeost Agents. 16:147-51.

Abhinandan, K R and Martin, A C R. Analysis and improvements to Kabat and structurally correct numbering of antibody variable domains. 2008; Mol Immunol, 45, 3832-3839.

Sequences Referred to in the Description

```
3A4 heavy chain variable region nucleotide sequence
                                                    SEQ ID NO.: 1
CAGATCCAGTTGGTGCAATCTGGACCTGAGATGGTGAAGCCTGGGGCTTCAGTGAAGATGTCCTGTAAG

GCTTCTGGATACACATTCACTGACGACTACATGAGCTGGGTGAAACAGAGCCATGGAAAGAGCCTTGAG

TGGATTGGAGATATTAATCCTTACAACGGTGATACTAACTACAACCAGAAGTTCAAGGGCAAGGCCATA

TTGACTGTAGACAAATCCTCCAGCACAGCCTACATGCAGCTCAACAGCCTGACATCGGAAGACTCAGCA

GTCTATTACTGTGCAAGAGACCCGGGGGCTATGGACTACTGGGGTCAAGGAACCTCAGTCACCGTCTCC

TCA

3A4 heavy chain variable region polypeptide sequence
                                                    SEQ ID NO.: 2
QTQLVQSGPEMVKPGASVKMSCKASGYTFTDDYMSWVKQSHGKSLEWIGDINPYNGDTNYNQKFKGKAI
LTVDKSSSTAYMQLNSLTSEDSAVYYCARDPGAMDYWGQGTSVTVSS 3A4 light chain variable region nucleotide sequence
                                                    SEQ ID NO.: 3
GATGTTGTGATGACCCAAACTCCACTCTCCCTGGCTGTCAGTCTTGGAGATCAAGCCTCCATCTCTTGC

AGATCTAGTCAGAGCCTTCTACATAGTAATGGAAACACCTATTTAGAATGGTACCTTCAGAAACCAGGC

CAGTCTCCAAAGCTCCTGATCCACACAGTTTCCAACCGATTTTCTGGGGTCCCAGACAGATTCAGTGGC

AGTGGATCAGGGACAGATTTCACACTCAAGATCAGCAGAGTGGAGGCTGAGGATCTGGGAGTTTATTAC

TGCTTTCAAGGTTCACATGTTCCGCTCACGTTCGGTGCTGGGACCAGGCTGGAGCTGAAA

3A4 light chain variable region polypeptide sequence
                                                    SEQ ID NO.: 4
DVVMTQTPLSLAVSLGDQASISCRSSQSLLHSNGNTYLEWYLQKPGQSPKLLIHTVSNRFSGVPDRFSG
SGSGTDFTLKISRVEAEDLGVYYCFQGSHVPLTFGAGTRLELK 3A4 heavy chain CDR1 polypeptide sequence
                                                    SEQ ID NO.: 5
GYTFTDDYMS 3A4 heavy chain CDR2 polypeptide sequence
                                                    SEQ ID NO.: 6
DINPYNGDTN 3A4 heavy chain CDR3 polypeptide sequence
                                                    SEQ ID NO.: 7
DPGAMDY 3A4 light chain CDR1 polypeptide sequence
                                                    SEQ ID NO.: 8
RSSQSLLHSNGNTYLE 3A4 light chain CDR2 polypeptide sequence
                                                    SEQ ID NO.: 9
TVSNRFS 3A4 light chain CDR3 polypeptide sequence
                                                    SEQ ID NO.: 10
FQGSHVPLT OGS1773
                                                    SEQ ID NO.: 11
GTAAGCAGCGCTGTGGCTGCACCATCTGTCTTC OGS1774
                                                    SEQ ID NO.: 12
GTAAGCGCTAGCCTAACACTCTCCCCTGTTGAAGC
``` human kappa constant nucleotide sequence

SEQ ID NO.: 13

GCTGTGGCTGCACCATCTGTCTTCATCTTCCCGCCATCTGATGAGCAGTTGAAATCTGGAACTGCCTCT
GTTGTGTGCCTGCTGAATAACTTCTATCCCAGAGAGGCCAAAGTACAGTGGAAGGTGGATAACGCCCTC
CAATCGGGTAACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACCCATCAGGGC
CTGAGCTCGCCCGTCACAAAGAGCTTCAACAGGGGAGAGTGTTAG human kappa constant polypeptide sequence

SEQ ID NO.: 14

AVAAPSVFIFPPSDEQLKSGTASVVCLLNNFYPREAKVQWKVDNALQSGNSQESVTEQDSKDSTYSLSS
TLTLSKADYEKHKVYACEVTHQGLSSPVTKSFNRGEC

SEQ ID NO.: 15

CTTGAGCCGGCGGATGGTCGAGGTGAGGTGTGGCAGGCTTGAGATCCAGCTGTTGGGGTGAGTACTCCC
TCTCAAAAGCGGGCATTACTTCTGCGCTAAGATTGTCAGTTTCCAAAAACGAGGAGGATTTGATATTCA
CCTGGCCCGATCTGGCCATACACTTGAGTGACAATGACATCCACTTTGCCTTTCTCTCCACAGGTGTCC
ACTCCCAGGTCCAAGTTTAAACGGATCTCTAGCGAATTCATGAACTTTCTGCTGTCTTGGGTGCATTGG
AGCCTTGCCTTGCTGCTCTACCTCCACCATGCCAAGTGGTCCCAGGCTTGAGACGGAGCTTACAGCGCT
GTGGCTGCACCATCTGTCTTCATCTTCCCGCCATCTGATGAGCAGTTGAAATCTGGAACTGCCTCTGTT
GTGTGCCTGCTGAATAACTTCTATCCCAGAGAGGCCAAAGTACAGTGGAAGGTGGATAACGCCCTCCAA
TCGGGTAACTCCCAGGAGAGTGTCACAGAGCAGGACAGCAAGGACAGCACCTACAGCCTCAGCAGCACC
CTGACGCTGAGCAAAGCAGACTACGAGAAACACAAAGTCTACGCCTGCGAAGTCACCCATCAGGGCCTG
AGCTCGCCCGTCACAAAGAGCTTCAACAGGGGAGAGTGTTAGGGTACCGCGGCCGCTTCGAATGAGATC
CCCCGACCTCGACCTCTGGCTAATAAAGGAAATTTATTTTCATTGCAATAGTGTGTTGGAATTTTTTGT
GTCTCTCACTCGGAAGGACATATGGGAGGGCAAATCATTTGGTCGAGATCCCTCGGAGATCTCTAGCTA
GAGCCCCGCCGCCGGACGAACTAAACCTGACTACGGCATCTCTGCCCCTTCTTCGCGGGGCAGTGCATG
TAATCCCTTCAGTTGGTTGGTACAACTTGCCAACTGGGCCCTGTTCCACATGTGACACGGGGGGGACC
AAACACAAAGGGGTTCTCTGACTGTAGTTGACATCCTTATAAATGGATGTGCACATTTGCCAACACTGA
GTGGCTTTCATCCTGGAGCAGACTTTGCAGTCTGTGGACTGCAACACAACATTGCCTTTATGTGTAACT
CTTGGCTGAAGCTCTTACACCAATGCTGGGGACATGTACCTCCCAGGGGCCCAGGAAGACTACGGGAG
GCTACACCAACGTCAATCAGAGGGGCCTGTGTAGCTACCGATAAGCGGACCCTCAAGAGGGCATTAGCA
ATAGTGTTTATAAGGCCCCCTTGTTAACCCTAAACGGGTAGCATATGCTTCCCGGGTAGTAGTATATAC
TATCCAGACTAACCCTAATTCAATAGCATATGTTACCCAACGGGAAGCATATGCTATCGAATTAGGGTT
AGTAAAAGGGTCCTAAGGAACAGCGATATCTCCCACCCCATGAGCTGTCACGGTTTTATTTACATGGGG
TCAGGATTCCACGAGGGTAGTGAACCATTTTAGTCACAAGGGCAGTGGCTGAAGATCAAGGAGCGGGCA
GTGAACTCTCCTGAATCTTCGCCTGCTTCTTCATTCTCCTTCGTTTAGCTAATAGAATAACTGCTGAGT
TGTGAACAGTAAGGTGTATGTGAGGTGCTCGAAAACAAGGTTTCAGGTGACGCCCCAGAATAAATTT
GGACGGGGGGTTCAGTGGTGGCATTGTGCTATGACACCAATATAACCCTCACAAACCCCTTGGGCAATA
AATACTAGTGTAGGAATGAAACATTCTGAATATCTTTAACAATAGAAATCCATGGGTGGGGACAAGCC
GTAAAGACTGGATGTCCATCTCACACGAATTTATGGCTATGGGCAACACATAATCCTAGTGCAATATGA
TACTGGGGTTATTAAGATGTGTCCCAGGCAGGGACCAAGACAGGTGAACCATGTTGTTACACTCTATTT
GTAACAAGGGGAAAGAGAGTGGACGCCGACAGCAGCGGACTCCACTGGTTGTCTCTAACACCCCGAAA
ATTAAACGGGGCTCCACGCCAATGGGCCCATAAACAAAGACAAGTGGCCACTCTTTTTTTTGAAATTG
TGGAGTGGGGGCACGCGTCAGCCCCCACACGCCGCCCTGCGGTTTTGGACTGTAAAATAAGGGTGTAAT
AACTTGGCTGATTGTAACCCCGCTAACCACTGCGGTCAAACCACTTGCCCACAAAACCACTAATGGCAC

-continued

```
CCCGGGGAATACCTGCATAAGTAGGTGGGCGGGCCAAGATAGGGGCGCGATTGCTGCGATCTGGAGGAC

AAATTACACACACTTGCGCCTGAGCGCCAAGCACAGGGTTGTTGGTCCTCATATTCACGAGGTCGCTGA

GAGCACGGTGGGCTAATGTTGCCATGGGTAGCATATACTACCCAAATATCTGGATAGCATATGCTATCC

TAATCTATATCTGGGTAGCATAGGCTATCCTAATCTATATCTGGGTAGCATATGCTATCCTAATCTATA

TCTGGGTAGTATATGCTATCCTAATTTATATCTGGGTAGCATAGGCTATCCTAATCTATATCTGGGTAG

CATATGCTATCCTAATCTATATCTGGGTAGTATATGCTATCCTAATCTGTATCCGGGTAGCATATGCTA

TCCTAATAGAGATTAGGGTAGTATATGCTATCCTAATTTATATCTGGGTAGCATATACTACCCAAATAT

CTGGATAGCATATGCTATCCTAATCTATATCTGGGTAGCATATGCTATCCTAATCTATATCTGGGTAGC

ATAGGCTATCCTAATCTATATCTGGGTAGCATATGCTATCCTAATCTATATCTGGGTAGTATATGCTAT

CCTAATTTATATCTGGGTAGCATAGGCTATCCTAATCTATATCTGGGTAGCATATGCTATCCTAATCTA

TATCTGGGTAGTATATGCTATCCTAATCTGTATCCGGGTAGCATATGCTATCCTCACGATGATAAGCTG

TCAAACATGAGAATTAATTCTTGAAGACGAAAGGGCCTCGTGATACGCCTATTTTTATAGGTTAATGTC

ATGATAATAATGGTTTCTTAGACGTCAGGTGGCACTTTTCGGGGAAATGTGCGCGGAACCCCTATTTGT

TTATTTTTCTAAATACATTCAAATATGTATCCGCTCATGAGACAATAACCCTGATAAATGCTTCAATAA

TATTGAAAAAGGAAGAGTATGAGTATTCAACATTTCCGTGTCGCCCTTATTCCCTTTTTTGCGGCATTT

TGCCTTCCTGTTTTTGCTCACCCAGAAACGCTGGTGAAAGTAAAAGATGCTGAAGATCAGTTGGGTGCA

CGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAA

GAGCAACTCGGTCGCCGCATACACTATTCTCAGAATGACTTGGTTGAGTACTCACCAGTCACAGAAAAG

CATCTTACGGATGGCATGACAGTAAGAGAATTATGCAGTGCTGCCATAACCATGAGTGATAACACTGCG

GCCAACTTACTTCTGACAACGATCGGAGGACCGAAGGAGCTAACCGCTTTTTTGCACAACATGGGGGAT

CATGTAACTCGCCTTGATCGTTGGGAACCGGAGCTGAATGAAGCCATACCAAACGACGAGCGTGACACC

ACGATGCCTGCAGCAATGGCAACAACGTTGCGCAAACTATTAACTGGCGAACTACTTACTCTAGCTTCC

CGGCAACAATTAATAGACTGGATGGAGGCGGATAAAGTTGCAGGACCACTTCTGCGCTCGGCCCTTCCG

GCTGGCTGGTTTATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGCAACTATGGATGAA

CGAAATAGACAGATCGCTGAGATAGGTGCCTCACTGATTAAGCATTGGTAACTGTCAGACCAAGTTTAC

TCATATATACTTTAGATTGATTTAAAACTTCATTTTTAATTTAAAAGGATCTAGGTGAAGATCCTTTTT

GATAATCTCATGACCAAAATCCCTTAACGTGAGTTTTCGTTCCACTGAGCGTCAGACCCCGTAGAAAAG

ATCAAAGGATCTTCTTGAGATCCTTTTTTTCTGCGCGTAATCTGCTGCTTGCAAACAAAAAAACCACCG

CTACCAGCGGTGGTTTGTTTGCCGGATCAAGAGCTACCAACTCTTTTTCCGAAGGTAACTGGCTTCAGC

AGAGCGCAGATACCAAATACTGTCCTTCTAGTGTAGCCGTAGTTAGGCCACCACTTCAAGAACTCTGTA

GCACCGCCTACATACCTCGCTCTGCTAATCCTGTTACCAGTGGCTGCTGCCAGTGGCGATAAGTCGTGT

CTTACCGGGTTGGACTCAAGACGATAGTTACCGGATAAGGCGCAGCGGTCGGGCTGAACGGGGGGTTCG

TGCACACAGCCCAGCTTGGAGCGAACGACCTACACCGAACTGAGATACCTACAGCGTGAGCATTGAGAA

AGCGCCACGCTTCCCGAAGGGAGAAAGGCGGACAGGTATCCGGTAAGCGGCAGGGTCGGAACAGGAGAG

CGCACGAGGGAGCTTCCAGGGGGAAACGCCTGGTATCTTTATAGTCCTGTCGGGTTTCGCCACCTCTGA

CTTGAGCGTCGATTTTTGTGATGCTCGTCAGGGGGCGGAGCCTATGGAAAAACGCCAGCAACGCGGCC

TTTTTACGGTTCCTGGCCTTTTGCTGGCCTTTTGCTCACATGTTCTTTCCTGCGTTATCCCCTGATTCT

GTGGATAACCGTATTACCGCCTTTGAGTGAGCTGATACCGCTCGCCGCAGCCGAACGACCGAGCGCAGC
```

-continued

```
GAGTCAGTGAGCGAGGAAGCGGAAGAGCGCCCAATACGCAAACCGCCTCTCCCCGCGCGTTGGCCGATT

CATTAATGCAGCTGGCACGACAGGTTTCCCGACTGGAAAGCGGGCAGTGAGCGCAACGCAATTAATGTG

AGTTAGCTCACTCATTAGGCACCCCAGGCTTTACACTTTATGCTTCCGGCTCGTATGTTGTGTGGAATT

GTGAGCGGATAACAATTTCACACAGGAAACAGCTATGACCATGATTACGCCAAGCTCTAGCTAGAGGTC

GACCAATTCTCATGTTTGACAGCTTATCATCGCAGATCCGGGCAACGTTGTTGCATTGCTGCAGGCGCA

GAACTGGTAGGTATGGCAGATCTATACATTGAATCAATATTGGCAATTAGCCATATTAGTCATTGGTTA

TATAGCATAAATCAATATTGGCTATTGGCCATTGCATACGTTGTATCTATATCATAATATGTACATTTA

TATTGGCTCATGTCCAATATGACCGCCATGTTGACATTGATTATTGACTAGTTATTAATAGTAATCAAT

TACGGGGTCATTAGTTCATAGCCCATATATGGAGTTCCGCGTTACATAACTTACGGTAAATGGCCCGCC

TGGCTGACCGCCCAACGACCCCCGCCCATTGACGTCAATAATGACGTATGTTCCCATAGTAACGCCAAT

AGGGACTTTCCATTGACGTCAATGGGTGGAGTATTTACGGTAAACTGCCCACTTGGCAGTACATCAAGT

GTATCATATGCCAAGTCCGCCCCCTATTGACGTCAATGACGGTAAATGGCCCGCCTGGCATTATGCCCA

GTACATGACCTTACGGGACTTTCCTACTTGGCAGTACATCTACGTATTAGTCATCGCTATTACCATGGT

GATGCGGTTTTGGCAGTACACCAATGGGCGTGGATAGCGGTTTGACTCACGGGGATTTCCAAGTCTCCA

CCCCATTGACGTCAATGGGAGTTTGTTTTGGCACCAAAATCAACGGGACTTTCCAAAATGTCGTAATAA

CCCCGCCCCGTTGACGCAAATGGGCGGTAGGCGTGTACGGTGGGAGGTCTATATAAGCAGAGCTCGTTT

AGTGAACCGTCAGATCCTCACTCTCTTCCGCATCGCTGTCTGCGAGGGCCAGCTGTTGGGCTCGCGGTT

GAGGACAAACTCTTCGCGGTCTTTCCAGTACTCTTGGATCGGAAACCCGTCGGCCTCCGAACGGTACTC

CGCCACCGAGGGACCTGAGCGAGTCCGCATCGACCGGATCGGAAAACCTCTCGAGAAAGGCGTCTAACC

AGTCACAGTCGCAAGGTAGGCTGAGCACCGTGGCGGGCGGCAGCGGGTGGCGGTCGGGGTTGTTTCTGG

CGGAGGTGCTGCTGATGATGTAATTAAAGTAGGCGGT

OGS18500                                          SEQ ID NO.: 16
ATGCCAAGTGGTCCCAGGCTGATGTTGTGATGACCCAAACTCC

OGS2084                                           SEQ ID NO:. 17
GGGAAGATGAAGACAGATGGTGCAGCCACAGTCCG

OGS1769                                           SEQ ID NO.: 18
GTAAGCGCTAGCGCCTCAACGAAGGGCCCATCTGTCTTTCCCCTGGCCCC

OGS1770                                           SEQ ID NO.: 19
GTAAGCGAATTCACAAGATTTGGGCTCAACTTTCTTG human immunoglobulin CH1 region nucleotide sequence
                                                  SEQ ID NO.: 20
GCCTCCACCAAGGGCCCATCGGTCTTCCCCCTGGCACCCTCCTCCAAGAGCACCTCTGGGGGCACAGCA

GCCCTGGGCTGCCTGGTCAAGGACTACTTCCCCGAACCGGTGACGGTGTCGTGGAACTCAGGCGCCCTG

ACCAGCGGCGTGCACACCTTCCCGGCTGTCCTACAGTCCTCAGGACTCTACTCCCTCAGCAGCGTGGTG

ACCGTGCCCTCCAGCAGCTTGGGCACCCAGACCTACATCTGCAACGTGAATCACAAGCCCAGCAACACC

AAGGTGGACAAGAAAGTTGAGCCCAAATCTTGT human immunoglobulin CH1 region polypeptide sequence
                                                  SEQ ID NO.: 21
ASTKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSC SEQ ID NO.: 22
CTTGAGCCGGCGGATGGTCGAGGTGAGGTGTGGCAGGCTTGAGATCCAGCTGTTGGGGTGAGTACTCCC

TCTCAAAAGCGGGCATTACTTCTGCGCTAAGATTGTCAGTTTCCAAAAACGAGGAGGATTTGATATTCA
```

-continued

```
CCTGGCCCGATCTGGCCATACACTTGAGTGACAATGACATCCACTTTGCCTTTCTCTCCACAGGTGTCC

ACTCCCAGGTCCAAGTTTGCCGCCACCATGGAGACAGACACACTCCTGCTATGGGTACTGCTGCTCTGG

GTTCCAGGTTCCACTGGCGGAGACGGAGCTTACGGGCCCATCTGTCTTTCCCCTGGCCCCCTCCTCCAA

GAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACT

CTACTCCCTCAGCAGCGTGGTGACCGTGCCCTCCAGCAGCTTGGGCACCCAGACCTACATCTGCAACGT

GAATCACAAGCCCAGCAACACCAAGGTGGACAAGAAAGTTGAGCCCAAATCTTGTGAATTCACTCACAC

ATGCCCACCGTGCCCAGCACCTGAACTCCTGGGGGGACCGTCAGTCTTCCTCTTCCCCCCAAAACCCAA

GGACACCCTCATGATCTCCCGGACCCCTGAGGTCACATGCGTGGTGGTGGACGTGAGCCACGAAGACCC

TGAGGTCAAGTTCAACTGGTACGTGGACGGCGTGGAGGTGCATAATGCCAAGACAAAGCCGCGGGAGGA

GCAGTACAACAGCACGTACCGTGTGGTCAGCGTCCTCACCGTCCTGCACCAGGACTGGCTGAATGGCAA

GGAGTACAAGTGCAAGGTCTCCAACAAAGCCCTCCCAGCCCCCATCGAGAAAACCATCTCCAAAGCCAA

AGGGCAGCCCCGAGAACCACAGGTGTACACCCTGCCCCCATCCCGGGATGAGCTGACCAAGAACCAGGT

CAGCCTGACCTGCCTGGTCAAAGGCTTCTATCCCAGCGACATCGCCGTGGAGTGGGAGAGCAATGGGCA

GCCGGAGAACAACTACAAGACCACGCCTCCCGTGCTGGACTCCGACGGCTCCTTCTTCCTCTACAGCAA

GCTCACCGTGGACAAGAGCAGGTGGCAGCAGGGGAACGTCTTCTCATGCTCCGTGATGCATGAGGCTCT

GCACAACCACTACACGCAGAAGAGCCTCTCCCTGTCTCCCGGGAAATGATCCCCCGACCTCGACCTCTG

GCTAATAAAGGAAATTTATTTTCATTGCAATAGTGTGTTGGAATTTTTTGTGTCTCTCACTCGGAAGGA

CATATGGGAGGGCAAATCATTTGGTCGAGATCCCTCGGAGATCTCTAGCTAGAGCCCCGCCGCCGGACG

AACTAAACCTGACTACGGCATCTCTGCCCCTTCTTCGCGGGCAGTGCATGTAATCCCTTCAGTTGGTT

GGTACAACTTGCCAACTGAACCCTAAACGGGTAGCATATGCTTCCCGGGTAGTAGTATATACTATCCAG

ACTAACCCTAATTCAATAGCATATGTTACCCAACGGGAAGCATATGCTATCGAATTAGGGTTAGTAAAA

GGGTCCTAAGGAACAGCGATGTAGGTGGGCGGGCCAAGATAGGGGCGCGATTGCTGCGATCTGGAGGAC

AAATTACACACACTTGCGCCTGAGCGCCAAGCACAGGGTTGTTGGTCCTCATATTCACGAGGTCGCTGA

GAGCACGGTGGGCTAATGTTGCCATGGGTAGCATATACTACCCAAATATCTGGATAGCATATGCTATCC

TAATCTATATCTGGGTAGCATAGGCTATCCTAATCTATATCTGGGTAGCATATGCTATCCTAATCTATA

TCTGGGTAGTATATGCTATCCTAATTTATATCTGGGTAGCATAGGCTATCCTAATCTATATCTGGGTAG

CATATGCTATCCTAATCTATATCTGGGTAGTATATGCTATCCTAATCTGTATCCGGGTAGCATATGCTA

TCCTAATAGAGATTAGGGTAGTATATGCTATCCTAATTTATATCTGGGTAGCATATACTACCCAAATAT

CTGGATAGCATATGCTATCCTAATCTATATCTGGGTAGCATATGCTATCCTAATCTATATCTGGGTAGC

ATAGGCTATCCTAATCTATATCTGGGTAGCATATGCTATCCTAATCTATATCTGGGTAGTATATGCTAT

CCTAATTTATATCTGGGTAGCATAGGCTATCCTAATCTATATCTGGGTAGCATATGCTATCCTAATCTA

TATCTGGGTAGTATATGCTATCCTAATCTGTATCCGGGTAGCATATGCTATCCTCACGATGATAAGCTG

TCAAACATGAGAATTAATTCTTGAAGACGAAAGGGCCTCGTGATACGCCTATTTTTATAGGTTAATGTC

ATGATAATAATGGTTTCTTAGACGTCAGGTGGCACTTTTCGGGGAAATGTGCGCGGAACCCCTATTTGT

TTATTTTTCTAAATACATTCAAATATGTATCCGCTCATGAGACAATAACCCTGATAAATGCTTCAATAA

TATTGAAAAAGGAAGAGTATGAGTATTCAACATTTCCGTGTCGCCCTTATTCCCTTTTTTGCGGCATTT

TGCCTTCCTGTTTTTGCTCACCCAGAAACGCTGGTGAAAGTAAAAGATGCTGAAGATCAGTTGGGTGCA

CGAGTGGGTTACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTGTTGACGCCGGGCAA

GAGCAACTCGGTCGCCGCATACACTATTCTCAGAATGACTTGGTTGAGTACTCACCAGTCACAGAAAAG
```

-continued

```
CATCTTACGGATGGCATGACAGTAAGAGAATTATGCAGTGCTGCCATAACCATGAGTGATAACACTGCG

GCCAACTTACTTCTGACAACGATCGGAGGACCGAAGGAGCTAACCGCTTTTTTGCACAACATGGGGGAT

CATGTAACTCGCCTTGATCGTTGGGAACCGGAGCTGAATGAAGCCATACCAAACGACGAGCGTGACACC

ACGATGCCTGCAGCAATGGCAACAACGTTGCGCAAACTATTAACTGGCGAACTACTTACTCTAGCTTCC

CGGCAACAATTAATAGACTGGATGGAGGCGGATAAAGTTGCAGGACCACTTCTGCGCTCGGCCCTTCCG

GCTGGCTGGTTTATTGCTGATAAATCTGGAGCCGGTGAGCGTGGGTCTCGCGGTATCATTGCAGCACTG

GGGCCAGATGGTAAGCCCTCCCGTATCGTAGTTATCTACACGACGGGGAGTCAGGCAACTATGGATGAA

CGAAATAGACAGATCGCTGAGATAGGTGCCTCACTGATTAAGCATTGGTAACTGTCAGACCAAGTTTAC

TCATATATACTTTAGATTGATTTAAAACTTCATTTTTAATTTAAAAGGATCTAGGTGAAGATCCTTTTT

GATAATCTCATGACCAAAATCCCTTAACGTGAGTTTTCGTTCCACTGAGCGTCAGACCCCGTAGAAAAG

ATCAAAGGATCTTCTTGAGATCCTTTTTTTCTGCGCGTAATCTGCTGCTTGCAAACAAAAAAACCACCG

CTACCAGCGGTGGTTTGTTTGCCGGATCAAGAGCTACCAACTCTTTTTCCGAAGGTAACTGGCTTCAGC

AGAGCGCAGATACCAAATACTGTCCTTCTAGTGTAGCCGTAGTTAGGCCACCACTTCAAGAACTCTGTA

GCACCGCCTACATACCTCGCTCTGCTAATCCTGTTACCAGTGGCTGCTGCCAGTGGCGATAAGTCGTGT

CTTACCGGGTTGGACTCAAGACGATAGTTACCGGATAAGGCGCAGCGGTCGGGCTGAACGGGGGGTTCG

TGCACACAGCCCAGCTTGGAGCGAACGACCTACACCGAACTGAGATACCTACAGCGTGAGCATTGAGAA

AGCGCCACGCTTCCCGAAGGGAGAAAGGCGGACAGGTATCCGGTAAGCGGCAGGGTCGGAACAGGAGAG

CGCACGAGGGAGCTTCCAGGGGGAAACGCCTGGTATCTTTATAGTCCTGTCGGGTTTCGCCACCTCTGA

CTTGAGCGTCGATTTTTGTGATGCTCGTCAGGGGGCGGAGCCTATGGAAAAACGCCAGCAACGCGGCC

TTTTTACGGTTCCTGGCCTTTTGCTGGCCTTTTGCTCACATGTTCTTTCCTGCGTTATCCCCTGATTCT

GTGGATAACCGTATTACCGCCTTTGAGTGAGCTGATACCGCTCGCCGCAGCCGAACGACCGAGCGCAGC

GAGTCAGTGAGCGAGGAAGCGTACATTTATATTGGCTCATGTCCAATATGACCGCCATGTTGACATTGA

TTATTGACTAGTTATTAATAGTAATCAATTACGGGGTCATTAGTTCATAGCCCATATATGGAGTTCCGC

GTTACATAACTTACGGTAAATGGCCCGCCTGGCTGACCGCCCAACGACCCCCGCCCATTGACGTCAATA

ATGACGTATGTTCCCATAGTAACGCCAATAGGGACTTTCCATTGACGTCAATGGGTGGAGTATTTACGG

TAAACTGCCCACTTGGCAGTACATCAAGTGTATCATATGCCAAGTCCGCCCCCTATTGACGTCAATGAC

GGTAAATGGCCCGCCTGGCATTATGCCCAGTACATGACCTTACGGGACTTTCCTACTTGGCAGTACATC

TACGTATTAGTCATCGCTATTACCATGGTGATGCGGTTTTGGCAGTACACCAATGGGCGTGGATAGCGG

TTTGACTCACGGGGATTTCCAAGTCTCCACCCCATTGACGTCAATGGGAGTTTGTTTTGGCACCAAAAT

CAACGGGACTTTCCAAAATGTCGTAATAACCCCGCCCCGTTGACGCAAATGGGCGGTAGGCGTGTACGG

TGGGAGGTCTATATAAGCAGAGCTCGTTTAGTGAACCGTCAGATCCTCACTCTCTTCCGCATCGCTGTC

TGCGAGGGCCAGCTGTTGGGCTCGCGGTTGAGGACAAACTCTTCGCGGTCTTTCCAGTACTCTTGGATC

GGAAACCCGTCGGCCTCCGAACGGTACTCCGCCACCGAGGGACCTGAGCGAGTCCGCATCGACCGGATC

GGAAAACCTCTCGAGAAAGGCGTCTAACCAGTCACAGTCGCAAGGTAGGCTGAGCACCGTGGCGGGCGG

CAGCGGGTGGCGGTCGGGGTTGTTTCTGGCGGAGGTGCTGCTGATGATGTAATTAAAGTAGGCGGT
```

OGS1879
SEQ ID NO.: 23
GGGTTCCAGGTTCCACTGGCCAGATCCAGTTGGTGCAATCTGG

OGS1810
SEQ ID NO.: 24
GGGGCCAGGGGAAAGACAGATGGGCCCTTCGTTGAGGC

SEQ ID NO.: 25
GTAAGCGGATCCATGGATGACGACGCGGCGCCC

```
                                                        SEQ ID NO.: 26
GTAAGCAAGCTTAGGCCGCTGGGACAGCGGAGGTGC

SEQ ID NO.: 27
GTAAGCAAGCTTGGCAGCAGCGCCAGGTCCAGC

SEQ ID NO.: 28
GAGGGGCATCAATCACACCGAGAAGTCACAGCCCCTCAACCACTGAGGTGTGGGGGGTAGGGATCTGC

ATTTCTTCATATCAACCCCACACTATAGGGCACCTAAATGGGTGGGCGGTGGGGGAGACCGACTCACTT

GAGTTTCTTGAAGGCTTCCTGGCCTCCAGCCACGTAATTGCCCCCGCTCTGGATCTGGTCTAGCTTCCG

GATTCGGTGGCCAGTCCGCGGGGTGTAGATGTTCCTGACGGCCCCAAAGGGTGCCTGAACGCCGCCGGT

CACCTCCTTCAGGAAGACTTCGAAGCTGGACACCTTCTTCTCATGGATGACGACGCGGCGCCCCGCGTA

GAAGGGGTCCCCGTTGCGGTACACAAGCACGCTCTTCACGACGGGCTGAGACAGGTGGCTGGACCTGGC

GCTGCTGCCGCTCATCTTCCCCGCTGGCCGCCGCCTCAGCTCGCTGCTTCGCGTCGGGAGGCACCTCCG

CTGTCCCAGCGGCCTCACCGCACCCAGGGCGCGGGATCGCCTCCTGAAACGAACGAGAAACTGACGAAT

CCACAGGTGAAAGAGAAGTAACGGCCGTGCGCCTAGGCGTCCACCCAGAGGAGACACTAGGAGCTTGCA

GGACTCGGAGTAGACGCTCAAGTTTTTCACCGTGGCGTGCACAGCCAATCAGGACCCGCAGTGCGCGCA

CCACACCAGGTTCACCTGCTACGGGCAGAATCAAGGTGGACAGCTTCTGAGCAGGAGCCGGAAACGCGC

GGGGCCTTCAAACAGGCACGCCTAGTGAGGGCAGGAGAGAGGAGGACGCACACACACACACACACACAA

ATATGGTGAAACCCAATTTCTTACATCATATCTGTGCTACCCTTTCCAAACAGCCTA

SEQ ID NO.: 29
MDDDAAPRVEGVPVAVHKHALHDGLRQVAGPGAAAAHLPRWPPPQLAASRREAPPLSQRPHRTQGAGSP
PETNEKLTNPQVKEK (variant light chain variable region)
                                                        SEQ ID NO.: 30
DXVMTQTPLSLXVXXGXXASISCRSSQSLLHSNGNTYLEWYLQKPGQSPXLLIHTVSNRFSG
VPDRFSGSGSGTDFTLKISRVEAEDXGVYYCFQGSHVPLTFGXGTXLEXK
``` wherein at least one of the amino acids identified by X is an amino acid substitution (conservative or non-conservative) in comparison with a corresponding amino acid in the polypeptide set forth in SEQ ID NO.:4. The amino acid substitution may be, for example conservative.

(variant light chain variable region)

SEQ ID NO.: 31

$DX_{a1}VMTQTPLSLX_{a2}VX_{a3}X_{a4}GX_{a5}X_{a6}ASISCRSSQSLLHSNGNTYLEWY$
$LQKPGQSPX_{a7}LLIHTVSNRFSGVPDRFSGSGSGTDFTLKISRVEAEDX_{a8}$
$GVYYCFQGSHVPLTFGX_{a9}GTX_{a10}LEX_{a11}K$

Wherein $X_{a1}$ may be a hydrophobic amino acid;

Wherein $X_{a2}$ may be A or P;

Wherein $X_{a3}$ may be neutral hydrophilic amino acid;

Wherein $X_{a4}$ may be L or P;

Wherein $X_{a5}$ may be an acidic amino acid;

Wherein $X_{a6}$ may be Q or P;

Wherein $X_{a7}$ may be a basic amino acid;

Wherein $X_{a8}$ may be a hydrophobic amino acid;

Wherein $X_{a9}$ may be A or Q;

Wherein $X_{a10}$ may be a basic amino acid; or

Wherein $X_{a11}$ may be a hydrophobic amino acid, wherein at least one of the amino acid identified by X is an amino acid substitution (conservative or non-conservative) in comparison with a corresponding amino acid in the polypeptide set forth in SEQ ID NO.:4.

(variant light chain variable region)

SEQ ID NO.: 32

$DX_{A1}VMTQTPLSLX_{A2}VX_{A3}X_{A4}GX_{A5}X_{A6}ASISCRSSQSLLHSNGNTYLEWY$
$LQKPGQSPX_{A7}LLIHTVSNRFSGVPDRFSGSGSGTDFTLKISRVEAEDX_{A8}$
$GVYYCFQGSHVPLTFGX_{A9}GTX_{A10}LEX_{A11}K$

Wherein $X_{A1}$ may be V or I

Wherein $X_{A2}$ may be A or P

Wherein $X_{A3}$ may be S or T

Wherein $X_{A4}$ may be L or P

Wherein $X_{A5}$ may be D or E

Wherein $X_{A6}$ may be Q or P

Wherein $X_{A7}$ may be K or Q

Wherein $X_{A8}$ may be L or V

Wherein $X_{A9}$ may be A or Q

Wherein $X_{A10}$ may be R or K or

Wherein $X_{A11}$ may be L or I, wherein at least one of the amino acid identified by X is an amino acid substitution (conservative or non-conservative) in comparison with a corresponding amino acid in the polypeptide set forth in SEQ ID NO.:4.

(variant 1 light chain variable region: Lvh1)

SEQ ID NO.: 33

```
DIVMTQTPLSLPVTPGEPASISCRSSQSLLHSNGNTYLEWYLQKPGQSP
QLLIYTVSNRFSGVPDRFSGSGSGTDFTLKISRVEAEDVGVYYCFQGSHV
PLTFGQGTKLEIK
```

-continued (variant 2 light chain variable region: Lvh2)
SEQ ID NO.: 34
DVVMTQTPLSLPVTPGEPASISCRSSQSLLHSNGNTYLEWYLQKPGQSPK
LLIYTVSNRFSGVPDRFSGSGSGTDFTLKISRVEAEDVGVYYCFQGSHVP
LTFGQGTKLEIK (variant heavy chain variable region)
SEQ ID NO.: 35
QXQLVQSGXEXXKPGASVKXSCKASGYTFTDDYMSWVXQXXGXXLEWXG
DINPYNGDTNYNQKFKGXXXXTXDXSXSTAYMXLXSLXSEDXAVYYCAR
DPGAMDYWGQGTXVTVSS wherein at least one of the amino acid identified by X is an amino acid substitution (conservative or non-conservative) in comparison with a corresponding amino acid in the polypeptide set forth in SEQ ID NO.:2. The amino acid substitution may be, for example conservative.

(variant heavy chain variable region)
SEQ ID NO.: 36
QX$_{b1}$QLVQSGX$_{b2}$EX$_{b3}$X$_{b4}$KPGASVKX$_{b5}$SCKASGYTFTDDYMSVWX$_{b6}$Q X$_{b7}$Xb$_{8}$GX$_{b9}$X$_{b10}$LEWX$_{b11}$GDINPYNGDTNYNQKFKGX$_{b12}$X$_{b13}$X$_{b14}$X$_{b15}$T X$_{b16}$DX$_{b17}$SX$_{b18}$STAYMX$_{b19}$LX$_{b20}$SLX$_{b21}$SEDX$_{b22}$AVYYCARDPGAMDYW GQGTX$_{b23}$VTVSS Wherein X$_{b1}$ may be a hydrophobic amino acid;
Wherein X$_{b2}$ may be P or A;
Wherein X$_{b3}$ may be a hydrophobic amino acid;
Wherein X$_{b4}$ may be V or K;
Wherein X$_{b5}$ may be a hydrophobic amino acid;
Wherein X$_{b6}$ may be a basic amino acid;
Wherein X$_{b7}$ may be S or A;
Wherein X$_{b8}$ may be H or P;
Wherein X$_{b9}$ may be a basic amino acid;
Wherein X$_{b10}$ may be S or G;
Wherein X$_{b11}$ may be a hydrophobic amino acid;
Wherein X$_{b12}$ may be a basic amino acid;
Wherein X$_{b13}$ may be a hydrophobic amino acid;
Wherein X$_{b14}$ may be I or T;
Wherein X$_{b15}$ may be a hydrophobic amino acid;
Wherein X$_{b16}$ may be a hydrophobic amino acid;
Wherein X$_{b17}$ may be K or T;
Wherein X$_{b18}$ may be a neutral hydrophilic amino acid;
Wherein X$_{b19}$ may be Q or E;
Wherein X$_{b20}$ may be N or S;
Wherein X$_{b21}$ may be T or R;
Wherein X$_{b22}$ may be a neutral hydrophilic amino acid; or
Wherein X$_{b23}$ may be S or L, wherein at least one of the amino acid identified by X is an amino acid substitution (conservative or non-conservative) in comparison with a corresponding amino acid in the polypeptide set forth in SEQ ID NO.:2.

(variant heavy chain variable region)
SEQ ID NO.: 37
QX$_{B1}$QLVQSGX$_{B2}$EX$_{B3}$X$_{B4}$KPGASVKX$_{B5}$SCKASGYTFTDDYMSWVX$_{B6}$QX$_{B7}$ X$_{B8}$GX$_{B9}$X$_{B10}$LEWX$_{B11}$GDINPYNGDTNYNQKFKGX$_{B12}$X$_{B13}$X$_{B14}$X$_{B15}$TX$_{B16}$D X$_{B17}$SX$_{B18}$STAYMX$_{B19}$LX$_{B20}$SLX$_{B21}$SEDX$_{B22}$AVYYCARDPGAMDYWGQGT

X$_{B23}$VTVSS

Wherein X$_{B1}$ may be I or V;
Wherein X$_{B2}$ may be P or A;
Wherein X$_{B3}$ may be M or V;
Wherein X$_{B4}$ may be V or K;
Wherein X$_{B5}$ may be M or V;
Wherein X$_{B6}$ may be K or R;
Wherein X$_{B7}$ may be S or A;
Wherein X$_{B8}$ may be H or P;
Wherein X$_{B9}$ may be K or Q;
Wherein X$_{B10}$ may be S or G;
Wherein X$_{B11}$ may be I or M;
Wherein X$_{B12}$ may be K or R;
Wherein X$_{B13}$ may be A or V;
Wherein X$_{B14}$ may be I or T;
Wherein X$_{B15}$ may be L or I;
Wherein X$_{B16}$ may be V or A;
Wherein X$_{B17}$ may be K or T;
Wherein X$_{B18}$ may be S or T;
Wherein X$_{B19}$ may be Q or E;
Wherein X$_{B20}$ may be N or S;
Wherein X$_{B21}$ may be T or R;
Wherein X$_{B22}$ may be S or T; or
Wherein X$_{B23}$ may be S or L, wherein at least one of the amino acid identified by X is an amino acid substitution (conservative or non-conservative) in comparison with a corresponding amino acid in the polypeptide set forth in SEQ ID NO.:2.

(variant 1 heavy chain variable region: Hvh1)
SEQ ID NO.: 38
QVQLVQSGAEVKKPGASVKVSCKASGYTFTDDYMSWVRQAPGQGLEWMGDINPYNGDTN
YNQKFKGRVTITADTSTSTAYMELSSLRSEDTAVYYCARDPGAMDYWGQGTLVTVSS (variant 2 heavy chain variable region: Hvh2)
SEQ ID NO.: 39
QIQLVQSGAEVKKPGASVKVSCKASGYTFTDDYMSWVRQAPGQGLEWMGDINPYNGDTNY
NQKFKGRVTITADKSTSTAYMELSSLRSEDTAVYYCARDPGAMDYWGQGTLVTVSS (variant 3 heavy chain variable region: Hvh3)
SEQ ID NO.: 40
QIQLVQSGAEVKKPGASVKVSCKASGYTFTDDYMSWVRQAPGQGLEWIGDINPYNGDTNY
NQKFKGRATLTVDKSTSTAYMELSSLRSEDTAVYYCARDPGAMDYWGQGTLVTVSS (variant 4 heavy chain variable region: Hvh4)
SEQ ID NO.: 41
QIQLVQSGAEVKKPGASVKVSCKASGYTFTDDYMSWVKQAPGQGLEWIGDINPYNGDTNY
NQKFKGKATLTVDKSTSTAYMELSSLRSEDTAVYYCARDPGAMDYWGQGTLVTVSS -continued 3A4 murine light (kappa) chain
SEQ ID NO: 42
DVVMTQTPLSLAVSLGDQASISCRSSQSLLHSNGNTYLEWYLQKPGQSPKLLIHTVSNRFSG

VPDRFSGSGSGTDFTLKISRVEAEDLGVYYCFQGSHVPLTFGAGTRLELKRTVAAPSVFIFPP

SDEQLKSGTASVVCLLNNFYPREAKVQWKVDNALQSGNSQESVTEQDSKDSTYSLSSTLTL

SKADYEKHKVYACEVTHQGLSSPVTKSFNRGEC

3A4 humanized light (kappa) chain variant 1; Lh1
SEQ ID NO: 43
DIVMTQTPLSLPVTPGEPASISCRSSQSLLHSNGNTYLEWYLQKPGQSPQLLIYTVSNRFSGV

PDRFSGSGSGTDFTLKISRVEAEDVGVYYCFQGSHVPLTFGQGTKLEIKRTVAAPSVFIFPPS

DEQLKSGTASVVCLLNNFYPREAKVQWKVDNALQSGNSQESVTEQDSKDSTYSLSSTLTLS

KADYEKHKVYACEVTHQGLSSPVTKSFNRGEC

3A4 humanized light (kappa) chain variant 2; Lh2
SEQ ID NO: 44
DVVMTQTPLSLPVTPGEPASISCRSSQSLLHSNGNTYLEWYLQKPGQSPKLLIYTVSNRFSG

VPDRFSGSGSGTDFTLKISRVEAEDVGVYYCFQGSHVPLTFGQGTKLEIKRTVAAPSVFIFPP

SDEQLKSGTASVVCLLNNFYPREAKVQWKVDNALQSGNSQESVTEQDSKDSTYSLSSTLTL

SKADYEKHKVYACEVTHQGLSSPVTKSFNRGEC

3A4 murine heavy (Igg1) chain
SEQ ID NO: 45
QIQLVQSGPEMVKPGASVKMSCKASGYTFTDDYMSWVKQSHGKSLEWIGDINPYNGDTNY

NQKFKGKAILTVDKSSSTAYMQLNSLTSEDSAVYYCARDPGAMDYWGQGTSVTVSSASTKG

PSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQGNVFSCSVMH

EALHNHYTQKSLSLSPGK

3A4 humanized heavy (Igg1) chain variant 1; Hh1
SEQ ID NO: 46
QVQLVQSGAEVKKPGASVKVSCKASGYTFTDDYMSWVRQAPGQGLEWMGDINPYNGDTN

YNQKFKGRVTITADTSTSTAYMELSSLRSEDTAVYYCARDPGAMDYWGQGTLVTVSSASTK

GPSVFPLAPSSKSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVM

HEALHNHYTQKSLSLSPGK

3A4 humanized heavy (Igg1) chain variant 2; Hh2
SEQ ID NO: 47
QIQLVQSGAEVKKPGASVKVSCKASGYTFTDDYMSWVRQAPGQGLEWMGDINPYNGDTNY

NQKFKGRVTITADKSTSTAYMELSSLRSEDTAVYYCARDPGAMDYWGQGTLVTVSSASTKG

PSVFPLAPSSKSTSGGTAALGCLVKDYFPEPVTVSWNSGALTSGVHTFPAVLQSSGLYSLSS

VVTVPSSSLGTQTYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQYNSTYRVVSVLT

-continued

VLHQDWLNGKEYKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQGNVFSCSVMH

EALHNHYTQKSLSLSPGK

3A4 humanized heavy (Igg1) chain variant 3; Hh3
SEQ ID NO: 48
QIQLVQSGAEVKKPGASVKVSCKASGYTFTDDYMSWVRQAPGQGLEWIGDINPYNGDTNY

NQKFKGRATLTVDKSTSTAYMELSSLRSEDTAVYYCARDPGAMDYWGQGTLVTVSSASTK

GPSVFPLAPSSKSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVM

HEALHNHYTQKSLSLSPGK

3A4 humanized heavy (Igg1) chain variant 4: Hh4
SEQ ID NO: 49
QIQLVQSGAEVKKPGASVKVSCKASGYTFTDDYMSWVKQAPGQGLEWIGDINPYNGDTNY

NQKFKGKATLTVDKSTSTAYMELSSLRSEDTAVYYCARDPGAMDYWGQGTLVTVSSASTK

GPSVFPLAPSSKSTSGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVM

HEALHNHYTQKSLSLSPGK

SEQ ID NO: 50
ATACCCAAGCTTGCCACCATGGAGACAGACACAC

SEQ ID NO: 51
ATACCCAAGCTTCATTTCCCGGGAGACAGGGAG

SEQ ID NO: 52
ATACCCAAGCTTGGGCCACCATGAACTTTCTGCTGTCTTGG

SEQ ID NO: 53
ATACCCAAGCTTCTAACACTCTCCCCTGTTGAAG pK-CR5
SEQ ID NO: 54
CTAAATTGTAAGCGTTAATATTTTGTTAAAATTCGCGTTAAATTTTGTTAAATCAGCTCAT

TTTTTAACCAATAGGCCGAAATCGGCAAAATCCCTTATAAATCAAAAGAATAGACCGAGA

TAGGGTTGAGTGTTGTTCCAGTTTGGAACAAGAGTCCACTATTAAAGAACGTGGACTCCA

ACGTCAAAGGGCGAAAAACCGTCTATCAGGGCGATGGCCCACTACGTGAACCATCACCC

TAATCAAGTTTTTTGGGGTCGAGGTGCCGTAAAGCACTAAATCGGAACCCTAAAGGGAG

CCCCCGATTTAGAGCTTGACGGGGAAAGCCGGCGAACGTGGCGAGAAAGGAAGGGAA

GAAAGCGAAAGGAGCGGGCGCTAGGGCGCTGGCAAGTGTAGCGGTCACGCTGCGCGT

AACCACCACACCCGCCGCGCTTAATGCGCCGCTACAGGGCGCGTCCCATTCGCCATTC

AGGCTGCGCAACTGTTGGGAAGGGCGATCGGTGCGGGCCTCTTCGCTATTACGCCAGC

TGGCGAAAGGGGATGTGCTGCAAGGCGATTAAGTTGGGTAACGCCAGGGTTTTCCCA

GTCACGACGTTGTAAAACGACGGCCAGTGAGCGCGCGTAATACGACTCACTATAGGGC

GAATTGGAGCTCCACCGCGGTGGCGGCCGCTCTAGAACTAGTGGATCCACATCGGCGC

GCCAAATGATTTGCCCTCCCATATGTCCTTCCGAGTGAGAGACACAAAAAATTCCAACAC

-continued

```
ACTATTGCAATGAAAATAAATTTCCTTTATTAGCCAGAGGTCGAGATTTAAATAAGCTTGC

TAGCAGATCTTTGGACCTGGGAGTGGACACCTGTGGAGAGAAAGGCAAAGTGGATGTCA

TTGTCACTCAAGTGTATGGCCAGATCGGGCCAGGTGAATATCAAATCCTCCTCGTTTTTG

GAAACTGACAATCTTAGCGCAGAAGTAATGCCCGCTTTTGAGAGGGAGTACTCACCCCA

ACAGCTGGATCTCAAGCCTGCCACACCTCACCTCGACCATCCGCCGTCTCAAGACCGCC

TACTTTAATTACATCATCAGCAGCACCTCCGCCAGAAACAACCCCGACCGCCACCCGCT

GCCGCCCGCCACGGTGCTCAGCCTACCTTGCGACTGTGACTGGTTAGACGCCTTTCTC

GAGAGGTTTTCCGATCCGGTCGATGCGGACTCGCTCAGGTCCCTCGGTGGCGGAGTAC

CGTTCGGAGGCCGACGGGTTTCCGATCCAAGAGTACTGGAAAGACCGCGAAGAGTTTG

TCCTCAACCGCGAGCCCAACAGCTGGCCCTCGCAGACAGCGATGCGGAAGAGAGTGAC

CGCGGAGGCTGGATCGGTCCCGGTGTCTTCTATGGAGGTCAAAACAGCGTGGATGGCG

TCTCCAGGCGATCTGACGGTTCACTAAACGAGCTCTGCTTATATAGGCCTCCCACCGTA

CACGCCTACCTCGACCCGGGTACCAATCTTATAATACAAACAGACCAGATTGTCTGTTTG

TTATAATACAAACAGACCAGATTGTCTGTTTGTTATAATACAAACAGACCAGATTGTCTGT

TTGTTATAATACAAACAGACCAGATTGTCTGTTTGTTATAATACAAACAGACCAGATTGTC

TGTTTGTTATAATACAAACAGACCAGATTGTCTGTTTGTTAAGGTTGTCGAGTGAAGACG

AAAGGGTTCATTAAGGCGCGCCGTCGACCTCGAGGGGGGCCCGGTACCCAGCTTTTG

TTCCCTTTAGTGAGGGTTAATTGCGCGCTTGGCGTAATCATGGTCATAGCTGTTTCCTGT

GTGAAATTGTTATCCGCTCACAATTCCACACAACATACGAGCCGGAAGCATAAAGTGTAA

AGCCTGGGGTGCCTAATGAGTGAGCTAACTCACATTAATTGCGTTGCGCTCACTGCCCG

CTTTCCAGTCGGGAAACCTGTCGTGCCAGCTGCATTAATGAATCGGCCAACGCGCGGG

GAGAGGCGGTTTGCGTATTGGGCGCTCTTCCGCTTCCTCGCTCACTGACTCGCTGCGCT

CGGTCGTTCGGCTGCGGCGAGCGGTATCAGCTCACTCAAAGGCGGTAATACGGTTATC

CACAGAATCAGGGGATAACGCAGGAAAGAACATGTGAGCAAAAGGCCAGCAAAAGGCC

AGGAACCGTAAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGACTATAAAGAT

ACCAGGCGTTTCCCCCTGGAAGCTCCCTCGTGCGCTCTCCTGTTCCGACCCTGCCGCTT

ACCGGATACCTGTCCGCCTTTCTCCCTTCGGGAAGCGTGGCGCTTTCTCATAGCTCACG

CTGTAGGTATCTCAGTTCGGTGTAGGTCGTTCGCTCCAAGCTGGGCTGTGTGCACGAAC

CCCCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTAGA

AGGACAGTATTTGGTATCTGCGCTCTGCTGAAGCCAGTTACCTTCGGAAAAAGAGTTGG

TAGCTCTTGATCCGGCAAACAAACCACCGCTGGTAGCGGTGGTTTTTTGTTTGCAAGCA

GCAGATTACGCGCAGAAAAAAAGGATCTCAAGAAGATCCTTTGATCTTTTCTACGGGGTC

TGACGCTCAGTGGAACGAAAACTCACGTTAAGGGATTTTGGTCATGAGATTATCAAAAAG

GATCTTCACCTAGATCCTTTTAAATTAAAAATGAAGTTTTAAATCAATCTAAAGTATATATG

AGTAAACTTGGTCTGACAGTTACCAATGCTTAATCAGTGAGGCACCTATCTCAGCGATCT

GTCTATTTCGTTCATCCATAGTTGCCTGACTCCCCGTCGTGTAGATAACTACGATACGGG

AGGGCTTACCATCTGGCCCCAGTGCTGCAATGATACCGCGAGACCCACGCTCACCGGC
```

```
TCCAGATTTATCAGCAATAAACCAGCCAGCCGGAAGGGCCGAGCGCAGAAGTGGTCCT

GCAACTTTATCCGCCTCCATCCAGTCTATTAATTGTTGCCGGGAAGCTAGAGTAAGTAGT

TCGCCAGTTAATAGTTTGCGCAACGTTGTTGCCATTGCTACAGGCATCGTGGTGTCACG

CTCGTCGTTTGGTATGGCTTCATTCAGCTCCGGTTCCCAACGATCAAGGCGAGTTACAT

GATCCCCCATGTTGTGCAAAAAAGCGGTTAGCTCCTTCGGTCCTCCGATCGTTGTCAGA

AGTAAGTTGGCCGCAGTGTTATCACTCATGGTTATGGCAGCACTGCATAATTCTCTTACT

GTCATGCCATCCGTAAGATGCTTTTCTGTGACTGGTGAGTACTCAACCAAGTCATTCTGA

GAATAGTGTATGCGGCGACCGAGTTGCTCTTGCCCGGCGTCAATACGGGATAATACCGC

GCCACATAGCAGAACTTTAAAAGTGCTCATCATTGGAAAACGTTCTTCGGGGCGAAAACT

CTCAAGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAGGCAAA

ATGCCGCAAAAAAGGGAATAAGGGCGACACGGAAATGTTGAATACTCATACTCTTCCTTT

TTCAATATTATTGAAGCATTTATCAGGGTTATTGTCTCATGAGCGGATACATATTTGAATG

TATTTAGAAAAATAAACAAATAGGGGTTCCGCGCACATTTCCCCGAAAAGTGCCAC pMPG-CR5
                                                        SEQ ID NO: 55
GTCGACGATACCGTGCACTTAATTAAGCGCGCTCGACCAAATGATTTGCCCTCCCATATG

TCCTTCCGAGTGAGAGACACAAAAAATTCCAACACACTATTGCAATGAAAATAAATTTCCT

TTATTAGCCAGAGGTCGAGGTCGGGGGATCCGTTTAAACTTGGACCTGGGAGTGGACAC

CTGTGGAGAGAAAGGCAAAGTGGATGTCATTGTCACTCAAGTGTATGGCCAGATCGGGC

CAGGTGAATATCAAATCCTCCTCGTTTTTGGAAACTGACAATCTTAGCGCAGAAGTAATG

CCCGCTTTTGAGAGGGAGTACTCACCCCAACAGCTGGATCTCAAGCCTGCCACACCTCA

CCTCGACCATCCGCCGTCTCAAGACCGCCTACTTTAATTACATCATCAGCAGCACCTCC

GCCAGAAACAACCCCGACCGCCACCCGCTGCCGCCCGCCACGGTGCTCAGCCTACCTT

GCGACTGTGACTGGTTAGACGCCTTTCTCGAGAGGTTTTCCGATCCGGTCGATGCGGAC

TCGCTCAGGTCCCTCGGTGGCGGAGTACCGTTCGGAGGCCGACGGGTTTCCGATCCAA

GAGTACTGGAAAGACCGCGAAGAGTTTGTCCTCAACCGCGAGCCCAACAGCTGGCCCT

CGCAGACAGCGATGCGGAAGAGAGTGACCGCGGAGGCTGGATCGGTCCCGGTGTCTT

CTATGGAGGTCAAAACAGCGTGGATGGCGTCTCCAGGCGATCTGACGGTTCACTAAACG

AGCTCTGCTTATATAGGCCTCCCACCGTACACGCCTACCTCGACCCGGGTACCAATCTT

ATAATACAAACAGACCAGATTGTCTGTTTGTTATAATACAAACAGACCAGATTGTCTGTTT

GTTATAATACAAACAGACCAGATTGTCTGTTTGTTATAATACAAACAGACCAGATTGTCTG

TTTGTTATAATACAAACAGACCAGATTGTCTGTTTGTTATAATACAAACAGACCAGATTGT

CTGTTTGTTAAGGTTGTCGAGTGAAGACGAAAGGGTTAATTAAGGCGCGCCGTCGACTA

GCTTGGCACGCCAGAAATCCGCGCGGTGGTTTTTGGGGGTCGGGGGTGTTTGGCAGCC

ACAGACGCCCGGTGTTCGTGTCGCGCCAGTACATGCGGTCCATGCCCAGGCCATCCAA

AAACCATGGGTCTGTCTGCTCAGTCCAGTCGTGGACCAGACCCCACGCAACGCCCAAAA

TAATAACCCCCACGAACCATAAACCATTCCCCATGGGGGACCCCGTCCCTAACCCACGG

GGCCAGTGGCTATGGCAGGGCCTGCCGCCCCGACGTTGGCTGCGAGCCCTGGGCCTT

CACCCGAACTTGGGGGGTGGGTGGGGAAAAGGAAGAAACGCGGGCGTATTGGCCCC

AATGGGGTCTCGGTGGGGTATCGACAGAGTGCCAGCCCTGGGACCGAACCCCGCGTTT

ATGAACAAACGACCCAACACCCGTGCGTTTTATTCTGTCTTTTTATTGCCGTCATAGCGC
```

-continued

```
GGGTTCCTTCCGGTATTGTCTCCTTCCGTGTTTCAGTTAGCCTCCCCCATCTCCCCTATT

CCTTTGCCCTCGGACGAGTGCTGGGGCGTCGGTTTCCACTATCGGCGAGTACTTCTACA

CAGCCATCGGTCCAGACGGCCGCGCTTCTGCGGGCGATTTGTGTACGCCCGACAGTCC

CGGCTCCGGATCGGACGATTGCGTCGCATCGACCCTGCGCCCAAGCTGCATCATCGAA

ATTGCCGTCAACCAAGCTCTGATAGAGTTGGTCAAGACCAATGCGGAGCATATACGCCC

GGAGCCGCGGCGATCCTGCAAGCTCCGGATGCCTCCGCTCGAAGTAGCGCGTCTGCTG

CTCCATACAAGCCAACCACGGCCTCCAGAAGAAGATGTTGGCGACCTCGTATTGGGAAT

CCCCGAACATCGCCTCGCTCCAGTCAATGACCGCTGTTATGCGGCCATTGTCCGTCAGG

ACATTGTTGGAGCCGAAATCCGCGTGCACGAGGTGCCGGACTTCGGGGCAGTCCTCGG

CCCAAAGCATCAGCTCATCGAGAGCCTGCGCGACGGACGCACTGACGGTGTCGTCCAT

CACAGTTTGCCAGTGATACACATGGGGATCAGCAATCGCGCATATGAAATCACGCCATG

TAGTGTATTGACCGATTCCTTGCGGTCCGAATGGGCCGAACCCGCTCGTCTGGCTAAGA

TCGGCCGCAGCGATCGCATCCATGGCCTCCGCGACCGGCTGCAGAACAGCGGGCAGTT

CGGTTTCAGGCAGGTCTTGCAACGTGACACCCTGTGCACGGCGGGAGATGCAATAGGT

CAGGCTCTCGCTGAATTCCCCAATGTCAAGCACTTCCGGAATCGGGAGCGCGGCCGAT

GCAAAGTGCCGATAAACATAACGATCTTTGTAGAAACCATCGGCGCAGCTATTTACCCGC

AGGACATATCCACGCCCTCCTACATCGAAGCTGAAAGCACGAGATTCTTCGCCCTCCGA

GAGCTGCATCAGGTCGGAGACGCTGTCGAACTTTTCGATCAGAAACTTCTCGACAGACG

TCGCGGTGAGTTCAGGCTTTTTCATATCTCATTGCCCGGGATCTGCGGCACGCTGTTGA

CGCTGTTAAGCGGGTCGCTGCAGGGTCGCTCGGTGTTCGAGGCCACACGCGTCACCTT

AATATGCGAAGTGGACCTGGGACCGCGCCGCCCCGACTGCATCTGCGTGTTCGAATTC

GCCAATGACAAGACGCTGGGCGGGGTTTGTGTCATCATAGAACTAAAGACATGCAAATA

TATTTCTTCCGGGGACACCGCCAGCAAACGCGAGCAACGGGCCACGGGGATGAAGCAG

GGCATGGCGGCCGACGCGCTGGGCTACGTCTTGCTGGCGTTCGCGACGCGAGGCTGG

ATGGCCTTCCCCATTATGATTCTTCTCGCTTCCGGCGGCATCGGGATGCCCGCGTTGCA

GGCCATGCTGTCCAGGCAGGTAGATGACGACCATCAGGGACAGCTTCAAGGATCGCTC

GCGGCTCTTACCAGCCTAACTTCGATCACTGGACCGCTGATCGTCACGGCGATTTATGC

CGCCTCGGCGAGCACATGGAACGGGTTGGCATGGATTGTAGGCGCCGCCCTATACCTT

GTCTGCCTCCCCGCGTTGCGTCGCGGTGCATGGAGCCGGGCCACCTCGACCTGAATGG

AAGCCGGCGGCACCTCGCTAACGGATTCACCACTCCAAGAATTGGAGCCAATCAATTCT

TGCGGAGAACTGTGAATGCGCAAACCAACCCTTGGCAGAACATATCCATCGCGTCCGCC

ATCTCCAGCAGCCGCACGCGGCGCAGCAAAAGGCCAGGAACCGTAAAAAGGCCGCGTT

GCTGGCGTTTTTCCATAGGCTCCGCCCCCCTGACGAGCATCACAAAAATCGACGCTCAA

GTCAGAGGTGGCGAAACCCGACAGGACTATAAAGATACCAGGCGTTTCCCCCTGGAAG

CTCCCTCGTGCGCTCTCCTGTTCCGACCCTGCCGCTTACCGGATACCTGTCCGCCTTTC

TCCCTTCGGGAAGCGTGGCGCTTTCTCATAGCTCACGCTGTAGGTATCTCAGTTCGGTG

TAGGTCGTTCGCTCCAAGCTGGGCTGTGTGCACGAACCCCCCGTTCAGCCCGACCGCT

GCGCCTTATCCGGTAACTATCGTCTTGAGTCCAACCCGGTAAGACACGACTTATCGCCA

CTGGCAGCAGCCACTGGTAACAGGATTAGCAGAGCGAGGTATGTAGGCGGTGCTACAG

AGTTCTTGAAGTGGTGGCCTAACTACGGCTACACTAGAAGGACAGTATTTGGTATCTGC
```

```
GCTCTGCTGAAGCCAGTTACCTTCGGAAAAAGAGTTGGTAGCTCTTGATCCGGCAAACA
AACCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACGAAA
ACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATAAA
CCAGCCAGCCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAATAGTTTGCGC
AACGTTGTTGCCATTGCTGCAGGCATCGTGGTGTCACGCTCGTCGTTTGGTATGGCTTC
ATTCAGCTCCGGTTCCCAACGATCAAGGCGAGTTACATGATCCCCCATGTTGTGCAAAAA
AGCGGTTAGCTCCTTCGGTCCTCCGATCGTTGTCAGAAGTAAGTTGGCCGCAGTGTTAT
CACTCATGGTTATGGCAGCACTGCATAATTCTCTTACTGTCATGCCATCCGTAAGATGCT
TTTCTGTGACTGGTGAGTACTCAACCAAGTCATTCTGAGAATAGTGTATGCGGCGACCGA
GTTGCTCTTGCCCGGCGTCAACACGGGATAATACCGCGCCACATAGCAGAACTTTAAAA
GTGCTCATCATTGGAAAACGTTCTTCGGGGCGAAAACTCTCAAGGATCTTACCGCTGTTG
AGATCCAGTTCGATGTAACCCACTCGTGCACCCAACTGATCTTCAGCATCTTTTACTTTC
ACCAGCGTTTCTGGGTGAGCAAAAACAGGAAGGCAAATGCCGCAAAAAAGGGAATAAG
GGCGACACGGAAATGTTGAATACTCATACTCTTCCTTTTTCAATATTATTGAAGCATTTAT
CAGGGTTATTGTCTCATGAGCGGATACATATTTGAATGTATTTAGAAAAATAAACAAATAG
GGGTTCCGCGCACATTTCCCCGAAAAGTGCCACCTGACGTCTAAGAAACCATTATTATCA
TGACATTAACCTATAAAAATAGGCGTATCACGAGGCCCTTTCGTCTTCAAGAATTCTCAT
GTTTGACAGCTTATCTCTAGCAGATCCGGAATTCCCCTCCCCAATTTAAATGAGGACCTA
ACCTGTGGAAATCTACTGATGTGGGAGGCTGTAACTGTACAAACAGAGGTTATTGGAATA
ACTAGCATGCTTAACCTTCATGCAGGGTCACAAAAAGTGCATGACGATGGTGGAGGAAA
ACCTATTCAAGGCAGTAATTTCCACTTCTTTGCTGTTGGTGGAGACCCCTTGGAAATGCA
GGGAGTGCTAATGAATTACAGGACAAAGTACCCAGATGGTACTATAACCCCTAAAAACCC
AACAGCCCAGTCCCAGGTAATGAATACTGACCATAAGGCCTATTTGGACAAAAACAATGC
TTATCCAGTTGAGTGCTGGGTTCCTGATCCTAGTAGAAATGAAAATACTAGGTATTTTGG
GACTTTCACAGGAGGGAAAATGTTCCCCCAGTACTTCATGTGACCAACACAGCTACCA
CAGTGTTGCTAGATGAACAGGGTGTGGGGCCTCTTTGTAAAGCTGATAGCCTGTATGTTT
CAGCTGCTGATATTTGTGGCCTGTTTACTAACAGCTCTGGAACACAACAGTGGAGAGGC
CTTGCAAGATATTTTAAGATCCGCCTGAGAAAAGATCTGTAAAGAATCCTTACCTAATTT
CCTTTTTGCTAAGTGACCTTATAAACAGGAGAACCCAGAGAGTGGATGGGCAGCCTATG
TATGGTATGGAATCCCAGGTAGAAGAGGTTAGGGTGTTTGATGGCACAGAAAGACTTCC
AGGGGACCCAGATATGATAAGATATATTGACAAACAGGGACAATTGCAAACCAAATGCT
TTAAACAGGTGCTTTTATTGTACATATACATTTAATAAATGCTGCTTTTGTATAAGCCACTT
TTAAGCTTGTGTTATTTTGGGGGTGGTGTTTTAGGCCTTTTAAAACACTGAAAGCCTTTAC
ACAAATGCAACTCTTGACTATGGGGGTCTGACCTTTGGGAATGTTCAGCAGGGGCTGAA
GTATCTGAGACTTGGGAAGAGCATTGTGATTGGGATTCAGTGCTTGATCCATGTCCAGA
```

GTCTTCAGTTTCTGAATCCTCTTCTCTTGTAATATCAAGAATACATTTCCCCATGCATATAT

TATATTTCATCCTTGAAAAAGTATACATACTTATCTCAGAATCCAGCCTTTCCTTCCATTCA

ACAATTCTAGAAGTTAAAACTGGGGTAGATGCTATTACAGAGGTAGAATGCTTCCTAAAC

CCAGAAATGGGGGATCTGC

3A4 humanized heavy chain CDR2 polypeptide sequence
                                              SEQ ID NO.: 56
DINPYNGDTNYNQKFKG

---

The invention claimed is:

1. A nucleic acid comprising a sequence encoding a light chain variable domain and/or a heavy chain variable domain of an antibody or antigen binding fragment thereof that specifically binds to kidney associated antigen 1 (SEQ ID NO.29), said light chain variable domain comprising complementarity determining regions having the amino acid sequence set forth in SEQ ID NO.8, SEQ ID NO.9 and SEQ ID NO.10 and said heavy chain variable domain comprising complementarity determining regions having the amino acid sequence set forth in SEQ ID NO.5, SEQ ID NO.6 and SEQ ID NO.7.

2. A vector or vectors comprising the nucleic acid of claim 1.

3. The vector or vectors of claim 2, wherein said vector or vectors comprise a constitutive or an inducible promoter.

4. An isolated cell comprising the nucleic acid of claim 1.

5. The isolated cell of claim 4, wherein said cell is capable of expressing, assembling and/or secreting an antibody or antigen binding fragment thereof.

6. A method of making an antibody or antigen binding fragment thereof comprising culturing the cell of claim 4, so that the antibody or antigen binding fragment thereof is produced.

7. The method of claim 6, further comprising recovering the antibody or antigen binding fragment thereof.

8. The method of claim 7, further comprising conjugating the antibody or antigen binding fragment thereof with a therapeutic or cytotoxic agent.

9. A nucleic acid comprising a sequence encoding a light chain variable domain and/or a heavy chain variable domain of an antibody or antigen binding fragment thereof that specifically binds to kidney associated antigen 1 (SEQ ID NO.:29), said light chain variable domain having an amino acid sequence selected from the group consisting of SEQ ID NO.:4, SEQ ID NO.:33 and SEQ ID NO.:34 and said heavy chain variable domain having an amino acid sequence selected from the group consisting of SEQ ID NO.:2, SEQ ID NO.:38, SEQ ID NO.:39, SEQ ID NO.:40 and SEQ ID NO.:41.

10. The nucleic acid of claim 9, wherein said nucleic acid comprises:
   a. a sequence encoding the light chain variable domain set forth in SEQ ID NO.:33 and/or the heavy chain variable domain set forth in SEQ ID NO.:41 or,
   b. a sequence encoding the light chain set forth in SEQ ID NO.:43 and/or the heavy chain set forth in SEQ ID NO.:49.

11. A vector or vectors comprising the nucleic acid of claim 9.

12. An isolated cell comprising the vector or vectors of claim 11.

13. A method of making an antibody or antigen binding fragment thereof comprising culturing the cell of claim 12 so that the antibody or antigen binding fragment thereof is produced.

14. The method of claim 13, further comprising recovering the antibody or antigen binding fragment thereof.

15. The method of claim 14, further comprising conjugating the antibody or antigen binding fragment thereof with a therapeutic or cytotoxic agent.

16. A cell constitutively- or inducibly-expressing an antibody or an antigen binding fragment thereof that specifically binds to kidney associated antigen 1 (SEQ ID NO.29), wherein said cell comprises a nucleic acid or nucleic acids comprising a sequence encoding a light chain variable domain comprising complementarity determining regions having the amino acid sequence set forth in SEQ ID NO.:8, SEQ ID NO.:9 and SEQ ID NO.:10 and a heavy chain variable domain comprising complementarity determining regions having the amino acid sequence set forth in SEQ ID NO.:5, SEQ ID NO.:6 and SEQ ID NO.: 7.

17. The cell of claim 16, wherein the nucleic acid or nucleic acids comprise a sequence encoding a light chain variable domain having an amino acid sequence selected from the group consisting of SEQ ID NO.:4, SEQ ID NO.:33 and SEQ ID NO.:34 and a heavy chain variable domain having an amino acid sequence selected from the group consisting of SEQ ID NO.:2, SEQ ID NO.:38, SEQ ID NO.:39, SEQ ID NO.:40 and SEQ ID NO.:41.

18. The cell of claim 16, wherein the nucleic acid or nucleic acids comprise:
 a. a sequence encoding a light chain variable domain having the amino acid sequence set forth in SEQ ID NO.:33 and a heavy chain variable domain having the amino acid sequence set forth in SEQ ID NO.:41 or,
 b. a sequence encoding a light chain having the amino acid sequence set forth in SEQ ID No.:43 and a heavy chain having the amino acid sequence set forth in SEQ ID NO.:49.

19. A method of making an antibody or antigen binding fragment thereof comprising culturing the cell of claim 16, so that the antibody or antigen binding fragment thereof is produced.

20. The method of claim 19, further comprising recovering the antibody or antigen binding fragment thereof.

21. The method of claim 20, further comprising conjugating the antibody or antigen binding fragment thereof with a therapeutic or cytotoxic agent.

\* \* \* \* \*